(12) United States Patent
Liu et al.

(10) Patent No.: US 11,965,021 B2
(45) Date of Patent: *Apr. 23, 2024

(54) CELLS EXPRESSING CHIMERIC ACTIVATING RECEPTORS AND CHIMERIC STIMULATING RECEPTORS AND USES THEREOF

(71) Applicant: EUREKA THERAPEUTICS, INC., Emeryville, CA (US)

(72) Inventors: Hong Liu, El Sobrante, CA (US); Pengbo Zhang, Fremont, CA (US); Lucas Horan, Emeryville, CA (US); Yiyang Xu, Pleasanton, CA (US); Binnaz K. Staley, San Carlos, CA (US); Lianxing Liu, San Francisco, CA (US); Hongruo Yun, San Francisco, CA (US)

(73) Assignee: EUREKA THERAPEUTICS, INC., Emeryville, CA (US)

( * ) Notice: Subject to any disclaimer, the term of this patent is extended or adjusted under 35 U.S.C. 154(b) by 801 days.

This patent is subject to a terminal disclaimer.

(21) Appl. No.: 16/608,366

(22) PCT Filed: Apr. 24, 2018

(86) PCT No.: PCT/US2018/029218
§ 371 (c)(1),
(2) Date: Oct. 25, 2019

(87) PCT Pub. No.: WO2018/200583
PCT Pub. Date: Nov. 1, 2018

(65) Prior Publication Data
US 2021/0107976 A1    Apr. 15, 2021

Related U.S. Application Data

(60) Provisional application No. 62/490,580, filed on Apr. 26, 2017, provisional application No. 62/490,578, (Continued)

(51) Int. Cl.
| | | |
|---|---|---|
| *C07K 14/705* | (2006.01) |
| *A61K 35/17* | (2015.01) |
| *A61K 39/00* | (2006.01) |
| *A61P 35/00* | (2006.01) |
| *C07K 14/725* | (2006.01) |
| *C07K 16/28* | (2006.01) |
| *C07K 16/30* | (2006.01) |
| *A61K 38/00* | (2006.01) |

(52) U.S. Cl.
CPC .......... *C07K 16/2803* (2013.01); *A61K 35/17* (2013.01); *A61P 35/00* (2018.01); *C07K 14/7051* (2013.01); *C07K 14/70521* (2013.01); *C07K 14/70578* (2013.01); *C07K 16/2809* (2013.01); *C07K 16/2827* (2013.01); *C07K 16/283* (2013.01); *C07K 16/2833* (2013.01); *C07K 16/2887* (2013.01); *C07K 16/303* (2013.01); *A61K 38/00* (2013.01); *A61K 2039/505* (2013.01); *C07K 2317/24* (2013.01); *C07K 2317/31* (2013.01); *C07K 2317/522* (2013.01); *C07K 2317/53* (2013.01); *C07K 2317/54* (2013.01); *C07K 2317/55* (2013.01); *C07K 2317/622* (2013.01); *C07K 2317/92* (2013.01); *C07K 2317/94* (2013.01); *C07K 2319/02* (2013.01); *C07K 2319/03* (2013.01); *C07K 2319/30* (2013.01); *C07K 2319/33* (2013.01)

(58) Field of Classification Search
CPC ..... A61K 35/17; A61P 35/00; C07K 14/7051; C07K 14/70521; C07K 2317/24
See application file for complete search history.

(56) References Cited

U.S. PATENT DOCUMENTS 3,753,357 A   8/1973  Schwartz
4,199,022 A   4/1980  Senkan et al.
(Continued)

FOREIGN PATENT DOCUMENTS

CN   102666576 A   9/2012
CN   103965362 A   8/2014
(Continued)

OTHER PUBLICATIONS

Abhinandan, K.R. et al. (Aug. 2008, e-pub. Jul. 9, 2008). "Analysis and Improvements To Kabat and Structurally Correct Numbering Of Antibody Variable Domain," Molecular Immunology 45(14):3832-3839.
(Continued)

*Primary Examiner* — Mark Halvorson
(74) *Attorney, Agent, or Firm* — MORRISON & FOERSTER LLP

(57) ABSTRACT

The present application provides immune cells (such as T cells) comprising a chimeric antibody-T cell receptor (TCR) construct (caTCR) and a chimeric signaling receptor (CSR) construct. The caTCR comprises an antigen-binding module that specifically binds to a target antigen and a T cell receptor module (TCRM) capable of recruiting at least one TCR-associated signaling molecule, and the CSR comprises a ligand-binding domain that specifically binds to a target ligand and a co-stimulatory signaling domain capable of providing a stimulatory signal to the immune cell. Also provided are methods of making and using these cells.

23 Claims, 20 Drawing Sheets
Specification includes a Sequence Listing.

Related U.S. Application Data filed on Apr. 26, 2017, provisional application No. 62/490,576, filed on Apr. 26, 2017.

(56) References Cited

U.S. PATENT DOCUMENTS

| | | |
|---|---|---|
| 4,559,298 A | 12/1985 | Fahy |
| 4,816,567 A | 3/1989 | Cabilly et al. |
| 5,229,275 A | 7/1993 | Goroff |
| 5,350,674 A | 9/1994 | Boenisch et al. |
| 5,399,346 A | 3/1995 | Anderson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,580,859 A | 12/1996 | Felgner et al. |
| 5,585,358 A | 12/1996 | Bialer et al. |
| 5,585,362 A | 12/1996 | Wilson et al. |
| 5,589,466 A | 12/1996 | Felgner et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,750,373 A | 5/1998 | Garrard et al. |
| 5,883,223 A | 3/1999 | Gray |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,446,179 B2 | 11/2008 | Jensen |
| 7,741,465 B1 | 6/2010 | Eshhar et al. |
| 8,784,821 B1 | 7/2014 | Kufer |
| 10,011,658 B2 | 7/2018 | Liu |
| 10,098,951 B2 | 10/2018 | Lu et al. |
| 10,208,285 B2 | 2/2019 | Baeuerle |
| 10,464,988 B2 | 11/2019 | Lu et al. |
| 10,822,389 B2 | 11/2020 | Lu et al. |
| 10,822,413 B2 | 11/2020 | Liu et al. |
| 11,613,573 B2 | 3/2023 | Horan et al. |
| 2004/0043401 A1 | 3/2004 | Sadelain et al. |
| 2005/0079574 A1 | 4/2005 | Bond |
| 2005/0119455 A1 | 6/2005 | Fuh et al. |
| 2005/0266000 A1 | 12/2005 | Bond et al. |
| 2006/0121005 A1 | 6/2006 | Berenson et al. |
| 2007/0071675 A1 | 3/2007 | Wu |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0118512 A1 | 5/2008 | Auf |
| 2008/0138336 A1 | 6/2008 | Damschroder |
| 2008/0311134 A1 | 12/2008 | Junutula et al. |
| 2009/0002360 A1 | 1/2009 | Chen et al. |
| 2009/0142349 A1 | 6/2009 | Rao-naik |
| 2010/0005543 A1 | 1/2010 | Sampson |
| 2010/0153133 A1 | 6/2010 | Angell et al. |
| 2010/0183564 A1 | 7/2010 | Boitano et al. |
| 2011/0286916 A1 | 11/2011 | Aste-amezaga |
| 2011/0311517 A1 | 12/2011 | Li |
| 2012/0251579 A1 | 10/2012 | Zender |
| 2013/0171152 A1 | 7/2013 | Spriggs et al. |
| 2013/0280220 A1 | 10/2013 | Ahmed et al. |
| 2014/0294841 A1 | 10/2014 | Scheinberg et al. |
| 2014/0370022 A1 | 12/2014 | Kim |
| 2015/0118237 A1 | 4/2015 | Kojoh |
| 2015/0183877 A1 | 7/2015 | Demarest et al. |
| 2015/0259436 A1 | 9/2015 | Scheinberg et al. |
| 2015/0274828 A1 | 10/2015 | Sun |
| 2015/0342993 A1* | 12/2015 | Kloss ............. A61K 39/001182 |
| | | 435/325 |
| 2016/0137715 A1 | 5/2016 | Molloy |
| 2016/0280796 A1 | 9/2016 | Scheinberg et al. |
| 2017/0088630 A1 | 3/2017 | Scheinberg et al. |
| 2017/0306303 A1* | 10/2017 | Taunton ............ A61K 39/0011 |
| 2018/0009892 A1 | 1/2018 | Liu et al. |
| 2018/0079815 A1 | 3/2018 | Liu |
| 2018/0085457 A1 | 3/2018 | Lu et al. |
| 2018/0118822 A1 | 5/2018 | Brentjens et al. |
| 2018/0118842 A1 | 5/2018 | Brentjens et al. |
| 2018/0127503 A1 | 5/2018 | Liu et al. |
| 2018/0134787 A1 | 5/2018 | Liu |
| 2018/0142016 A1 | 5/2018 | Wong et al. |
| 2018/0148503 A1 | 5/2018 | Scheinberg et al. |
| 2018/0208658 A1 | 7/2018 | Liu |
| 2018/0230193 A1* | 8/2018 | Loew ................ C07K 14/7051 |
| 2018/0258261 A1 | 9/2018 | Motz et al. |
| 2018/0258187 A1 | 9/2018 | Cheung et al. |
| 2018/0371085 A1 | 12/2018 | Brentjens et al. |
| 2019/0022216 A1 | 1/2019 | Lu et al. |
| 2019/0030071 A1* | 1/2019 | De Berardinis ..... C12N 5/0636 |
| 2019/0144563 A1 | 5/2019 | Scheinberg et al. |
| 2019/0248865 A1 | 8/2019 | Lu et al. |
| 2019/0256571 A1 | 8/2019 | Baeuerle |
| 2019/0276540 A1 | 9/2019 | Baeuerle |
| 2019/0284262 A1 | 9/2019 | Scheinberg et al. |
| 2019/0315859 A1 | 10/2019 | Liu et al. |
| 2019/0382504 A1 | 12/2019 | Liu et al. |
| 2020/0087400 A1 | 3/2020 | Liu et al. |
| 2020/0115434 A1 | 4/2020 | Lu |
| 2020/0115448 A1 | 4/2020 | Liu et al. |
| 2020/0115470 A1 | 4/2020 | Cheung et al. |
| 2020/0123249 A1 | 4/2020 | Brentjens et al. |
| 2020/0123250 A1 | 4/2020 | Brentjens et al. |
| 2020/0123266 A1 | 4/2020 | Brentjens et al. |
| 2020/0207828 A1 | 7/2020 | Baeuerle |
| 2021/0017280 A1 | 1/2021 | Cui et al. |
| 2021/0093666 A1 | 4/2021 | Staley et al. |
| 2021/0101954 A1 | 4/2021 | Horan et al. |
| 2021/0107992 A1 | 4/2021 | Zhang et al. |
| 2021/0163624 A1 | 6/2021 | Scheinberg et al. |
| 2021/0253665 A1 | 8/2021 | Lu et al. |
| 2021/0277117 A1 | 9/2021 | Liu et al. |
| 2021/0388081 A1 | 12/2021 | Brentjens et al. |
| 2021/0403597 A1 | 12/2021 | Spriggs et al. |
| 2022/0185910 A1 | 6/2022 | Liu et al. |
| 2022/0235143 A1 | 7/2022 | Spriggs et al. |
| 2022/0315660 A1 | 10/2022 | Brentjens et al. |
| 2023/0048360 A1 | 2/2023 | Zhang et al. |

FOREIGN PATENT DOCUMENTS

| | | | |
|---|---|---|---|
| CN | 104087592 A | 10/2014 | |
| CN | 104769103 A | 7/2015 | |
| CN | 104853766 A | 8/2015 | |
| CN | 105331585 A | 2/2016 | |
| CN | 103319595 B | 12/2016 | |
| EP | 0340793 A2 | 8/1995 | |
| EP | 0340793 B1 | 8/1995 | |
| EP | 2155789 A2 | 2/2010 | |
| EP | 3445787 A1 | 2/2019 | |
| EP | 3558348 A1 | 10/2019 | |
| EP | 3638295 A1 | 4/2020 | |
| JP | H02174681 A | 7/1990 | |
| JP | 2014512812 A | 5/2014 | |
| JP | 2015516818 A | 6/2015 | |
| JP | 2015528298 A | 9/2015 | |
| JP | 2015535689 A | 12/2018 | |
| JP | 2020513754 A | 5/2020 | |
| RU | 2529373 C2 | 9/2014 | |
| WO | WO 94/09131 | * 4/1994 | ............. C12N 15/10 |
| WO | WO-1997/02342 A1 | 1/1997 | |
| WO | WO-1997/17852 A1 | 5/1997 | |
| WO | WO-2001/29058 A1 | 4/2001 | |
| WO | 2001077342 A1 | 10/2001 | |

(56) References Cited

FOREIGN PATENT DOCUMENTS

| | | |
|---|---|---|
| WO | WO-2001/96584 A2 | 12/2001 |
| WO | WO-2003/048731 A2 | 6/2003 |
| WO | WO-2003/068201 A2 | 6/2003 |
| WO | WO-2003/068201 A3 | 8/2003 |
| WO | WO-2005/116072 A2 | 12/2005 |
| WO | WO-2005/116072 A3 | 12/2005 |
| WO | WO-2006/106905 A1 | 10/2006 |
| WO | WO-2007/034489 A2 | 3/2007 |
| WO | WO-2007/131092 A2 | 11/2007 |
| WO | 2007143104 A2 | 12/2007 |
| WO | WO-2007/034489 A3 | 12/2007 |
| WO | 2008137475 A2 | 11/2008 |
| WO | 2011119979 A2 | 9/2011 |
| WO | 2012050374 A2 | 4/2012 |
| WO | 2012135854 A2 | 10/2012 |
| WO | 2012135854 A3 | 3/2013 |
| WO | 2013166051 A1 | 11/2013 |
| WO | WO-2014/011988 A2 | 1/2014 |
| WO | 2014039523 A1 | 3/2014 |
| WO | WO-2014/039523 A1 | 3/2014 |
| WO | 2014055668 A1 | 4/2014 |
| WO | WO-2014/055668 A1 | 4/2014 |
| WO | 2014093855 A1 | 6/2014 |
| WO | 2014134165 A1 | 9/2014 |
| WO | 2014153470 A2 | 9/2014 |
| WO | WO-2014/123165 A1 | 9/2014 |
| WO | WO-2014/144622 A2 | 9/2014 |
| WO | WO-2014/152878 A2 | 9/2014 |
| WO | 2015017214 A1 | 2/2015 |
| WO | WO-2015/063069 A1 | 5/2015 |
| WO | WO-2015/070061 A1 | 5/2015 |
| WO | WO-2015/070078 A1 | 5/2015 |
| WO | WO-2014/144622 A3 | 6/2015 |
| WO | 2016042461 A1 | 3/2016 |
| WO | 2016071343 A1 | 5/2016 |
| WO | WO-2016/090312 A6 | 6/2016 |
| WO | WO-2016/090320 A1 | 6/2016 |
| WO | WO-2016/090327 A2 | 6/2016 |
| WO | WO-2016/090329 A2 | 6/2016 |
| WO | WO-2016/090337 A1 | 6/2016 |
| WO | WO-2016/090327 A3 | 7/2016 |
| WO | WO-2016/142768 A1 | 9/2016 |
| WO | WO-2016/149368 A1 | 9/2016 |
| WO | WO-2016/154047 A2 | 9/2016 |
| WO | WO-2016/161390 A1 | 10/2016 |
| WO | 2016187349 A1 | 11/2016 |
| WO | WO-2016/154047 A3 | 11/2016 |
| WO | WO-2016/182957 A1 | 11/2016 |
| WO | WO-2016/187216 A1 | 11/2016 |
| WO | WO-2016/187220 A2 | 11/2016 |
| WO | WO-2016/191246 A2 | 12/2016 |
| WO | WO-2016/199141 A2 | 12/2016 |
| WO | WO-2016/199414 A3 | 12/2016 |
| WO | WO-2016/201124 A2 | 12/2016 |
| WO | WO-2016/210129 A1 | 12/2016 |
| WO | WO-2016/210365 A2 | 12/2016 |
| WO | WO-2016/210365 A3 | 12/2016 |
| WO | 2017004252 A1 | 1/2017 |
| WO | WO-2017/015634 A2 | 1/2017 |
| WO | WO-2017/015634 A3 | 1/2017 |
| WO | 2017025038 A1 | 2/2017 |
| WO | 2017044699 A1 | 3/2017 |
| WO | WO-2017/066136 A2 | 4/2017 |
| WO | WO-2017/070608 A1 | 4/2017 |
| WO | 2017096120 A1 | 6/2017 |
| WO | 2017124001 A2 | 7/2017 |
| WO | 2018057967 A2 | 3/2018 |
| WO | 2018119298 A1 | 6/2018 |
| WO | 2018148454 A1 | 8/2018 |
| WO | 2018200586 A1 | 11/2018 |
| WO | WO-2018/200582 A1 | 11/2018 |
| WO | WO-2018/200583 A1 | 11/2018 |
| WO | WO-2018/200585 A1 | 11/2018 |
| WO | 2019191704 A1 | 10/2019 |
| WO | 2019245991 A1 | 12/2019 |
| WO | 2020102555 A1 | 5/2020 |
| WO | 2020227538 A1 | 11/2020 |
| WO | 2021016609 A1 | 1/2021 |
| WO | 2022026759 A1 | 2/2022 |

OTHER PUBLICATIONS

Adolf-Bryfogle, J et al. (2015, e-pub. Nov. 11, 2014). "PylgClassify: A Database Of Antibody CDR Structural Classifications," Nucleic Acids Res., 43:D432-D438.

Ahuja, R. et al. (Sep. 10, 2014). "Human Oncogenic Viruses and Cancer," Current Science 107(5):768-785.

Al-Lazikani, B. et al. (1997). "Standard Conformations for the Canonical Structures of Immunoglobulins," J. Mol. Biol. 273:927-948.

Anderson, W.F. (May 8, 1992). "Human Gene Therapy," Science 256(5058):808-813.

Arakawa, T. et al. (Nov. 11, 1994). "Formation of Heterodimers from Three Neurotrophins, Nerve Growth Factor, Neurotrophin-3, and Brain-derived Neurotrophic Factor," J. Biol. Chem. 269:27833-27839.

Ashwood-Smith, M.J. (Jun. 24, 1961). "Preservation of Mouse Bone Marrow at -79° C. with Dimethyl Sulphoxide," Nature 190:1204-1205.

Barrett, D.M. et al. (2014; e-published on Nov. 20, 2013). "Chimeric Antigen Receptor Therapy for Cancer," Annu. Rev. Med. 65:333-347, 18 pages.

Bender, M.A. et al. (May 1, 1960). "Preservation of Viable Bone Marrow Cells by Freezing," Journal of Applied Physiology 15(3):520-524.

Berge, I.J.M. et al. (Dec. 1998). "Selective Expansion of a Peripheral Blood CD8+ Memory T Cell Subset Expressing Both Granzyme B and L-Selectin During Primary Viral Infection in Renal Allograft Recipients," Transplant Proc. 30(8):3975-3977.

Blattman, J.N. et al. (Jul. 9, 2004). "Cancer Immunotherapy: A Treatment for the Masses," Science 305(5681):200-205.

Boerner, P. et al. (Jul. 1, 1991). "Production of Antigen-Specific Human Monoclonal Antibodies From In Vitro-Primed Human Splenocytes," The Journal of Immunology 147(1): 86-95.

Brentjens, R.J. et al. (Nov. 3, 2011). "Safety and Persistence of Adoptively Transferred Autologous CD19-Targeted T Cells in Patients with Relapsed or Chemotherapy Refractory B-Cell Leukemias," Blood 118(18):4817-4828.

Brinkmann, U. et al. (2017, e-pub. Jan. 10, 2017). "The Making of Bispecific Antibodies," mABS 9(2):182-212.

Brodeur, B.R. et al. (1987). "Mouse-Human Myeloma Partners for the Production Monoclonal Antibody Production of Heterohybridomas," Chapter 4 in Techniques and Applications, Marcel Dekker, Inc., New York, pp. 51-63.

Brown, M. et al. (Jun. 5, 1987). "Lac Repressor Can Regulate Expression From a Hybrid SV40 Early Promoter Containing a Lac Operator in Animal Cells," Cell 49(5):603-612.

Brüggemann, M. et al. (1993). "Designer Mice: The Production of Human Antibody Repertoires in Transgenic Animals," Year in Immunol. 7:33-40.

Call, Me et al. (Dec. 27, 2002). "The Organizing Principle in the Formation of the T Cell Receptor-CD3 Complex," Cell. 111(7):967-979, 23 pages.

Carter P. (Feb. 1, 2001). "Bispecific Human IgG by Design," J Immunol Methods 248(1-2):7-15.

Cheever, M.A. et al. (Sep. 1, 2009). "The Prioritization of Cancer Antigens: A National Cancer Institute Pilot Project For the Acceleration of Translational Research," Clin. Cancer Res. 15(17):5323-5337.

Chen, W. et al. (2016, e-pub. Apr. 13, 2016). "Improving the CH1-CK Heterodimerization and Pharmacokinetics of 4Dm2m, A Novel Potent CD4-Antibody Fusion Protein Against HIV-1," mAbs 8(4): 761-774.

Chmielewski, M. (Sep. 2011; e-pub. Jul. 8, 2011). "IL-12 Release by Engineered T Cells Expressing Chimeric Antigen Receptors Can Effectively Muster an Antigen-Independent Macrophage Response

(56) References Cited

OTHER PUBLICATIONS on Tumor Cells That Have Shut Down Tumor Antigen Expression," *Cancer Research* 71(17):5697-5706.
Chothia, C. et al. (1987). "Canonical Structures for the Hypervariable Regions of Immunoglobulins," *J. Mol. Biol.* 196:901-917.
Chowdhury, P.S. (2008). "Engineering Hot Spots for Affinity Enhancement of Antibodies," Chapter 11 in *Methods in Molecular Biology*, M. Welschof (eds.) et al., Humana Press Inc., Totowa, NJ, 207:179-196.
Clackson et al. (Aug. 15, 1991). "Making Antibody Fragments Using Phage Display Libraries," *Nature* 352:624-628.
Clipstone, N.A. et al. (Jun. 25, 1992). "Identification of Calcineurin as a Key Signaling Enzyme In T-Lymphocyte Activation," *Nature* 357(6380):695-697. (Abstract Only).
Cohen, C.J., et al. (Sep. 1, 2006). "Enhanced Antitumor Activity of Murine-Human Hybrid T-Cell Receptor (TCR) in Human Lymphocytes is Associated with Improved Pairing and TCR/CD3 Stability" Cancer Res 66(17):8878-8886.
Cohen, CJ. et al. (Sep.-Oct. 2003). "Recombinant Antibodies with MHC-Restricted, Peptide-Specific, T-Cell Receptor-Like Specificity: New Tools to Study Antigen Presentation and TCR-Peptide-MHC Interactions," *J. Mol. Recognit.* 16(5):324-332.
Cole et al. (1985). "The EBV-Hybridoma Technique and Its Application to Human Lung Cancer," in *Monoclonal Antibodies and Cancer Therapy*, Ralph A. Reisfeld (ed.) et al., Alan R. Liss, Inc. p. 77-96.
Cunningham, B.C. et al. (Jun. 2, 1989). "High Resolution Epitope Mapping of hGH-Receptor Interactions by Alanine-Scanning Mutagenesis," *Science* 244:1081-1085.
Datta, R. et al. (Nov. 1, 1992). "Ionizing Radiation Activates Transcription of the *EGR1* Gene Via CArG Elements," *Proc. Natl. Acad. Sci. USA* 89(21):10149-10153.
Davila, M.L. et al. (Dec. 1, 2012). "How do CARs work? Early Insight from Recent Clinical Studies Targeting CD19," *Oncoimmunology* 1(9): 1577-1583.
Davis, M.M. et al. (Apr. 1998). "Ligand Recognition By $\alpha\beta$ T Cell Receptors," *Annual Review of Immunology* 16:523-544.
Davis, M.M. et al. (Aug. 4, 1988). "T-Cell Antigen Receptor Genes and T-Cell Recognition," *Nature* 334(6181):395-402.
Digiammarino, E.L. et al. (Sep. 1, 2011). "Ligand Association Rates to the Innervariable-Domain of a Dual-Variable-Domain Immunoglobulin Are Significantly Impacted By Linker Design, "mAbs 3(5):487-494.
Dillon, N. (May 1993). "Regulating Gene Expression in Gene Therapy," *TIBTECH* 11(5):167-173.
Dudley, M.E. et al. (Apr. 1, 2005). "Adoptive Cell Transfer Therapy Following Non-Myeloablative but Lymphodepleting Chemotherapy for the Treatment of Patients with Refractory Metastatic Melanoma," *J. Clin. Oncol.* 23(10):2346-2357, 24 pages.
Durand, D. et al. (Apr. 1988). "Characterization of Antigen Receptor Response Elements within the Interleukin-2 Enhancer," *Molec. Cell. Biol.* 8(2):1715-1724.
Edgar, R.C. (2004; e-published on Mar. 19, 2004). "MUSCLE: Multiple Sequence Alignment With High Accuracy and High Throughput," *Nucleic Acids Research* 32(5):1792-1797.
Edgar, R.C. (Aug. 19, 2004). "MUSCLE: A Multiple Sequence Alignment Method With Reduced Time and Space Complexity," *BMC Bioinformatics* 5(1):113, pp. 1-19.
Ehrenmann, F. et al. (Jan. 2010, e-pub. Nov. 9, 2009). "IMGT/3Dstructure-DB and IMGT/DomainGapAlign: a database and a tool for immunoglobulins or antibodies, T cell receptors, MHC, IgSF and MhcSF," Nucleic Acids Res. 38: D301-D307.
Engberg, J. et al. (Mar. 1999). "Recombinant Antibodies with the Antigen-Specific, MHC Restricted Specificity of T Cells: Novel Reagents for Basic and Clinical Investigations and Immunotherapy," *Immunotechnology* 4(3-4):273-278.
Eshhar, Z. et al. (1990). "Chimeric T Cell Receptor Which Incorporates the Anti-Tumour Specificity of a Monoclonal Antibody with the Cytolytic Activity of T Cells: A Model System for Immunotherapeutical Approach," *Br. J. Cancer* 62(Suppl. X):27-29.

Fellouse, F.A. et al. (Aug. 24, 2004). "Synthetic Antibodies from a Four-Amino-Acid Code: A Dominant Role for Tyrosine in Antigen Recognition," *Proc. Natl. Acad. Sci. USA* 101(34):12467-12472.
Fishwild, D.M. et al. (Jul. 1996). "High-avidity Human IgG$_k$ Monoclonal Antibodies from a Novel Strain of Minilocus Transgenic Mice," *Nature Biotechnology* 14:845-851.
Fletcher, J. et al. (May 4, 2012). "A Basis Set of de Novo Coiled-Coil Peptide Oligomers for Rational Protein Design and Synthetic Biology," ACS Synth. Biol. 1(6):240-250. (Abstract Only).
Friedmann-Morvinski, D. et al. (Apr. 15, 2005). "Redirected Primary T Cells Harboring a Chimeric Receptor Require Costimulation for their Antigen-Specific Activation," *Blood* 105(8):3087-3093.
Garland, R.J et al. (Jul. 30, 1999). "The Use of Teflon Cell Culture Bags to Expand Functionally Active CD8+ Cytotoxic T Lymphocytes," *Journal of Immunological Methods* 227(1-2):53-63.
Gingrich, J.R. et al. (1998). "Inducible Gene Expression in the Nervous System of Transgenic Mice," *Annual Rev. Neurosci.* 21:377-405.
Girardi, M. (2006). "Immunosurveillance and Immunoregulation by $\gamma\delta$ T Cells" *J. Invest. Dermatol.* 126(1):25-31.
Goding, J.W. (1986). "Production of Monoclonal Antibodies," Chapter 3 in *Monoclonal Antibodies: Principles and Practice*, Academic Press, New York, pp. 56-103.
Griffiths, A.D. et al. (1993). "Human Anti-Self Antibodies with High Specificity from Phage Display Libraries," *The EMBO Journal* 12(2):725-734.
Gross, G et al. (1992). "Endowing T Cells with Antibody Specificity Using Chimeric T Cell Receptors," *FASEB J.* 6(15):3370-3378.
Gross, G. et al. (Dec. 1, 1989). "Expression of Immunoglobulin-T-Cell Receptor Chimeric Molecules as Functional Receptors With Antibody-Type Specificity," *Proc. Natl. Acad. Sci. USA.* 86(24):10024-10028.
Gunasekaran, K. et al. (Jun. 18, 2010; e-published on Apr. 16, 2010). "Enhancing Antibody Fc Heterodimer Formation Through Electrostatic Steering Effects: Applications to Bispecific Molecules and Monovalent IgG," *J Biol Chem.* 285(25):19637-19646.
Haanen, J. et al. (Nov. 1, 1999). "Selective Expansion of Crossreactive CD8+ Memory T Cells by Viral Variants," *J. Exp. Med.* 190(9):1319-1328.
Hayes, S.M. et al. (Jun. 2002). "Distinct Structure and Signaling Potential of the $\gamma\delta$TCR Complex," *Immunity* 16(6):827-838.
Hoet, R.M. et al. (Mar. 2005; e-published on Feb. 20, 2005). "Generation of High-Affinity Human Antibodies By Combining Donor-Derived and Synthetic Complementarity-Determining-Region Diversity," *Nature Biotechnology* 23(3):344-348.
Hoogenboom, H.R. (2001). "Overview of Antibody Phage-Display Technology and Its Applications," Chapter 1 in *Methods in Molecular Biology*, O'Brien (ed.) et al., Human Press, Totowa, NJ, 178:1-37.
Hoogenboom, H.R. et al. (1992). "By-Passing Immunization—Human Antibodies from Synthetic Repertoires of Germline V$_H$ Gene Segments Rearranged in Vitro," J. Mol. Biol. 227:381-388.
Honegger, A. et al. (2001). "Yet Another Numbering Scheme for Immunoglobulin Variable Domains: An Automatic Modeling and Analysis Tool," J. Mol. Biol. 309:657-670.
Hsu, P.D. et al. (Jun. 5, 2014). "Development and Applications of CRISPR-Cas9 for Genome Engineering," *Cell* 157(6):1262-1278.
International Preliminary Report on Patentability dated Nov. 7, 2019, for International Patent Application No. PCT/US2018/029217, filed Apr. 24, 2018, 11 pages.
International Preliminary Report on Patentability dated Nov. 7, 2019, for International Patent Application No. PCT/US2018/029218, filed Apr. 24, 2018, 8 pages.
International Preliminary Report on Patentability dated Nov. 7, 2019, for International Patent Application No. PCT/US2018/029220, filed Apr. 24, 2018, 10 pages.
International Search Report dated Jul. 18, 2018, for International Patent Application No. PCT/US2018/029217, filed Apr. 24, 2018, 10 pages.
International Search Report dated Jul. 18, 2018, for International Patent Application No. PCT/US2018/029218, filed Apr. 24, 2018, 8 pages.

(56) References Cited

OTHER PUBLICATIONS

International Search Report dated Jul. 18, 2018, for International Patent Application No. PCT/US2018/029220, filed Apr. 24, 2018, 6 pages.
Jakobovits, A. et al. (Mar. 18, 1993). "Germ-Line Transmission and Expression of a Human-Derived Yeast Artificial Chromosome," *Nature* 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *PNAS USA* 90:2551-2555.
Jiang, W. et al. (2015; e-published on Jul. 22, 2015). "CRISPR-Cas: New Tools for Genetic Manipulations from Bacterial Immunity Systems," *Annu. Rev. Microbiol.* 69:209-228.
Jones, P.T. et al. (May 29, 1986). "Replacing the Complementarity Determining Regions in a Human Antibody with those from a Mouse," *Nature* 321:522-525.
Kabat, E.A. et al. (1991). U.S. Department of Health and Human Services—Public Health Service National Institutes of health, in *Sequences of Proteins of Immunological Interest*, eighty five pages.
Kabat, E.A. et al. (Oct. 10, 1977). "Unusual Distributions of Amino Acids in Complementarity-Determining (Hypervariable) Segments of Heavy and Light Chains of Immunoglobulins and their Possible Roles in Specificity of Antibody-combining Sites," *The Journal of Biological Chemistry* 252(19):6609-6616.
Kam, N.W.S et al. (Aug. 16, 2005). "Carbon Nanotubes as Multifunctional Biological Transporters and Near-Infrared Agents for Selective Cancer Cell Destruction," *Proc. Natl. Acad. Sci. USA* 102(33):11600-11605.
Kim, J.H. et al. (Apr. 2011). "High Cleavage Efficiency of a 2A Peptide Derived from Porcine Teschovirus-1 in Human Cell Lines, Zebrafish and Mice," *PloS One* 6(4):e18556, pp. 1-8.
Kobayashi, E. et al. (2014; e-published on Jan. 1, 2014). "A Novel System for Cloning Human TCRs," *Oncoimmunology* 3(1):e27258-1-e27258-2.
Kobayashi et al. (2008). "Induction of EBV-Latent Membrane Protein 1-Specific MHC Class II-Restricted T-Cell Responses Against Natural Killer Lymphoma Cells,"*Cancer Res.* 68(3):901-908.
Kochenderfer, J.N. et al. (Nov. 18, 2010; e-published on Jul. 28, 2010). "Eradication of B-Lineage Cells and Regression of Lymphoma in a Patient Treated With Autologous T Cells Genetically Engineered to Recognize CD19," *Blood* 116(20):4099-4102.
Köhler G. et al. (Aug. 7, 1975). "Continuous Cultures of Fused Cells Secreting Antibody of Predefined Specificity," *Nature* 256:495-497.
Kostelney, S.A. et al. (Mar. 1, 1992). "Formation of a bispecific antibody by the use of leucine zippers," J. Immunol, 148(5):1547-1553.
Kozbor, D. et al. (Dec. 1984). "A Human Hybrid Myeloma for Production of Human Monoclonal Antibodies," *The Journal of Immunology* 133(6):3001-3005.
Kremer, E.J. et al. (Jan. 1995). "Adenovirus and Adeno-Associated Virus Mediated Gene Transfer," *British Medical Bulletin* 51(1):31-44.
Kuhns, M.S. (Jun. 25, 2012). "TCR Signaling Emerges from the Sum of Many Parts," *Front Immunol.* 3(Article 159):1-13.
Kunert, A. et al. (Nov. 8, 2013). "TCR-Engineered T Cells Meet New Challenges to Treat Solid Tumors: Choice of Antigen, T Cell Fitness, and Sensitization of Tumor Milieu," *Front. Immunol.* 4(Article 363):1-16.
Kuwana, Y. et al. (Dec. 31, 1987). "Expression of Chimeric Receptor Composed of Immunoglobulin-Derived V Regions and T-Cell Receptor-Derived C Regions," *Biochem. Biophys. Res. Commun.* 149(3):960-968.
Lee, C.V et al. (2004). "Bivalent Antibody Phage Display Mimics Natural Immunoglobulin,"*Journal of Immunological Methods* 284(1-2):119-132.
Lee, C.V. et al. (2004). "High-Affinity Human Antibodies from Phage-Displayed Synthetic Fab Libraries with a Single Framework Scaffold," *J. Mol. Biol.* 340(5):1073-1093.

Lefranc, M.P. et al. (Jan. 2003). "IMGT Unique Numbering For Immunoglobulin and T Cell Receptor Variable Domains and Ig Superfamily V-Like Domains," Dev. Comp. Immunol. 27(1):55-77.
Lefranc, M.-P. et al. (Dec. 1986). "Genetic Polymorphism and Exon Changes of the Constant Regions of The Human T-Cell Rearranging Gene γ," *Proc. Natl. Acad. Sci. USA* 83:9596-9600.
Lewis, J.P. et al. (Jan.-Feb. 1967). "The Effect of Cooling Regimens on the Transplantation Potential of Marrow," *Transfusion* 7(1):17-32.
Linner, J.G. et al. (Sep. 1986). "A New Technique for Removal of Amorphous Phase Tissue Water Without Ice Crystal Damage: A Preparative Method for Ultrastructural Analysis and Immunoelectron Microscopy," *J. Histochem. Cytochem.* 34(9):1123-1135.
Livesey, S.A. et al. (May 21, 1987). "Cryofixation Taking on a New Look," *Nature* 327:255-256.
Lonberg, N. et al. (1995). "Human Antibodies from Transgenic Mice," *Intern. Rev. Immunol.*, 13:65-93.
Lonberg, N. et al. (Apr. 28, 1994). "Antigen-Specific Human Antibodies from Mice Comprising Four Distinct Genetic Modifications," *Nature* 368:856-859.
Louis, C.U. et al. (Dec. 1, 2011; e-published on Oct. 7, 2011). "Antitumor Activity and Long-Term Fate of Chimeric Antigen Receptor-Positive T Cells in Patients With Neuroblastoma," *Blood* 118(23):6050-6056.
Lovelock, J.E. (Feb. 1, 1954). "The Protective Action of Neutral Solutes Against Haemolysis by Freezing and Thawing,"*Biochem. J.* 56(2):265-270.
Lovelock, J.E. et al. (May 16, 1959). "Prevention of Freezing Damage to Living Cells by Dimethyl Sulphoxide," *Nature* 183(4672):1394-1395.
MacCallum, R.M. et al. (1996). "Antibody-Antigen Interactions: Contact Analysis and Binding Site Topography," *J. Mol. Biol.* 262:732-745.
Mader, S. et al. (Jun. 1993). "A Steroid-inducible Promoter for the Controlled Overexpression of Cloned Genes in Eukaryotic Cells," *Proc. Natl. Acad. Sci. USA* 90:5603-5607.
Manome, Y. et al. (1993). "Coinduction of C-Jun Gene Expression and Internucleosomal DNA Fragmentation by Ionizing Radiation," *Biochemistry* 32(40):10607-10613.
Marks, J.D. et al. (1991). "By-Passing Immunization—Human Antibodies from V-Gene Libraries Displayed on Phage," *J. Mol. Biol.* 222:581-597.
Marks, J.D. et al. (2003). "Selection of Human Antibodies from Phage Display Libraries," Chapter 8 in *Methods in Molecular Biology*, B.K.C. Lo, ed., Humana Press Inc., Totowa, N.J., 248:161-175.
Marks, J.D. et al. (Jul. 1992). "By-Passing Immunization: Building High Affinity Human Antibodies by Chain Shuffling," *Bio/Technology*, 10:779-783.
Maude, S.L. et al. (Oct. 16, 2014). "Chimeric Antigen Receptor T Cells for Sustained Remissions in Leukemia," *N. Engl. J. Med.* 371(16):1507-1517, 17 pages.
Mazur, P. (1977). "The Role of Intracellular Freezing in the Death of Cells Cooled at Supraoptimal Rates," *Cryobiology* 14(3):251-272.
Mazur, P. (May 22, 1970). "Cryobiology: The Freezing of Biological Systems," *Science* 168(3934):939-949.
McCafferty, J. et al. (Dec. 6, 1990). "Phage Antibodies: Filamentous Phage Displaying Antibody Variable Domains," *Nature* 348:552-554.
Miller, A.D. (Jun. 11, 1992). "Human Gene Therapy Comes of Age," *Nature* 357(6378):455-460.
Mitani, K. et al. (May 1993). "Delivering Therapeutic Genes—Matching Approach and Application," *Trends in Biotechnology (TIBTECH)* 11(5):162-166.
Morrison, S.L. (Apr. 28, 1994). "Success in Specification," *Nature* 368:812-813.
Morrison, S.L. et al. (Nov. 1984). "Chimeric Human Antibody Molecules: Mouse Antigen-Binding Domains with Human Constant Region Domains," *Proc. Natl. Acad. Sci. USA* 81:6851-6855.
Müller, K.M. et al. (1998). "The First Constant Domain ($C_H1$ and $C_L$) of an Antibody Used as Heterodimerization Domain for Bispecific Miniantibodies," *FEBS Letters* 422(2):259-264.

(56) References Cited

OTHER PUBLICATIONS

Munson, P.J. et al. (1980). "LIGAND: A Versatile Computerized Approach for Characterization of Ligand-Binding Systems," *Analytical Biochemistry* 107:220-239.
Nabel, G.J. et al. (May 1993). "Direct Gene Transfer for Immunotherapy and Immunization," *Trends in Biotechnology* 11(5):211-215.
Neuberger, M. (Jul. 1996). "Generating High-Avidity Human Mabs in Mice," *Nature Biotechnology* 14:826, one page.
O'Connell, M.R. et al. (Dec. 11, 2014; e-published on Sep. 28, 2014). "Programmable RNA Recognition and Cleavage by CRISPR/Cas9," *Nature* 516(7530):263-266, 23 pages.
Oren, R. et al. (2014). "Functional Comparison of Engineered T Cells Carrying a Native TCR Versus TCR-Like Antibody-Based Chimeric Antigen Receptors Indicates Affinity/Avidity Thresholds," *The Journal of Immunology* 193(11):5733-5743.
Phan, T.T. et al. (Sep. 1960). "Survival of Mouse Bone-Marrow Cells Frozen and Thawed in Solutions of Amino Acids," *Exp. Cell Res.* 20(3):651-654.
Presta, L.G. (1992). "Antibody Engineering," *Current Opinion in Structural Biology* 2:593-596.
Radziejewski, C. et al. (Dec. 1, 1993). "Heterodimers of the Neurotrophic Factors: Formation, Isolation, and Differential Stability," *Biochem.* 32(48):13350-13356. (Abstract Only).
Rapatz, G. et al. (Jul.-Aug. 1968). "Preservation of Erythrocytes in Blood Containing Various Cryoprotective Agents, Frozen at Various Rates and Brought to a Given Final Temperature," *Cryobiology* 5(1):18-25.
Riechmann, et al. (Mar. 24, 1988). "Reshaping Human Antibodies for Therapy," *Nature* 332:323-327.
Rinfret, A.P. (Apr. 1960). "Factors Affecting the Erythrocyte During Rapid Freezing and Thawing," *Annals of the New York Academy of Sciences* 85:576-594.
Robbins, P.F. et al. (Mar. 1, 2015; e-published on Dec. 23, 2014). "A Pilot Trial Using Lymphocytes Genetically Engineered With an NY-ESO-1-Reactive T-Cell Receptor: Long-Term Follow-Up and Correlates with Response," *Clin. Cancer Res.* 21(5):1019-1027, 19 pages.
Rosenberg, S.A. (May 17, 2001). "Progress In Human Tumour Immunology and Immunotherapy," *Nature* 411(6835):380-384. (Abstract ONLY).
Rosenberg, S.A. et al. (Apr. 2008). "Adoptive Cell Transfer: A Clinical Path to Effective Cancer Immunotherapy," *Nat. Rev. Cancer* 8(4):299-308, 22 pages.
Rosenberg, S.A. et al. (Apr. 3, 2015). "Adoptive Cell Transfer as Personalized Immunotherapy for Human Cancer," *Science* 348(6230):62-68.
Rowe, A.W. et al. (1962). "109-Cell, Tissue Culture," *Federation Proceedings* 21:157, three pages.
Rowe, A.W. et al. (1962). "Controlled Rate Freezing of Bone Marrow," *Blood* 20:636-637.
Rowe, A.W. et al. (Jul.-Aug. 1966). "Biochemical Aspects of Cryoprotective Agents in Freezing and Thawing," *Cryobiology* 3(1):12-18.
Sahu, G.K. et al. (Nov. 2013, e-pub. Sep. 6, 2013). "Anti-HIV designer T Cells Progressively Eradicate a Latently Infected Cell Line by Sequentially Inducing HIV Reactivation then Killing the Newly Gp 120-Positive Cells," *Virology* 446(0):268-275.
Schuler et al. SYFPEITHI, Database for Searching and T-Cell Epitope Prediction. in Immunoinfonnatics Methods in Molecular Biology, vol. 409(1): 75-93, 2007 [152/195].
Sergeeva, A. et al. (Apr. 21, 2011, e-pub. Feb. 4, 2011). "An Anti-PR1/HLA-A2 T-Cell Receptor-Like Antibody Mediates Complement-Dependent Cytotoxicity Against Acute Myeloid Leukemia Progenitor Cells," *Blood* 117(16):4262-4272.
Sidhu, S.S. et al. (2004). "Phage-Displayed Antibody Libraries of Synthetic Heavy Chain Complementarity Determining Regions," *J. Mol. Biol.* 338(2): 299-310.
Simione, F.P., Jr. (Nov.-Dec. 1992). "Key Issues Relating to the Genetic Stability and Preservation of Cells and Cell Banks," *J. Parenter. Sci. Technol.* 46(6):226-232.

Singh, H. et al. (Dec. 1, 2001). "ProPred: Prediction of HLA-DR Binding Sites," *Bioinformatics* 17(12):1236-1237.
Spencer, D.M. (Nov. 12, 1993). "Controlling Signal Transduction with Synthetic Ligands," *Science* 262(5136):1019-1024.
Spitzer, G. et al. (Jun. 15, 1980). "High-Dose Combination Chemotherapy with Autologous Bone Marrow Transplantation in Adult Solid Tumors," *Cancer* 45:3075-3085.
Steinmetz, A. et al. (2016, e-pub.Mar. 16, 2016). "CODV-Ig, A Universal Bispecific Tetravalent and Multifunctional Immunoglobulin Format for Medical Applications," *MABS* 8(5):867-878, with Supplementary material, 59 pages.
Stiff, P.J. et al. (Feb. 1983). "Unfractionated Human Marrow Cell Cryopreservation Using Dimethylsulfoxide and Hydroxyethyl Starch," *Cryobiology* 20(1):17-24.
Takihara, Y. et al. (Aug. 1988). "Sequence and Organization of the Diversity, Joining, and Constant Region Genes of the Human T-Cell δ-chain Locus," *Proc. Natl. Acad. Sci. USA* 85:6097-6101.
Thomas, F. et al. (Mar. 11, 2013). "A Set of de Novo Designed Parallel Heterodimeric Coiled Coils with Quantified Dissociation Constants in the Micromolar to Sub-nanomolar Regime," *J. Am. Chem. Soc.* 135(13):5161-5166.
Torikai, H. et al. (Jun. 2012, e-pub. Apr. 24, 2012). "A Foundation For Universal T-Cell Based Imununotherapy: T Cells Engineered to Express a CD19-Specific Chimeric-Antigen-Receptor and Eliminate Expression of Endogenous TCR," *Blood* 119(24):5697-5705.
Tutt, A. et al. (Jul. 1, 1991) "Trispecific F(ab')3 Derivatives That Use Cooperative Signaling Via the TCR/CD3 Complex and CD2 to Activate and Redirect Resting Cytotoxic T Cells," *J. Immunol.* 147(1):60-69.
U.S. Appl. No. 15/769,724, filed Apr. 19, 2018, by Lu et al. (A U.S. Patent Application is not submitted herewith pursuant to the waiver of 37 C.F.R. § 1.98(a)(2)(iii) issued by the Office dated Sep. 21, 2004.).
U.S. Appl. No. 16/667,781, filed Oct. 29, 2019, by Lu et al. (A U.S. Patent Application is not submitted herewith pursuant to the waiver of 37 C.F.R. § 1.98(a)(2)(iii) issued by the Office dated Sep. 21, 2004.).
U.S. Appl. No. 16/608,336, filed Oct. 25, 2019, for Lucas Horan et al. (A U.S. Patent Application is not submitted herewith pursuant to the waiver of 37 C.F.R. § 1.98(a)(2)(iii) issued by the Office dated Sep. 21, 2004.).
U.S. Appl. No. 16/608,362, filed Oct. 25, 2019, for Binnaz K. Staley et al. (A U.S. Patent Application is not submitted herewith pursuant to the waiver of 37 C.F.R. § 1.98(a)(2)(iii) issued by the Office dated Sep. 21, 2004.).
Ui-Tei, K. et al. (Aug. 18, 2000). "Sensitive Assay of RNA Interference In *Drosophila* and Chinese Hamster Cultured Cells Using Firefly Luciferase Gene as Target," *FEBS Letters* 479(3):79-82.
Van Brunt, J. (Oct. 1988). "Molecular Farming: Transgenic Animals as Bioreactors," *Biotechnology* 6(10):1149-1154.
Van Der Veken, L.T. et al. (Jan. 1, 2009). "αβ T Cell Receptor Transfer to γδ T Cells Generates Functional Effector Cells without Mixed TCR Dimers In Vivo," *J. Immunol.* 182(1):164-170.
Verhoeyen, M. et al. (1988). "Reshaping Human Antibodies: Grafting and Antilysozyme Activity," *Science* 239:1534-1536.
Vigne, E. et al. (Jun. 1995). "Third-generation Adenovectors for Gene Therapy," *Restorative Neurology and Neuroscience* 8(1-2):35-36.
Wang, J.-H et al. (Nov. 2012). "The Structural Basis of αβ T-Lineage Immune Recognition: TCR Docking Topologies, Mechanotransduction, and Co-Receptor Function," *Immunol Rev.* 250(1):102-119, 32 pages.
Wang, W. et al. (Jan. 2007). "Antibody Structure, Instability, and Formulation," *Journal of Pharmaceutical Sciences* 96(1):1-26.
White, J. H. (Jun. 1993). "A steroid-inducible promoter for the controlled overexpression of cloned genes in eukaryotic cells," *Proc. Natl. Acad. Sci. USA* 90:5603-5607.
Winter, G. et al. (1994). "Making Antibodies by Phage Display Technology," *Ann. Rev. Immunol.*, 12:433-455.
Written Opinion of the International Searching Authority dated Jul. 18, 2018, for International Patent Application No. PCT/US2018/029217, filed Apr. 24, 2018, 9 pages.

(56) References Cited

OTHER PUBLICATIONS

Written Opinion of the International Searching Authority dated Jul. 18, 2018, for International Patent Application No. PCT/US2018/029218, filed Apr. 24, 2018, 6 pages.
Written Opinion of the International Searching Authority dated Jul. 18, 2018, for International Patent Application No. PCT/US2018/029220, filed Apr. 24, 2018, 8 pages.
Wu, X. et al. (Jan. 22, 2015). "Protein Design of IgG/TCR Chimeras for the Co-Expression of Fab-like Moieties Within Bispecific Antibodies," *MABS* 7(2):364-376.
Wu, Y.J. et al. (Sep. 1, 1988). "Signal Transduction of Gamma/Delta T Cell Antigen Receptor With a Novel Mitogenic Anti-Delta Antibody," J. Immunol 141(5):1476-1479. (Abstract Only).
Yu, M. et al. Jan. 1, 1994). "Progress Towards Gene Therapy for HIV Infection," *Gene Therapy* 1(1): 13-26.
Yun, C.O. et al. (Sep.-Oct. 2000). "Targeting of T Lymphocytes to Melanoma Cells Through Chimeric Anti-GD3 Immunoglobulin T-Cell Receptors," *Neoplasia* 2(5):449-459.
Zhang, L. et al. (Apr. 2011, e-pub. Feb. 1, 2011). "Improving Adoptive T Cell Therapy by Targeting and Controlling IL-12 Expression to the Tumor Environment," Molecular therapy 19(4):751-759.
Almåsbak, H. et al. (2016). "CAR T Cell Therapy: A Game Changer in Cancer Treatment," Journal of Immunology Research 2016(Article ID 5474602), ten pages.
Beckman, R.A. et al. (Jan. 15, 2007, e-pub. Dec. 11, 2006). "Antibody Constructs in Cancer Therapy, Protein Engineering Strategies to Improve Exposure in Solid Tumors," Cancer 109(2):170-179.
Bei, R. et al. (Oct. 2011). "Alpha Fetoprotein is More than a Hepatocellular Cancer Biomarker: From Spontaneous Immune Response in Cancer Patients to the Development of an AFP-Based Cancer Vaccine," Current Molecular Medicine 11(7):564-581.
Broere, F. et al. (2011). "T Cell Subsets and T Cell-Mediated Immunity," in Principles of Immunopharmacology, 3rd Revised and extended Edition, Nijkamp, F.P. et al. (eds.), Springer, Basel, AG, pp. 15-27.
Butterfield, L.H. et al. (Dec. 1, 2003). "T-Cell Responses to HLA-A*0201 Immunodominant Peptides Derived from □-Fetoprotein in Patients with Hepatocellular Cancer," Clinical Cancer Research 9(16 pt. 1):5902-5908.
Butterfield, L.H. et al. (Apr. 15, 2001). "T Cell Responses to HLA-A*0201-Restricted Peptides Derived from Human α Fetoprotein," The Journal of Immunology 166(8):5300-5308.
Butterfield, L.H. et al. (Jul. 1, 1999). "Generation of Human T-Cell Responses to an HLA-A2.1-Restricted Peptide Epitope Derived From a-Fetoprotein," Cancer Res. 59(13):3134-3142.
Call, M.E. (2005, Oct. 19, 2004). "The T Cell Receptor: Critical Role of the Membrane Environment in Receptor Assembly and Function," Annu. Rev. Immunol. 23:101-125.
Chames, P. et al. (Jul. 15, 2002). "TCR-Like Human Antibodies Expressed on Human CTLs Mediate Antibody Affinity-Dependent Cytolytic Activity," The Journal of Immunology 169(2):1110-1118.
Chang, A.Y. et al. (Aug. 2, 2016). "Opportunities And Challenges For TCR Mimic Antibodies In Cancer Therapy." Expert Opinion on Biological Therapy 16(8):979-987, 18 pages,.
Chen, C. et al. (Sep. 1, 1992). "Generation and Analysis Of Random Point Mutations In An Antibody CDR2 Sequence: Many Mutated Antibodies Lose Their Ability To Bind Antigen," J. Exp. Med. 176(3):855-866.
Collier, S. et al. (2006). "Discrepancy in CD3-Transmembrane Peptide Activity Between In Vitro and In Vivo T-Cell Inhibition," Scandinavian Journal of Immunology 64:388-391.
Communication Pursuant to Article 94(3) EPC, dated Feb. 25, 2022, for EP Patent Application No. 18789935.6, filed on Nov. 25, 2019, 6 pages.
Communication Pursuant to Article 94(3) EPC, dated Mar. 1, 2022, for EP Patent Application No. 18791852.9, filed on Nov. 25, 2019, 5 pages.
Dahan, R. et al. (Feb. 2012). "T-Cell-Receptor-Like Antibodies-Generation, Function and Applications," Expert Reviews in Molecular Medicine 14(e6):1-17.
Dao, T. et al. (Mar. 13, 2013). "Targeting the Intracellular WT1 Oncogene Product With a Therapeutic Human Antibody," Sci. Transl. Med. 5(176):176ra33, 22 pages.
Denkberg, G. et al. (Sep. 1, 2003). "Selective Targeting of Melanoma and APCs Using a Recombinant Antibody with TCR-Like Specificity Directed Toward a Melanoma Differentiation Antigen," (2003). J. Immunol. 171(5):2197-2207.
Edwards, B.M. et al. (Nov. 14, 2003). "The Remarkable Flexibility of the Human Antibody Repertoire; Isolation of Over One Thousand Different Antibodies to a Single Protein, Blys," J. Mol. Biol. 334(1):103-118.
Extended European Search Report dated Feb. 3, 2021, for European Patent No. 18791852.9, filed Nov. 25, 2019, 11 pages.
Fesnak, A.D. et al. (Aug. 23, 2016, e-pub Aug. 23, 2017). "Engineered T Cells: The Promise and Challenges of Cancer Immunotherapy," Nature Reviews Cancer 16(9):566-581.
Gura, T. (1997). "Systems for Identifying New Drugs Are Often Faulty," Science 278(5340):1041-1042, , 5 pages.
Hammer, O. (Sep. 1, 2012), "CD19 as an Attractive Target for Antibody-Based Therapy," mAbs 4(5):571-577.
Harris, D.T. et al. (Mar. 2016). "Adoptive T Cell Therapies: A Comparison of T Cell Receptors and Chimeric Antigen Receptors," Trends Pharmacol Sci. 37(3):220-230, 21 pages.
Hiasa, A. et al. (Feb. 26, 2009). "Rapid αβ TCR-Mediated Responses in γδ T Cells Transduced With Cancer-Specific TCR Genes," Gene Therapy 16:620-628.
Kuball, J. et al. (Mar. 15, 2007; e-pub. Nov. 2, 2006). "Facilitating Matched Pairing and Expression of TCR Chains Introduced into Human T Cells," Blood 109(6):2331-2338.
Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.
Manolios, N. et al. (1994). "The T Cell Antigen Receptor Alpha and Beta Chains Interact Via Distinct Regions with CD3 Chains," 24:84-92.
Marcu-Malina, V. et al. (Jul. 7, 2011; e-pub. May 12, 2011). "Redirecting αβT Cells Against Cancer Cells by Transfer of a Broadly Tumor-Reactive γδT-Cells Receptor," Blood 118(1):50-59.
Mariuzza, R.A. et al. (1987). "The Structural Basis of Antigen-Antibody Recognition," Annu. Rev. Biophys. Biophys. Chem. 16:139-159.
Martin, S.F. et al. (Mar. 19, 1998). "Application Of Alme3-Mediated Amidation Reactions To Solution Phase Peptide Synthesis," Tetrahedron Letters 39(12):1517-1520.
Muller, S. et al. (Dec. 2008). "Spliceosomal Peptide P140 for Immunotherapy of Systemic Lupus Erthematosus: Results of an Early Phase II Clinical Trial." Arthritis & Rheumatism: Offical Journal of the American College of Rheumatology 58(12):3783-3883.
Murphy, K. (2012). Janeway's Immunobiology, pp.x-xix, 868 p, (TOC and Index only).
Peipp. M. et al. (Aug. 2002). "Bispecific Antibodies Trageting Cancer Cells," BioChem. Soc Trans, 30(4):507-511.
Purbhoo. M.A. et al. (2006). "Quantifying and Imaging NY-ESO-1/LAGE-1-Derived Epitopes on Tumor Cells Using High Affinity T Cell Receptors," J Immunol 176(12):7308-7316.
Ridgway, J.B.B. et al. (1996). "'Knobs-Into-Holes' Engineering of Antibody CH3 Domains for Heavy Chain Heterodimerization," Protein Engineering 9(7):617-621.
Rosenberg, S.A. et al. (Dec. 22, 1988). "Use Of Tumor-Infiltrating Lymphocytes and Interleukin-2 in the Immunotherapy of Patients With Metastatic Melanoma. A Preliminary Report," N Engl J Med. 319(25):1676-1680.
Sadelain, M. et al. (Jan. 1, 2003). "Targeting Tumours With Genetically Enhanced T Lymphocytes," Nature Reviews Cancer 3(1):35-45.
Scheinberg, D.A. et al. (May 2013). "Reaching Un-Drugable Intracellular Targets with the Long Arm of Antibodies," Oncotarget 4(5):647-648.

(56) References Cited

OTHER PUBLICATIONS

Sela-Chulang, I et al. (Oct. 8, 2013). "The Structural Basis of Antibody-Antigen Recognition," Front Immunol. 4(302): 1-13.
Singer, M. et al. (1998). Genes and Genomes vol. 1 "Mir" Moskva 1:63-64. (English translation attached).
Sloviter, H.A. et al. (Dec. 1, 1962). "Recovery and Transfusion of Human Erythrocytes after freezing in Polyglycol Solutions," Nature 196(4857):899-900.
Stewart-Jones, G. et al. (Apr. 7, 2009). "Rational Development of High-Affinity T-Cell Receptor-Like Antibodies," Proceedings of the National Academy of Sciences 106(14):5784-5788.
Sun, L. et al. (Aug. 7, 2015). "Engineered Cytotoxic T Lymphocytes with AFP-Specific TCR Gene for Adoptive Immunotherapy in Hepatocellular Carcinoma," Tumor Biology 37(1):799-806.
Tao, D. et al. (Mar. 13, 2013). "Targeting the Intracellular WT1 Oncogene Product with a Therapeutic Human Antibody," Science Translational Medicine, American Association For The Advancement of Science 5(176):176ra, 26 pages.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Weidanz, J.A. et al. (2011). "TCR-Like Biomolecules Target Peptide/MHC Class I Complexes on the Surface of Infected and Cancerous Cells," Int. Rev. Immunol. 30(5-6):328-340, pp. 1-13.
Wilkie, S. et al. (Apr. 17, 2012). "Dual Targeting of ErbB2 and MUC1 in Breast Cancer Using Chimeric Antigen Receptors Engineered to Provide Complementary Signaling," Journal of Clinical Immunology 32(5):1059-1070.
Willemsen, R.A. et al. (Aug. 2000). "Grafting Primary Human T Lymphocytes With Cancer-Specific Chimeric Single Chain and Two Chain TCR," Gene Therapy 7(16):1369-1377.
Wucherpfennig, K.W. et al. (Apr. 2010). "Structural Biology of the T-Cell Receptor: Insights into Receptor Assembly, Ligand Recognition, and Initiation of Signaling," Cold Spring Harb Perspect Biol. 2(4):a005140, pp. 1-14.
Zhang, G. et al. (Jan. 6, 2014). "Anti-Melanoma Activity of T-Cells Redirected with a TCR-like Chimeric Antigen Receptor," Scientific Reports 4:3571:1-8.
Zhang, J. et al. (Jul. 19, 2019). "The Emerging World of TCR-T Cell Trials Against Cancer: A Systematic Review," Technology In Cancer Research & Treatment 18: 1-13.
Zhang, T. et al. (2004; e-pub. May 21, 2004). "Transgenic TCR Expression: Comparison of Single Chain with Full-Length Receptor Constructs for T-Cell Function," Cancer Gene Therapy 11:487-496.
Zheng, J. et al. (Dec. 2013; e-pub. Aug. 3, 2013). "A Novel Antibody-Like TCRγδ-Ig Fusion Protein Exhibits Antitumor Activity Against Human Ovarian Carcinoma," Cancer Letters 341(2):150-158.
Colman, P.M. (1994). "Effects of Amino Acid Sequence Changes on Antibody-Antigen Interactions," Research in Immunology 145(1):33-36.
Genbank Accession No. AAQ57272.1. (Aug. 27, 2003). "T Cell Receptor Delta-Chain [*Homo sapiens*]," 2 pages.
Genbank Accession No. AGE01788.1. (Feb. 16, 2013). "T Cell Receptor Delta-Chain [*Homo sapiens*]," 2 pages.
Genbank Accession No. CC173893.1. (Aug. 13, 2012). "T Cell Receptor B Chain [*Homo sapiens*]," 2 pages.
Genbank Accession No. CC173895.1. (Aug. 13, 2012). "T Cell Receptor A Chain *Homo sapiens*]," 2 pages.
Pan, Q. et al. (Jan. 2007). "Blocking Neuropilin-1 Function Has an Additive Effect with Anti-VEGF to Inhibit Tumor Growth," Cancer Cell 11:53-67.
Rudikoff, S. et al. (Mar. 1982). "Single Amino Acid Substitution Altering Antigen-Binding Specificity," Proc. Natl. Acad. Sci. USA 79:1979-1983.
Zah, E. et al. (Jun. 2016). "T-Cell Expressing CD19/CD20 Bispecific Chimeric Antigen Receptors Prevent Antigen Escape by Malignant B Cells," Cancer Immunol. Res. 4(6):498-508.
Lanitis, E. et al. (Jul. 1, 2013). "Chimeric Antigen Receptor T Cells With Dissociated Signaling Domains Exhibit Focused Anti-tumor Activity With Reduced Potential for Toxicity in Vivo," Cancer Immunol. Res. 1(1):43-53, 20 pages.
Su, C. (Jan. 15, 2017). "The Influence of Constant-Domain Replacement on the Function of TCR," China Excellent master's Dissertation Full Text Database, Medicine and Health technology, E059-15, 69 pages, (Translation of Abstract Only).
Fujio, K. et al. (2000). "Functional Reconstitution of Class II MHC-Restricted T Cell Immunity Mediated by Retroviral Transfer of the αβ TCR Complex," The Journal of Immunology 165:528-532.
International Search Report and Written Opinion dated Nov. 13, 2020, for International Patent Application No. PCT/US2043629, filed Jul. 24, 2020, 9 pages.
International Search Report and Written Opinion dated Nov. 9, 2021, for International Patent Application No. PCT/US21/43776, filed Jul. 29, 2021, 9 pages.
Lee, S.Y. et al. (Sep. 1996). "CD30/TNF Receptor-Associated Factor Interaction: $NF_\kappa B$ Activation and Binding Specificity," Proc. Natl. Acad. Sci. USA 93:9699-9703.
Gilfillan, M.C. et al. (1998). "Expression of the Costimulatory Receptor CD30 is Regulated by Both CD28 and Cytokines," The Journal of Immunology 160:2180-2187.
Schneider, D. et al. (2017). "A Tandem CD19/CD20 CAR Lentiviral Vector Drives On-Target and Off-Target Antigen Modulation in Leukemia Cell Lines," Journal for Immuno Therapy of Cancer 5:42, 17 pages.

\* cited by examiner

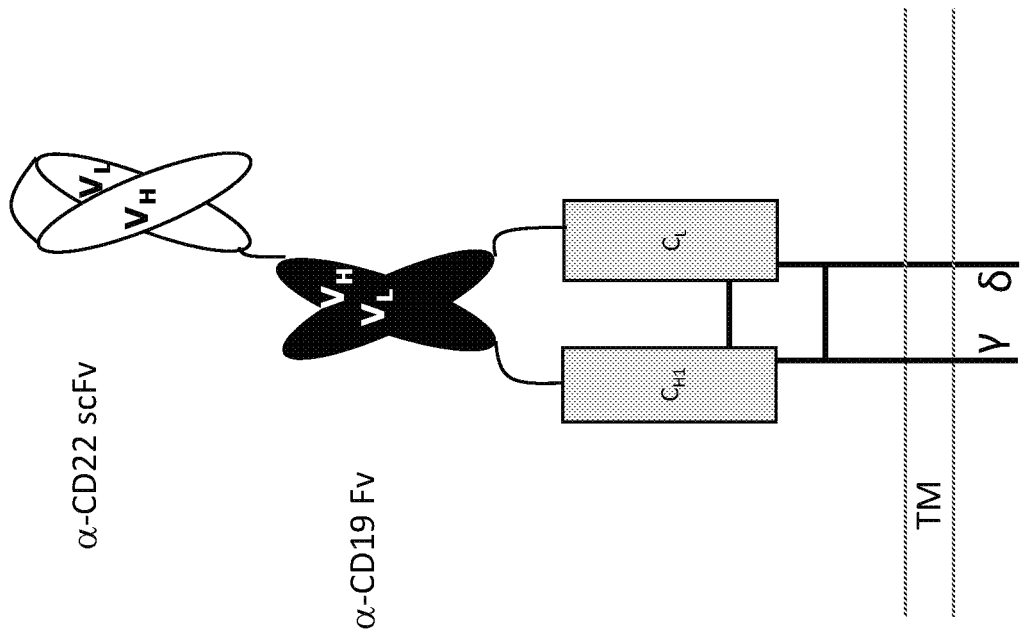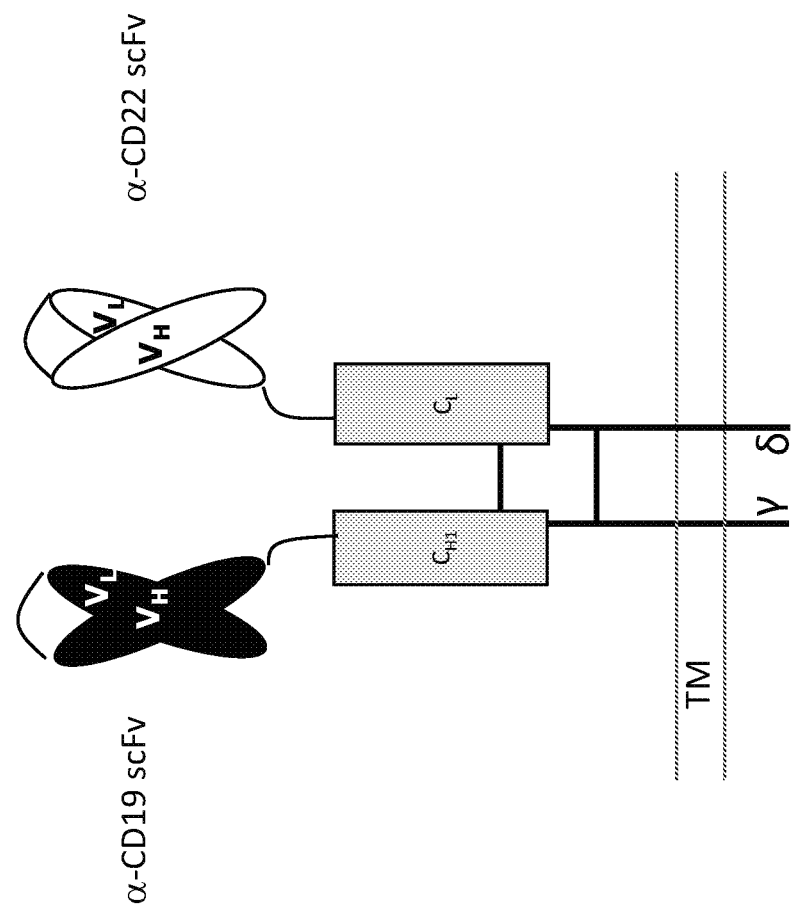
FIG. 13C
FIG. 13D

CELLS EXPRESSING CHIMERIC ACTIVATING RECEPTORS AND CHIMERIC STIMULATING RECEPTORS AND USES THEREOF

CROSS-REFERENCE TO RELATED APPLICATION

This application is a national stage application under 35 U.S.C. § 371 of International Application No. PCT/US2018/029218, filed on Apr. 24, 2018, which claims priority to U.S. Provisional Application No. 62/490,576, filed on Apr. 26, 2017, U.S. Provisional Application No. 62/490,578, filed on Apr. 26, 2017, and U.S. Provisional Application No. 62/490,580, filed on Apr. 26, 2017, the contents of which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 7500420010000SEQLIST.txt, date recorded: Oct. 14, 2019, size: 107 KB).

FIELD OF THE INVENTION

The invention relates to immune cells (such as T cells) comprising a chimeric antibody-T cell receptor (TCR) construct (caTCR) and a chimeric signaling receptor (CSR) construct. The caTCR comprises an antigen-binding module that specifically binds to a target antigen and a T cell receptor module (TCRM) capable of recruiting at least one TCR-associated signaling molecule, and the CSR comprises a ligand-binding domain that specifically binds to a target ligand and a co-stimulatory signaling domain capable of providing a stimulatory signal to the immune cell.

BACKGROUND OF THE INVENTION

T-cell mediated immunity is an adaptive process of developing antigen (Ag)-specific T lymphocytes to eliminate viruses, bacterial, parasitic infections or malignant cells. It can also involve aberrant recognition of self-antigen, leading to autoimmune inflammatory diseases. The Ag specificity of T lymphocytes is based on recognition through the T Cell Receptor (TCR) of unique antigenic peptides presented by Major Histocompatibility Complex (MIIC) molecules on Ag-presenting cells (APC) (Broere, et al., Principles of Immunopharmacology, 2011). Each T lymphocyte expresses a unique TCR on the cell surface as the result of developmental selection upon maturation in the thymus. The TCR occurs in two forms as either an αβ heterodimer or as a γδ heterodimer. T cells express either the αβ form or the γδ form TCR on the cell surface. The four chains, α/β/γ/δ, all have a characteristic extracellular structure consisting of a highly polymorphic "immunoglobulin variable region"-like N-terminal domain and an "immunoglobulin constant region"-like second domain. Each of these domains has a characteristic intra-domain disulfide bridge. The constant region is proximal to the cell membrane, followed by a connecting peptide, a transmembrane region and a short cytoplasmic tail. The covalent linkage between the 2 chains of the heterodimeric TCR is formed by the cysteine residue located within the short connecting peptide sequence bridging the extracellular constant domain and the transmembrane region which forms a disulfide bond with the paired TCR chain cysteine residue at the corresponding position (The T cell Receptor Factsbook, 2001).

The αβ and γδ TCRs are associated with the non-polymorphic membrane-bound CD3 proteins to form the functional octameric TCR-CD3 complex, consisting of the TCR heterodimer and three dimeric signaling molecules, CD3δ/ε, CD3γ/ε and CD3ζ/ζ or ζ/η. Ionizable residues in the transmembrane domain of each subunit form a polar network of interactions that hold the complex together. For T cell activation, the TCR N-terminal variable regions recognize the peptide/MHC complex presented on the surface of target cell, whereas the CD3 proteins participate in signal transduction (Call et al., Cell. 111(7):967-79, 2002; The T cell Receptor Factsbook, 2001).

αβ TCR, also called conventional TCR, is expressed on most lymphocytes and consists of the glycosylated polymorphic α and β chains. Different a TCRs can discriminate among different peptides embedded in the surfaces of MHC II (mostly expressed on APC cell surfaces) and MHC I (expressed on all nucleated cells) molecules, whose dimensions and shapes are relatively constant. The γδ TCR, though structurally similar to the αβ TCR, recognizes carbohydrate-, nucleotide-, or phosphor-carrying antigens in a fashion independent of MHC presentation (The T cell Receptor Factsbook, 2001; Girardi et al., J. Invest. Dermatol. 126(1): 25-31, 2006; Hayes et al., Immunity. 16(6):827-38, 2002).

In the past two decades, fundamental advances in immunology and tumor biology, combined with the identification of a large number of tumor antigens, have led to significant progress in the field of cell-based immunotherapy. T cell therapy occupies a large space in the field of cell-based immunotherapy, with the goal of treating cancer by transferring autologous and ex vivo expanded T cells to patients, and has resulted in some notable antitumor responses (Blattman et al., Science. 305(5681):200-5, 2004). For example, the administration of naturally occurring tumor infiltrating lymphocytes (TILs) expanded ex vivo mediated an objective response rate ranging from 50-70% in melanoma patients, including bulky invasive tumors at multiple sites involving liver, lung, soft tissue and brain (Rosenberg et al., Nat. Rev. Cancer. 8(4):299-308, 2008; Dudley M E et al., J. Clin. Oncol. 23(10):2346-57, 2005).

A major limitation to the widespread application of TIL therapy is the difficulty in generating human T cells with antitumor potential. As an alternative approach, exogenous high-affinity TCRs can be introduced into normal autologous T cells of the patients through T cell engineering. The adoptive transfer of these cells into lympho-depleted patients has been shown to mediate cancer regression in cancers such as melanoma, colorectal carcinoma, and synovial sarcoma (Kunert R et al., Front. Immunol. 4:363, 2013). A recent phase I clinical trial using anti NY-ESO-1 TCRs against synovial sarcoma reported an overall response rate of 66% and complete response was achieved in one of the patients receiving the T cell therapy (Robbins P F et al., Clin. Cancer Res. 21(5):1019-27, 2015).

One of the advantages of TCR-engineered T cell therapy is that it can target the entire array of potential intracellular tumor-specific proteins, which are processed and delivered to the cell surface through MHC presentation. Furthermore, the TCR is highly sensitive and can be activated by just a few antigenic peptide/MHC molecules, which in turn can trigger a cytolytic T cell response, including cytokine secretion, T cell proliferation and cytolysis of defined target cells. Therefore, compared with antibody or small molecule therapies, TCR-engineered T cells are particularly valuable for their ability to kill target cells with very few copies of target intracellular antigens (Kunert R et al., *Front. Immunol.* 4:363, 2013).

However, unlike therapeutic antibodies, which are mostly discovered through hybridoma or display technologies, identification of target-specific TCRs requires the establishment of target peptide/MHC specific TCR clones from patient T cells and screening for the right α-β chain combination that has the optimal target antigen-binding affinity. Very often, phage/yeast display is employed after cloning of the TCR from patient T cells to further enhance the target binding affinity of the TCR. The whole process requires expertise in many areas and is time-consuming (Kobayashi E et al., *Oncoimmunology.* 3(1):e27258, 2014). The difficulties in the TCR discovery process have largely impeded the widespread application of TCR-engineered T cell therapy. It has also been hampered by treatment-related toxicity, in particularly with TCRs against antigens that are over-expressed on tumor cells but also expressed on healthy cells, or with TCRs recognizing off-target peptide/MHC complexes (Rosenberg S A et al., *Science.* 348(6230):62-8, 2015).

A different approach has been developed in recent years to engage T cells for targeted cancer immunotherapy. This new approach is called Chimeric Antigen Receptor T cell Therapy (CAR-T). It merges the exquisite targeting specificity of monoclonal antibodies with the potent cytotoxicity and long-term persistence provided by cytotoxic T cells. A CAR is composed of an extracellular domain that recognizes a cell surface antigen, a transmembrane region, and an intracellular signaling domain. The extracellular domain consists of the antigen-binding variable regions from the heavy and light chains of a monoclonal antibody that are fused into a single-chain variable fragment (scFv). The intracellular signaling domain contains an immunoreceptor tyrosine-based activation motif (ITAM), such as those from CD3ζ or FcRγ, and one or more co-stimulatory signaling domains, such as those from CD28, 4-1BB or OX40 (Barrett D M et al., *Annu. Rev. Med.* 65:333-47, 2014; Davila M L et al., *Oncoimmunology.* 1(9):1577-1583, 2012). Binding of target antigens by CARs grafted onto a T cell surface can trigger T cell effector functions independent of TCR-peptide/MHC complex interaction. Thus, T cells equipped with CARs can be redirected to attack a broad variety of cells, including those that do not match the MHC type of the TCRs on the T cells but express the target cell-surface antigens. This approach overcomes the constraints of MHC-restricted TCR recognition and avoids tumor escape through impairments in antigen presentation or MHC molecule expression. Clinical trials have shown clinically significant antitumor activity of CAR-T therapy in neuroblastoma (Louis C U et al., *Blood.* 118(23):6050-6056, 2011), B-ALL (Maude, S L, et al., *New England Journal of Medicine* 371:16:1507-1517, 2014), CLL (Brentjens, R J, et al. *Blood* 118:18:4817-4828, 2011), and B cell lymphoma (Kochenderfer, I N, et al. *Blood* 116:20:4099-4102, 2010). In one study, a 90% complete remission rate in 30 patients with B-ALL treated with CD19-CAR T therapy was reported (Maude, S L, et al., supra).

All CARs studied so far have been directed to tumor antigens with high cell surface expression. To target low-copy number cell-surface tumor antigens and intracellular tumor antigens, which represent 95% of all known tumor-specific antigens, there is a need to develop more potent and effective engineered cell therapies (Cheever, et al., *Clin. Cancer Res.* 15(17):5323-37, 2009).

Several attempts have been made to engineer chimeric receptor molecules having antibody specificity with T cell receptor effector functions. See, for example, Kuwana, Y, et al., *Biochem. Biophys. Res. Commun.* 149(3):960-968, 1987; Gross, G, et al., *Proc. Nat. Acad. Sci. USA.* 86:10024-10028, 1989; Gross, G & Eshhar, Z, *FASEB J.* 6(15):3370-3378, 1992; and U.S. Pat. No. 7,741,465. To this date, none of these chimeric receptors have been adopted for clinical use, and novel designs for antibody-TCR chimeric receptors with improved expression and functionality in human T cells are needed.

The disclosures of all publications, patents, patent applications and published patent applications referred to herein are hereby incorporated herein by reference in their entirety. PCT Application Number PCT/US2016/058305 is hereby incorporated herein by reference in its entirety.

BRIEF SUMMARY OF THE INVENTION

The present application in one aspect provides immune cells (such as T cells) comprising a chimeric antibody-T cell receptor (TCR) construct (caTCR) and a chimeric signaling receptor (CSR) construct. The caTCR comprises an antigen-binding module that specifically binds to a target antigen and a T cell receptor module (TCRM) capable of recruiting at least one TCR-associated signaling molecule, and the CSR comprises a ligand-binding domain that specifically binds to a target ligand and a co-stimulatory signaling domain capable of providing a stimulatory signal to the immune cell.

In some embodiments, there is provided an immune cell comprising: a) a chimeric antibody-T cell receptor (TCR) construct (caTCR) comprising: i) an antigen binding module that specifically binds to a target antigen; and ii) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule; and b) a chimeric signaling receptor (CSR) comprising: i) a ligand-binding module that is capable of binding or interacting with a target ligand; ii) a transmembrane module; and iii) a co-stimulatory immune cell signaling module that is capable of providing a co-stimulatory signal to the immune cell, wherein the ligand-binding module and the co-stimulatory immune cell signaling module are not derived from the same molecule, and wherein the CSR lacks a functional primary immune cell signaling domain.

In some embodiments, there is provided one or more nucleic acids encoding a caTCR and CSR as described here, wherein the caTCR and CSR each consist of one or more polypeptide chains encoded by the one or more nucleic acids.

In some embodiments, there is provided one or more nucleic acids encoding: a) a chimeric antibody-T cell receptor (TCR) construct (caTCR) comprising: i) an antigen binding module that specifically binds to a target antigen; and ii) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule, and wherein the caTCR consists of one or more polypeptide chains; and b) a chimeric signaling receptor (CSR) comprising: i) a ligand-binding module that is capable of binding or interacting with a target ligand; ii) a transmembrane module; and iii) a co-stimulatory immune cell signaling module that is capable of providing a co-stimulatory signal to the immune cell, wherein the ligand-binding module and the co-stimulatory immune cell signaling module are not derived from the same molecule, wherein the CSR lacks a functional primary immune cell signaling domain, and wherein the CSR consists of one or more polypeptide chains.

In some embodiments, there is provided one or more vectors comprising one or more nucleic acids as described herein.

In some embodiments, there is provided a composition comprising one or more nucleic acids or one or more vectors as described herein.

In some embodiments, there is provided an immune cell comprising one or more nucleic acids or one or more vectors as described herein.

In some embodiments, there is provided a pharmaceutical composition comprising an immune cell as described herein, and a pharmaceutically acceptable carrier.

In some embodiments, there is provided a method of killing a target cell presenting a target antigen, comprising contacting the target cell with an immune cell as described herein.

In some embodiments, there is provided a method of treating a target antigen-associated disease in an individual in need thereof, comprising administering to the individual an effective amount of a pharmaceutical composition as described herein.

In some embodiments, there is provided a method of providing a co-stimulatory signal to an immune cell comprising a caTCR or transduced with a nucleic acid encoding a caTCR, comprising introducing into said cell one or more nucleic acids or one or more vectors as described herein.

BRIEF DESCRIPTION OF THE DRAWINGS

FIGS. 13A-13E show schematic structures of exemplary bispecific caTCR molecules.

DETAILED DESCRIPTION OF THE INVENTION

Figure 1:
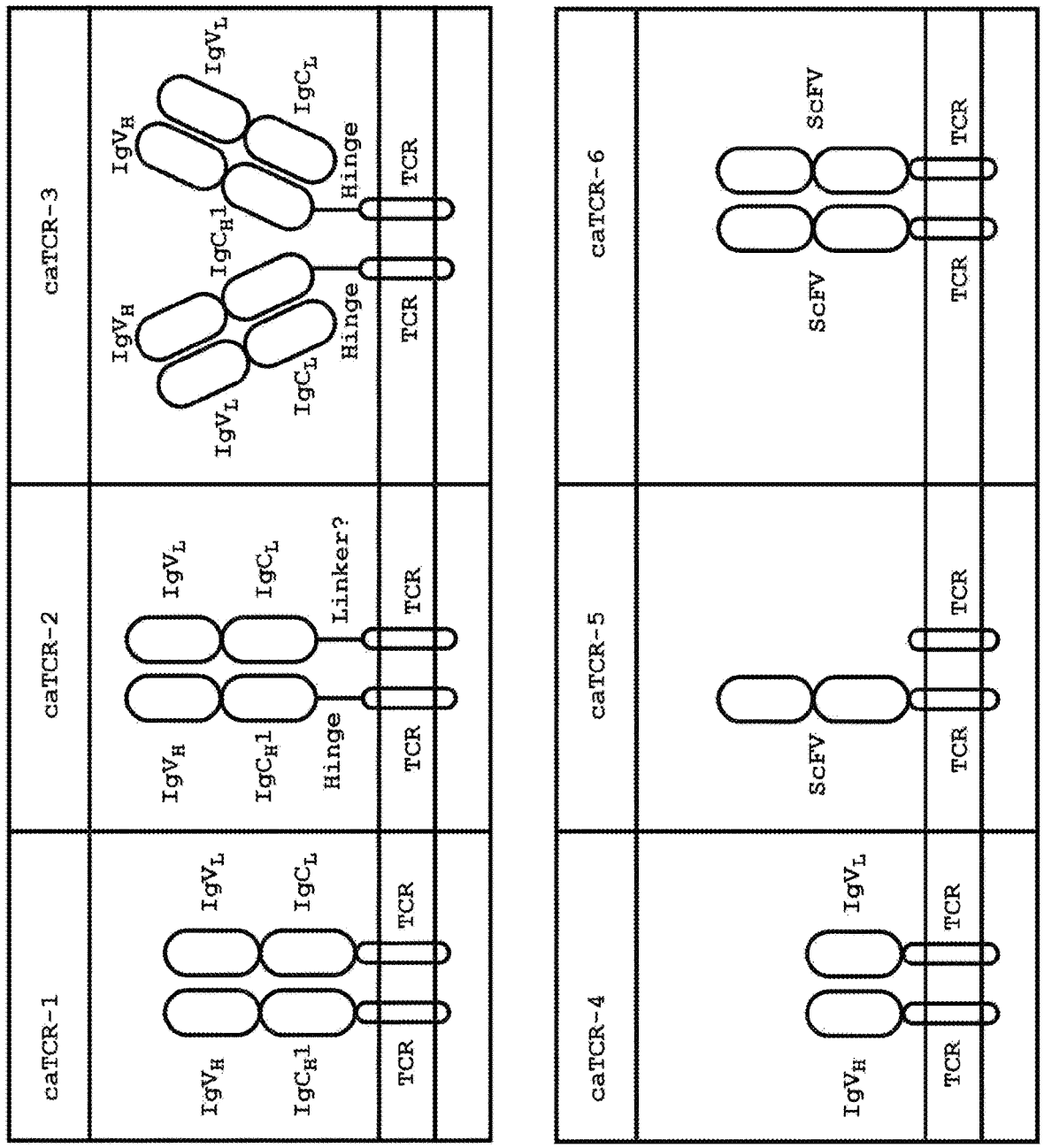
FIG. 1 shows a schematic representation of several caTCR molecules having different antigen-binding modules.

The present application provides immune cells (such as T cells) comprising a chimeric antibody-T cell receptor (TCR) construct (caTCR) and a chimeric signaling receptor (CSR) construct. The caTCR comprises an antigen-binding module that specifically binds to a target antigen and a T cell receptor module (TCRM) capable of recruiting at least one TCR-associated signaling molecule. The CSR comprises a ligand-binding domain that specifically binds to a target ligand and a co-stimulatory immune cell signaling domain capable of providing a stimulatory signal to the immune cell, and does not comprise a functional primary immune cell signaling sequence. The target antigen and target ligand can be proteins expressed on the cell surface or complexes comprising a peptide and an MHC protein (referred to herein as a "pMHC complex," or "pMHC"), such as an MHC-presented disease-associated antigen peptide on the surface of a diseased cell. caTCRs are regulated by the naturally occurring machinery that controls T cell receptor activation, and signaling through the CSR is capable of potentiating the immune response mediated by the caTCR.

We have developed a series of novel T cells comprising caTCR and CSR constructs. They exhibited potent cytotoxicity against target-bearing tumor cells, with increased cytokine expression in response to target cell engagement as compared to cells expressing only the caTCR in the absence of the CSR. Inclusion of the CSR in these cells further enhanced degranulation, proliferation, and viability as compared to cells expressing only the caTCR.

The present application thus provides immune cells comprising a caTCR specific for a target antigen and a CSR specific for a target ligand, wherein the caTCR comprises an antigen-binding module that specifically binds to the target antigen and a T cell receptor module (TCRM) capable of recruiting at least one TCR-associated signaling molecule, and wherein the CSR a) comprises a ligand-binding domain that specifically binds to the target ligand and a co-stimulatory immune cell signaling domain capable of providing a stimulatory signal to the immune cell and b) does not comprise a functional primary immune cell signaling sequence. The caTCR can take any of a number of formats with variations in the antigen-binding module and/or TCRM. For example, the caTCR can have an antigen-binding module comprising a moiety selected from the group consisting of a Fab, a Fab', a (Fab')$_2$, an Fv, and an scFv, and a TCRM comprising one or more sequences derived from an α/β or γ/δ TCR, including variants in one or more of the transmembrane domain, connecting peptide, and intracellular domain. See FIG. 1. In some embodiments, the antigen-binding module is multispecific (such as bispecific). The CSR can similarly have a ligand-binding module comprising a moiety selected from the group consisting of a Fab, a Fab', a (Fab')$_2$, an Fv, and an scFv. In some embodiments, the target antigen and the target ligand are the same. In some embodiments, the antigen-binding module of the caTCR and the ligand-binding module of the CSR are the same, or comprise the same sequences conferring antigen specificity, such as CDRs or variable domains. In some embodiments, the target antigen and the target ligand are different.

In yet other aspects, there are provided a) one or more nucleic acids encoding a caTCR and a CSR, b) immune cells comprising one or more nucleic acids encoding a caTCR and a CSR, and c) compositions comprising immune cells comprising i) a caTCR and a CSR, or ii) one or more nucleic acids encoding the caTCR and the CSR. The compositions can be pharmaceutical compositions.

Also provided are methods of making and using immune cells comprising a caTCR and a CSR for treatment purposes, as well as kits and articles of manufacture useful for such methods. Further provided are methods of treating a disease using immune cells comprising a caTCR and a CSR.

Definitions

The term "antibody" or "antibody moiety" includes full-length antibodies and antigen-binding fragments thereof. A full-length antibody comprises two heavy chains and two light chains. The variable regions of the light and heavy chains are responsible for antigen-binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as lgG1 (γ1 heavy chain), lgG2 (γ2 heavy chain), lgG3 (γ3 heavy chain), lgG4 (γ4 heavy chain), lgA1 (α1 heavy chain), or lgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

As used herein, a first antibody moiety "competes" for binding to a target antigen with a second antibody moiety when the first antibody moiety inhibits target antigen-binding of the second antibody moiety by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds" or "is specific for" refers to measurable and reproducible interactions, such as binding between a target and an antibody or antibody moiety that is determinative of the presence of the target in the presence of a heterogeneous population of molecules, including biological molecules. For example, an antibody moiety that specifically binds to a target (which can be an epitope) is an antibody moiety that binds the target with greater affinity, avidity, more readily, and/or with greater duration than its bindings to other targets. In some embodiments, an antibody moiety that specifically binds to an antigen reacts with one or more antigenic determinants of the antigen (for example a cell surface antigen or a peptide/MHC protein complex) with a binding affinity that is at least about 10 times its binding affinity for other targets.

The term "T cell receptor," or "TCR," refers to a heterodimeric receptor composed of αβ or γδ chains that pair on the surface of a T cell. Each α, β, γ, and δ chain is composed of two Ig-like domains: a variable domain (V) that confers antigen recognition through the complementarity determining regions (CDR), followed by a constant domain (C) that is anchored to cell membrane by a connecting peptide and a transmembrane (TM) region. The TM region associates with the invariant subunits of the CD3 signaling apparatus. Each of the V domains has three CDRs. These CDRs interact with a complex between an antigenic peptide bound to a protein encoded by the major histocompatibility complex (pMHC) (Davis and Bjorkman (1988) Nature, 334, 395-402; Davis et al. (1998) Annu Rev Immunol, 16, 523-544; Murphy (2012), xix, 868 p.).

The term "TCR-associated signaling molecule" refers to a molecule having a cytoplasmic immunoreceptor tyrosine-based activation motif (ITAM) that is part of the TCR-CD3 complex. TCR-associated signaling molecules include CD3γε, CD3δε, and ζζ (also known as CD3ζ or CD3ζζ).

"Activation", as used herein in relation to a cell expressing CD3, refers to the state of the cell that has been sufficiently stimulated to induce a detectable increase in downstream effector functions of the CD3 signaling pathway, including, without limitation, cellular proliferation and cytokine production.

The term "module" when referring to a portion of a protein is meant to include structurally and/or functionally related portions of one or more polypeptides which make up the protein. For example, a transmembrane module of a dimeric receptor may refer to the portions of each polypeptide chain of the receptor that span the membrane. A module may also refer to related portions of a single polypeptide chain. For example, a transmembrane module of a monomeric receptor may refer to portions of the single polypeptide chain of the receptor that span the membrane. A module may also include only a single portion of a polypeptide.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., J. Mol. Biol., 273: 927-948 (1997); MacCallum et al., J. Mol. Biol. 262:732-745 (1996); Abhinandan and Martin, Mol. Immunol., 45: 3832-3839 (2008); Lefranc M. P. et al., Dev. Comp. Immunol., 27: 55-77 (2003); and Honegger and Plückthun, J. Mol. Biol., 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, Mol. Immunol., 45: 3832-3839 (2008); Ehrenmann F. et al., Nucleic Acids Res., 38: D301-D307 (2010); and Adolf-Bryfogle J. et al., Nucleic Acids Res., 43: D432-D438 (2015). The contents of the references cited in this paragraph are incorporated herein by reference in their entireties for use in the present invention and for possible inclusion in one or more claims herein.

TABLE 1

CDR DEFINITIONS

|  | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Phückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

The term "fully synthetic" in reference to an antibody or antibody moiety means that the antibody or antibody moiety has fixed naturally occurring $V_H/V_L$ framework pairings, but non-naturally occurring (i.e., synthetic) sequences of all 6 CDRs of both heavy and light chains.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Homology" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are "homologous" at that position. The "percent of homology" or "percent sequence identity" between two sequences is a function of the number of matching or homologous positions shared by the two sequences divided by the number of positions compared times 100, considering any conservative substitutions as part of the sequence identity. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5): 1792-1797, 2004; Edgar, R. C., *BMC Bioinformatics* 5(1): 113, 2004).

The "$C_H1$ domain" of a human IgG Fc region (also referred to as "C1" of "H1" domain) usually extends from about amino acid 118 to about amino acid 215 (EU numbering system).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "inducible promoter" refers to a promoter whose activity can be regulated by adding or removing one or more specific signals. For example, an inducible promoter may activate transcription of an operably linked nucleic acid under a specific set of conditions, e.g., in the presence of an inducing agent or conditions that activates the promoter and/or relieves repression of the promoter.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of the disease (such as, for example, tumor volume in cancer). The methods of the invention contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

An "effective amount" of a caTCR or composition comprising a caTCR as disclosed herein is an amount sufficient to carry out a specifically stated purpose. An "effective amount" can be determined empirically and by known methods relating to the stated purpose.

The term "therapeutically effective amount" refers to an amount of a caTCR or composition comprising a caTCR as disclosed herein, effective to "treat" a disease or disorder in an individual. In the case of cancer, the therapeutically effective amount of a caTCR or composition comprising a caTCR as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent a caTCR or composition comprising a caTCR as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that improves progression free survival of a patient. In the case of infectious disease, such as viral infection, the therapeutically effective amount of a caTCR or composition comprising a caTCR as disclosed herein can reduce the number of cells infected by the pathogen; reduce the production or release of pathogen-derived antigens; inhibit (i.e., slow to some extent and preferably stop) spread of the pathogen to uninfected cells; and/or relieve to some extent one or more symptoms associated with the infection. In some embodiments, the therapeutically effective amount is an amount that extends the survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

caTCR Plus CSR Immune Cells

The present invention provides an immune cell (such as a T cell) presenting on its surface a caTCR and a CSR according to any of the caTCRs and CSRs described herein (such an immune cell is also referred to herein as a "caTCR plus CSR immune cell"). In some embodiments, the immune cell comprises nucleic acid encoding the caTCR and CSR, wherein the caTCR and CSR are expressed from the nucleic acid and localized to the immune cell surface. In some embodiments, the immune cell is a T cell. In some embodiments, the immune cell is selected from the group consisting of a cytotoxic T cell, a helper T cell, a natural killer T cell, and a suppressor T cell. In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the T cell is a γδ T cell and the TCR-TMs of the introduced caTCR comprise sequences derived from TCR α and β chains. In some embodiments, the immune cell is modified to block or decrease the expression of one or both of the endogenous TCR subunits of the immune cell. For example, in some embodiments, the immune cell is an αβ T cell modified to block or decrease the expression of the TCR α and/or β chains or the immune cell is a γδ T cell modified to block or decrease the expression of the TCR γ and/or δ chains. Modifications of cells to disrupt gene expression include any such techniques known in the art, including for example RNA interference (e.g., siRNA, shRNA, miRNA), gene editing (e.g., CRISPR- or TALEN-based gene knockout), and the like.

For example, in some embodiments, there is provided an immune cell (such as a T cell) comprising nucleic acid encoding a caTCR according to any of the caTCRs described herein and a CSR according to any of the CSRs described herein, wherein the caTCR and CSR are expressed from the nucleic acid and localized to the immune cell surface. In some embodiments, the nucleic acid comprises a first caTCR nucleic acid sequence encoding a first caTCR polypeptide chain of the caTCR, a second caTCR nucleic acid sequence encoding a second caTCR polypeptide chain of the caTCR, and a CSR nucleic acid sequence encoding a CSR polypeptide chain of the CSR. In some embodiments, the first and second caTCR nucleic acid sequences and CSR nucleic acid sequence are each contained in different vectors. In some embodiments, some or all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses). In some embodiments, one or more of the vectors is integrated into the host genome of the immune cell. In some embodiments, the first and second caTCR nucleic acid sequences and CSR nucleic acid sequence are each under the control of different promoters. In some embodiments, some or all of the promoters have the same sequence. In some embodiments, some or all of the promoters have different sequences. In some embodiments, some or all of the nucleic acid sequences are under the control of a single promoter. In some embodiments, some or all of the promoters are inducible. In some embodiments, the immune cell is selected from the group consisting of a cytotoxic T cell, a helper T cell, a natural killer T cell, and a suppressor T cell.

Thus, in some embodiments, there is provided a caTCR plus CSR immune cell (such as a T cell) expressing on its surface a caTCR according to any of the caTCRs described herein and a CSR according to any of the CSRs described herein, wherein the caTCR plus CSR immune cell comprises a) a first caTCR nucleic acid sequence encoding a first caTCR polypeptide chain of the caTCR; b) a second caTCR nucleic acid sequence encoding a second caTCR polypeptide chain of the caTCR; and c) a CSR nucleic acid sequence encoding a CSR polypeptide chain of the CSR, wherein the first and second caTCR polypeptide chains are expressed from the first and second caTCR nucleic acid sequences to form the caTCR, wherein the CSR polypeptide chain is expressed from the CSR nucleic acid to form the CSR, and wherein the caTCR and CSR localize to the surface of the immune cell. In some embodiments, the first caTCR nucleic acid sequence is contained in a first vector (such as a lentiviral vector), the second caTCR nucleic acid sequence is contained in a second vector (such as a lentiviral vector), and the CSR nucleic acid sequence is contained in a third vector (such as a lentiviral vector). In some embodiments, some or all of the first and second caTCR nucleic acid sequences and CSR nucleic acid sequence are contained in the same vector (such as a lentiviral vector). In some embodiments, each of the first and second caTCR nucleic acid sequences and CSR nucleic acid sequence are, individually, operably linked to a promoter. In some embodiments, some or all of the nucleic acid sequences are under the control of a single promoter. In some embodiments, some or all of the promoters have the same sequence. In some embodiments, some or all of the promoters have different sequences. In some embodiments, some or all of the promoters are inducible. In some embodiments, some or all of the vectors are viral vectors (such as lentiviral vectors). In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the immune cell is a γδ T cell and the TCR-TMs of the introduced caTCR comprise sequences derived from TCR α and β chains. In some embodiments, the immune cell is modified to block or decrease the expression of one or both of its endogenous TCR subunits. For example, in some embodiments, the immune cell is an αβ T cell modified to block or decrease the expression of the TCR α and/or β chains, or the immune cell is a γδ T cell modified to block or decrease the expression of the TCR γ and/or δ chains. In some embodiments, the immune cell is selected from the group consisting of a cytotoxic T cell, a helper T cell, a natural killer T cell, and a suppressor T cell. In some embodiments, some or all of the vectors are viral vectors (such as lentiviral vectors) integrated into the host genome of the immune cell.

In some embodiments, there is provided a caTCR plus CSR immune cell (such as a T cell) expressing on its surface a caTCR according to any of the caTCRs described herein and a CSR according to any of the CSRs described herein, wherein the caTCR plus CSR immune cell comprises a) a first vector comprising a first promoter operably linked to a first caTCR nucleic acid sequence encoding a first caTCR polypeptide chain of the caTCR; b) a second vector comprising a second promoter operably linked to a second caTCR nucleic acid sequence encoding a second caTCR polypeptide chain of the caTCR; and c) a third vector comprising a third promoter operably linked to a CSR nucleic acid sequence encoding a CSR polypeptide chain of the CSR, wherein the first and second caTCR polypeptide chains are expressed from the first and second caTCR nucleic acid sequences to form the caTCR and the CSR polypeptide chain is expressed from the CSR nucleic acid sequence to form the CSR, and wherein the caTCR and CSR localize to the surface of the immune cell. In some embodiments, some or all of the promoters have the same sequence. In some embodiments, some or all of the promoters have different sequences. In some embodiments, some or all of the promoters are inducible. In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the immune cell is a γδ T cell and the TCR-TMs of the introduced caTCR comprise sequences derived from TCR α and β chains. In some embodiments, the immune cell is modified to block or decrease the expression of one or both of its endogenous TCR subunits. For example, in some embodiments, the immune cell is an αβ T cell modified to block or decrease the expression of the TCR α and/or β chains, or the immune cell is a γδ T cell modified to block or decrease the expression of the TCR γ and/or δ chains. In some embodiments, the immune cell is selected from the group consisting of a cytotoxic T cell, a helper T cell, a natural killer T cell, and a suppressor T cell. In some embodiments, the first and second vectors are viral vectors (such as lentiviral vectors) integrated into the host genome of the immune cell.

In some embodiments, there is provided a caTCR plus CSR immune cell (such as a T cell) expressing on its surface a caTCR according to any of the caTCRs described herein and a CSR according to any of the CSRs described herein, wherein the caTCR plus CSR immune cell comprises a) a first vector comprising i) a first promoter operably linked to a first caTCR nucleic acid sequence encoding a first caTCR polypeptide chain of the caTCR and ii) a second promoter operably linked to a second caTCR nucleic acid sequence encoding a second caTCR polypeptide chain of the caTCR; and b) a second vector comprising a third promoter operably linked to a CSR nucleic acid sequence encoding a CSR polypeptide chain of the CSR, wherein the first and second caTCR polypeptide chains are expressed from the first and second caTCR nucleic acid sequences to form the caTCR and the CSR polypeptide chain is expressed from the CSR nucleic acid sequence to form the CSR, and wherein the caTCR localizes to the surface of the immune cell. In some embodiments, some or all of the promoters have the same sequence. In some embodiments, some or all of the promoters have different sequences. In some embodiments, some or all of the promoters are inducible. In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the immune cell is a γδ T cell and the TCR-TMs of the introduced caTCR comprise sequences derived from TCR α and β chains. In some embodiments, the immune cell is modified to block or decrease the expression of one or both of its endogenous TCR subunits. For example, in some embodiments, the immune cell is an αβ T cell modified to block or decrease the expression of the TCR α and/or β chains, or the immune cell is a γδ T cell modified to block or decrease the expression of the TCR γ and/or δ chains. In some embodiments, the immune cell is selected from the group consisting of a cytotoxic T cell, a helper T cell, a natural killer T cell, and a suppressor T cell. In some embodiments, the first and second vectors are viral vectors (such as lentiviral vectors) integrated into the host genome of the immune cell. It is to be appreciated that embodiments where any of the nucleic acid sequences are swapped are also contemplated, such as where the first or second caTCR nucleic acid sequence is swapped with the CSR nucleic acid sequence.

In some embodiments, there is provided a caTCR plus CSR immune cell (such as a T cell) expressing on its surface a caTCR according to any of the caTCRs described herein and a CSR according to any of the CSRs described herein, wherein the caTCR plus CSR immune cell comprises a) a first vector comprising i) a first caTCR nucleic acid sequence encoding a first caTCR polypeptide chain of the caTCR and ii) a second caTCR nucleic acid sequence encoding a second caTCR polypeptide chain of the caTCR, wherein the first and second caTCR nucleic acid sequences are under the control of a first promoter; and b) a second vector comprising a second promoter operably linked to a CSR nucleic acid sequence encoding a CSR polypeptide chain of the CSR, wherein the first and second caTCR polypeptide chains are expressed from the first and second caTCR nucleic acid sequences to form the caTCR and the CSR polypeptide chain is expressed from the CSR nucleic acid sequence to form the CSR, and wherein the caTCR and CSR localize to the surface of the immune cell. In some embodiments, the first promoter is operably linked to the 5' end of the first caTCR nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first caTCR nucleic acid sequence to the 5' end of the second caTCR nucleic acid sequence, wherein the first caTCR nucleic acid sequence and the second caTCR nucleic acid sequence are transcribed as a single RNA under the control of the promoter. In some embodiments, the first promoter is operably linked to the 5' end of the second caTCR nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second caTCR nucleic acid sequence to the 5' end of the first caTCR nucleic acid sequence, wherein the first caTCR nucleic acid sequence and the second caTCR nucleic acid sequence are transcribed as a single RNA under the control of the promoter. In some embodiments, the first and/or second promoters have the same sequence. In some embodiments, the first and/or second promoters have different sequences. In some embodiments, the first and/or second promoters are inducible. In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the immune cell is a γδ T cell and the TCR-TMs of the introduced caTCR comprise sequences derived from TCR α and β chains. In some embodiments, the immune cell is modified to block or decrease the expression of one or both of its endogenous TCR subunits. For example, in some embodiments, the immune cell is an αβ T cell modified to block or decrease the expression of the TCR α and/or β chains, or the immune cell is a γδ T cell modified to block or decrease the expression of the TCR γ and/or δ chains. In some embodiments, the immune cell is selected from the group consisting of a cytotoxic T cell, a helper T cell, a natural killer T cell, and a suppressor T cell. In some embodiments, the vector is a viral vector (such as a lentiviral vector) integrated into the host genome of the immune cell. It is to be appreciated that embodiments where any of the nucleic acid sequences are swapped are also contemplated, such as where the first or second caTCR nucleic acid sequence is swapped with the CSR nucleic acid sequence.

In some embodiments, there is provided a caTCR plus CSR immune cell (such as a T cell) expressing on its surface a caTCR according to any of the caTCRs described herein and a CSR according to any of the CSRs described herein, wherein the caTCR plus CSR immune cell comprises a vector comprising a) a first caTCR nucleic acid sequence encoding a first caTCR polypeptide chain of the caTCR; b) a second caTCR nucleic acid sequence encoding a second caTCR polypeptide chain of the caTCR; and c) a CSR nucleic acid sequence encoding a CSR polypeptide chain of the CSR, wherein the first and second caTCR nucleic acid sequences and the CSR nucleic acid sequence are under the control of a single promoter; wherein the first and second caTCR polypeptide chains are expressed from the first and second caTCR nucleic acid sequences to form the caTCR and the CSR polypeptide chain is expressed from the CSR nucleic acid sequence to form the CSR, and wherein the caTCR and CSR localize to the surface of the immune cell. In some embodiments, the promoter is operably linked to one of the nucleic acid sequences, which is linked to the other nucleic acid sequences by nucleic acid linkers selected, individually, from the group consisting of an internal ribosomal entry site (IRES) and a nucleic acid encoding a self-cleaving 2A peptide (such as P2A, T2A, E2A, or F2A), such that the first and second caTCR nucleic acid sequences and the CSR nucleic acid sequence are transcribed as a single RNA under the control of the promoter. In some embodiments, the promoter is inducible. In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the immune cell is a γδ T cell and the TCR-TMs of the introduced caTCR comprise sequences derived from TCR α and β chains. In some embodiments, the immune cell is modified to block or decrease the expression of one or both of its endogenous TCR subunits. For example, the immune cell is an αβ T cell modified to block or decrease the expression of the TCR α and/or β chains, or the immune cell is a γδ T cell modified to block or decrease the expression of the TCR γ and/or δ chains. In some embodiments, the immune cell is selected from the group consisting of a cytotoxic T cell, a helper T cell, a natural killer T cell, and a suppressor T cell. In some embodiments, the vector is a viral vector (such as a lentiviral vector) integrated into the host genome of the immune cell.

Chimeric Antibody/T Cell Receptor (caTCR) Constructs

In one aspect, the target antigen-specific chimeric antibody/T cell receptor (caTCR) described herein specifically binds to a target antigen (such as a cell surface antigen or a peptide/MHC complex) and is capable of recruiting at least one TCR-associated signaling molecule (such as CD3δε, CD3γε, and/or ζζ). In some embodiments, the caTCR comprises naturally occurring TCR domains. In some embodiments, the caTCR comprises at least one non-naturally occurring TCR domain. The caTCR comprises an antigen-binding module that provides the antigen specificity and a T cell receptor module (TCRM) that allows for CD3 recruitment and signaling. The antigen-binding module is not a naturally occurring T cell receptor antigen-binding moiety. In some embodiments, the antigen-binding module is linked to the amino terminus of a polypeptide chain in the TCRM. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific). The TCRM comprises a transmembrane module derived from the transmembrane domains of one or more TCRs (TCR-TMs), such as an αβ and/or γδ TCR, and optionally further comprises one or both of the connecting peptides or fragments thereof of a TCR and/or one or more TCR intracellular domains or fragments thereof. In some embodiments, the TCRM comprises two polypeptide chains, each polypeptide chain comprising, from amino terminus to carboxy terminus, a connecting peptide, a transmembrane domain, and optionally a TCR intracellular domain. In some embodiments, the TCRM comprises one or more non-naturally occurring TCR domains. For example, in some embodiments, the TCRM comprises one or two non-naturally occurring TCR transmembrane domains. A non-naturally occurring TCR domain may be a corresponding domain of a naturally occurring TCR modified by substitution of one or more amino acids, and/or by replacement of a portion of the corresponding domain with a portion of an analogous domain from another TCR. The caTCR may comprise a first polypeptide chain and a second polypeptide chain, wherein the first and second polypeptide chains together form the antigen-binding module and the TCRM. In some embodiments, the first and second polypeptide chains are separate polypeptide chains, and the caTCR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the caTCR further comprises one or more T cell co-stimulatory signaling sequences. The one or more co-stimulatory signaling sequences can be, individually, all or a portion of the intracellular domain of a co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the one or more co-stimulatory signaling sequences are between the first TCR-TM and the first TCR intracellular domain and/or between the second TCR-TM and the second TCR intracellular domain. In some embodiments, the one or more co-stimulatory signaling sequences are carboxy-terminal to the first TCRD and/or the second TCRD. In some embodiments, the caTCR lacks a T cell co-stimulatory signaling sequence. In some embodiments, the caTCR further comprises a stabilization module comprising a first stabilization domain and a second stabilization domain, wherein the first and second stabilization domains have a binding affinity for each other that stabilizes the caTCR. In some embodiments, the stabilization module is located between the antigen-binding module and the TCRM. In some embodiments, the caTCR further comprises a spacer module between any two caTCR modules or domains. In some embodiments, the spacer module comprises one or more peptide linkers connecting two caTCR modules or domains.

The caTCRs described herein may have one or more features described in this section. It is intended that any of the features for each component of the caTCR (e.g., antigen-binding module, TCRD, TCR-TM, spacer module, stabilization module, T cell co-stimulation sequences, and various linkers etc.) described herein can be combined with each other, with any of the features of the CSR, and with any of the features of the SSE as if each and every combination is individually described.

In some embodiments, the antigen-binding module (such as an antibody moiety) specifically binds to a target antigen with a) an affinity that is at least about 10 (including for example at least about any of 10, 20, 30, 40, 50, 75, 100, 200, 300, 400, 500, 750, 1000 or more) times its binding affinity for other molecules; or b) a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to other molecules. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

Examples of stabilization domains include an Fc region; a hinge region; a $C_H3$ domain; a $C_H4$ domain; a $C_H1$ or $C_L$ domain; a leucine zipper domain (e.g., a jun/fos leucine zipper domain, see, e.g., Kostelney et al, *J. Immunol,* 148: 1547-1553, 1992; or a yeast GCN4 leucine zipper domain); an isoleucine zipper domain; a dimerizing region of a dimerizing cell-surface receptor (e.g., interleukin-8 receptor (IL-8R); or an integrin heterodimer such as LFA-1 or GPIIIb/IIIa); a dimerizing region of a secreted, dimerizing ligand (e.g., nerve growth factor (NGF), neurotrophin-3 (NT-3), interleukin-8 (IL-8), vascular endothelial growth factor (VEGF), or brain-derived neurotrophic factor (BDNF); see, e.g., Arakawa et al, *J. Biol. Chem.* 269:27833-27839, 1994, and Radziejewski et al, *Biochem.* 32: 1350, 1993); a coiled coil dimerization domain (see, for example, WO2014152878; Fletcher et al, *ACS Synth. Biol.* 1:240-250, 2012; and Thomas et al., *J. Am. Chem. Soc.* 135(13):5161-5166, 2013); and a polypeptide comprising at least one cysteine residue (e.g., from about one, two, or three to about ten cysteine residues) such that disulfide bond(s) can form between the polypeptide and a second polypeptide comprising at least one cysteine residue.

In some embodiments, the TCRM described herein comprises a) a first T cell receptor domain (TCRD) comprising a first TCR transmembrane domain (TCR-TM) and b) a second TCRD comprising a second TCR-TM, wherein the TCRM facilitates recruitment of at least one TCR-associated signaling molecule. In some embodiments, both of the TCR-TMs are naturally occurring. In some embodiments, at least one of the TCR-TMs is non-naturally occurring. In some embodiments, both of the TCR-TMs are non-naturally occurring. In some embodiments, the first TCR-TM is derived from one of the transmembrane domains of a T cell receptor (such as an αβ TCR or a γδ TCR) and the second TCR-TM is derived from the other transmembrane domain of the T cell receptor. In some embodiments, the TCRM allows for enhanced recruitment of the at least one TCR-associated signaling molecule as compared to a TCRM comprising the transmembrane domains of the T cell receptor. Recruitment of TCR-associated signaling molecules can be determined by methods known in the art, such as FACS analysis for TCR-CD3 complex surface expression or co-immunoprecipitation of CD3 subunits with the caTCR.

For example, in some embodiments, the first TCR-TM of a TCRM described herein comprises, consists essentially of, or consists of the transmembrane domain of the TCR α chain (e.g., GenBank Accession No: CCI73895) or a variant thereof and the second TCR-TM of the TCRM comprises, consists essentially of, or consists of the transmembrane domain of the TCR R chain (e.g., GenBank Accession No: CCI73893) or a variant thereof. In some embodiments, the first TCR-TM comprises, consists essentially of, or consists of the transmembrane domain of the TCR δ chain (e.g., GenBank Accession No: AAQ57272) or a variant thereof and the second TCR-TM comprises, consists essentially of, or consists of the transmembrane domain of the TCR γ chain (e.g., GenBank Accession No: AGE91788) or a variant thereof. In some embodiments, the first and second TCR-TMs of a TCRM described herein comprise, consist essentially of, or consist of the transmembrane domain of a TCR α chain constant domain (e.g., SEQ ID NO: 1) or a variant thereof and the transmembrane domain of a TCR β chain constant domain (e.g., SEQ ID NO: 2) or a variant thereof, respectively. In some embodiments, the first and second TCR-TMs comprise, consist essentially of, or consist of the transmembrane domain of a TCR δ chain constant domain (e.g., SEQ ID NO: 3) or a variant thereof and the transmembrane domain of a TCR γ chain constant domain (e.g., SEQ ID NO: 4) or a variant thereof, respectively. In some embodiments, the first and second TCR-TMs comprise, consist essentially of, or consist of the amino acid sequences of SEQ ID NOs: 5 and 6, or variants thereof, respectively. In some embodiments, the first and second TCR-TMs comprise, consist essentially of, or consist of the amino acid sequences of SEQ ID NOs: 7 and 8, or variants thereof, respectively. Variants of the transmembrane domains include, without limitation, transmembrane domains with one or more amino acid substitutions compared to the reference sequence. In some embodiments, a variant transmembrane domain comprises no more than 5 amino acid substitutions compared to the reference sequence. In some embodiments, the first TCRD further comprises a first connecting peptide amino-terminal to the transmembrane domain and/or the second TCRD further comprises a second connecting peptide amino-terminal to the transmembrane domain. In some embodiments, the first connecting peptide comprises all or a portion of the connecting peptide of the TCR subunit from which the first TCR-TM is derived, or a variant thereof, and/or the second connecting peptide comprises all or a portion of the connecting peptide of the TCR subunit from which the second TCR-TM is derived, or a variant thereof. In some embodiments, the first and/or second connecting peptides comprise, consist essentially of, or consist of all or a portion of the connecting peptide of a TCR α chain constant domain (e.g., SEQ ID NO: 1) or a variant thereof and all or a portion of the connecting peptide of a TCR β chain constant domain (e.g., SEQ ID NO: 2) or a variant thereof, respectively. In some embodiments, the first and/or second connecting peptides comprise, consist essentially of, or consist of all or a portion of the connecting peptide of SEQ ID NO: 27 or 28, or a variant thereof, and all or a portion of the connecting peptide of SEQ ID NO: 29 or 30, or a variant thereof, respectively. In some embodiments, the first and/or second connecting peptides comprise, consist essentially of, or consist of all or a portion of the connecting peptide of a TCR δ chain constant domain (e.g., SEQ ID NO: 3) or a variant thereof and all or a portion of the connecting peptide of a TCR γ chain constant domain (e.g., SEQ ID NO: 4) or a variant thereof, respectively. In some embodiments, the first and/or second connecting peptides comprise, consist essentially of, or consist of all or a portion of the connecting peptide of SEQ ID NO: 31 or 32, or a variant thereof, and all or a portion of the connecting peptide of SEQ ID NO: 33 or 34, or a variant thereof, respectively. In some embodiments, the first TCRD further comprises a first TCR intracellular domain carboxy-terminal to the first TCR-TM and/or the second TCRD further comprises a second TCR intracellular domain carboxy-terminal to the second TCR-TM. In some embodiments, the first TCR intracellular domain comprises all or a portion of the intracellular domain of the TCR subunit from which the first TCR-TM is derived, or a variant thereof, and/or the second TCR intracellular domain comprises all or a portion of the intracellular domain of the TCR subunit from which the second TCR-TM is derived, or a variant thereof. In some embodiments, the second TCR intracellular domains comprise any one of the amino acid sequences of SEQ ID NOs: 35-36, or variants thereof. In some embodiments, the first TCRD is a fragment of one chain of a naturally occurring TCR, or a variant thereof, and/or the second TCRD is a fragment of the other chain of the naturally occurring TCR, or a variant thereof. In some embodiments, at least one of the TCRDs is non-naturally occurring. In some embodiments, the first and second TCRDs are linked by a disulfide bond. In some embodiments, the first and second TCRDs are linked by a disulfide bond between a residue in the first connecting peptide and a residue in the second connecting peptide. In some embodiments, the TCRM is capable of recruiting at least one TCR-associated signaling molecule selected from the group consisting of CD3δε, CD3γε, and ζζ. In some embodiments, the TCRM is capable of recruiting each of CD3δε, CD3γε, and ζζ to form a caTCR-CD3 complex (i.e., promotes caTCR-CD3 complex formation).

Contemplated caTCR constructs include, for example, caTCRs that specifically bind to cell surface antigens, caT-CRs that specifically bind to cell surface-presented peptide/MHC complexes, and caTCRs that specifically bind to both cell surface antigens and cell surface-presented peptide/MHC complexes.

In some embodiments, the antigen-binding module is an antibody moiety selected from the group consisting of a Fab, a Fab', a (Fab')2, an Fv, or a single chain Fv (scFv). In some embodiments, the antibody moiety is monospecific. In some embodiments, the antibody moiety is multi-specific. In some embodiments, the antibody moiety is bispecific. In some embodiments, the antibody moiety is a tandem scFv, a diabody (Db), a single chain diabody (scDb), a dual-affinity retargeting (DART) antibody, a dual variable domain (DVD) antibody, a chemically cross-linked antibody, a heteromultimeric antibody, or a heteroconjugate antibody. In some embodiments, the antibody moiety is a tandem scFv comprising two scFvs linked by a peptide linker. In some embodiments, the antibody moiety is two scFvs that are not directly linked. In some embodiments, the antibody moiety is fully human, semi-synthetic with human antibody framework regions, or humanized.

In some embodiments, the antigen-binding module comprises a first antigen-binding domain comprising a $V_H$ antibody domain and a second antigen-binding domain comprising a $V_L$ antibody domain. In some embodiments, the $V_H$ antibody domain and $V_L$ antibody domain CDRs are derived from the same antibody moiety. In some embodiments, some of the $V_H$ antibody domain and $V_L$ antibody domain CDRs are derived from different antibody moieties. In some embodiments, the $V_H$ antibody domain and/or $V_L$ antibody domain are human, humanized, chimeric, semi-synthetic, or fully synthetic.

In some embodiments, the antigen-binding module is an antibody moiety that is semi-synthetic, comprising fully human sequences and one or more synthetic regions. In some embodiments, the antigen-binding module is a semi-synthetic antibody moiety, comprising a fully human $V_L$ and a semi-synthetic $V_H$ comprising fully human FR1, HC-CDR1, FR2, HC-CDR2, FR3, and FR4 regions and a synthetic HC-CDR3. In some embodiments, the semi-synthetic $V_H$ comprises a fully synthetic HC-CDR3 having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length. In some embodiments, the semi-synthetic $V_H$ or the synthetic HC-CDR3 is obtained from a semi-synthetic library (such as a semi-synthetic human library) comprising fully synthetic HC-CDR3 regions having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length, wherein each amino acid in the sequence is, independently from one another, randomly selected from the standard human amino acids, minus cysteine. In some embodiments, the synthetic HC-CDR3 is from about 10 to about 19 (such as about any of 10, 11, 12, 13, 14, 15, 16, 17, 18 or 19) amino acids in length. In some embodiments, the antigen-binding module is a semi-synthetic antibody moiety, comprising a semi-synthetic $V_L$ and a semi-synthetic $V_H$. In some embodiments, the antigen-binding module is a fully-synthetic antibody moiety, comprising fixed human $V_H/V_L$ framework pairings, but randomized and synthetic sequences for all 6 CDRs of both heavy and light chains.

The antigen-binding module in some embodiments is an antibody moiety comprising specific CDR sequences derived from one or more antibody moieties (such as a monoclonal antibody) or certain variants of such sequences comprising one or more amino acid substitutions. In some embodiments, the amino acid substitutions in the variant sequences do not substantially reduce the ability of the antigen-binding module to bind the target antigen. Alterations that substantially improve target antigen binding affinity or affect some other property, such as specificity and/or cross-reactivity with related variants of the target antigen, are also contemplated.

In some embodiments, the stabilization module is derived from an antibody moiety. For example, in some embodiments, the stabilization module comprises a first stabilization domain comprising a $C_H1$ antibody domain or variant thereof and a second stabilization domain comprising a $C_L$ antibody domain or variant thereof. In another embodiment, the stabilization module comprises a first stabilization domain comprising a $C_H3$ antibody domain or variant thereof and a second stabilization domain comprising a $C_H3$ antibody domain or a variant thereof. In some embodiments, antibody heavy chain constant domains (e.g., $C_H1$ or $C_H3$) contained in the stabilization module are derived from an IgG (e.g., IgG1, IgG2, IgG3, or IgG4), IgA (e.g., IgA1 or IgA2), IgD, IgM, or IgE heavy chain, optionally human. In some embodiments, an antibody heavy chain constant domain (e.g., $C_H1$ or $C_H3$) contained in the stabilization module is a variant comprising one or more modifications (e.g., amino acid substitutions, insertions, and/or deletions) compared to the sequence from which it is derived. In some embodiments, antibody light chain constant domains ($C_L$) contained in the stabilization module are derived from a kappa or lambda light chain, optionally human. In some embodiments, an antibody light chain constant domain ($C_L$) contained in the stabilization module is a variant comprising one or more modifications (e.g., amino acid substitutions, insertions, and/or deletions) compared to the sequence from which it is derived. In some embodiments, the first and/or second stabilization domains comprise one or more modifications that do not substantially alter their binding affinity for each other. In some embodiments, the first and/or second stabilization domains comprise one or more modifications that increase their binding affinity for each other and/or introduce a non-naturally occurring disulfide bond. In some embodiments, the stabilization module comprises a knob-into-hole modification (see, for example, Carter P. *J Immunol Methods.* 248:7-15, 2001). For example, in some embodiments, the stabilization module comprises antibody constant domain regions (e.g., $C_H3$ domains) comprising a knob-into-hole modification. In some embodiments, the stabilization module comprises antibody constant domain regions (e.g., $C_H3$ domains) modified by electrostatic steering to enhance their association (see, for example, WO2006106905 and Gunasekaran K, et al. *J Biol Chem.* 285:19637-46, 2010). In some embodiments, the first and second stabilization domains are linked by a disulfide bond.

In some embodiments, the caTCR comprises an antigen-binding module described herein linked to a TCRM described herein, optionally including a stabilization module. For example, in the some embodiments, the caTCR comprises the antigen-binding module linked to the N-terminus of one or both of the TCRDs. In some embodiments, the caTCR comprises a stabilization module between a TCRM and an antigen-binding module. In some embodiments, the caTCR further comprises a spacer module between any two caTCR modules or domains. In some embodiments, the spacer module comprises one or more peptide linkers between about 5 to about 70 (such as about any of 5, 10, 15, 20, 25, 30, 35, 40, 45, 50, 55, 60, 65, or 70, including any ranges between these values) amino acids in length. In some embodiments, the caTCR further comprises one or more accessory intracellular domains. In some embodiments, the one or more accessory intracellular domains are carboxy-terminal to the first and/or second TCRD. In some embodiments, the one or more accessory intracellular domains are between the first TCR-TM and the first TCR intracellular domain and/or between the second TCR-TM and the second TCR intracellular domain. In some embodiments, the one or more accessory intracellular domains comprise, individually, a TCR co-stimulatory domain. In some embodiments, the TCR co-stimulatory domain comprises all or a portion of the intracellular domain of an immune co-stimulatory molecule (such as CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like). In some embodiments, the TCR co-stimulatory domain comprises all or a portion of the amino acid sequence of any one of SEQ ID NOs: 51-56, or a variant thereof.

In some embodiments, the antigen-binding module specifically binds a cell surface antigen. In some embodiments, the cell surface antigen is selected from the group consisting of a protein, a carbohydrate, and a lipid. In some embodiments, the cell surface antigen is a disease-associated antigen expressed in a diseased cell. In some embodiments, the antigen-binding module specifically binds a complex comprising a peptide and an MHC protein. Peptide/MHC complexes include, for example, a surface-presented complex comprising a peptide derived from a disease-associated antigen expressed in a diseased cell and an MHC protein. In some embodiments, the full-length disease-associated antigen is not normally expressed on the surface of the diseased cell (e.g., the disease-associated antigen is an intracellular or secreted protein). In some embodiments, the disease is cancer and the disease-associated antigen is a tumor-associated antigen expressed in a cancer cell. In some embodiments, the tumor-associated antigen is an oncoprotein. In some embodiments, the oncoprotein is the result of a mutation in a proto-oncogene, and the oncoprotein comprises a neoepitope comprising the mutation. For example, in some embodiments, the antigen-binding module specifically binds a cell surface tumor-associated antigen (e.g., an oncoprotein comprising a neoepitope). In some embodiments, the antigen-binding module specifically binds a complex comprising a peptide derived from a tumor-associated antigen (e.g., an oncoprotein comprising a neoepitope) not normally expressed on the surface of a cancer cell (e.g., an intracellular or secreted tumor-associated antigen) and an MHC protein. In some embodiments, the disease is viral infection and the disease-associated antigen is a virus-associated antigen expressed in an infected cell. For example, in some embodiments, the antigen-binding module specifically binds a cell surface virus-associated antigen. In some embodiments, the antigen-binding module specifically binds a complex comprising a peptide derived from a virus-associated antigen not normally expressed on the surface of a virus-infected cell (e.g., an intracellular or secreted virus-associated antigen) and an MHC protein. In some embodiments, the caTCR construct binds the target antigen with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values).

In some embodiments, the caTCR comprises an antigen-binding module that specifically binds to a cell surface antigen, wherein the cell surface antigen is CD19, CD20, CD22, CD47, GPC-3, ROR1, ROR2, BCMA, GPRC5D, or FCRL5, including variants or mutants thereof. Specific binding to a full antigen, e.g., a cell surface antigen, is sometimes referred to as "non-MHC-restricted binding".

In some embodiments, the caTCR comprises an antigen-binding module that specifically binds to a complex comprising a peptide and an MHC protein, wherein the peptide is derived from a protein selected from the group consisting of WT-1, AFP, HPV16-E7, NY-ESO-1, PRAME, EBV-LMP2A, HIV-1, KRAS, Histone H3.3, and PSA, including variants or mutants thereof. Specific binding to a complex comprising a peptide and an MHC protein is sometimes referred to as "MHC-restricted binding".

In some embodiments, the caTCR comprises an antigen-binding module that specifically binds to a complex comprising a peptide derived from a disease-associated antigen (such as a tumor-associated or virally-encoded antigen) and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01.

In some embodiments, the caTCR comprises an antigen-binding module that specifically binds to a complex comprising a peptide derived from a disease-associated antigen (such as a tumor-associated or virally-encoded antigen) and an MHC class II protein, wherein the MHC class II protein is HLA-DP, HLA-DQ, or HLA-DR. In some embodiments, the MHC class II protein is HLA-DP. In some embodiments, the MHC class II protein is HLA-DQ. In some embodiments, the MHC class II protein is HLA-DR.

In some embodiments, the caTCR described herein comprises a) an antigen-binding module that specifically binds to a target antigen, and b) a TCRM comprising first and second TCR-TMs derived from the transmembrane domains of a TCR (such as an αβTCR or a γδTCR), wherein the TCRM is capable of recruiting at least one TCR-associated signaling molecule. In some embodiments, the antigen-binding module is linked to the amino-terminus of one or more polypeptide chains in the TCRM. For example, in some embodiments, the TCRM comprises two polypeptide chains, and the antigen-binding module is linked to the amino-terminus of one or both of the TCRM polypeptide chains. In some embodiments, the first and second TCR-TMs are naturally occurring. In some embodiments, at least one of the TCR-TMs is non-naturally occurring. In some embodiments, the first and second TCR-TMs are non-naturally occurring. In some embodiments, the TCRM further comprises at least one connecting peptide or fragment thereof of the TCR amino-terminal to a TCR-TM. In some embodiments, the TCRM further comprises at least one TCR intracellular domain comprising a sequence from an intracellular domain of the TCR carboxy-terminal to a TCR-TM. In some embodiments, the TCRM comprises TCRDs derived from fragments of the TCR chains. In some embodiments, at least one of the TCRDs is non-naturally occurring. In some embodiments, the caTCR further comprises at least one accessory intracellular domain comprising a T cell co-stimulatory signaling sequence (such as from CD27, CD28, 4-1BB (CD137), OX40, CD30, or CD40) carboxy-terminal to a TCR-TM. In some embodiments, the caTCR lacks a co-stimulatory signaling sequence. In some embodiments, the antigen-binding module is an antibody moiety. In some embodiments, the antibody moiety comprises a $V_H$ antibody domain and a $V_L$ antibody domain. In some embodiments, the antibody moiety is human, humanized, chimeric, semi-synthetic, or fully synthetic. In some embodiments, the caTCR further comprises a stabilization module comprising a first stabilization domain and a second stabilization domain, wherein the first and second stabilization domains have a binding affinity for each other that stabilizes the caTCR. In some embodiments, the stabilization module comprises at least one disulfide bond linking the stabilization domains. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the T cell receptor transmembrane domains. In some embodiments, the TCRM promotes caTCR-CD3 complex formation. In some embodiments, there is a spacer module between any two caTCR modules or domains. In some embodiments, the caTCR is a heteromultimer, such as a heterodimer. For example, in some embodiments, the caTCR is a heterodimer comprising a first polypeptide chain comprising the first TCRD and a second polypeptide chain comprising the second TCRD, wherein the antigen-binding module is linked to the first and/or second polypeptide chains. In some embodiments, the antigen-binding module is multispecific (such as bispecific).

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the TCR is an αβ TCR and the first and second TCR-TMs are derived from TCR α and β subunit transmembrane domains. In some embodiments, the TCR is a γδ TCR and the first and second TCR-TMs are derived from TCR γ and δ subunit transmembrane domains. In some embodiments, the first TCRD further comprises a first TCR connecting peptide or a fragment thereof and/or the second TCRD further comprises a second TCR connecting peptide or a fragment thereof. In some embodiments, the first connecting peptide comprises all or a portion of the connecting peptide of the TCR subunit from which the first TCR-TM is derived, or a variant thereof, and/or the second connecting peptide comprises all or a portion of the connecting peptide of the TCR subunit from which the second TCR-TM is derived, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR subunit from which the first TCR-TM is derived and/or the second TCR intracellular domain comprises a sequence from the intracellular domain of the TCR subunit from which the second TCR-TM is derived. In some embodiments, the first TCRD is a fragment of the TCR subunit from which the first TCR-TM is derived and/or the second TCRD is a fragment of the TCR subunit from which the second TCR-TM is derived. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the T cell receptor transmembrane domains. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the transmembrane domains of a naturally occurring a TCR and a second TCRD comprising a second TCR-TM derived from the other transmembrane domain of the naturally occurring a TCR, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the first TCRD further comprises a first TCR connecting peptide or a fragment thereof and/or the second TCRD further comprises a second TCR connecting peptide or a fragment thereof. In some embodiments, the first connecting peptide comprises all or a portion of the connecting peptide of the TCR subunit from which the first TCR-TM is derived, or a variant thereof, and/or the second connecting peptide comprises all or a portion of the connecting peptide of the TCR subunit from which the second TCR-TM is derived, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR subunit from which the first TCR-TM is derived and/or the second TCR intracellular domain comprises a sequence from the intracellular domain of the TCR subunit from which the second TCR-TM is derived. In some embodiments, the first TCRD is a fragment of the TCR subunit from which the first TCR-TM is derived and/or the second TCRD is a fragment of the TCR subunit from which the second TCR-TM is derived. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the naturally occurring a T cell receptor transmembrane domains. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the transmembrane domains of a naturally occurring γδ TCR and a second TCRD comprising a second TCR-TM derived from the other transmembrane domain of the naturally occurring γδ TCR, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the first TCRD further comprises a first TCR connecting peptide or a fragment thereof and/or the second TCRD further comprises a second TCR connecting peptide or a fragment thereof. In some embodiments, the first connecting peptide comprises all or a portion of the connecting peptide of the TCR subunit from which the first TCR-TM is derived, or a variant thereof, and/or the second connecting peptide comprises all or a portion of the connecting peptide of the TCR subunit from which the second TCR-TM is derived, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR subunit from which the first TCR-TM is derived and/or the second TCR intracellular domain comprises a sequence from the intracellular domain of the TCR subunit from which the second TCR-TM is derived. In some embodiments, the first TCRD is a fragment of the TCR subunit from which the first TCR-TM is derived and/or the second TCRD is a fragment of the TCR subunit from which the second TCR-TM is derived. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the naturally occurring γδ T cell receptor transmembrane domains. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from a transmembrane domain contained in one of the amino acid sequences of SEQ ID NO: 1 and SEQ ID NO: 2 and a second TCRD comprising a second TCR-TM derived from a transmembrane domain contained in the other amino acid sequence, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of a connecting peptide contained in any one of the amino acid sequences of SEQ ID NOs: 1-4, or a variant thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of an intracellular domain contained in any one of SEQ ID NOs: 1-4, or a variant thereof. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of the transmembrane domains contained in SEQ ID NOs: 1 and 2. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from a transmembrane domain contained in one of the amino acid sequences of SEQ ID NO: 1 and SEQ ID NO: 2 and a second TCRD comprising a second TCR-TM derived from a transmembrane domain contained in the other amino acid sequence, wherein at least one of the TCR-TMs comprises one or more (such as 2, 3, 4, 5, or more) amino acid substitutions compared to the amino acid sequence from which it is derived, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, one or more (such as 2, 3, 4, 5, or more) amino acid substitutions compared to the amino acid sequence from which it is derived. In some embodiments, the first TCR-TM and/or the second TCR-TM each comprise, independently from one another, no more than 5 amino acid substitutions compared to the amino acid sequences from which they are derived. In some embodiments, at least one of the TCR-TMs comprises a single amino acid substitution compared to the amino acid sequence from which it is derived. In some embodiments, each of the TCR-TMs comprises a single amino acid substitution compared to the amino acid sequence from which it is derived. In some embodiments, at least one of the substituted amino acids in the first TCR-TM is positioned such that in the caTCR it can interact with at least one of the substituted amino acids in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of a connecting peptide contained in any one of the amino acid sequences of SEQ ID NOs: 1-4, or a variant thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of an intracellular domain contained in any one of SEQ ID NOs: 1-4, or a variant thereof. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of the transmembrane domains contained in SEQ ID NOs: 1 and 2. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from a transmembrane domain contained in one of the amino acid sequences of SEQ ID NO: 1 and SEQ ID NO: 2 and a second TCRD comprising a second TCR-TM derived from a transmembrane domain contained in the other amino acid sequence, wherein at least one of the TCR-TMs comprises a chimeric sequence comprising a portion of consecutive amino acids from a transmembrane domain contained in SEQ ID NO: 3 or 4, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, a chimeric sequence comprising a portion of consecutive amino acids from a transmembrane domain contained in SEQ ID NO: 3 or 4. In some embodiments, the first TCR-TM and/or the second TCR-TM each comprise, independently from one another, a chimeric sequence comprising a portion of no more than about 10 (such as no more than about 9, 8, 7, 6, 5, or fewer) consecutive amino acids from a transmembrane domain contained in SEQ ID NO: 3 or 4. In some embodiments, the chimeric sequence in the first or second TCR-TM is from a transmembrane domain contained in SEQ ID NO: 3 and the chimeric sequence in the other TCR-TM is from a transmembrane domain contained in SEQ ID NO: 4. In some embodiments, the chimeric sequence in the first TCR-TM is positioned such that it can interact with the chimeric sequence in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of a connecting peptide contained in any one of the amino acid sequences of SEQ ID NOs: 1-4, or a variant thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of an intracellular domain contained in any one of SEQ ID NOs: 1-4, or a variant thereof. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of the transmembrane domains contained in SEQ ID NOs: 1 and 2. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from a transmembrane domain contained in one of the amino acid sequences of SEQ ID NO: 3 and SEQ ID NO: 4 and a second TCRD comprising a second TCR-TM derived from a transmembrane domain contained in the other amino acid sequence, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of a connecting peptide contained in any one of the amino acid sequences of SEQ ID NOs: 1-4, or a variant thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of an intracellular domain contained in any one of SEQ ID NOs: 1-4, or a variant thereof. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δ, CD3γε, and ζζ. In some embodiments, the TCRM allows for enhanced recruitment of the at least one TCR-associated signaling molecule as compared to a TCRM comprising T cell receptor transmembrane domains having the sequences of the transmembrane domains contained in SEQ ID NOs: 3 and 4. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from a transmembrane domain contained in one of the amino acid sequences of SEQ ID NO: 3 and SEQ ID NO: 4 and a second TCRD comprising a second TCR-TM derived from a transmembrane domain contained in the other amino acid sequence, wherein at least one of the TCR-TMs comprises one or more (such as 2, 3, 4, 5, or more) amino acid substitutions compared to the amino acid sequence from which it is derived, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, one or more (such as 2, 3, 4, 5, or more) amino acid substitutions compared to the amino acid sequence from which it is derived. In some embodiments, the first TCR-TM and/or the second TCR-TM each comprise, independently from one another, no more than 5 amino acid substitutions compared to the amino acid sequences from which they are derived. In some embodiments, at least one of the TCR-TMs comprises a single amino acid substitution compared to the amino acid sequence from which it is derived. In some embodiments, each of the TCR-TMs comprises a single amino acid substitution compared to the amino acid sequence from which it is derived. In some embodiments, at least one of the substituted amino acids in the first TCR-TM is positioned such that in the caTCR it can interact with at least one of the substituted amino acids in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of a connecting peptide contained in any one of the amino acid sequences of SEQ ID NOs: 1-4, or a variant thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of an intracellular domain contained in any one of SEQ ID NOs: 1-4, or a variant thereof. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of the transmembrane domains contained in SEQ ID NOs: 3 and 4. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from a transmembrane domain contained in one of the amino acid sequences of SEQ ID NO: 3 and SEQ ID NO: 4 and a second TCRD comprising a second TCR-TM derived from a transmembrane domain contained in the other amino acid sequence, wherein at least one of the TCR-TMs comprises a chimeric sequence comprising a portion of consecutive amino acids from a transmembrane domain contained in SEQ ID NO: 1 or 2, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, a chimeric sequence comprising a portion of consecutive amino acids from a transmembrane domain contained in SEQ ID NO: 1 or 2. In some embodiments, the first TCR-TM and/or the second TCR-TM each comprise, independently from one another, a chimeric sequence comprising a portion of no more than about 10 (such as no more than about 9, 8, 7, 6, 5, or fewer) consecutive amino acids from a transmembrane domain contained in SEQ ID NO: 1 or 2. In some embodiments, the chimeric sequence in the first or second TCR-TM is from a transmembrane domain contained in SEQ ID NO: 1 and the chimeric sequence in the other TCR-TM is from a transmembrane domain contained in SEQ ID NO: 2. In some embodiments, the chimeric sequence in the first TCR-TM is positioned such that it can interact with the chimeric sequence in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of a connecting peptide contained in any one of the amino acid sequences of SEQ ID NOs: 1-4, or a variant thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of an intracellular domain contained in any one of SEQ ID NOs: 1-4, or a variant thereof. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of the transmembrane domains contained in SEQ ID NOs: 3 and 4. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the amino acid sequences of SEQ ID NO: 5 and SEQ ID NO: 6 and a second TCRD comprising a second TCR-TM derived from the other amino acid sequence, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 5 and 6. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the amino acid sequences of SEQ ID NO: 5 and SEQ ID NO: 6 and a second TCRD comprising a second TCR-TM derived from the other amino acid sequence, wherein at least one of the TCR-TMs comprises one or more (such as 2, 3, 4, 5, or more) amino acid substitutions compared to the amino acid sequence from which it is derived, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, one or more (such as 2, 3, 4, 5, or more) amino acid substitutions compared to the amino acid sequence from which it is derived. In some embodiments, the first TCR-TM and/or the second TCR-TM each comprise, independently from one another, no more than 5 amino acid substitutions compared to the amino acid sequences from which they are derived. In some embodiments, at least one of the TCR-TMs comprises a single amino acid substitution compared to the amino acid sequence from which it is derived. In some embodiments, each of the TCR-TMs comprises a single amino acid substitution compared to the amino acid sequence from which it is derived. In some embodiments, at least one of the substituted amino acids in the first TCR-TM is positioned such that in the caTCR it can interact with at least one of the substituted amino acids in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δ, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 5 and 6. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the amino acid sequences of SEQ ID NO: 5 and SEQ ID NO: 6 and a second TCRD comprising a second TCR-TM derived from the other amino acid sequence, wherein at least one of the TCR-TMs comprises a chimeric sequence comprising a portion of consecutive amino acids from SEQ ID NO: 7 or 8, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, a chimeric sequence comprising a portion of consecutive amino acids from SEQ ID NO: 7 or 8. In some embodiments, the first TCR-TM and/or the second TCR-TM each comprise, independently from one another, a chimeric sequence comprising a portion of no more than about 10 (such as no more than about 9, 8, 7, 6, 5, or fewer) consecutive amino acids from SEQ ID NO: 7 or 8. In some embodiments, the chimeric sequence in the first or second TCR-TM is from SEQ ID NO: 7 and the chimeric sequence in the other TCR-TM is from SEQ ID NO: 8. In some embodiments, the chimeric sequence in the first TCR-TM is positioned such that it can interact with the chimeric sequence in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 5 and 6. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the amino acid sequences of SEQ ID NO: 7 and SEQ ID NO: 8 and a second TCRD comprising a second TCR-TM derived from the other amino acid sequence, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, both of the TCR-TMs are naturally occurring. In some embodiments, at least one of the TCR-TMs is non-naturally occurring. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the amino acid sequences of SEQ ID NO: 7 and SEQ ID NO: 8 and a second TCRD comprising a second TCR-TM derived from the other amino acid sequence, wherein at least one of the TCR-TMs comprises one or more (such as 2, 3, 4, 5, or more) amino acid substitutions compared to the amino acid sequence from which it is derived, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, one or more (such as 2, 3, 4, 5, or more) amino acid substitutions compared to the amino acid sequence from which it is derived. In some embodiments, the first TCR-TM and/or the second TCR-TM each comprise, independently from one another, no more than 5 amino acid substitutions compared to the amino acid sequences from which they are derived. In some embodiments, at least one of the TCR-TMs comprises a single amino acid substitution compared to the amino acid sequence from which it is derived. In some embodiments, each of the TCR-TMs comprises a single amino acid substitution compared to the amino acid sequence from which it is derived. In some embodiments, at least one of the substituted amino acids in the first TCR-TM is positioned such that in the caTCR it can interact with at least one of the substituted amino acids in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δ, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

In some embodiments, the caTCR described herein specifically binds a target antigen, comprising a) a first TCRD comprising a first TCR-TM derived from one of the amino acid sequences of SEQ ID NO: 7 and SEQ ID NO: 8 and a second TCRD comprising a second TCR-TM derived from the other amino acid sequence, wherein at least one of the TCR-TMs comprises a chimeric sequence comprising a portion of consecutive amino acids from SEQ ID NO: 5 or 6, and the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, each of the TCR-TMs comprises, independently from one another, a chimeric sequence comprising a portion of consecutive amino acids from SEQ ID NO: 5 or 6. In some embodiments, the first TCR-TM and/or the second TCR-TM each comprise, independently from one another, a chimeric sequence comprising a portion of no more than about 10 (such as no more than about 9, 8, 7, 6, 5, or fewer) consecutive amino acids from SEQ ID NO: 5 or 6. In some embodiments, the chimeric sequence in the first or second TCR-TM is from SEQ ID NO: 5 and the chimeric sequence in the other TCR-TM is from SEQ ID NO: 6. In some embodiments, the chimeric sequence in the first TCR-TM is positioned such that it can interact with the chimeric sequence in the second TCR-TM. In some embodiments, the first TCRD further comprises a first TCR connecting peptide or a fragment thereof and/or the second TCRD further comprises a second TCR connecting peptide or a fragment thereof. In some embodiments, the first connecting peptide and the second connecting peptide each comprise, independently from one another, the amino acid sequence of any one of SEQ ID NOs: 27-34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain and the second TCR intracellular domain each comprise, independently from one another, the amino acid sequence of SEQ ID NO: 35 or 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (such as bispecific).

The different aspects are discussed in various sections below in further detail.

TCR-TM Variants

In some embodiments, the TCR-TMs of a caTCR are derived from a T cell receptor, wherein at least one of the TCR-TMs is non-naturally occurring. Non-naturally occurring TCR-TMs derived from a T cell receptor include a transmembrane domain from a T cell receptor that has been modified by substitution of one or more amino acids. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal (either in primary sequence or spatially) to an amino acid in the TCRM involved in binding CD3. For example, in some embodiments, at least one of the substituted amino acids is separated from an amino acid in the TCRM involved in binding CD3 by no more than 3 (such as 0, 1, 2, or 3) amino acids. In some embodiments, at least one of the substituted amino acids is separated from an amino acid in the TCRM involved in binding CD3 by no more than about 15 (such as no more than about any of 14, 12, 10, 8, 6, 4, 2, or 1) angstroms. In some embodiments, each of the substituted amino acids is proximal to an amino acid in the TCRM involved in binding CD3.

For example, in some embodiments, a non-naturally occurring TCR-TM derived from a T cell receptor comprises, consists essentially of, or consists of the transmembrane domain of an α, β, γ, or δ TCR subunit modified by substitution of one or more amino acid residues. In some embodiments, the transmembrane domain of the TCR subunit is modified by substitution of no more than 5 amino acid residues. In some embodiments, the transmembrane domain of the TCR subunit is modified by substitution of a single amino acid residue. In some embodiments, at least one of the substituted amino acids is substituted with a residue more hydrophobic than the corresponding unsubstituted residue.

In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

Thus, in some embodiments, a non-naturally occurring TCR-TM derived from a T cell receptor described herein comprises, consists essentially of, or consists of the transmembrane domain of an α TCR subunit comprising the amino acid sequence of a transmembrane domain contained in SEQ ID NO: 1 (e.g., SEQ ID NO: 5), modified by substitution of one or more amino acid residues. In some embodiments, the transmembrane domain of the α TCR subunit is modified by substitution of no more than 5 amino acid residues in the transmembrane domain contained in SEQ ID NO: 1. In some embodiments, the transmembrane domain of the α TCR subunit is modified by substitution of a single amino acid residue in the transmembrane domain contained in SEQ ID NO: 1. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, a non-naturally occurring TCR-TM derived from a T cell receptor described herein comprises, consists essentially of, or consists of the transmembrane domain of an α TCR subunit comprising the amino acid sequence of SEQ ID NO: 5, modified by substitution of one or more amino acid residues. In some embodiments, the transmembrane domain of the α TCR subunit is modified by substitution of no more than 5 amino acid residues in SEQ ID NO: 5. In some embodiments, the transmembrane domain of the α TCR subunit is modified by substitution of a single amino acid residue in SEQ ID NO: 5. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, a non-naturally occurring TCR-TM derived from a T cell receptor described herein comprises, consists essentially of, or consists of the transmembrane domain of a β TCR subunit comprising the amino acid sequence of a transmembrane domain contained in SEQ ID NO: 2 (e.g., SEQ ID NO: 6), modified by substitution of one or more amino acid residues. In some embodiments, the transmembrane domain of the β TCR subunit is modified by substitution of no more than 5 amino acid residues in the transmembrane domain contained in SEQ ID NO: 2. In some embodiments, the transmembrane domain of the β TCR subunit is modified by substitution of a single amino acid residue in the transmembrane domain contained in SEQ ID NO: 2. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, a non-naturally occurring TCR-TM derived from a T cell receptor described herein comprises, consists essentially of, or consists of the transmembrane domain of a TCR subunit comprising the amino acid sequence of SEQ ID NO: 6, modified by substitution of one or more amino acid residues. In some embodiments, the transmembrane domain of the β TCR subunit is modified by substitution of no more than 5 amino acid residues in SEQ ID NO: 6. In some embodiments, the transmembrane domain of the β TCR subunit is modified by substitution of a single amino acid residue in SEQ ID NO: 6. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, a non-naturally occurring TCR-TM derived from a T cell receptor described herein comprises, consists essentially of, or consists of the transmembrane domain of a δ TCR subunit comprising the amino acid sequence of a transmembrane domain contained in SEQ ID NO: 3 (e.g., SEQ ID NO: 7), modified by substitution of one or more amino acid residues. In some embodiments, the transmembrane domain of the δ TCR subunit is modified by substitution of no more than 5 amino acid residues in the transmembrane domain contained in SEQ ID NO: 3. In some embodiments, the transmembrane domain of the δ TCR subunit is modified by substitution of a single amino acid residue in the transmembrane domain contained in SEQ ID NO: 3. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, the non-naturally occurring TCR-TM comprises the amino acid sequence of the transmembrane domain contained in SEQ ID NO: 3 (e.g., SEQ ID NO: 7), modified by one or more substitutions (such as substitutions with more hydrophobic residues) in amino acids corresponding to the following amino acids in SEQ ID NO: 7: L4, M6, V12, N15, F245, and L25. In some embodiments, the non-naturally occurring TCR-TM comprises the amino acid sequence of the transmembrane domain contained in SEQ ID NO: 3 modified by substitutions (such as substitutions with more hydrophobic residues) in amino acids corresponding to V12 and N15 in SEQ ID NO: 7. In some embodiments, the non-naturally occurring TCR-TM comprises the amino acid sequence of the transmembrane domain contained in SEQ ID NO: 3 modified by one or more substitutions corresponding to the following substitutions in SEQ ID NO: 7: L4C, M6V, V12F, N15S, F245S, and L25S. In some embodiments, the non-naturally occurring TCR-TM comprises the amino acid sequence of the transmembrane domain contained in SEQ ID NO: 3 modified by substitutions corresponding to V12F and N15S substitutions in SEQ ID NO: 7. In some embodiments, the non-naturally occurring TCR-TM comprises the amino acid sequence of any one of SEQ ID NOs: 9-13.

In some embodiments, a non-naturally occurring TCR-TM derived from a T cell receptor described herein comprises, consists essentially of, or consists of the transmembrane domain of a δ TCR subunit comprising the amino acid sequence of SEQ ID NO: 7, modified by substitution of one or more amino acid residues. In some embodiments, the transmembrane domain of the δ TCR subunit is modified by substitution of no more than 5 amino acid residues in SEQ ID NO: 7. In some embodiments, the transmembrane domain of the δ TCR subunit is modified by substitution of a single amino acid residue in SEQ ID NO: 7. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, the non-naturally occurring TCR-TM comprises the amino acid sequence of SEQ ID NO: 7 modified by one or more substitutions (such as substitutions with more hydrophobic residues) in amino acids corresponding to the following amino acids in SEQ ID NO: 7: L4, M6, V12, N15, F245, and L25. In some embodiments, the non-naturally occurring TCR-TM comprises the amino acid sequence of SEQ ID NO: 7 modified by substitutions (such as substitutions with more hydrophobic residues) in amino acids corresponding to V12 and N15 in SEQ ID NO: 7. In some embodiments, the non-naturally occurring TCR-TM comprises the amino acid sequence of SEQ ID NO: 7 modified by one or more substitutions corresponding to the following substitutions in SEQ ID NO: 7: L4C, M6V, V12F, N15S, F245S, and L25S. In some embodiments, the non-naturally occurring TCR-TM comprises the amino acid sequence of SEQ ID NO: 7 modified by substitutions corresponding to V12F and N15S substitutions in SEQ ID NO: 7. In some embodiments, the non-naturally occurring TCR-TM comprises the amino acid sequence of any one of SEQ ID NOs: 9-13.

In some embodiments, a non-naturally occurring TCR-TM derived from a T cell receptor described herein comprises, consists essentially of, or consists of the transmembrane domain of a γ TCR subunit comprising the amino acid sequence of a transmembrane domain contained in SEQ ID NO: 4 (e.g., SEQ ID NO: 8), modified by substitution of one or more amino acid residues. In some embodiments, the transmembrane domain of the γ TCR subunit is modified by substitution of no more than 5 amino acid residues in the transmembrane domain contained in SEQ ID NO: 4. In some embodiments, the transmembrane domain of the γ TCR subunit is modified by substitution of a single amino acid residue in the transmembrane domain contained in SEQ ID NO: 4. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, the non-naturally occurring TCR-TM comprises the amino acid sequence of the transmembrane domain contained in SEQ ID NO: 4 (e.g., SEQ ID NO: 8), modified by one or more substitutions (such as substitutions with more hydrophobic residues) in amino acids corresponding to the following amino acids in SEQ ID NO: 8: Y1, Y2, M3, L5, L8, V12, V13, F15, A16, I18, C19, C20, and C21. In some embodiments, the non-naturally occurring TCR-TM comprises the amino acid sequence of the transmembrane domain contained in SEQ ID NO: 4 modified by substitutions (such as substitutions with more hydrophobic residues) in amino acids corresponding to Y2, M3, A16, and I18 in SEQ ID NO: 8. In some embodiments, the non-naturally occurring TCR-TM comprises the amino acid sequence of the transmembrane domain contained in SEQ ID NO: 4 modified by substitutions (such as substitutions with more hydrophobic residues) in amino acids corresponding to L8, V12, and F15 in SEQ ID NO: 8. In some embodiments, the non-naturally occurring TCR-TM comprises the amino acid sequence of the transmembrane domain contained in SEQ ID NO: 4 modified by one or more substitutions corresponding to the following substitutions in SEQ ID NO: 8: Y1Q, Y2L, Y2I, M3V, M3I, L5C, L8F, V12F, V13Y, F15S, A16V, A16, I18V, I18L, C19M, C20M, and C21G. In some embodiments, the non-naturally occurring TCR-TM comprises the amino acid sequence of the transmembrane domain contained in SEQ ID NO: 4 modified by substitutions corresponding to Y2L, M3V, A16V, and I18V substitutions in SEQ ID NO: 8. In some embodiments, the non-naturally occurring TCR-TM comprises the amino acid sequence of the transmembrane domain contained in SEQ ID NO: 4 modified by substitutions corresponding to Y2I, M3I, A16I, and I18L substitutions in SEQ ID NO: 8. In some embodiments, the non-naturally occurring TCR-TM comprises the amino acid sequence of the transmembrane domain contained in SEQ ID NO: 4 modified by substitutions corresponding to L8F, V12F, and F15S substitutions in SEQ ID NO: 8. In some embodiments, the non-naturally occurring TCR-TM comprises the amino acid sequence of any one of SEQ ID NOs: 14-26.

In some embodiments, a non-naturally occurring TCR-TM derived from a T cell receptor described herein comprises, consists essentially of, or consists of the transmembrane domain of a γ TCR subunit comprising the amino acid sequence of SEQ ID NO: 8, modified by substitution of one or more amino acid residues. In some embodiments, the transmembrane domain of the γ TCR subunit is modified by substitution of no more than 5 amino acid residues in SEQ ID NO: 8. In some embodiments, the transmembrane domain of the γ TCR subunit is modified by substitution of a single amino acid residue in SEQ ID NO: 8. In some embodiments, at least one of the substituted amino acids is substituted with a residue more hydrophobic than the corresponding unsubstituted residue. In some embodiments, each of the substituted amino acids is substituted with a residue more hydrophobic than the corresponding unsubstituted residue. In some embodiments, at least one of the substituted amino acids is proximal to an amino acid in the TCRM involved in binding CD3. In some embodiments, each of the substituted amino acids is proximal to an amino acid in the TCRM involved in binding CD3.

In some embodiments, the non-naturally occurring TCR-TM comprises the amino acid sequence of SEQ ID NO: 8 modified by one or more substitutions (such as substitutions with more hydrophobic residues) in amino acids corresponding to the following amino acids in SEQ ID NO: 8: Y1, Y2, M3, L5, L8, V12, V13, F15, A16, I18, C19, C20, and C21. In some embodiments, the non-naturally occurring TCR-TM comprises the amino acid sequence of SEQ ID NO: 8 modified by substitutions (such as substitutions with more hydrophobic residues) in amino acids corresponding to Y2, M3, A16, and I18 in SEQ ID NO: 8. In some embodiments, the non-naturally occurring TCR-TM comprises the amino acid sequence of SEQ ID NO: 8 modified by substitutions (such as substitutions with more hydrophobic residues) in amino acids corresponding to L8, V12, and F15 in SEQ ID NO: 8. In some embodiments, the non-naturally occurring TCR-TM comprises the amino acid sequence of SEQ ID NO: 8 modified by one or more substitutions corresponding to the following substitutions in SEQ ID NO: 8: Y1Q, Y2L, Y2I, M3V, M3I, L5C, L8F, V12F, V13Y, F15S, A16V, A16, I18V, I18L, C19M, C20M, and C21G. In some embodiments, the non-naturally occurring TCR-TM comprises the amino acid sequence of SEQ ID NO: 8 modified by substitutions corresponding to Y2L, M3V, A16V, and I18V substitutions in SEQ ID NO: 8. In some embodiments, the non-naturally occurring TCR-TM comprises the amino acid sequence of SEQ ID NO: 8 modified by substitutions corresponding to Y2I, M3I, A16, and I18L substitutions in SEQ ID NO: 8. In some embodiments, the non-naturally occurring TCR-TM comprises the amino acid sequence of SEQ ID NO: 8 modified by substitutions corresponding to L8F, V12F, and F15S substitutions in SEQ ID NO: 8. In some embodiments, the non-naturally occurring TCR-TM comprises the amino acid sequence of any one of SEQ ID NOs: 14-26.

In some embodiments, the caTCR described herein specifically binds a target antigen, comprising a) a first TCRD comprising a first TCR-TM comprising, consisting essentially of, or consisting of any one of the amino acid sequences of SEQ ID NOs: 7 and 9-13, and a second TCRD comprising a second TCR-TM comprising, consisting essentially of, or consisting of the amino acid sequence of any one of SEQ ID NOs: 8 and 14-26, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs. In some embodiments, at least one of the TCR-TMs is non-naturally occurring. In some embodiments, the first TCR-TM and second TCR-TM are selected according to any of the caTCRs listed in Table 2. In some embodiments, the first TCRD further comprises a first TCR connecting peptide or a fragment thereof and/or the second TCRD further comprises a second TCR connecting peptide or a fragment thereof. In some embodiments, the first connecting peptide comprises the amino acid sequence SEQ ID NO: 31 or 32, or a variant thereof, and/or the second connecting peptide comprises the amino acid sequence SEQ ID NO: 33 or 34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the second TCR intracellular domain comprises the amino acid sequence of SEQ ID NO: 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv).

TABLE 2

| caTCR ID | First TCR-TM (δ subunit) | Second TCR-TM (γ subunit) |
|---|---|---|
| TM0 | VLGLRMLFAKTVA VNFLLTAKLFFL (SEQ ID NO: 7) | YYMYLLLLLKSVVY FAIITCCLL (SEQ ID NO: 8) |
| TM1 | VLGLRMLFAKTVA VNFLLTAKLFSL (SEQ ID NO: 9) | YYMYLLLLLKSVVY FAIITCCLL (SEQ ID NO: 8) |
| TM2 | VLGLRMLFAKTVA VNFLLTAKLFFL (SEQ ID NO: 7) | YYMYLLLLLKSVVY FAIITCCLLRRTAF (SEQ ID NO: 14) |
| TM3 | VLGLRMLFAKTVA VNFLLTAKLFFL (SEQ ID NO: 7) | YYMYLLLLLKSVVY FAIITCGLLRRTAF (SEQ ID NO: 15) |
| TM4 | VLGLRMLFAKTVA VNFLLTAKLFFL (SEQ ID NO: 7) | YLVYLLLLLKSVVY FVIVTCCLLRRTAF (SEQ ID NO: 16) |
| TM5 | VLGLRVLFAKTVA VNFLLTAKLFFL (SEQ ID NO: 10) | YLVYLLLLLKSVVY FVIVTCCLLRRTAF (SEQ ID NO: 16) |
| TM6 | VLGLRMLFAKTVA VNFLLTAKLFFL (SEQ ID NO: 7) | YLMYLLLLLKSVVY FAIITCCLLRRTAF (SEQ ID NO: 17) |
| TM7 | VLGLRMLFAKTVA VNFLLTAKLFFL (SEQ ID NO: 7) | YYVYLLLLLKSVVY FAIITCCLLRRTAF (SEQ ID NO: 18) |
| TM8 | VLGLRMLFAKTVA VNFLLTAKLFFL (SEQ ID NO: 7) | YYMYLLLLLKSVVY FVIITCCLLRRTAF (SEQ ID NO: 19) |
| TM9 | VLGLRMLFAKTVA VNFLLTAKLFFL (SEQ ID NO: 7) | YYMYLLLLLKSVVY FAIVTCCLLRRTAF (SEQ ID NO: 20) |
| TM10 | VLGLRMLFAKTVA VNFLLTAKLFFL (SEQ ID NO: 7) | YYTYLLLLLKSVVY FAIITCCLLRRTAF (SEQ ID NO: 21) |

TABLE 2-continued

| caTCR ID | First TCR-TM (δ subunit) | Second TCR-TM (γ subunit) |
|---|---|---|
| TM11 | VLGLRMLFAKTVA VNFLLTAKLFFL (SEQ ID NO: 7) | YITYLLLLLKSVVY FIILTCCLLRRTAF (SEQ ID NO: 22) |
| TM12 | VLGCRMLFAKTVA VNFLLTAKLFFL (SEQ ID NO: 11) | YYMYCLLLLKSVVY FAIITCCLLRRTAF (SEQ ID NO: 23) |
| TM13 | VLGLRMLFAKTFA VSFLLTAKLFFL (SEQ ID NO: 12) | YYMYLLLFLKSFVY SAIITCCLLRRTAF (SEQ ID NO: 24) |
| TM14 | VLGLRMLFAKTVA VNFLLTAKLFFL (SEQ ID NO: 7) | YYMYLLLLLKSVVY FAIITMCLLRRTAF (SEQ ID NO: 25) |
| TM15 | VLGLRMLFAKTVA VNFLLTAKLFFS (SEQ ID NO: 13) | QYMYLLLLLKSVVY FAIITCCLLRRTAF (SEQ ID NO: 26) |

Antigen-Binding Modules

In some embodiments, according to any of the caTCRs described herein, the antigen-binding module is an antibody moiety. In some embodiments, the antibody moiety is selected from the group consisting of a Fab, a Fab', a (Fab')2, an Fv, and a single chain Fv (scFv). In some embodiments, where the antibody moiety is a multimer comprising a first antibody moiety chain and a second antibody moiety chain, the caTCR comprises the first TCRD linked to the first or second antibody moiety chain and the second TCRD linked to the other antibody moiety chain. In some embodiments, the antibody moiety specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the antibody moiety specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof.

In some embodiments, according to any of the caTCRs described herein, the antigen-binding module is an antibody moiety comprising $C_H1$ and $C_L$ domains. In some embodiments, the $C_H1$ domain is derived from an IgG (e.g, IgG1, IgG2, IgG3, or IgG4) heavy chain, optionally human. In some embodiments, the $C_H1$ domain is a variant comprising one or more modifications (e.g., amino acid substitutions, insertions, and/or deletions) compared to the sequence from which it is derived. In some embodiments, the $C_H1$ domain comprises the amino acid sequence of any one of SEQ ID NOs: 37-47, or a variant thereof. In some embodiments, the $C_H1$ domain comprises the amino acid sequence of SEQ ID NO: 37, or a variant thereof. In some embodiments, the $C_L$ domain is derived from a kappa or lambda light chain, optionally human. In some embodiments, the $C_L$ domain is a variant comprising one or more modifications (e.g., amino acid substitutions, insertions, and/or deletions) compared to the sequence from which it is derived. In some embodiments, the $C_L$ domain comprises the amino acid sequence of SEQ ID NO: 48, or a variant thereof. In some embodiments, the $C_H1$ and/or $C_L$ domains comprise one or more modifications that do not substantially alter their binding affinity for each other. In some embodiments, the $C_H1$ and/or $C_L$ domains comprise one or more modifications that increase their binding affinity for each other and/or introduce a non-naturally occurring disulfide bond.

In some embodiments, according to any of the caTCRs described herein comprising an antibody moiety that specifically binds to a target antigen, the antibody moiety comprises the CDRs or variables domains ($V_H$ and/or $V_L$ domains) of an antibody moiety specific for the target antigen. In some embodiments, the antibody moiety comprises the CDRs or variables domains ($V_H$ and/or $V_L$ domains) of an antibody moiety specific for CD19 (see, e.g., WO2017066136A2). In some embodiments, the antibody moiety comprises the CDRs or variables domains ($V_H$ and/or $V_L$ domains) of an antibody moiety specific for CD19 (e.g., $V_H$ domain comprising, consisting essentially of, or consisting of the amino acid sequence of SEQ ID NO: 58 and/or $V_L$ domain comprising, consisting essentially of, or consisting of the amino acid sequence of SEQ ID NO: 59, or CDRs contained therein). In some embodiments, the antibody moiety comprises the CDRs or variables domains ($V_H$ and/or $V_L$ domains) of an antibody moiety specific for CD20 (e.g., $V_H$ domain comprising, consisting essentially of, or consisting of the amino acid sequence of SEQ ID NO: 60 and/or $V_L$ domain comprising, consisting essentially of, or consisting of the amino acid sequence of SEQ ID NO: 61, or CDRs contained therein). In some embodiments, the antibody moiety comprises the CDRs or variables domains ($V_H$ and/or $V_L$ domains) of an antibody moiety specific for CD22 (see, e.g., U.S. Ser. No. 62/650,955 filed Mar. 30, 2018, the contents of which are incorporated herein by reference in their entirety). In some embodiments, the antibody moiety comprises the CDRs or variables domains ($V_H$ and/or $V_L$ domains) of an antibody moiety specific for CD22 (e.g., $V_H$ domain comprising, consisting essentially of, or consisting of the amino acid sequence of SEQ ID NO: 101 and/or $V_L$ domain comprising, consisting essentially of, or consisting of the amino acid sequence of SEQ ID NO: 102, or CDRs contained therein). In some embodiments, the antibody moiety comprises the CDRs or variables domains ($V_H$ and/or $V_L$ domains) of an antibody moiety specific for GPC3 (see, e.g., U.S. Ser. No. 62/490,586 filed Apr. 26, 2017, the contents of which are incorporated herein by reference in their entirety). In some embodiments, the antibody moiety comprises the CDRs or variables domains ($V_H$ and/or $V_L$ domains) of an antibody moiety specific for GPC3 (e.g., $V_H$ domain comprising, consisting essentially of, or consisting of the amino acid sequence of SEQ ID NO: 64 and/or $V_L$ domain comprising, consisting essentially of, or consisting of the amino acid sequence of SEQ ID NO: 65, or CDRs contained therein). In some embodiments, the antibody moiety comprises the CDRs or variables domains ($V_H$ and/or $V_L$ domains) of an antibody moiety specific for ROR1 (see, e.g., WO2016/187220 and WO2016/187216). In some embodiments, the antibody moiety comprises the CDRs or variables domains ($V_H$ and/or $V_L$ domains) of an antibody moiety specific for ROR2 (see, e.g., WO2016/142768). In some embodiments, the antibody moiety comprises the CDRs or variables domains ($V_H$ and/or $V_L$ domains) of an antibody moiety specific for BCMA (see, e.g., WO2016/090327 and WO2016/090320). In some embodiments, the antibody moiety comprises the CDRs or variables domains ($V_H$ and/or $V_L$ domains) of an antibody moiety specific for GPRC5D (see, e.g., WO2016/090329 and WO2016/090312). In some embodiments, the antibody moiety comprises the CDRs or variables domains ($V_H$ and/or $V_L$ domains) of an antibody moiety specific for FCRL5 (see, e.g., WO2016/090337). In some embodiments, the antibody moiety comprises the CDRs or variables domains (V$_H$ and/or V$_L$ domains) of an antibody moiety specific for WT-1 (see, e.g., WO2012/135854, WO2015/070078, and WO2015/070061). In some embodiments, the antibody moiety comprises the CDRs or variables domains (V$_H$ and/or V$_L$ domains) of an antibody moiety specific for AFP (see, e.g., WO2016/161390). In some embodiments, the antibody moiety comprises the CDRs or variables domains (V$_H$ and/or V$_L$ domains) of an antibody moiety specific for HPV16-E7 (see, e.g., WO2016/182957). In some embodiments, the antibody moiety comprises the CDRs or variables domains (V$_H$ and/or V$_L$ domains) of an antibody moiety specific for NY-ESO-1 (see, e.g., WO2016/210365). In some embodiments, the antibody moiety comprises the CDRs or variables domains (V$_H$ and/or V$_L$ domains) of an antibody moiety specific for PRAME (see, e.g., WO2016/191246). In some embodiments, the antibody moiety comprises the CDRs or variables domains (V$_H$ and/or V$_L$ domains) of an antibody moiety specific for EBV-LMP2A (see, e.g., WO2016/201124). In some embodiments, the antibody moiety comprises the CDRs or variables domains (V$_H$ and/or V$_L$ domains) of an antibody moiety specific for KRAS (see, e.g., WO2016/154047). In some embodiments, the antibody moiety comprises the CDRs or variables domains (V$_H$ and/or V$_L$ domains) of an antibody moiety specific for PSA (see, e.g., WO2017/015634). In some embodiments, the antibody moiety is a Fab comprising one Fab chain comprising a V$_H$ domain and a C$_H$1 domain, and another Fab chain comprising a V$_L$ domain and a C$_L$ domain. In some embodiments, the C$_H$1 domain comprises the amino acid sequence of any one of SEQ ID NOs: 37-47 and/or the C$_L$ domain comprises the amino acid sequence of SEQ ID NO: 48. In some embodiments, the C$_H$1 domain comprises, consists essentially of, or consists of the amino acid sequence of SEQ ID NO: 37 and the C$_L$ domain comprises, consists essentially of, or consists of the amino acid sequence of SEQ ID NO: 48.

caTCR Constructs

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) an antibody moiety that specifically binds to the target antigen, wherein the antibody moiety is linked to the first and/or second TCRDs. In some embodiments, the antibody moiety is selected from the group consisting of a Fab, a Fab', a (Fab')2, an Fv, and a single chain Fv (scFv). In some embodiments, the antibody moiety specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the antibody moiety specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the stabilization module is located between the TCRM and the antibody moiety. In some embodiments, both of the TCR-TMs are naturally occurring. In some embodiments, at least one of the TCR-TMs is non-naturally occurring.

In some embodiments, the caTCR described herein specifically binds a target antigen, comprising a) a first TCRD comprising a first TCR-TM comprising, consisting essentially of, or consisting of any one of the amino acid sequences of SEQ ID NOs: 7 and 9-13 and a second TCRD comprising a second TCR-TM comprising, consisting essentially of, or consisting of the amino acid sequence of any one of SEQ ID NOs: 8 and 14-26, wherein the first and second TCRDs form a TCRM that is capable of recruiting at least one TCR-associated signaling molecule; and b) an antibody moiety that specifically binds to the target antigen, wherein the antibody moiety is linked to the first and/or second TCRDs. In some embodiments, the first TCR-TM and second TCR-TM are selected according to any of the caTCRs listed in Table 2. In some embodiments, the antibody moiety is selected from the group consisting of a Fab, a Fab', a (Fab')2, an Fv, and a single chain Fv (scFv). In some embodiments, the antibody moiety specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the antibody moiety specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the first TCRD further comprises a first TCR connecting peptide or a fragment thereof and/or the second TCRD further comprises a second TCR connecting peptide or a fragment thereof. In some embodiments, the first connecting peptide comprises the amino acid sequence SEQ ID NO: 31 or 32, or a variant thereof, and/or the second connecting peptide comprises the amino acid sequence SEQ ID NO: 33 or 34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the second TCR intracellular domain comprises the amino acid sequence of SEQ ID NO: 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains. In some embodiments, both of the TCR-TMs are naturally occurring. In some embodiments, at least one of the TCR-TMs is non-naturally occurring.

In some embodiments, the caTCR described herein specifically binds a target antigen, comprising a) a first TCRD comprising a first TCR-TM and a second TCRD comprising a second TCR-TM, wherein the first and second TCR-TMs comprise, consist essentially of, or consist of the amino acid sequences of SEQ ID NOs: 7 and 8, 9 and 8, 7 and 14, 7 and 15, 7 and 16, 10 and 16, 7 and 17, 7 and 18, 7 and 19, 7 and 20, 7 and 21, 7 and 22, 11 and 23, 12 and 24, 7 and 25, or 13 and 26, respectively, and wherein the first and second TCRDs form a TCRM that is capable of recruiting at least one TCR-associated signaling molecule; and b) an antibody moiety that specifically binds to the target antigen, wherein the antibody moiety is linked to the first and/or second TCRDs. For example, in some embodiments, the caTCR described herein specifically binds a target antigen, comprising a) a first TCRD comprising a first TCR-TM comprising, consisting essentially of, or consisting of the amino acid sequence of SEQ ID NO: 7, and a second TCRD comprising a second TCR-TM comprising, consisting essentially of, or consisting of the amino acid sequence of SEQ ID NO: 8, wherein the first and second TCRDs form a TCRM that is capable of recruiting at least one TCR-associated signaling molecule; and b) an antibody moiety that specifically binds to the target antigen, wherein the antibody moiety is linked to the first and/or second TCRDs. In some embodiments, the antibody moiety is selected from the group consisting of a Fab, a Fab', a (Fab')2, an Fv, and a single chain Fv (scFv). In some embodiments, the antibody moiety specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the antibody moiety specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the first TCRD further comprises a first TCR connecting peptide or a fragment thereof and/or the second TCRD further comprises a second TCR connecting peptide or a fragment thereof. In some embodiments, the first connecting peptide comprises the amino acid sequence SEQ ID NO: 31 or 32, or a variant thereof, and/or the second connecting peptide comprises the amino acid sequence SEQ ID NO: 33 or 34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the second TCR intracellular domain comprises the amino acid sequence of SEQ ID NO: 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains.

In some embodiments, the caTCR described herein specifically binds a target antigen, comprising a) a first polypeptide chain comprising a first antigen-binding domain comprising a first Fab chain linked to a first TCRD comprising a first TCR-TM derived from one of the transmembrane domains of a TCR; and b) a second polypeptide chain comprising a second antigen-binding domain comprising a second Fab chain linked to a second TCRD comprising a second TCR-TM derived from the other transmembrane domain of the TCR, wherein the first and second TCRDs form a TCRM that is capable of recruiting at least one TCR-associated signaling molecule, and wherein the first and second Fab chains form a Fab-like antigen-binding module that specifically binds the target antigen. In some embodiments, a) the first Fab chain comprises $V_H$ and $C_H1$ antibody domains and the second Fab chain comprises $V_L$ and $C_L$ antibody domains; or b) the first Fab chain comprises $V_L$ and $C_L$ antibody domains and the second Fab chain comprises $V_H$ and $C_H1$ antibody domains. For example, in some embodiments, the caTCR comprises a) a first polypeptide chain comprising a first Fab chain comprising $V_H$ and $C_H1$ antibody domains linked to the first TCRD and b) a second Fab chain comprising $V_L$ and $C_L$ antibody domains linked to the second TCRD. In some embodiments, the caTCR comprises a) a first Fab chain comprising $V_L$ and $C_L$ antibody domains linked to the first TCRD and b) a second Fab chain comprising $V_H$ and $C_H1$ antibody domains linked to the second TCRD. In some embodiments, there is a peptide linker between one or both of the TCRDs and their linked Fab chain. In some embodiments, there is a disulfide bond between a residue in the $C_H1$ domain and a residue in the $C_L$ domain. In some embodiments, the $C_H1$ and/or $C_L$ domains comprise one or more modifications that increase the binding affinity of the Fab chains for each other. In some embodiments, the $C_H1$ and $C_L$ domains are swapped, such that one of the Fab chains comprises $V_H$ and $C_L$ antibody domains and the other Fab chain comprises $V_L$ and $C_H1$ antibody domains. In some embodiments, the Fab-like antigen-binding module specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the Fab-like antigen-binding module specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the first or second stabilization domain is located between first TCRD and its linked Fab chain and the other stabilization domain is located between the second TCRD and its linked Fab chain. In some embodiments, both of the TCR-TMs are naturally occurring. In some embodiments, at least one of the TCR-TMs is non-naturally occurring.

In some embodiments, the caTCR described herein specifically binds a target antigen, comprising a) a first polypeptide chain comprising a first antigen-binding domain comprising a first Fab chain linked to a first TCRD comprising a first TCR-TM comprising, consisting essentially of, or consisting of any one of the amino acid sequences of SEQ ID NOs: 7 and 9-13; and b) a second polypeptide chain comprising a second antigen-binding domain comprising a second Fab chain linked to a second TCRD comprising a second TCR-TM comprising, consisting essentially of, or consisting of the amino acid sequence of any one of SEQ ID NOs: 8 and 14-26, wherein the first and second TCRDs form a TCRM that is capable of recruiting at least one TCR-associated signaling molecule, and wherein the first and second Fab chains form a Fab-like antigen-binding module that specifically binds the target antigen. In some embodiments, the first TCR-TM and second TCR-TM are selected according to any of the caTCRs listed in Table 2. In some embodiments, a) the first Fab chain comprises $V_H$ and $C_H1$ antibody domains and the second Fab chain comprises $V_L$ and $C_L$ antibody domains; or b) the first Fab chain comprises $V_L$ and $C_L$ antibody domains and the second Fab chain comprises $V_H$ and $C_H1$ antibody domains. In some embodiments, the $C_H1$ domain comprises the amino acid sequence of any one of SEQ ID NOs: 37-47 and/or the $C_L$ domain comprises the amino acid sequence of SEQ ID NO: 48. In some embodiments, the $C_H1$ domain comprises, consists essentially of, or consists of the amino acid sequence of SEQ ID NO: 37 and the $C_L$ domain comprises, consists essentially of, or consists of the amino acid sequence of SEQ ID NO: 48. In some embodiments, the Fab-like antigen-binding module specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the Fab-like antigen-binding module specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the first TCRD further comprises a first TCR connecting peptide or a fragment thereof and/or the second TCRD further comprises a second TCR connecting peptide or a fragment thereof. In some embodiments, the first connecting peptide comprises the amino acid sequence SEQ ID NO: 31 or 32, or a variant thereof, and/or the second connecting peptide comprises the amino acid sequence SEQ ID NO: 33 or 34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the second TCR intracellular domain comprises the amino acid sequence of SEQ ID NO: 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains. In some embodiments, both of the TCR-TMs are naturally occurring. In some embodiments, at least one of the TCR-TMs is non-naturally occurring.

In some embodiments, the caTCR described herein specifically binds a target antigen, comprising a) a first polypeptide chain comprising a first antigen-binding domain comprising a first Fab chain linked to a first TCRD comprising a first TCR-TM and a second polypeptide chain comprising a second antigen-binding domain comprising a second Fab chain linked to a second TCRD comprising a second TCR-TM, wherein the first and second TCR-TMs comprise, consist essentially of, or consist of the amino acid sequences of SEQ ID NOs: 7 and 8, 9 and 8, 7 and 14, 7 and 15, 7 and 16, 10 and 16, 7 and 17, 7 and 18, 7 and 19, 7 and 20, 7 and 21, 7 and 22, 11 and 23, 12 and 24, 7 and 25, or 13 and 26, respectively, wherein the first and second TCRDs form a TCRM that is capable of recruiting at least one TCR-associated signaling molecule, and wherein the first and second Fab chains form a Fab-like antigen-binding module that specifically binds the target antigen. In some embodiments, a) the first Fab chain comprises $V_H$ and $C_H1$ antibody domains and the second Fab chain comprises $V_L$ and $C_L$ antibody domains; or b) the first Fab chain comprises $V_L$ and $C_L$ antibody domains and the second Fab chain comprises $V_H$ and $C_H1$ antibody domains. In some embodiments, the $C_H1$ domain comprises the amino acid sequence of any one of SEQ ID NOs: 37-47 and/or the $C_L$ domain comprises the amino acid sequence of SEQ ID NO: 48. In some embodiments, the $C_H1$ domain comprises, consists essentially of, or consists of the amino acid sequence of SEQ ID NO: 37 and the $C_L$ domain comprises, consists essentially of, or consists of the amino acid sequence of SEQ ID NO: 48. In some embodiments, the Fab-like antigen-binding module specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the Fab-like antigen-binding module specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the first TCRD further comprises a first TCR connecting peptide or a fragment thereof and/or the second TCRD further comprises a second TCR connecting peptide or a fragment thereof. In some embodiments, the first connecting peptide comprises the amino acid sequence SEQ ID NO: 31 or 32, or a variant thereof, and/or the second connecting peptide comprises the amino acid sequence SEQ ID NO: 33 or 34, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the second TCR intracellular domain comprises the amino acid sequence of SEQ ID NO: 36, or a variant thereof. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising T cell receptor transmembrane domains having the sequences of SEQ ID NOs: 7 and 8. In some embodiments, the TCRM promotes caTCR-CD3 complex formation. In some embodiments, there is a spacer module between any two caTCR modules or domains.

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) a Fab' that specifically binds to the target antigen, wherein the Fab' comprises a first Fab' chain comprising $V_H$, $C_H 1$, and partial hinge antibody domains and a second Fab' chain comprising $V_L$ and $C_L$ antibody domains, and wherein the first Fab' chain is linked to the first or second TCRD and the second Fab' chain is linked to the other TCRD. In some embodiments, there is a peptide linker between one or both of the TCRDs and their linked Fab' chain. In some embodiments, there is a disulfide bond between a residue in the $C_H 1$ domain and a residue in the $C_L$ domain. In some embodiments, the $C_H 1$ and/or $C_L$ domains comprise one or more modifications that increase the binding affinity of the Fab' chains for each other. In some embodiments, the $C_H 1$ and $C_L$ domains are swapped, such that the first Fab' chain comprises $V_H$, $C_L$, and partial hinge antibody domains and the second Fab' chain comprises $V_L$ and $C_H 1$ domains. In some embodiments, the Fab' specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the Fab' specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the first or second stabilization domain is located between first TCRD and its linked Fab' chain and the other stabilization domain is located between the second TCRD and its linked Fab' chain. In some embodiments, both of the TCR-TMs are naturally occurring. In some embodiments, at least one of the TCR-TMs is non-naturally occurring.

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) a (Fab')2 that specifically binds to the target antigen, wherein the (Fab')2 comprises first and second (Fab')2 chains comprising $V_H$, $C_H 1$, and partial hinge antibody domains and third and fourth (Fab')2 chains comprising $V_L$ and $C_L$ antibody domains, and wherein the first (Fab')2 chain is linked to the first or second TCRD and the second (Fab')2 chain is linked to the other TCRD. In some embodiments, there is a peptide linker between one or both of the TCRDs and their linked (Fab')2 chain. In some embodiments, there is a disulfide bond between a residue in a $C_H 1$ domain and a residue in a $C_L$ domain. In some embodiments, the $C_H 1$ and/or $C_L$ domains comprise one or more modifications that increase the binding affinity of the (Fab')2 chains for each other. In some embodiments, the $C_H 1$ and $C_L$ domains are swapped, such that the first and second (Fab')2 chains comprise $V_H$, $C_L$, and partial hinge antibody domains and the third and fourth (Fab')2 chains comprise $V_L$ and $C_H 1$ domains. In some embodiments, the (Fab')2 specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the (Fab')2 specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the first or second stabilization domain is located between first TCRD and its linked (Fab')2 chain and the other stabilization domain is located between the second TCRD and its linked (Fab')2 chain. In some embodiments, both of the TCR-TMs are naturally occurring. In some embodiments, at least one of the TCR-TMs is non-naturally occurring.

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) an Fv that specifically binds to the target antigen, wherein the Fv comprises a first Fv chain comprising a $V_H$ antibody domain and a second Fv chain comprising a $V_L$ antibody domain, and wherein the first Fv chain is linked to the first or second TCRD and the second Fv chain is linked to the other TCRD. In some embodiments, there is a peptide linker between one or both of the TCRDs and their linked Fv chain. In some embodiments, the Fv specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the Fv specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the first or second stabilization domain is located between first TCRD and its linked Fv chain and the other stabilization domain is located between the second TCRD and its linked Fv chain. In some embodiments, both of the TCR-TMs are naturally occurring. In some embodiments, at least one of the TCR-TMs is non-naturally occurring.

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) a first scFv that specifically binds to the target antigen, wherein the first scFv comprises $V_H$ and $V_L$ antibody domains, and wherein the first scFv is linked to the first or second TCRD. In some embodiments, the caTCR further comprises a second antigen-binding module linked to the first scFv or to the TCRD that is not linked to the first scFv. In some embodiments, the second antigen-binding module specifically binds to the target antigen. In some embodiments, the second antigen-binding module specifically binds to an antigen other than the target antigen. In some embodiments, the second antigen-binding module is a second scFv. In some embodiments, there is a peptide linker between the first scFv and its linked TCRD and/or between the second antigen-binding module and its linked scFv or TCRD. In some embodiments, the scFv specifically binds a cell surface antigen including, without limitation, CD19, CD20, CD22, CD47, GPC-3, ROR1, ROR2, BCMA, GPRC5D, and FCRL5, including variants or mutants thereof. In some embodiments, the scFv specifically binds a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the first or second stabilization domain is located between first scFv and its linked TCRD and the other stabilization domain is linked to the second TCRD. In some embodiments, both of the TCR-TMs are naturally occurring. In some embodiments, at least one of the TCR-TMs is non-naturally occurring.

In some embodiments, the caTCR described herein specifically binds a target antigen, comprising a) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule; and b) a first scFv that specifically binds to the target antigen and a second scFv, wherein the first and second scFvs comprise $V_H$ and $V_L$ antibody domains, and wherein the first scFv is linked to the first or second TCRD and the second scFv is linked to the other TCRD. In some embodiments, the second TCRD specifically binds to the target antigen. In some embodiments, the second scFv comprises, consists essentially of, or consists of the amino acid sequence of the first scFv. In some embodiments, the second scFv specifically binds to an antigen other than the target antigen. In some embodiments, the first and/or second scFvs specifically bind, individually, a cell surface antigen including, without limitation, CD19, CD20, CD22, CD47, GPC-3, ROR1, ROR2, BCMA, GPRC5D, and FCRL5, including variants or mutants thereof. In some embodiments, the first and/or second scFvs specifically bind, individually, a peptide/MHC complex, wherein the peptide is derived from a protein including, without limitation, WT-1, AFP, HPV16-E7, NY-ESO-1, PRAME, EBV-LMP2A, HIV-1, KRAS, Histone H3.3, and PSA, including variants or mutants thereof. In some embodiments, the caTCR further comprises a stabilization module comprising a first stabilization domain and a second stabilization domain, wherein the first and second stabilization domains have a binding affinity for each other that stabilizes the caTCR. In some embodiments, the first or second stabilization domain is located between first scFv and its linked TCRD and the other stabilization domain is located between the second scFv and its linked TCRD. In some embodiments, both of the TCR-TMs are naturally occurring. In some embodiments, at least one of the TCR-TMs is non-naturally occurring.

Multispecific caTCRs

In some embodiments, the caTCR is a multispecific caTCR that specifically binds to two or more (e.g., 2, 3, 4, or more) different target antigens or epitopes. In some embodiments, the multispecific caTCR specifically binds to two or more (e.g., 2, 3, 4, or more) different target antigens. In some embodiments, the multispecific caTCR specifically binds to two or more (e.g., 2, 3, 4, or more) different epitopes on the same target antigen. In some embodiments, the multispecific caTCR comprises an antigen-binding module for each antigen or epitope. In some embodiments, the multispecific caTCR comprises more than two antigen-binding module for at least one antigen or epitope. In some embodiments, the multispecific caTCR comprises a multispecific antigen-binding module comprising two or more (e.g., 2, 3, 4, or more) antigen-binding domains each specifically binding to an antigen or epitope. In some embodiments, the multispecific caTCR is bispecific. In some embodiments, the multispecific caTCR is trispecific.

Multi-specific molecules are molecules that have binding specificities for at least two different antigens or epitopes (e.g., bispecific antibodies have binding specificities for two antigens or epitopes). Multi-specific caTCRs with more than two valencies and/or specificities are also contemplated. Bispecific antibodies have been described, e.g., see, Brinkmann U. and Kontermann R. E. (2017) *MABS*, 9(2), 182-212. Trispecific antibodies can be prepared. See, Tutt et al. *J. Immunol.* 147: 60 (1991). It is to be appreciated that one of skill in the art could select appropriate features of individual multi-specific molecules known in the art to form a multi-specific caTCR.

In some embodiments, the caTCR (also referred herein as "multispecific caTCR") comprises: a) a multispecific (e.g., bispecific) antigen-binding module comprising a first antigen-binding domain that specifically binds to a first target antigen and a second antigen-binding domain that specifically binds to a second target antigen; and b) a TCRM comprising a first TCRD (TCRD1) comprising a first TCR-TM and a second TCRD (TCRD2) comprising a second TCR-TM; wherein the TCRM facilitates recruitment of at least one TCR-associated signaling molecule. In some embodiments, the first TCRD further comprises a first TCR connecting peptide or a fragment thereof and/or the second TCRD further comprises a second TCR connecting peptide or a fragment thereof. In some embodiments, the first connecting peptide comprises all or a portion of the connecting peptide of the TCR subunit from which the first TCR-TM is derived, or a variant thereof, and/or the second connecting peptide comprises all or a portion of the connecting peptide of the TCR subunit from which the second TCR-TM is derived, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR subunit from which the first TCR-TM is derived and/or the second TCR intracellular domain comprises a sequence from the intracellular domain of the TCR subunit from which the second TCR-TM is derived. In some embodiments, the first TCRD is a fragment of the TCR subunit from which the first TCR-TM is derived and/or the second TCRD is a fragment of the TCR subunit from which the second TCR-TM is derived. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise an antibody moiety, such as $C_H1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the naturally occurring a T cell receptor transmembrane domains. In some embodiments, the TCRM promotes caTCR-CD3 complex formation. In some embodiments, there is a spacer module between any two caTCR modules or domains. In some embodiments, both the first TCR-TM and the second TCR-TM are naturally occurring. In some embodiments, at least one of the TCR-TMs is non-naturally occurring. In some embodiments, the first TCR-TM comprises up to 5 amino acid substitutions (e.g., a single amino acid substitution) compared to the transmembrane domain from which it is derived and/or the second TCR-TM comprises up to 5 amino acid substitutions (e.g., a single amino acid substitution) compared to the transmembrane domain from which it is derived. In some embodiments, a substituted amino acid in the first TCR-TM is proximal to a substituted amino acid in the second TCR-TM. In some embodiments, one or more substituted amino acids are proximal to an amino acid in the first or second TCR-TM involved in binding to CD3. In some embodiments, one or more (e.g., each) substituted amino acids are more hydrophobic than their corresponding unsubstituted amino acid. In some embodiments, the first TCR-TM comprises the amino acid sequence of any one of SEQ ID NOs: 7 and 9-13, and wherein the second TCR-TM comprises the amino acid sequence of any one of SEQ ID NOs: 8 and 14-26.

Exemplary structures of bispecific caTCRs are shown in FIGS. 13A-13E, in which the target antigens are CD19 and CD22, but a skilled person in the art would readily appreciate that bispecific caTCRs targeting other target antigens or epitopes may be prepared using the same structural formats.

Figure 13B:
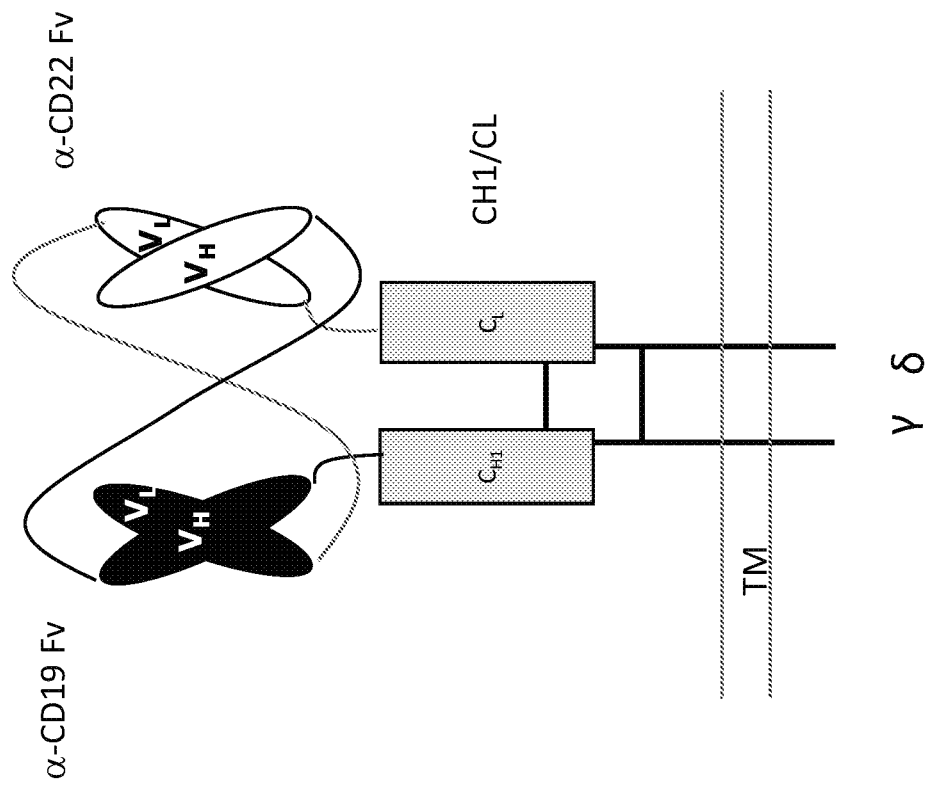
Figure 13A:
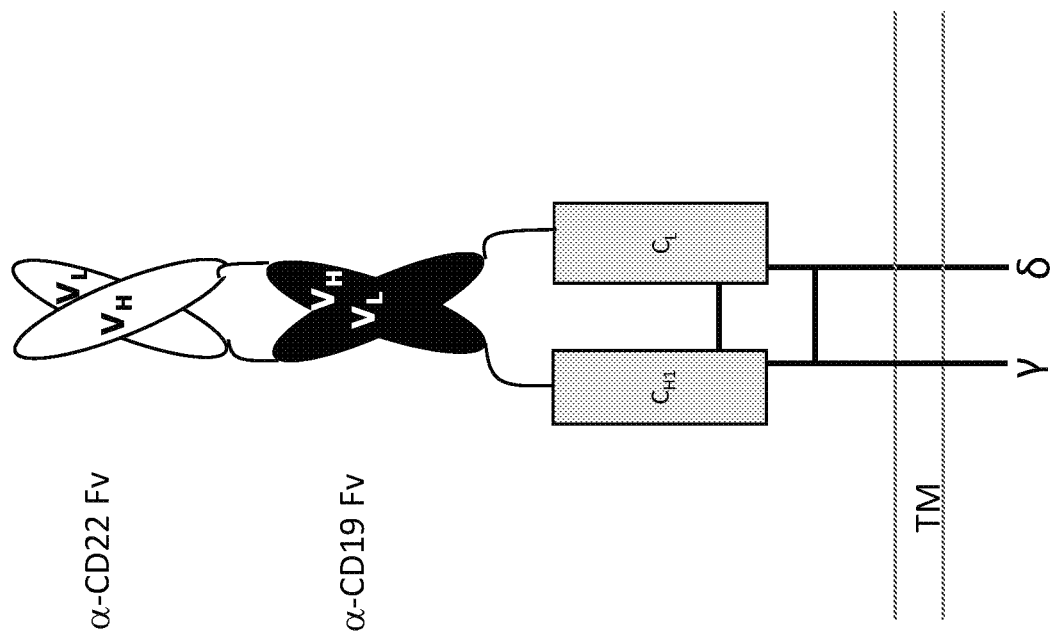

For example, dual-variable domains (DVD) derived from DVD IgGs (see, DiGiammarino et al., mAbs 3(5): 487-494) can be used as a bispecific antigen-binding module in the caTCR (FIG. 13A). Various linkers for fusion of the outer variable domain and inner variable domain have been developed and optimized for DVD-Igs, which may be useful in constructing bispecific caTCRs having a DVD module. However, the variable domain stacking approach in DVD modules may affect the folding and target binding affinity of the inner variable domain. The linkers between the two variable domains and the order of the two variable domains may affect the efficacy of the caTCR.

In some embodiments, the caTCR comprises: a) a multispecific (e.g., bispecific) antigen-binding module comprising a Fv that specifically binds to a first target antigen and a Fab that specifically binds to a second target antigen; and b) a TCRM comprising a first TCRD (TCRD1) comprising a first TCR-TM and a second TCRD (TCRD2) comprising a second TCR-TM; wherein the TCRM facilitates recruitment of at least one TCR-associated signaling molecule.

In some embodiments, the caTCR comprises: (i) a first polypeptide chain comprising from the N-terminus to the C-terminus: $V_H1$-L1-$V_H2$-$C_H1$-TCRD1; and a second polypeptide chain comprising from the N-terminus to the C-terminus: $V_L1$-L2-$V_L2$-$C_L$-TCRD2; (ii) a first polypeptide chain comprising from the N-terminus to the C-terminus: $V_H1$-L1-$V_L2$-$C_L$-TCRD1; and a second polypeptide chain comprising from the N-terminus to the C-terminus: $V_L1$-L2-$V_H2$-$C_H1$-TCRD2; (iii) a first polypeptide chain comprising from the N-terminus to the C-terminus: $V_L1$-L1-$V_H2$-$C_H1$-TCRD1; and a second polypeptide chain comprising from the N-terminus to the C-terminus: $V_H1$-L2-$V_L2$-$C_L$-TCRD2; or (iv) a first polypeptide chain comprising from the N-terminus to the C-terminus: $V_L1$-L1-$V_L2$-$C_L$-TCRD1; and a second polypeptide chain comprising from the N-terminus to the C-terminus: $V_H1$-L2-$V_H2$-$C_H1$-TCRD2, wherein $V_H1$ and $V_L1$ form a first antigen-binding domain that specifically binds to a first target antigen, and $V_{H2}$ and $V_{L2}$ form a second antigen-binding domain that specifically binds to a second target antigen, wherein TCRD1 and TCRD2 form a TCRM that facilitates recruitment of at least one TCR-associated signaling molecule, and wherein L1 and L2 are peptide linkers. In some embodiments, L1 and/or L2 are about 5 to about 50 (e.g., about 5-10, about 10-15, or about 15-30) amino acids long. In some embodiments, L1 and L2 have the same length. In some embodiment, L1 and L2 have the same amino acid sequence. In some embodiments, L1 and L2 have different lengths. In some embodiments, L1 and L2 have different amino acid sequences. An exemplary bispecific caTCR is shown in FIG. 13A.

Cross-over dual variable domains (CODV) derived from CODV-IgGs (see, Steinmetz, et al.; mAbs (2016), 8(5): 867-878) can be used as a bispecific antigen-binding module in the caTCR (FIG. 13B). CODV allows relatively unobstructed antigen-binding sites for each Fv. Various linkers for fusion of the heavy chain and light chain variable regions have been developed and optimized for CODV-Igs, which may be useful in constructing bispecific caTCRs having a CODV module. However, proper folding of the CODV module can be challenging, and long linkers used in the CODV module can be a potential source of immunogenicity and susceptible to proteolytic cleavage.

In some embodiments, the caTCR comprises: a) a multispecific (e.g., bispecific) antigen-binding module comprising a first Fv that specifically binds to a first target antigen and a second Fv that specifically binds to a second target antigen; and b) a TCRM comprising a first TCRD (TCRD1) comprising a first TCR-TM and a second TCRD (TCRD2) comprising a second TCR-TM; wherein the TCRM facilitates recruitment of at least one TCR-associated signaling molecule. In some embodiments, the caTCR further comprises a $C_H1$ and a $C_L$.

In some embodiments, the caTCR comprises: (i) a first polypeptide chain comprising from the N-terminus to the C-terminus: $V_H1$-L1-$V_H2$-$C_H1$-TCRD1, and a second polypeptide chain comprising from the N-terminus to the C-terminus: $V_L2$-L2-$V_L1$-$C_L$-TCRD2; or (ii) a first polypeptide chain comprising from the N-terminus to the C-terminus: $V_L1$-L1-$V_L2$-$C_L$-TCRD1, and a second polypeptide chain comprising from the N-terminus to the C-terminus: $V_H2$-L2-$V_H1$-$C_H1$-TCRD2, wherein $V_H1$ and $V_L1$ form a first antigen-binding domain that specifically binds to a first target antigen, and $V_H2$ and $V_L2$ form a second antigen-binding domain that specifically binds to a second target antigen, wherein TCRD1 and TCRD2 form a TCRM that facilitates recruitment of at least one TCR-associated signaling molecule, and wherein L1 and L2 are peptide linkers. In some embodiments, L1 and/or L2 are about 5 to about 50 (e.g., about 5-20, about 15-30, or about 30-50) amino acids long. In some embodiments, L1 and L2 have the same length. In some embodiment, L1 and L2 have the same amino acid sequence. In some embodiments, L1 and L2 have different lengths. In some embodiments, L1 and L2 have different amino acid sequences. An exemplary bispecific caTCR is shown in FIG. 13B.

Bispecific antigen-binding modules derived from scFv-fusion proteins, such as those described in Chen et al., mAbs 8(4): 761-774, may be used in a bispecific caTCR (FIG. 13C). Expression of bispecific antibodies having a similar fusion format has demonstrated proper folding and stability of this format. Various linkers for fusion of the scFvs to the constant domains have been developed and optimized for these bispecific antibodies, which may be useful in constructing bispecific caTCRs having a similar scFv fusion domain. However, steric hindrance between the scFvs may compromise binding of the scFvs to their target antigens.

In some embodiments, the caTCR comprises: a) a multispecific (e.g., bispecific) antigen-binding module comprising a first scFv that specifically binds to a first target antigen and a second scFv that specifically binds to a second target antigen; and b) a TCRM comprising a first TCRD (TCRD1) comprising a first TCR-TM and a second TCRD (TCRD2) comprising a second TCR-TM; wherein the TCRM facilitates recruitment of at least one TCR-associated signaling molecule. In some embodiments, the caTCR further comprises a $C_H1$ and a $C_L$.

In some embodiments, the caTCR comprises: (i) a first polypeptide chain comprising from the N-terminus to the C-terminus: scFv1-L1-$C_H1$-TCRD1, and a second polypeptide chain comprising from the N-terminus to the C-terminus: scFv2-L2-$C_L$-TCRD2; or (ii) a first polypeptide chain comprising from the N-terminus to the C-terminus: scFv2-L1-$C_H1$-TCRD1, and a second polypeptide chain comprising from the N-terminus to the C-terminus: scFv1-L2-$C_L$-TCRD2; wherein scFv1 specifically binds to a first target antigen and scFv2 specifically binds to a second target antigen, wherein TCRD1 and TCRD2 form a TCRM that facilitates recruitment of at least one TCR-associated signaling molecule, and wherein L1 and L2 are peptide linkers. In some embodiments, L1 and/or L2 are about 5 to about 50 (e.g., about 5-10, about 10-15, or about 15-30) amino acids long. In some embodiments, L1 and L2 have the same length. In some embodiment, L1 and L2 have the same amino acid sequence. In some embodiments, L1 and L2 have different lengths. In some embodiments, L1 and L2 have different amino acid sequences. An exemplary bispecific caTCR is shown in FIG. 13C.

Bispecific antigen-binding modules derived from an IgG-scFv bispecific antibody or a Fab-scFv-Fc bispecific antibody may be used in a bispecific caTCR. In one format (FIG. 13D), an scFv is attached to either the $V_H$ or $V_L$ of a Fab, which allows greater flexibility of the scFv and thus greater access of the Fab to its target antigen. However, the scFv-Fab module may have stability issues. In a second format (FIG. 13E), a Fab is fused to a first TCRD and an scFv is fused to a second TCRD.

In some embodiments, the caTCR comprises: a) a multispecific (e.g., bispecific) antigen-binding module comprising a scFv that specifically binds to a first target antigen and a Fab that specifically binds to a second target antigen; and b) a TCRM comprising a first TCRD (TCRD1) comprising a first TCR-TM and a second TCRD (TCRD2) comprising a second TCR-TM; wherein the TCRM facilitates recruitment of at least one TCR-associated signaling molecule.

In some embodiments, the caTCR comprises: (i) a first polypeptide chain comprising from the N-terminus to the C-terminus: scFv-L1-$V_H$-$C_H1$-TCRD1, and a second polypeptide chain comprising from the N-terminus to the C-terminus: $V_L$—$C_L$-TCRD2; or (ii) a first polypeptide chain comprising from the N-terminus to the C-terminus: $V_H$—$C_H1$-TCRD1, and a second polypeptide chain comprising from the N-terminus to the C-terminus: scFv-L2-$V_L$-$C_L$-TCRD2; wherein the scFv specifically binds to a first target antigen, and the $V_H$ and $V_L$ form a second antigen-binding domain that specifically binds to a second target antigen, wherein TCRD1 and TCRD2 form a TCRM that facilitates recruitment of at least one TCR-associated signaling molecule, and wherein L1 and L2 are peptide linkers. In some embodiments, L1 and/or L2 are about 5 to about 50 (e.g., about 5-10, about 10-15, or about 15-30) amino acids long. An exemplary bispecific caTCR is shown in FIG. 13D.

Figure 13E:
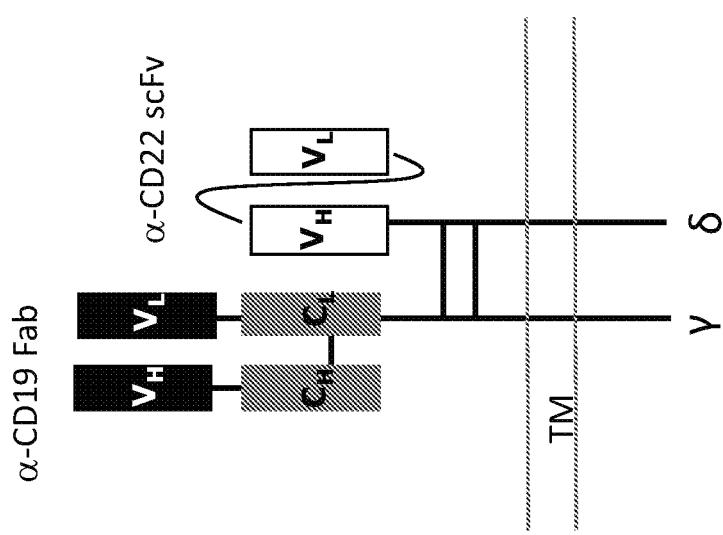

In some embodiments, the caTCR comprises: (i) a first polypeptide chain comprising from the N-terminus to the C-terminus: $V_L$-$C_L$-L1-TCRD1, a second polypeptide chain comprising from the N-terminus to the C-terminus: $V_H$-$C_H1$, and a third polypeptide chain comprising from the N-terminus to the C-terminus: scFv-L2-TCRD2; (ii) a first polypeptide chain comprising from the N-terminus to the C-terminus: $V_H$-$C_H1$-L1-TCRD1, a second polypeptide chain comprising from the N-terminus to the C-terminus: $V_L$-$C_L$, and a third polypeptide chain comprising from the N-terminus to the C-terminus: scFv-L2-TCRD2; (iii) a first polypeptide chain comprising from the N-terminus to the C-terminus: scFv-L1-TCRD1, a second polypeptide chain comprising from the N-terminus to the C-terminus: $V_H$-$C_H1$, and a third polypeptide chain comprising from the N-terminus to the C-terminus: $V_L$-$C_L$-L2-TCRD2; or (iv) a first polypeptide chain comprising from the N-terminus to the C-terminus: scFv-L1-TCRD1, a second polypeptide chain comprising from the N-terminus to the C-terminus: $V_L$-$C_L$, and a third polypeptide chain comprising from the N-terminus to the C-terminus: $V_H$-$C_H1$-L2-TCRD2; wherein the scFv specifically binds to a first target antigen, and the $V_H$ and $V_L$ form a second antigen-binding domain that specifically binds to a second target antigen, wherein TCRD1 and TCRD2 form a TCRM that facilitates recruitment of at least one TCR-associated signaling molecule, and wherein L1 and L2 are peptide linkers. In some embodiments, L1 and/or L2 are about 5 to about 50 (e.g., about 5-10, about 10-15, or about 15-30) amino acids long. An exemplary bispecific caTCR is shown in FIG. 13E. The length of the peptide linker between the scFv and the TCRD and the length of the peptide linker between the Fab and the TCRD can be optimized as they may affect the accessibility of the scFv and the Fab to their target antigens.

The multispecific antigen-binding module of the multispecific caTCR may specifically bind to any suitable combination of target antigens or epitopes. In some embodiments, the multispecific antigen-binding module specifically binds to at least one cell surface antigen. In some embodiments, the at least one cell surface antigen is selected from the group consisting of CD19, CD20, CD22, CD47, GPC-3, ROR1, ROR2, BCMA, GPRC5D, and FCRL5, including variants or mutants thereof. In some embodiments, the multispecific antigen-binding module specifically binds to at least one peptide/MHC complex. In some embodiments, the at least one peptide/MHC complex comprises a peptide derived from a protein selected from the group consisting of WT-1, AFP, HPV16-E7, NY-ESO-1, PRAME, EBV-LMP2A, HIV-1, KRAS, Histone H3.3, and PSA, including variants or mutants thereof. In some embodiments, the multispecific antigen-binding module specifically binds to a first cell surface antigen and a second cell surface antigen. In some embodiments, the multispecific antigen-binding module specifically binds to CD19 and CD22. In some embodiments, the multispecific antigen-binding module specifically binds to CD19 and CD20. In some embodiments, the multispecific antigen-binding module specifically binds to a first peptide/MHC complex and a second peptide/MHC complex. In some embodiments, the multispecific antigen-binding module specifically binds a cell surface antigen and a peptide/MHC complex.

Chimeric Co-Stimulatory Receptor (CSR) Constructs

The ligand-specific chimeric co-stimulatory receptor (CSR) described herein specifically binds to a target ligand (such as a cell surface antigen or a peptide/MHC complex) and is capable of stimulating an immune cell on the surface of which it is functionally expressed upon target ligand binding. The CSR comprises a ligand-binding module that provides the ligand-binding specificity, a transmembrane module, and a co-stimulatory immune cell signaling module that allows for stimulating the immune cell. The CSR lacks a functional primary immune cell signaling sequence. In some embodiments, the CSR lacks any primary immune cell signaling sequence. In some embodiments, the CSR comprises a single polypeptide chain comprising the ligand-binding module, transmembrane module, and co-stimulatory signaling module. In some embodiments, the CSR comprises a first polypeptide chain and a second polypeptide chain, wherein the first and second polypeptide chains together form the ligand-binding module, transmembrane module, and co-stimulatory signaling module. In some embodiments, the first and second polypeptide chains are separate polypeptide chains, and the CSR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the expression of the CSR in the caTCR plus CSR immune cell is inducible. In some embodiments, the expression of the CSR in the caTCR plus CSR immune cell is inducible upon signaling through the caTCR.

Examples of co-stimulatory immune cell signaling domains for use in the CSRs of the invention include the cytoplasmic sequences of co-receptors of the T cell receptor (TCR), which can act in concert with a caTCR to initiate signal transduction following caTCR engagement, as well as any derivative or variant of these sequences and any synthetic sequence that has the same functional capability.

Under some circumstances, signals generated through the TCR alone are insufficient for full activation of the T cell and that a secondary or co-stimulatory signal is also required. Thus, in some embodiments, T cell activation is mediated by two distinct classes of intracellular signaling sequence: those that initiate antigen-dependent primary activation through the TCR (referred to herein as "primary T cell signaling sequences") and those that act in an antigen-independent manner to provide a secondary or co-stimulatory signal (referred to herein as "co-stimulatory T cell signaling sequences").

Primary immune cell signaling sequences that act in a stimulatory manner may contain signaling motifs which are known as immunoreceptor tyrosine-based activation motifs or ITAMs. Examples of ITAM-containing primary immune cell signaling sequences include those derived from TCRζ, FcRγ, FcRβ, CD37, CD36, CD3, CD5, CD22, CD79a, CD79b, and CD66d. A "functional" primary immune cell signaling sequence is a sequence that is capable of transducing an immune cell activation signal when operably coupled to an appropriate receptor. "Non-functional" primary immune cell signaling sequences, which may comprises fragments or variants of primary immune cell signaling sequences, are unable to transduce an immune cell activation signal. The CSRs described herein lack a functional primary immune cell signaling sequence, such as a functional signaling sequence comprising an ITAM. In some embodiments, the CSRs lack any primary immune cell signaling sequence.

The co-stimulatory immune cell signaling sequence can be a portion of the intracellular domain of a co-stimulatory molecule including, for example, CD27, CD28, 4-1BB (CD137), OX40, CD27, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the target ligand is a cell surface antigen. In some embodiments, the target ligand is a peptide/MHC complex. In some embodiments, the target ligand is the same as the target antigen of a caTCR expressed in the same immune cell. In some embodiments, the target ligand is different than the target antigen of a caTCR expressed in the same immune cell. In some embodiments, the target ligand is a molecule presented on the surface of a cell presenting the target antigen. For example, in some embodiments, the target antigen of the caTCR is a cancer-associated antigen presented on a cancer cell, and the target ligand is a ubiquitous molecule expressed on the surface of the cancer cell, such as an integrin. In some embodiments, the target ligand is a disease-associated ligand. In some embodiments, the target ligand is a cancer-associated ligand. In some embodiments, the cancer-associated ligand is, for example, CD19, CD20, CD22, CD47, IL4, GPC-3, ROR1, ROR2, BCMA, GPRC5D, or FCRL5. In some embodiments, the cancer-associated ligand is a peptide/NMC complex comprising a peptide derived from a protein including WT-1, AFP, HPV16-E7, NY-ESO-1, PRAME, EBV-LMP2A, and PSA. In some embodiments, the target ligand is a virus-associated ligand. In some embodiments, the target ligand is an immune checkpoint molecule. In some embodiments, the immune checkpoint molecule includes PD-L1, PD-L2, CD80, CD86, ICOSL, B7-H3, B7-H4, HVEM, 4-1BBL, OX40L, CD70, CD40, and GAL9. In some embodiments, the target ligand is an apoptotic molecule. In some embodiments, the apoptotic molecule includes FasL, FasR, TNFR1, and TNFR2.

In some embodiments, the ligand-binding module is an antibody moiety. In some embodiments, the antibody moiety is a Fab, a Fab', a (Fab')2, an Fv, or a single chain Fv (scFv). In some embodiments, the antibody moiety specifically binds a cell surface antigen including, without limitation, CD19, CD20, CD22, CD47, GPC-3, ROR1, ROR2, BCMA, GPRC5D, and FCRL5. In some embodiments, the antibody moiety specifically binds a peptide/NMC complex, wherein the peptide is derived from a protein including, without limitation, WT-1, AFP, HPV16-E7, NY-ESO-1, PRAME, EBV-LMP2A, and PSA. In some embodiments, the antibody moiety comprises the CDRs or variables domains ($V_H$ and/or $V_L$ domains) of an antibody moiety specific for CD19 (see, e.g., WO2017066136A2). In some embodiments, the antibody moiety comprises the CDRs or variables domains ($V_H$ and/or $V_L$ domains) of an antibody moiety specific for CD19 (e.g., $V_H$ domain comprising, consisting essentially of, or consisting of the amino acid sequence of SEQ ID NO: 58 and/or $V_L$ domain comprising, consisting essentially of, or consisting of the amino acid sequence of SEQ ID NO: 59, or CDRs contained therein). In some embodiments, the antibody moiety comprises the CDRs or variables domains ($V_H$ and/or $V_L$ domains) of an antibody moiety specific for CD20 (e.g., $V_H$ domain comprising, consisting essentially of, or consisting of the amino acid sequence of SEQ ID NO: 60 and/or $V_L$ domain comprising, consisting essentially of, or consisting of the amino acid sequence of SEQ ID NO: 61, or CDRs contained therein). In some embodiments, the antibody moiety comprises the CDRs or variables domains ($V_H$ and/or $V_L$ domains) of an antibody moiety specific for CD22 (see, e.g., U.S. Ser. No. 62/650,955 filed Mar. 30, 2018). In some embodiments, the antibody moiety comprises the CDRs or variables domains ($V_H$ and/or $V_L$ domains) of an antibody moiety specific for CD22 (e.g., $V_H$ domain comprising, consisting essentially of, or consisting of the amino acid sequence of SEQ ID NO: 101 and/or $V_L$ domain comprising, consisting essentially of, or consisting of the amino acid sequence of SEQ ID NO: 102, or CDRs contained therein). In some embodiments, the antibody moiety comprises the CDRs or variables domains ($V_H$ and/or $V_L$ domains) of an antibody moiety specific for GPC3 (see, e.g., U.S. Ser. No. 62/490,586 filed Apr. 26, 2017). In some embodiments, the antibody moiety comprises the CDRs or variables domains ($V_H$ and/or $V_L$ domains) of an antibody moiety specific for GPC3 (e.g., $V_H$ domain comprising, consisting essentially of, or consisting of the amino acid sequence of SEQ ID NO: 64 and/or $V_L$ domain comprising, consisting essentially of, or consisting of the amino acid sequence of SEQ ID NO: 65, or CDRs contained therein). In some embodiments, the antibody moiety comprises the CDRs or variables domains ($V_H$ and/or $V_L$ domains) of an antibody moiety specific for ROR1 (see, e.g., WO2016/187220 and WO2016/187216). In some embodiments, the antibody moiety comprises the CDRs or variables domains ($V_H$ and/or $V_L$ domains) of an antibody moiety specific for ROR2 (see, e.g., WO2016/142768). In some embodiments, the antibody moiety comprises the CDRs or variables domains ($V_H$ and/or $V_L$ domains) of an antibody moiety specific for BCMA (see, e.g., WO2016/090327 and WO2016/090320). In some embodiments, the antibody moiety comprises the CDRs or variables domains ($V_H$ and/or $V_L$ domains) of an antibody moiety specific for GPRC5D (see, e.g., WO2016/090329 and WO2016/090312). In some embodiments, the antibody moiety comprises the CDRs or variables domains ($V_H$ and/or $V_L$ domains) of an antibody moiety specific for FCRL5 (see, e.g., WO2016/090337). In some embodiments, the antibody moiety comprises the CDRs or variables domains ($V_H$ and/or $V_L$ domains) of an antibody moiety specific for WT-1 (see, e.g., WO2012/135854, WO2015/070078, and WO2015/070061). In some embodiments, the antibody moiety comprises the CDRs or variables domains ($V_H$ and/or $V_L$ domains) of an antibody moiety specific for AFP (see, e.g., WO2016/161390). In some embodiments, the antibody moiety comprises the CDRs or variables domains ($V_H$ and/or $V_L$ domains) of an antibody moiety specific for HPV16-E7 (see, e.g., WO2016/182957). In some embodiments, the antibody moiety comprises the CDRs or variables domains ($V_H$ and/or $V_L$ domains) of an antibody moiety specific for NY-ESO-1 (see, e.g., WO2016/210365). In some embodiments, the antibody moiety comprises the CDRs or variables domains ($V_H$ and/or $V_L$ domains) of an antibody moiety specific for PRAME (see, e.g., WO2016/191246). In some embodiments, the antibody moiety comprises the CDRs or variables domains ($V_H$ and/or $V_L$ domains) of an antibody moiety specific for EBV-LMP2A (see, e.g., WO2016/201124). In some embodiments, the antibody moiety comprises the CDRs or variables domains ($V_H$ and/or $V_L$ domains) of an antibody moiety specific for KRAS (see, e.g., WO2016/154047). In some embodiments, the antibody moiety comprises the CDRs or variables domains ($V_H$ and/or $V_L$ domains) of an antibody moiety specific for PSA (see, e.g., WO2017/015634).

In some embodiments, the ligand-binding module is (or is derived from) all or a portion of the extracellular domain of a receptor for the target ligand. In some embodiments, the receptor includes, for example, FasR, TNFR1, TNFR2, PD-1, CD28, CTLA-4, ICOS, BTLA, KIR, LAG-3, 4-1BB, OX40, CD27, and TIM-3.

In some embodiments, the transmembrane module comprises one or more transmembrane domains derived from, for example, CD28, CD3ε, CD3ζ, CD45, CD4, CD5, CD8, CD9, CD16, CD22, CD33, CD37, CD64, CD80, CD86, CD134, CD137, or CD154.

In some embodiments, the co-stimulatory signaling module comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the co-stimulatory signaling molecule comprises a fragment of CD28 comprising the amino acid sequence of SEQ ID NO: 51. In some embodiments, the co-stimulatory signaling molecule comprises a fragment of CD28 comprising the amino acid sequence of SEQ ID NO: 52. In some embodiments, the co-stimulatory signaling molecule comprises a fragment of 4-1BB comprising the amino acid sequence of SEQ ID NO: 53. In some embodiments, the co-stimulatory signaling molecule comprises a fragment of 4-1BB comprising the amino acid sequence of SEQ ID NO: 54. In some embodiments, the co-stimulatory signaling molecule comprises a fragment of CD8 comprising the amino acid sequence of SEQ ID NO: 57. In some embodiments, the co-stimulatory signaling molecule comprises a fragment of OX40 comprising the amino acid sequence of SEQ ID NO: 55. In some embodiments, the co-stimulatory signaling molecule comprises a fragment of OX40 comprising the amino acid sequence of SEQ ID NO: 56. In some embodiments, the co-stimulatory signaling molecule comprises a fragment of CD27 comprising the amino acid sequence of SEQ ID NO: 86 or 87. In some embodiments, the co-stimulatory signaling molecule comprises a fragment of CD30 comprising the amino acid sequence of SEQ ID NO: 88 or 89.

In some embodiments, the CSR further comprises a spacer module between any of the ligand-binding module, the transmembrane module, and the co-stimulatory signaling module. In some embodiments, the spacer module comprises one or more peptide linkers connecting two CSR modules. In some embodiments, the spacer module comprises one or more peptide linkers between about 5 to about 70 (such as about any of 5, 10, 15, 20, 25, 30, 35, 40, 45, 50, 55, 60, 65, or 70, including any ranges between these values) amino acids in length.

In some embodiments, the ligand-binding module (such as an antibody moiety) specifically binds to a target antigen with a) an affinity that is at least about 10 (including for example at least about any of 10, 20, 30, 40, 50, 75, 100, 200, 300, 400, 500, 750, 1000 or more) times its binding affinity for other molecules; or b) a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to other molecules. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

In some embodiments, the CSR described herein specifically binds to a target ligand (such as a cell surface antigen or a peptide/MHC complex), comprising a) a target ligand-binding domain (LBD); b) a transmembrane domain; and c) and a co-stimulatory signaling domain, wherein the CSR is capable of stimulating an immune cell on the surface of which it is functionally expressed upon target ligand binding. In some embodiments, the target ligand is a cell surface antigen. In some embodiments, the target ligand is a peptide/MHC complex. In some embodiments, the target ligand is the same as the target antigen of a caTCR expressed in the same immune cell. In some embodiments, the target ligand is different from the target antigen of a caTCR expressed in the same immune cell. In some embodiments, the target ligand is a disease-associated ligand. In some embodiments, the target ligand is a cancer-associated ligand. In some embodiments, the cancer-associated ligand is, for example, CD19, CD20, CD22, CD47, IL4, GPC-3, ROR1, ROR2, BCMA, GPRC5D, or FCRL5. In some embodiments, the cancer-associated ligand is a peptide/MHC complex comprising a peptide derived from a protein including WT-1, AFP, HPV16-E7, NY-ESO-1, PRAME, EBV-LMP2A, and PSA. In some embodiments, the target ligand is a virus-associated ligand. In some embodiments, the target ligand is an immune checkpoint molecule. In some embodiments, the immune checkpoint molecule includes PD-L1, PD-L2, CD80, CD86, ICOSL, B7-H3, B7-H4, HVEM, 4-1BBL, OX40L, CD70, CD40, and GAL9. In some embodiments, the target ligand is an apoptotic molecule. In some embodiments, the apoptotic molecule includes FasL, FasR, TNFR1, and TNFR2. In some embodiments, the ligand-binding domain is an antibody moiety. In some embodiments, the antibody moiety is a Fab, a Fab', a (Fab')2, an Fv, or a single chain Fv (scFv). In some embodiments, the ligand-binding domain is (or is derived from) all or a portion of the extracellular domain of a receptor for the target ligand. In some embodiments, the receptor includes, for example, FasR, TNFR1, TNFR2, PD-1, CD28, CTLA-4, ICOS, BTLA, KIR, LAG-3, 4-1BB, OX40, CD27, and TIM-3. In some embodiments, the transmembrane domain comprises a transmembrane domain derived from a transmembrane protein including, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the CSR comprises a fragment of a transmembrane protein (fTMP), wherein the fTMP comprises the CSR transmembrane domain. In some embodiments, the co-stimulatory signaling domain comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR comprises a fragment of an immune cell co-stimulatory molecule (fCSM), wherein the fCSM comprises the CSR transmembrane domain and CSR co-stimulatory signaling domain. In some embodiments, the CSR further comprises a spacer domain between any of the ligand-binding domain, the transmembrane domain, and the co-stimulatory signaling domain. In some embodiments, the spacer domain comprises a peptide linker connecting two CSR domains.

In some embodiments, the CSR described herein specifically binds to a target ligand, comprising a) a target ligand-binding domain; b) a transmembrane domain; and c) and a co-stimulatory signaling domain, wherein the target ligand is a cell surface antigen, and wherein the CSR is capable of stimulating an immune cell on the surface of which it is functionally expressed upon target ligand binding. In some embodiments, the target ligand is the same as the target antigen of a caTCR expressed in the same immune cell. In some embodiments, the target ligand is different from the target antigen of a caTCR expressed in the same immune cell. In some embodiments, the target ligand is a disease-associated ligand. In some embodiments, the target ligand is a cancer-associated ligand. In some embodiments, the cancer-associated ligand is, for example, CD19, CD20, CD22, CD47, IL4, GPC-3, ROR1, ROR2, BCMA, GPRC5D, or FCRL5. In some embodiments, the target ligand is a virus-associated ligand. In some embodiments, the target ligand is an immune checkpoint molecule. In some embodiments, the immune checkpoint molecule includes PD-L1, PD-L2, CD80, CD86, ICOSL, B7-H3, B7-H4, HVEM, 4-1BBL, OX40L, CD70, CD40, and GAL9. In some embodiments, the target ligand is an apoptotic molecule. In some embodiments, the apoptotic molecule includes FasL, FasR, TNFR1, and TNFR2. In some embodiments, the ligand-binding domain is an antibody moiety. In some embodiments, the antibody moiety is a Fab, a Fab', a (Fab')2, an Fv, or a single chain Fv (scFv). In some embodiments, the ligand-binding domain is (or is derived from) all or a portion of the extracellular domain of a receptor for the target ligand. In some embodiments, the receptor includes, for example, FasR, TNFR1, TNFR2, PD-1, CD28, CTLA-4, ICOS, BTLA, KIR, LAG-3, 4-1BB, OX40, CD27, and TIM-3. In some embodiments, the transmembrane domain comprises a transmembrane domain derived from a transmembrane protein including, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the CSR comprises a fragment of a transmembrane protein (fTMP), wherein the fTMP comprises the CSR transmembrane domain. In some embodiments, the co-stimulatory signaling domain comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR comprises a fragment of an immune cell co-stimulatory molecule (fCSM), wherein the fCSM comprises the CSR transmembrane domain and CSR co-stimulatory signaling domain. In some embodiments, the CSR further comprises a spacer domain between any of the ligand-binding domain, the transmembrane domain, and the co-stimulatory signaling domain. In some embodiments, the spacer domain comprises a peptide linker connecting two CSR domains.

In some embodiments, the CSR described herein specifically binds to a target ligand, comprising a) a target ligand-binding domain; b) a transmembrane domain; and c) and a co-stimulatory signaling domain, wherein the target ligand is a peptide/MHC complex, and wherein the CSR is capable of stimulating an immune cell on the surface of which it is functionally expressed upon target ligand binding. In some embodiments, the target ligand is the same as the target antigen of a caTCR expressed in the same immune cell. In some embodiments, the target ligand is different from the target antigen of a caTCR expressed in the same immune cell. In some embodiments, the target ligand is a disease-associated ligand. In some embodiments, the target ligand is a cancer-associated ligand. In some embodiments, the cancer-associated ligand is a peptide/MHC complex comprising a peptide derived from a protein including WT-1, AFP, HPV16-E7, NY-ESO-1, PRAME, EBV-LMP2A, and PSA. In some embodiments, the target ligand is a virus-associated ligand. In some embodiments, the ligand-binding domain is an antibody moiety. In some embodiments, the antibody moiety is a Fab, a Fab', a (Fab')2, an Fv, or a single chain Fv (scFv). In some embodiments, the transmembrane domain comprises a transmembrane domain derived from a trans-membrane protein including, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the CSR comprises a fragment of a transmembrane protein (fTMP), wherein the fTMP comprises the CSR transmembrane domain. In some embodiments, the co-stimulatory signaling domain comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR comprises a fragment of an immune cell co-stimulatory molecule (fCSM), wherein the fCSM comprises the CSR transmembrane domain and CSR co-stimulatory signaling domain. In some embodiments, the CSR further comprises a spacer domain between any of the ligand-binding domain, the transmembrane domain, and the co-stimulatory signaling domain. In some embodiments, the spacer domain comprises a peptide linker connecting two CSR domains.

In some embodiments, the CSR described herein specifically binds to a target ligand (such as a cell surface antigen or a peptide/MHC complex), comprising a) a target ligand-binding domain; b) a transmembrane domain; and c) and a co-stimulatory signaling domain, wherein the ligand-binding domain is an antibody moiety, and wherein the CSR is capable of stimulating an immune cell on the surface of which it is functionally expressed upon target ligand binding. In some embodiments, the target ligand is a cell surface antigen. In some embodiments, the target ligand is a peptide/MHC complex. In some embodiments, the target ligand is the same as the target antigen of a caTCR expressed in the same immune cell. In some embodiments, the target ligand is different from the target antigen of a caTCR expressed in the same immune cell. In some embodiments, the target ligand is a disease-associated ligand. In some embodiments, the target ligand is a cancer-associated ligand. In some embodiments, the cancer-associated ligand is, for example, CD19, CD20, CD22, CD47, IL4, GPC-3, ROR1, ROR2, BCMA, GPRC5D, or FCRL5. In some embodiments, the cancer-associated ligand is a peptide/MHC complex comprising a peptide derived from a protein including WT-1, AFP, HPV16-E7, NY-ESO-1, PRAME, EBV-LMP2A, and PSA. In some embodiments, the target ligand is a virus-associated ligand. In some embodiments, the target ligand is an immune checkpoint molecule. In some embodiments, the immune checkpoint molecule includes PD-L1, PD-L2, CD80, CD86, ICOSL, B7-H3, B7-H4, HVEM, 4-1BBL, OX40L, CD70, CD40, and GAL9. In some embodiments, the target ligand is an apoptotic molecule. In some embodiments, the apoptotic molecule includes FasL, FasR, TNFR1, and TNFR2. In some embodiments, the antibody moiety is a Fab, a Fab', a (Fab')2, an Fv, or a single chain Fv (scFv). In some embodiments, the transmembrane domain comprises a transmembrane domain derived from a transmembrane protein including, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the CSR comprises a fragment of a transmembrane protein (fTMP), wherein the fTMP comprises the CSR transmembrane domain. In some embodiments, the co-stimulatory signaling domain comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR comprises a fragment of an immune cell co-stimulatory molecule (fCSM), wherein the fCSM comprises the CSR transmembrane domain and CSR co-stimulatory signaling domain. In some embodiments, the CSR further comprises a spacer domain between any of the ligand-binding domain, the transmembrane domain, and the co-stimulatory signaling domain. In some embodiments, the spacer domain comprises a peptide linker connecting two CSR domains. In some embodiments, the CSR domains are selected according to any of the CSRs listed in Table 3.

TABLE 3

| CSR ID | Spacer following LBD (SEQ ID NO) | fTMP (SEQ ID NO) | fCSM (SEQ ID NO) | Full CSR domain (no LBD; SEQ ID NO) |
|---|---|---|---|---|
| 1 | 103 | — | 51 | 90 |
| 2 | 104 | 57 | 54 | 91 |
| 3 | 104 | — | 53 | 92 |
| 4 | 104 | 57 | 87 | 93 |
| 5 | 104 | — | 86 | 94 |
| 6 | 104 | 57 | 89 | 95 |

TABLE 3-continued

| CSR ID | Spacer following LBD (SEQ ID NO) | fTMP (SEQ ID NO) | fCSM (SEQ ID NO) | Full CSR domain (no LBD; SEQ ID NO) |
|---|---|---|---|---|
| 7 | 104 | — | 88 | 96 |
| 8 | 104 | 57 | 56 | 97 |
| 9 | 104 | — | 55 | 98 |

In some embodiments, the CSR comprises an fCSM of CD28. In some embodiments, the CSR comprises: a) a target ligand-binding domain; b) a CD8 transmembrane domain comprising the amino acid sequence of SEQ ID NO: 57; and c) a fragment of CD28 comprising the amino acid sequence of SEQ ID NO: 52. In some embodiments, the CSR comprises: a) a target ligand-binding domain; and b) a fragment of CD28 comprising the amino acid sequence of SEQ ID NO: 51. In some embodiments, the CSR comprises: a target ligand-binding domain and a CSR domain comprising the amino acid sequence of SEQ ID NO: 90.

In some embodiments, the CSR comprises an fCSM of 4-1BB. In some embodiments, the CSR comprises: a) a target ligand-binding domain; b) a CD8 transmembrane domain comprising the amino acid sequence of SEQ ID NO: 57; and c) a fragment of 4-1BB comprising the amino acid sequence of SEQ ID NO: 54. In some embodiments, the CSR comprises: a) a target ligand-binding domain; and b) a fragment of 4-1BB comprising the amino acid sequence of SEQ ID NO: 53. In some embodiments, the CSR comprises: a target ligand-binding domain and a CSR domain comprising the amino acid sequence of SEQ ID NO: 91 or 92.

In some embodiments, the CSR comprises an fCSM of CD27. In some embodiments, the CSR comprises: a) a target ligand-binding domain; b) a CD8 transmembrane domain comprising the amino acid sequence of SEQ ID NO: 57; and c) a fragment of CD27 comprising the amino acid sequence of SEQ ID NO: 87. In some embodiments, the CSR comprises: a) a target ligand-binding domain; and b) a fragment of CD27 comprising the amino acid sequence of SEQ ID NO: 86. In some embodiments, the CSR comprises: a target ligand-binding domain and a CSR domain comprising the amino acid sequence of SEQ ID NO: 93 or 94.

In some embodiments, the CSR comprises an fCSM of CD30. In some embodiments, the CSR comprises: a) a target ligand-binding domain; b) a CD8 transmembrane domain comprising the amino acid sequence of SEQ ID NO: 57; and c) a fragment of CD30 comprising the amino acid sequence of SEQ ID NO: 89. In some embodiments, the CSR comprises: a) a target ligand-binding domain; and b) a fragment of CD30 comprising the amino acid sequence of SEQ ID NO: 88. In some embodiments, the CSR comprises: a target ligand-binding domain and a CSR domain comprising the amino acid sequence of SEQ ID NO: 95 or 96.

In some embodiments, the CSR comprises an fCSM of OX40. In some embodiments, the CSR comprises: a) a target ligand-binding domain; b) a CD8 transmembrane domain comprising the amino acid sequence of SEQ ID NO: 57; and c) a fragment of OX40 comprising the amino acid sequence of SEQ ID NO: 56. In some embodiments, the CSR comprises: a) a target ligand-binding domain; and b) a fragment of OX40 comprising the amino acid sequence of SEQ ID NO: 55. In some embodiments, the CSR comprises: a target ligand-binding domain and a CSR domain comprising the amino acid sequence of SEQ ID NO: 97 or 98.

In some embodiments, the CSR described herein specifically binds to a target ligand (such as a cell surface antigen or a peptide/MHC complex), comprising a) a target ligand-binding domain; b) a transmembrane domain; and c) a co-stimulatory signaling domain, wherein the ligand-binding domain is (or is derived from) all or a portion of the extracellular domain of a receptor for the target ligand, and wherein the CSR is capable of stimulating an immune cell on the surface of which it is functionally expressed upon target ligand binding. In some embodiments, the target ligand is a cell surface antigen. In some embodiments, the target ligand is the same as the target antigen of a caTCR expressed in the same immune cell. In some embodiments, the target ligand is different from the target antigen of a caTCR expressed in the same immune cell. In some embodiments, the target ligand is a disease-associated ligand. In some embodiments, the target ligand is a cancer-associated ligand. In some embodiments, the cancer-associated ligand is, for example, CD19, CD20, CD22, CD47, IL4, GPC-3, ROR1, ROR2, BCMA, GPRC5D, or FCRL5. In some embodiments, the target ligand is an immune checkpoint molecule. In some embodiments, the immune checkpoint molecule includes PD-L1, PD-L2, CD80, CD86, ICOSL, B7-H3, B7-H4, HVEM, 4-1BBL, OX40L, CD70, CD40, and GAL9. In some embodiments, the target ligand is an apoptotic molecule. In some embodiments, the apoptotic molecule includes FasL, FasR, TNFR1, and TNFR2. In some embodiments, the target ligand receptor includes, for example, FasR, TNFR1, TNFR2, PD-1, CD28, CTLA-4, ICOS, BTLA, KIR, LAG-3, 4-1BB, OX40, CD27, and TIM-3. In some embodiments, the transmembrane domain comprises a transmembrane domain derived from, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the co-stimulatory signaling domain comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR further comprises a spacer domain between any of the ligand-binding domain, the transmembrane domain, and the co-stimulatory signaling domain. In some embodiments, the spacer domain comprises a peptide linker connecting two CSR domains.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; and b) a fragment of CD28 comprising, consisting essentially of, or consisting of the amino acid sequence of SEQ ID NO: 51 or 52. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the scFv comprises, consists essentially of, or consists of the amino acid sequence of SEQ ID NO: 77. In some embodiments, the fragment of CD28 comprises the amino acid sequence of SEQ ID NO: 51. In some embodiments, the CSR comprises the amino acid sequence of SEQ ID NO: 90. In some embodiments, the CSR comprises, from amino terminus to carboxy terminus, the scFv, a peptide linker comprising SEQ ID NO: 103, and the fragment of CD28. In some embodiments, the CSR comprises, consists essentially of, or consists of the amino acid sequence of SEQ ID NO: 80.

In some embodiments, the CSR described herein specifically binds to CD20, comprising a) an scFv comprising a $V_H$ domain having the amino acid sequence of SEQ ID NO: 60 and a $V_L$ domain having the amino acid sequence of SEQ ID NO: 61; and b) a fragment of CD28 comprising, consisting essentially of, or consisting of the amino acid sequence of SEQ ID NO: 51 or 52. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the scFv comprises, consists essentially of, or consists of the amino acid sequence of SEQ ID NO: 78. In some embodiments, the fragment of CD28 comprises the amino acid sequence of SEQ ID NO: 51. In some embodiments, the CSR comprises, from amino terminus to carboxy terminus, the scFv, a peptide linker comprising SEQ ID NO: 103, and the fragment of CD28. In some embodiments, the CSR comprises, consists essentially of, or consists of the amino acid sequence of SEQ ID NO: 81.

In some embodiments, the CSR described herein specifically binds to GPC3, comprising a) an scFv comprising a $V_H$ domain having the amino acid sequence of SEQ ID NO: 64 and a $V_L$ domain having the amino acid sequence of SEQ ID NO: 65; and b) a fragment of CD28 comprising, consisting essentially of, or consisting of the amino acid sequence of SEQ ID NO: 51 or 52. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the scFv comprises, consists essentially of, or consists of the amino acid sequence of SEQ ID NO: 79. In some embodiments, the fragment of CD28 comprises the amino acid sequence of SEQ ID NO: 51. In some embodiments, the CSR comprises, from amino terminus to carboxy terminus, the scFv, a peptide linker comprising SEQ ID NO: 103, and the fragment of CD28. In some embodiments, the CSR comprises, consists essentially of, or consists of the amino acid sequence of SEQ ID NO: 82.

In some embodiments, the CSR described herein specifically binds to CD20, comprising a) an scFv comprising a $V_H$ domain having the amino acid sequence of SEQ ID NO: 60 and a $V_L$ domain having the amino acid sequence of SEQ ID NO: 61; and b) a fragment of CD28 comprising, consisting essentially of, or consisting of the amino acid sequence of SEQ ID NO: 51 or 52. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the scFv comprises, consists essentially of, or consists of the amino acid sequence of SEQ ID NO: 78. In some embodiments, the fragment of CD28 comprises the amino acid sequence of SEQ ID NO: 51. In some embodiments, the CSR comprises, from amino terminus to carboxy terminus, the scFv, a peptide linker comprising SEQ ID NO: 103, and the fragment of CD28. In some embodiments, the CSR comprises, consists essentially of, or consists of the amino acid sequence of SEQ ID NO: 81.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; and b) a fragment of 4-1BB comprising, consisting essentially of, or consisting of the amino acid sequence of SEQ ID NO: 53 or 54. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the fragment of 4-1BB comprises the amino acid sequence of SEQ ID NO: 53. In some embodiments, the CSR comprises, from amino terminus to carboxy terminus, the scFv, a peptide linker comprising SEQ ID NO: 104, and the fragment of 4-1BB.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; b) a fragment of CD8 comprising, consisting essentially of, or consisting of the amino acid sequence of SEQ ID NO: 57; and c) a fragment of 4-1BB comprising, consisting essentially of, or consisting of the amino acid sequence of SEQ ID NO: 54. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the CSR comprises, from amino terminus to carboxy terminus, the scFv, a peptide linker comprising SEQ ID NO: 104, the fragment of CD8, and the fragment of 4-1BB.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; b) a fragment of CD8 comprising, consisting essentially of, or consisting of the amino acid sequence of SEQ ID NO: 57; and c) a fragment of OX40 comprising, consisting essentially of, or consisting of the amino acid sequence of SEQ ID NO: 57. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the CSR comprises, from amino terminus to carboxy terminus, the scFv, a peptide linker comprising SEQ ID NO: 104, the fragment of CD8, and the fragment of OX40.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; and b) a fragment of OX40 comprising, consisting essentially of, or consisting of the amino acid sequence of SEQ ID NO: 56 or 57. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the fragment of OX40 comprises the amino acid sequence of SEQ ID NO: 56. In some embodiments, the CSR comprises, from amino terminus to carboxy terminus, the scFv, a peptide linker comprising SEQ ID NO: 104, and the fragment of OX40.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; b) a fragment of CD8 comprising, consisting essentially of, or consisting of the amino acid sequence of SEQ ID NO: 57; and c) a fragment of CD27 comprising, consisting essentially of, or consisting of the amino acid sequence of SEQ ID NO: 87. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the CSR comprises, from amino terminus to carboxy terminus, the scFv, a peptide linker comprising SEQ ID NO: 104, the fragment of CD8, and the fragment of CD27.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; and b) a fragment of CD27 comprising, consisting essentially of, or consisting of the amino acid sequence of SEQ ID NO: 86 or 87. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the fragment of CD27 comprises the amino acid sequence of SEQ ID NO: 86. In some embodiments, the CSR comprises, from amino terminus to carboxy terminus, the scFv, a peptide linker comprising SEQ ID NO: 104, and the fragment of CD27.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; b) a fragment of CD8 comprising, consisting essentially of, or consisting of the amino acid sequence of SEQ ID NO: 57; and c) a fragment of CD30 comprising, consisting essentially of, or consisting of the amino acid sequence of SEQ ID NO: 89. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the CSR comprises, from amino terminus to carboxy terminus, the scFv, a peptide linker comprising SEQ ID NO: 104, the fragment of CD8, and the fragment of CD30.

In some embodiments, the CSR described herein specifically binds to CD19, comprising a) an scFv comprising a $V_H$ domain having the amino acid sequence of SEQ ID NO: 58 and a $V_L$ domain having the amino acid sequence of SEQ ID NO: 59; and b) a fragment of CD30 comprising, consisting essentially of, or consisting of the amino acid sequence of SEQ ID NO: 88 or 89. In some embodiments, the scFv comprises, from amino terminus to carboxy terminus, the $V_L$ domain, a peptide linker comprising the amino acid sequence of SEQ ID NO: 76, and the $V_H$ domain. In some embodiments, the fragment of CD30 comprises the amino acid sequence of SEQ ID NO: 88. In some embodiments, the CSR comprises, from amino terminus to carboxy terminus, the scFv, a peptide linker comprising SEQ ID NO: 104, and the fragment of CD30.

In some embodiments, the expression of the CSR in the caTCR plus CSR immune cell is inducible. In some embodiments, the caTCR plus CSR immune cell comprises a nucleic acid sequence encoding the CSR operably linked to an inducible promoter, including any of the inducible promoters described herein. In some embodiments, the expression of the CSR in the caTCR plus CSR immune cell is inducible upon signaling through the caTCR. In some such embodiments, the caTCR plus CSR immune cell comprises a nucleic acid sequence encoding the CSR operably linked to a promoter or regulatory element responsive to signaling through the caTCR. In some embodiments, the nucleic acid sequence encoding the CSR is operably linked to a nuclear-factor of the activated T-cell (NFAT)-derived promoter. In some embodiments, the NFAT-derived promoter is an NFAT-derived minimal promoter (see for example Durand, D. et. al., *Molec. Cell. Biol.* 8, 1715-1724 (1988); Clipstone, N A, Crabtree, G R. *Nature.* 1992 357(6380): 695-7; Chmielewski, M., et al. *Cancer research* 71.17 (2011): 5697-5706; and Zhang, L., et al. *Molecular therapy* 19.4 (2011): 751-759). In some embodiments, the NFAT-derived promoter comprises the nucleotide sequence of SEQ ID NO: 85. In some embodiments, the nucleic acid sequence encoding the CSR is operably linked to an IL-2 promoter.

Secretory Secondary Effector (SSE) Constructs

In some embodiments, the caTCR plus CSR immune cell (such as a T cell) is capable of secreting a secretory secondary effector (SSE). Such an immune cell is also referred herein as a "caTCR plus CSR and SSE immune cell." The SSE enhances the immune response mediated by a caTCR plus CSR and SSE immune cell in which it is functionally expressed and secreted from. In some embodiments, the SSE is capable of redirecting other immune cells (such as bystander T cells or NK cells) to target disease cells (such as target cancer cells). In some embodiments, the SSE is a multispecific antibody (such as a bispecific antibody) targeting an immune cell (such as a T cell or NK cell) and a disease cell (such as a cancer cell). In some embodiments, the SSE protects the caTCR plus CSR and SSE immune cell from an immunosuppressive environment, such as an immunosuppressive tumor environment. In some embodiments, the SSE provides autocrine activation of stimulatory receptors on the caTCR plus CSR and SSE immune cell. In some embodiments, the SSE is an exogenous growth factor or stimulatory cytokine. In some embodiments, the expression of the SSE in the caTCR plus CSR and SSE immune cell is inducible. In some embodiments, the expression of the SSE in the caTCR plus CSR and SSE immune cell is inducible upon signaling through the caTCR.

In some embodiments, the SSE is a multispecific antibody (such as a bispecific antibody) targeting a T cell and a disease cell. In some embodiments, the SSE comprises an antibody moiety that specifically binds to a surface antigen of a T cell. In some embodiments, the T cell surface antigen is CD3. In some embodiments, the SSE comprises an antibody moiety that specifically binds to a disease-associated antigen (such as a cancer-associated antigen). In some embodiments, the disease-associated antigen is a surface antigen of a disease cell (such as a cancer cell). In some embodiments, the disease-associated antigen is glypican-3 (GPC3), CD47, mucin-16 (MUC16), CD19, CD20, CD22, EpCAM, EGFR, HER2, CEA, PSMA, AFP, PSA, BCMA, FCRL5, NY-ESO, HPV16, or FoxP3, including variants or mutants thereof. In some embodiments, the SSE is a multispecific antibody selected from the group consisting of a tandem scFv, a diabody (Db), a single chain diabody (scDb), a dual-affinity retargeting (DART) antibody, and a dual variable domain (DVD) antibody. In some embodiments, the SSE is a bispecific antibody. In some embodiments, the SSE is a tandem scFv comprising a first scFv targeting the T cell surface antigen and a second scFv targeting the disease-associated antigen.

In some embodiments, the SSE is a tandem scFv comprising a first scFv targeting CD3 and a second scFv targeting a disease-associated antigen. In some embodiments, the disease-associated antigen is GPC3, CD47, MUC16, CD19, CD20, CD22, EpCAM, EGFR, HER2, CEA, PSMA, AFP, PSA, BCMA, FCRL5, NY-ESO, HPV16, or FoxP3, including variants or mutants thereof.

In some embodiments, the SSE is a tandem scFv comprising a first scFv targeting CD3 and a second scFv targeting GPC3. In some embodiments, the second scFv comprises a $V_H$ domain comprising, consisting essentially of, or consisting of the amino acid sequence of SEQ ID NO:

64 and a $V_L$ domain comprising, consisting essentially of, or consisting of the amino acid sequence of SEQ ID NO: 65. In some embodiments, the $V_H$ domain is amino-terminal to the $V_L$ domain. In some embodiments, the $V_L$ domain is amino-terminal to the $V_H$ domain. In some embodiments, the second scFv comprises, consists essentially of, or consists of the amino acid sequence of SEQ ID NO: 79. In some embodiments, the first scFv is amino-terminal to the second scFv. In some embodiments, the second scFv is amino-terminal to the first scFv. In some embodiments, the SSE comprises, consists essentially of, or consists of the amino acid sequence of SEQ ID NO: 105.

In some embodiments, the SSE is a tandem scFv comprising a first scFv targeting CD3 and a second scFv targeting CD47. In some embodiments, the SSE is a tandem scFv comprising a first scFv targeting CD3 and a second scFv targeting MUC16.

In some embodiments, the SSE is a multispecific antibody (such as a bispecific antibody) targeting an NK cell and a disease-associated antigen (such as a cancer-associated antigen). In some embodiments, the SSE comprises an antibody moiety that specifically binds to a surface antigen of an NK cell. In some embodiments, the NK cell surface antigen is CD16a. In some embodiments, the SSE comprises an antibody moiety that specifically binds to a disease-associated antigen (such as a cancer-associated antigen). In some embodiments, the disease-associated antigen is a surface antigen of a disease cell (such as a cancer cell). In some embodiments, the disease-associated antigen is GPC3, CD47, MUC16, CD19, CD20, CD22, EpCAM, EGFR, HER2, CEA, PSMA, AFP, PSA, BCMA, FCRL5, NY-ESO, HPV16, or FoxP3, including variants or mutants thereof. In some embodiments, the SSE is a multispecific antibody selected from the group consisting of a tandem scFv, a diabody (Db), a single chain diabody (scDb), a dual-affinity retargeting (DART) antibody, and a dual variable domain (DVD) antibody. In some embodiments, the SSE is a bispecific antibody. In some embodiments, the SSE is a tandem scFv comprising a first scFv targeting the NK cell surface antigen and a second scFv targeting the disease-associated antigen.

In some embodiments, the SSE is a tandem scFv comprising a first scFv targeting CD16a and a second scFv targeting a disease-associated antigen. In some embodiments, the disease-associated antigen is GPC3, CD47, MUC16, CD19, CD20, CD22, EpCAM, EGFR, HER2, CEA, PSMA, AFP, PSA, BCMA, FCRL5, NY-ESO, HPV16, or FoxP3, including variants or mutants thereof.

In some embodiments, the SSE is a tandem scFv comprising a first scFv targeting CD16a and a second scFv targeting GPC3. In some embodiments, the SSE is a tandem scFv comprising a first scFv targeting CD16a and a second scFv targeting CD47. In some embodiments, the SSE is a tandem scFv comprising a first scFv targeting CD16a and a second scFv targeting MUC16.

In some embodiments, the SSEs described herein comprises an antibody moiety that specifically binds to a disease-associated antigen, wherein the antibody moiety comprises the CDRs or variables domains ($V_H$ and/or $V_L$ domains) of an antibody moiety specific for the disease-associated antigen. In some embodiments, the antibody moiety comprises the CDRs or variables domains ($V_H$ and/or $V_L$ domains) of an antibody moiety specific for CD19 (see, e.g., WO2017066136A2). In some embodiments, the antibody moiety comprises the CDRs or variables domains ($V_H$ and/or $V_L$ domains) of an antibody moiety specific for CD19 (e.g., $V_H$ domain comprising, consisting essentially of, or consisting of the amino acid sequence of SEQ ID NO: 58 and/or $V_L$ domain comprising, consisting essentially of, or consisting of the amino acid sequence of SEQ ID NO: 59, or CDRs contained therein). In some embodiments, the antibody moiety comprises the CDRs or variables domains ($V_H$ and/or $V_L$ domains) of an antibody moiety specific for CD20 (e.g., $V_H$ domain comprising, consisting essentially of, or consisting of the amino acid sequence of SEQ ID NO: 60 and/or $V_L$ domain comprising, consisting essentially of, or consisting of the amino acid sequence of SEQ ID NO: 61, or CDRs contained therein). In some embodiments, the antibody moiety comprises the CDRs or variables domains ($V_H$ and/or $V_L$ domains) of an antibody moiety specific for CD22 (see, e.g., U.S. Ser. No. 62/650,955 filed Mar. 30, 2018, the contents of which are incorporated herein by reference in their entirety). In some embodiments, the antibody moiety comprises the CDRs or variables domains ($V_H$ and/or $V_L$ domains) of an antibody moiety specific for CD22 (e.g., $V_H$ domain comprising, consisting essentially of, or consisting of the amino acid sequence of SEQ ID NO: 101 and/or $V_L$ domain comprising, consisting essentially of, or consisting of the amino acid sequence of SEQ ID NO: 102, or CDRs contained therein). In some embodiments, the antibody moiety comprises the CDRs or variables domains ($V_H$ and/or $V_L$ domains) of an antibody moiety specific for GPC3 (see, e.g., U.S. Ser. No. 62/490,586 filed Apr. 26, 2017, the contents of which are incorporated herein by reference in their entirety). In some embodiments, the antibody moiety comprises the CDRs or variables domains ($V_H$ and/or $V_L$ domains) of an antibody moiety specific for GPC3 (e.g., $V_H$ domain comprising, consisting essentially of, or consisting of the amino acid sequence of SEQ ID NO: 64 and/or $V_L$ domain comprising, consisting essentially of, or consisting of the amino acid sequence of SEQ ID NO: 65, or CDRs contained therein). In some embodiments, the antibody moiety comprises the CDRs or variables domains ($V_H$ and/or $V_L$ domains) of an antibody moiety specific for ROR1 (see, e.g., WO2016/187220 and WO2016/187216). In some embodiments, the antibody moiety comprises the CDRs or variables domains ($V_H$ and/or $V_L$ domains) of an antibody moiety specific for ROR2 (see, e.g., WO2016/142768). In some embodiments, the antibody moiety comprises the CDRs or variables domains ($V_H$ and/or $V_L$ domains) of an antibody moiety specific for BCMA (see, e.g., WO2016/090327 and WO2016/090320). In some embodiments, the antibody moiety comprises the CDRs or variables domains ($V_H$ and/or $V_L$ domains) of an antibody moiety specific for GPRC5D (see, e.g., WO2016/090329 and WO2016/090312). In some embodiments, the antibody moiety comprises the CDRs or variables domains ($V_H$ and/or $V_L$ domains) of an antibody moiety specific for FCRL5 (see, e.g., WO2016/090337). In some embodiments, the antibody moiety comprises the CDRs or variables domains ($V_H$ and/or $V_L$ domains) of an antibody moiety specific for WT-1 (see, e.g., WO2012/135854, WO2015/070078, and WO2015/070061). In some embodiments, the antibody moiety comprises the CDRs or variables domains ($V_H$ and/or $V_L$ domains) of an antibody moiety specific for AFP (see, e.g., WO2016/161390). In some embodiments, the antibody moiety comprises the CDRs or variables domains ($V_H$ and/or $V_L$ domains) of an antibody moiety specific for HPV16-E7 (see, e.g., WO2016/182957). In some embodiments, the antibody moiety comprises the CDRs or variables domains ($V_H$ and/or $V_L$ domains) of an antibody moiety specific for NY-ESO-1 (see, e.g., WO2016/210365). In some embodiments, the antibody moiety comprises the CDRs or variables domains ($V_H$ and/or $V_L$ domains) of an antibody moiety specific for PRAME (see, e.g., WO2016/191246). In some embodiments, the antibody moiety comprises the CDRs or variables domains ($V_H$ and/or $V_L$ domains) of an antibody moiety specific for EBV-LMP2A (see, e.g., WO2016/201124). In some embodiments, the antibody moiety comprises the CDRs or variables domains ($V_H$ and/or $V_L$ domains) of an antibody moiety specific for KRAS (see, e.g., WO2016/154047). In some embodiments, the antibody moiety comprises the CDRs or variables domains ($V_H$ and/or $V_L$ domains) of an antibody moiety specific for PSA (see, e.g., WO2017/015634). In some embodiments, the antibody moiety is an scFv. In some embodiments, the SSE is a tandem scFv comprising a) a first scFv that specifically binds to a surface antigen of a T cell (such as CD3) or an NK cell (such as CD16a) and b) the antibody moiety, wherein the antibody moiety is a second scFv. In some embodiments, the SSE comprises the first and second scFvs connected by a peptide linker. In some embodiments, the first scFv is amino-terminal to the second scFv. In some embodiments, the second scFv is amino-terminal to the first scFv.

In some embodiments, the SSE is a multispecific antibody (such as a bispecific antibody) targeting one or more soluble immunosuppressive agents. Such an SSE can act as a trap to sequester the soluble immunosuppressive agents from their targets, thereby reducing their immunosuppressive effects. In some embodiments, the SSE comprises one or more antibody moieties that specifically bind to one or more soluble immunosuppressive agents. In some embodiments, the immunosuppressive agents are immunosuppressive cytokines. In some embodiments, the immunosuppressive cytokines include TGF-β family members (such as TGF-β1 to 4), IL-4, and IL-10, including variants or mutants thereof. In some embodiments, the SSE is a multispecific antibody selected from the group consisting of a tandem scFv, a diabody (Db), a single chain diabody (scDb), a dual-affinity retargeting (DART) antibody, and a dual variable domain (DVD) antibody. In some embodiments, the SSE is a bispecific antibody. For example, in some embodiments, the SSE is a tandem scFv comprising a first scFv targeting a first immunosuppressive cytokine (such as TGFβ) and a second scFv targeting a second immunosuppressive cytokine (such as IL-4).

In some embodiments, the SSE is an antibody moiety targeting an immune checkpoint molecule. In some embodiments, the SSE is an antagonist of an inhibitory immune checkpoint molecule. In some embodiments, the inhibitory immune checkpoint molecule is selected from the group consisting of PD-1, PD-L1, CTLA-4, HVEM, BTLA, KIR, LAG-3, TIM-3, and A2aR. In some embodiments, the SSE is an agonist of a stimulatory immune checkpoint molecule. In some embodiments, the stimulatory immune checkpoint molecule is selected from the group consisting of CD28, ICOS, 4-1BB, OX40, CD27, and CD40. In some embodiments, the antibody moiety is a full-length antibody, a Fab, a Fab', a (Fab')2, an Fv, or a single chain Fv (scFv). In some embodiments, the antibody moiety is an scFv.

In some embodiments, the SSE is an antagonistic antibody moiety targeting PD-1. In some embodiments, the antibody moiety comprises the CDRs or variables domains ($V_H$ and/or $V_L$ domains) of an antagonistic antibody moiety specific for PD-1 (see, e.g., WO2016/210129). In some embodiments, the antagonistic antibody moiety is a full-length antibody, a Fab, a Fab', a (Fab')2, an Fv, or a single chain Fv (scFv). In some embodiments, the antagonistic antibody moiety is an scFv.

In some embodiments, the SSE is an antagonistic antibody moiety targeting CD47. In some embodiments, the antagonistic antibody moiety comprises the CDRs or variables domains ($V_H$ and/or $V_L$ domains) of an antagonistic antibody moiety specific for CD47 (e.g., $V_H$ domain comprising, consisting essentially of, or consisting of the amino acid sequence of SEQ ID NO: 66 and/or $V_L$ domain comprising, consisting essentially of, or consisting of the amino acid sequence of SEQ ID NO: 67, or CDRs contained therein). In some embodiments, the antagonistic antibody moiety is a full-length antibody, a Fab, a Fab', a (Fab')2, an Fv, or a single chain Fv (scFv). In some embodiments, the antagonistic antibody moiety is an scFv.

In some embodiments, the SSE comprises an antibody moiety that binds to a target antigen with a) an affinity that is at least about 10 (including for example at least about any of 10, 20, 30, 40, 50, 75, 100, 200, 300, 400, 500, 750, 1000 or more) times its binding affinity for other molecules; or b) a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to other molecules. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

In some embodiments, the SSE is a soluble molecule that specifically binds a ligand of an immunosuppressive receptor. In some embodiments, the SSE comprises a ligand-binding domain derived from the extracellular domain of the immunosuppressive receptor. In some embodiments, the ligand-binding domain is a portion of the extracellular domain of the receptor. In some embodiments, the immunosuppressive receptor is selected from the group consisting of FasR, TNFR1, TNFR2, SIRPα, PD-1, CD28, CTLA-4, ICOS, BTLA, KIR, LAG-3, 4-1BB, OX40, CD27, CD40, and TIM-3.

In some embodiments, the SSE is a soluble molecule that specifically binds to and antagonizes an immunosuppressive receptor. In some embodiments, the SSE comprises a receptor-binding domain derived from the extracellular domain of a ligand for the immunosuppressive receptor. In some embodiments, the receptor-binding domain is a portion of the extracellular domain of the ligand. In some embodiments, the ligand is selected from the group consisting of FasL, PD-L1, PD-L2, CD47, CD80, CD86, ICOSL, HVEM, 4-1BBL, OX40L, CD70, CD40L, and GAL9.

In some embodiments, the SSE is an exogenous stimulatory cytokine. An exogenous cytokine described herein is a cytokine expressed from an exogenous gene. In some embodiments, the exogenous stimulatory cytokine is an IL-12 family member. In some embodiments, the IL-12 family member is IL-12, IL-23, IL-27, or IL-35. In some embodiments, the exogenous stimulatory cytokine is IL-2, IL-15, IL-18, or IL-21. In some embodiments, the exogenous stimulatory cytokine is capable of providing autocrine activation of receptors for the cytokine on the caTCR plus CSR and SSE immune cell.

In some embodiments, the expression of the SSE in the caTCR plus CSR and SSE immune cell is inducible. In some embodiments, the caTCR plus CSR and SSE immune cell comprises a nucleic acid sequence encoding the SSE operably linked to an inducible promoter, including any of the inducible promoters described herein. In some embodiments, the expression of the SSE in the caTCR plus CSR and SSE immune cell is inducible upon signaling through the caTCR. In some such embodiments, the caTCR plus CSR and SSE immune cell comprises a nucleic acid sequence encoding the SSE operably linked to a promoter or regulatory element responsive to signaling through the caTCR. In some embodiments, the nucleic acid sequence encoding the SSE is operably linked to a nuclear-factor of the activated T-cell (NFAT)-derived promoter. In some embodiments, the NFAT-derived promoter is an NFAT-derived minimal promoter (see for example Durand, D. et. al., *Molec. Cell. Biol.* 8, 1715-1724 (1988); Clipstone, N A, Crabtree, G R. Nature. 1992 357(6380): 695-7; Chmielewski, M., et al. *Cancer research* 71.17 (2011): 5697-5706; and Zhang, L., et al. *Molecular therapy* 19.4 (2011): 751-759). In some embodiments, the NFAT-derived promoter comprises the nucleotide sequence of SEQ ID NO: 85. In some embodiments, the nucleic acid sequence encoding the SSE is operably linked to an IL-2 promoter.

Nucleic Acids

Nucleic acid molecules encoding the caTCRs, CSRs and/or SSEs described herein are also contemplated. In some embodiments, according to any of the caTCRs, CSRs and SSEs described herein, there is provided a nucleic acid (or a set of nucleic acids) encoding the caTCR, CSR and/or SSE.

The present invention also provides vectors in which a nucleic acid of the present invention is inserted.

In brief summary, the expression of a caTCR and/or CSR and/or SSE described herein by a nucleic acid encoding the caTCR and/or CSR and/or SSE can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to, a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405.

An exemplary inducible promoter system for use in the present invention is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli*. (See, Brown et al., Cell 49:603-612 (1987). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

Another exemplary inducible promoter system for use in the present invention is the nuclear-factor of the activated T-cell (NFAT) system. The NFAT family of transcription factors are important regulators of T cell activation. NFAT response elements are found, for example, in the IL-2 promoter (see for example Durand, D. et. al., *Molec. Cell. Biol.* 8, 1715-1724 (1988); Clipstone, N A, Crabtree, G R. *Nature.* 1992 357(6380): 695-7; Chmielewski, M., et al. *Cancer research* 71.17 (2011): 5697-5706; and Zhang, L., et al. *Molecular therapy* 19.4 (2011): 751-759). In some embodiments, an inducible promoter described herein comprises one or more (such as 2, 3, 4, 5, 6, or more) NFAT response elements. In some embodiments, the inducible promoter comprises 6 NFAT response elements, for example, comprising the nucleotide sequence of SEQ ID NO: 83. In some embodiments, an inducible promoter described herein comprises one or more (such as 2, 3, 4, 5, 6, or more) NFAT response elements linked to a minimal promoter, such as a minimal TA promoter. In some embodiments, the minimal TA promoter comprises the nucleotide sequence of SEQ ID NO: 84. In some embodiments, the inducible promoter comprises the nucleotide sequence of SEQ ID NO: 85.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a caTCR and/or a CSR according to any of the caTCRs, CSRs and SSEs described herein. In some embodiments, the nucleic acid comprises one or more nucleic acid sequences encoding all of the polypeptide chains of the caTCR. In some embodiments, the nucleic acid comprises one or more nucleic acid sequences encoding all of the polypeptide chains of the CSR. In some embodiments, the nucleic acid comprises one or more nucleic acid sequences encoding all of the polypeptide chains of the caTCR and the CSR. In some embodiments, each of the one or more nucleic acid sequences is contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

For example, in some embodiments, the caTCR is a dimer comprising a first caTCR polypeptide chain and a second caTCR polypeptide chain and the CSR is a monomer comprising a single CSR polypeptide chain, and the nucleic acid comprises a first nucleic acid sequence encoding the first caTCR polypeptide chain, a second nucleic acid encoding the second caTCR chain, and a third nucleic acid sequence encoding the CSR polypeptide chain. In some embodiments, the first nucleic acid sequence is contained in a first vector, the second nucleic acid sequence is contained in a second vector, and the third nucleic acid sequence is contained in a third vector. In some embodiments, the first and second nucleic acid sequences are contained in a first vector, and the third nucleic acid sequence is contained in a second vector. In some embodiments, the first and third nucleic acid sequences are contained in a first vector, and the second nucleic acid sequence is contained in a second vector. In some embodiments, the second and third nucleic acid sequences are contained in a first vector, and the first nucleic acid sequence is contained in a second vector. In some embodiments, the first, second, and third nucleic acid sequences are contained in the same vector. In some embodiments, the first nucleic acid sequence is under the control of a first promoter, the second nucleic acid sequence is under the control of a second promoter, and the third nucleic acid sequence is under the control of a third promoter. In some embodiments, some or all of the first, second, and third promoters have the same sequence. In some embodiments, some or all of the first, second, and third promoters have different sequences. In some embodiments, some or all of the first, second, and third nucleic acid sequences are expressed as a single transcript under the control of a single promoter in a multicistronic vector. See for example Kim, J H, et al., PLoS One 6(4):e18556, 2011. In some embodiments, one or more of the promoters are inducible. In some embodiments, the third nucleic acid sequence encoding the CSR polypeptide chain is operably linked to an inducible promoter. In some embodiments, the inducible promoter comprises one or more elements responsive to immune cell activation, such as NFAT response elements.

In some embodiments, some or all of the first, second, and third nucleic acid sequences have similar (such as substantially or about the same) expression levels in a host cell (such as a T cell). In some embodiments, some of the first, second, and third nucleic acid sequences have expression levels in a host cell (such as a T cell) that differ by at least about two (such as at least about any of 2, 3, 4, 5, or more) times. Expression can be determined at the mRNA or protein level. The level of mRNA expression can be determined by measuring the amount of mRNA transcribed from the nucleic acid using various well-known methods, including Northern blotting, quantitative RT-PCR, microarray analysis and the like. The level of protein expression can be measured by known methods including immunocytochemical staining, enzyme-linked immunosorbent assay (ELISA), western blot analysis, luminescent assays, mass spectrometry, high performance liquid chromatography, high-pressure liquid chromatography-tandem mass spectrometry, and the like.

It is to be understood that the features of the embodiments described herein can be adapted and combined to encompass embodiments comprising any number of nucleic acid sequences, e.g., where the nucleic acid encoding the caTCR and/or CSR and/or SSE comprises five or more nucleic acid sequences (e.g., where the caTCR and SSE each comprises 2 or more distinct polypeptide chains).

Thus, in some embodiments, there is provided nucleic acid encoding a) a dimeric caTCR comprising a first caTCR polypeptide chain and a second caTCR polypeptide chain according to any of the caTCRs described herein, the nucleic acid comprising i) a first caTCR nucleic acid sequence encoding the first caTCR polypeptide chain, and ii) a second caTCR nucleic acid sequence encoding the second caTCR polypeptide chain; and b) a monomeric CSR comprising a single CSR polypeptide chain according to any of the CSRs described herein, the nucleic acid further comprising a CSR nucleic acid sequence encoding the CSR polypeptide chain. In some embodiments, the first caTCR nucleic acid sequence is contained in a first vector (such as a lentiviral vector), the second caTCR nucleic acid sequence is contained in a second vector (such as a lentiviral vector), and the CSR nucleic acid sequence is contained in a third vector (such as a lentiviral vector). In some embodiments, some or all of the first and second caTCR nucleic acid sequences and CSR nucleic acid sequence are contained in the same vector (such as a lentiviral vector). In some embodiments, each of the first and second caTCR nucleic acid sequences and CSR nucleic acid sequence are, individually, operably linked to a promoter. In some embodiments, some or all of the promoters have the same sequence. In some embodiments, some or all of the promoters have different sequences. In some embodiments, some or all of the promoters are inducible. In some embodiments, the CSR nucleic acid sequence is operably linked to an inducible promoter. In some embodiments, the inducible promoter comprises one or more elements responsive to immune cell activation. In some embodiments, the CSR nucleic acid sequence is operably linked to an NFAT-derived promoter. In some embodiments, some or all of the vectors are viral vectors (such as lentiviral vectors).

In some embodiments, there is provided a) a first vector (such as a lentiviral vector) comprising nucleic acid encoding a dimeric caTCR comprising a first caTCR polypeptide chain and a second caTCR polypeptide chain according to any of the caTCRs described herein comprising i) a first promoter operably linked to a first caTCR nucleic acid sequence encoding the first caTCR polypeptide chain; and ii) a second promoter operably linked to a second caTCR nucleic acid sequence encoding the second caTCR polypeptide chain; and b) a second vector (such as a lentiviral vector) comprising nucleic acid encoding a monomeric CSR comprising a CSR polypeptide chain according to any of the CSRs described herein comprising a third promoter operably linked to a CSR nucleic acid sequence encoding the CSR polypeptide chain. In some embodiments, some or all of the promoters have the same sequence. In some embodiments, some or all of the promoters have different sequences. In some embodiments, some or all of the promoters are inducible. In some embodiments, the first and/or second vectors are viral vectors (such as lentiviral vectors).

In some embodiments, there is provided a) a first vector (such as a lentiviral vector) comprising nucleic acid encoding a dimeric caTCR comprising a first caTCR polypeptide chain and a second caTCR polypeptide chain according to any of the caTCRs described herein comprising i) a first caTCR nucleic acid sequence encoding the first caTCR polypeptide chain; and ii) a second caTCR nucleic acid sequence encoding the second caTCR polypeptide chain, wherein the first and second caTCR nucleic acid sequences are under the control of a first promoter; and b) a second vector (such as a lentiviral vector) comprising nucleic acid encoding a monomeric CSR comprising a CSR polypeptide chain according to any of the CSRs described herein comprising a second promoter operably linked to a CSR nucleic acid sequence encoding the CSR polypeptide chain. In some embodiments, the first promoter is operably linked to the 5' end of the first caTCR nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of first caTCR nucleic acid sequence to the 5' end of the second caTCR nucleic acid sequence, wherein the first caTCR nucleic acid sequence and the second caTCR nucleic acid sequence are transcribed as a single RNA under the control of the first promoter. In some embodiments, the first promoter is operably linked to the 5' end of the second caTCR nucleic acid sequence, and there is nucleic acid linker selected from the group consisting of an internal ribosomal entry site (IRES) and a nucleic acid encoding a self-cleaving 2A peptide (such as P2A, T2A, E2A, or F2A) linking the 3' end of second caTCR nucleic acid sequence to the 5' end of the first caTCR nucleic acid sequence, wherein the first caTCR nucleic acid sequence and the second caTCR nucleic acid sequence are transcribed as a single RNA under the control of the first promoter. In some embodiments, the first and/or second promoters are inducible. In some embodiments, the first and/or second vectors are viral vectors (such as lentiviral vectors). It is to be appreciated that embodiments where any of the nucleic acid sequences are swapped are also contemplated, such as where the first or second caTCR nucleic acid sequence is swapped with the CSR nucleic acid sequence.

In some embodiments, there is provided a vector (such as a viral vector, e.g., a lentiviral vector) comprising a) nucleic acid encoding a dimeric caTCR comprising a first caTCR polypeptide chain and a second caTCR polypeptide chain according to any of the caTCRs described herein comprising i) a first caTCR nucleic acid sequence encoding the first caTCR polypeptide chain; and ii) a second caTCR nucleic acid sequence encoding the second caTCR polypeptide chain; and b) nucleic acid encoding a monomeric CSR comprising a CSR polypeptide chain according to any of the CSRs described herein comprising a CSR nucleic acid sequence encoding the CSR polypeptide chain, wherein the first and second caTCR nucleic acid sequences are under the control of a first promoter, and wherein the CSR nucleic acid sequence is under the control of a second promoter. In some embodiments, the first promoter is operably linked to one of the caTCR nucleic acid sequences, which is linked to the other caTCR nucleic acid sequence by a nucleic acid linker selected from the group consisting of an internal ribosomal entry site (IRES) and a nucleic acid encoding a self-cleaving 2A peptide (such as P2A, T2A, E2A, or F2A), such that the first and second caTCR nucleic acid sequences are transcribed as a single RNA under the control of the first promoter. In some embodiments, the first and/or second promoters are inducible. In some embodiments, the second promoter is an inducible promoter. In some embodiments, the inducible promoter comprises one or more elements responsive to immune cell activation. In some embodiments, the second promoter is an NFAT-derived promoter. In some embodiments, the NFAT-derived promoter comprises the nucleotide sequence of SEQ ID NO: 85. In some embodiments, the vector is a viral vector (such as a lentiviral vector).

In some embodiments, there is provided a vector (such as a lentiviral vector) comprising a) nucleic acid encoding a dimeric caTCR comprising a first caTCR polypeptide chain and a second caTCR polypeptide chain according to any of the caTCRs described herein comprising i) a first caTCR nucleic acid sequence encoding the first caTCR polypeptide chain; and ii) a second caTCR nucleic acid sequence encoding the second caTCR polypeptide chain; and b) nucleic acid encoding a monomeric CSR comprising a CSR polypeptide chain according to any of the CSRs described herein comprising a CSR nucleic acid sequence encoding the CSR polypeptide chain, wherein the first and second caTCR nucleic acid sequences and the CSR nucleic acid sequence are under the control of a single promoter. In some embodiments, the promoter is operably linked to one of the nucleic acid sequences, which is linked to the other nucleic acid sequences by nucleic acid linkers selected, individually, from the group consisting of an internal ribosomal entry site (IRES) and a nucleic acid encoding a self-cleaving 2A peptide (such as P2A, T2A, E2A, or F2A), such that the first and second caTCR nucleic acid sequences and the CSR nucleic acid sequence are transcribed as a single RNA under the control of the promoter. In some embodiments, the promoter is inducible. In some embodiments, the vector is a viral vector (such as a lentiviral vector).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human, cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Preparation of caTCRs, CSRs and SSEs

In some embodiments, according to any of the caTCRs, CSRs and SSEs described herein comprising an antibody moiety, the antibody moiety (e.g., Fab, Fab', (Fab')2, Fv, or scFv) comprises sequences derived from a monoclonal antibody. In some embodiments, the antibody moiety comprises $V_H$ and $V_L$ domains, or variants thereof, from the monoclonal antibody. In some embodiments, the antibody moiety further comprises $C_H1$ and $C_L$ domains, or variants thereof, from the monoclonal antibody. Monoclonal antibodies can be prepared, e.g., using hybridoma methods, such as those described by Kohler and Milstein, Nature, 256:495 (1975) and Sergeeva et al., Blood, 117(16):4262-4272.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest, or a complex comprising at least two molecules, such as a complex comprising a peptide and an MHC protein. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. See, e.g., Goding, Monoclonal Antibodies: Principles and Practice (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia Human myeloma and mouse-human heteromyeloma cell lines also have been described for the production of human monoclonal antibodies. Kozbor, J. Immunol., 133:3001 (1984); Brodeur et al. Monoclonal Antibody Production Techniques and Applications (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones can be sub-cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub-clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the caTCRs, CSRs and SSEs described herein comprising an antibody moiety, the antibody moiety comprises sequences from a clone selected from an antibody moiety library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., Methods in Molecular Biology 178:1-37 (O'Brien et al., ed., Human Press, Totowa, N.J., 2001) and further described, e.g., in McCafferty et al., Nature 348:552-554; Clackson et al., Nature 352: 624-628 (1991); Marks et al., J. Mol. Biol. 222: 581-597 (1992); Marks and Bradbury, Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Nat. Acad. Sci. USA 101(34): 12467-12472 (2004); and Lee et al., J. Immunol. Methods 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The antibody moiety can be prepared using phage display to screen libraries for antibodies specific to the target antigen (such as a peptide/MHC class I/II complex or a cell surface antigen). The library can be a human scFv phage display library having a diversity of at least one×$10^9$ (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al. *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target antigen with high affinity can be selected by iterative binding of phage to the target antigen, which is bound to a solid support (such as, for example, beads for solution panning or mammalian cells for cell panning), followed by removal of non-bound phage and by elution of specifically bound phage. In an example of solution panning, the target antigen can be biotinylated for immobilization to a solid support. The biotinylated target antigen is mixed with the phage library and a solid support, such as streptavidin-conjugated Dynabeads M-280, and then target antigen-phage-bead complexes are isolated. The bound phage clones are then eluted and used to infect an appropriate host cell, such as *E. coli* XL1-Blue, for expression and purification. In an example of cell panning, T2 cells (a TAP-deficient, HLA-A*02:01$^+$ lymphoblast cell line) loaded with an AFP peptide are mixed with the phage library, after which the cells are collected and the bound clones are eluted and used to infect an appropriate host cell for expression and purification. The panning can be performed for multiple (such as about any of 2, 3, 4, 5, 6 or more) rounds with either solution panning, cell panning, or a combination of both, to enrich for phage clones binding specifically to the target antigen. Enriched phage clones can be tested for specific binding to the target antigen by any methods known in the art, including for example ELISA and FACS.

Human and Humanized Antibody Moieties

The caTCR, CSR and SSE antibody moieties can be human or humanized. Humanized forms of non-human (e.g., murine) antibody moieties are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody moiety nor in the imported CDR or framework sequences. In general, the humanized antibody moiety can comprise substantially all of at least one, and typically two, variable domains, in which all or substantially all of the CDR regions correspond to those of a non-human immunoglobulin, and all or substantially all of the FR regions are those of a human immunoglobulin consensus sequence. See, e.g., Jones et al., *Nature*, 321: 522-525 (1986); Riechmann et al., *Nature*, 332: 323-329 (1988); Presta, *Curr. Op. Struct. Biol.*, 2:593-596 (1992).

Generally, a humanized antibody moiety has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature*, 321: 522-525 (1986); Riechmann et al., *Nature*, 332: 323-327 (1988); Verhoeyen et al., *Science*, 239: 1534-1536 (1988)), by substituting rodent CDRs or CDR sequences for the corresponding sequences of a human antibody moiety. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA*, 90:2551 (1993);

Jakobovits et al., *Nature,* 362:255-258 (1993); Bruggemann et al., *Year in Immunol.,* 7:33 (1993); U.S. Pat. Nos. 5,545, 806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., *BioTechnology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Human antibodies may also be generated by in vitro activated B cells (see U.S. Pat. Nos. 5,567,610 and 5,229, 275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985) and Boerner et al., *J. Immunol.,* 147(1): 86-95 (1991).

Additional Variants

In some embodiments, amino acid sequence variants of the antigen-binding modules provided herein are contemplated. For example, it may be desirable to improve the binding affinity and/or other biological properties of the antigen-binding module. Amino acid sequence variants of an antigen-binding module may be prepared by introducing appropriate modifications into the nucleotide sequence encoding the antigen-binding module, or by peptide synthesis. Such modifications include, for example, deletions from, and/or insertions into and/or substitutions of residues within the amino acid sequences of the antigen-binding module. Any combination of deletion, insertion, and substitution can be made to arrive at the final construct, provided that the final construct possesses the desired characteristics, e.g., antigen-binding.

In some embodiments, antigen-binding module variants having one or more amino acid substitutions are provided. Sites of interest for substitutional mutagenesis include the HVRs and FRs of antibody moieties. Amino acid substitutions may be introduced into an antigen-binding module of interest and the products screened for a desired activity, e.g., retained/improved antigen binding or decreased immunogenicity.

Conservative substitutions are shown in Table 4 below.

TABLE 4

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |

TABLE 4-continued

CONSERVATIVE SUBSTITITIONS

| Original Residue | Exemplary Substitutions | Preferred Substitutions |
|---|---|---|
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;
b. neutral hydrophilic: Cys, Ser, Thr, Asn, Gln;
c. acidic: Asp, Glu;
d. basic: His, Lys, Arg;
e. residues that influence chain orientation: Gly, Pro;
f. aromatic: Trp, Tyr, Phe.

Non-conservative substitutions will entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody moiety affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody moiety to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antigen-binding module that may be targeted for mutagenesis is called "alanine scanning mutagenesis" as described by Cunningham and Wells (1989) *Science,* 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antigen-binding module with antigen is affected. Further substitutions may be introduced at the amino acid locations demonstrating functional sensitivity to the initial substitutions. Alternatively, or additionally, a crystal structure of an antigen-antigen-binding module complex can be determined to identify contact points between the antigen-binding module and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antigen-binding module with an N-terminal methionyl residue. Other insertional variants of the antigen-binding module include the fusion to the N- or C-terminus of the antigen-binding module to an enzyme (e.g., for ADEPT) or a polypeptide which increases the serum half-life of the antigen-binding module.

Derivatives

In some embodiments, a caTCR according to any of the caTCRs described herein and/or a CSR according to any of the CSRs described herein and/or an SSE according to any of the SSEs described herein may be further modified to contain additional nonproteinaceous moieties that are known in the art and readily available. The moieties suitable for derivatization of the caTCR and/or CSR and/or SSE include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the caTCR and/or CSR and/or SSE may vary, and if more than one polymer are attached, they can be the same or different molecules. In general, the number and/or type of polymers used for derivatization can be determined based on considerations including, but not limited to, the particular properties or functions of the caTCR and/or CSR and/or SSE to be improved, whether the caTCR and/or CSR and/or SSE derivative will be used in a therapy under defined conditions, etc.

In some embodiments, conjugates of a caTCR and/or CSR and/or SSE and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the caTCR- and/or CSR- and/or SSE-nonproteinaceous moiety are killed.

Preparation of caTCR Plus CSR Immune Cells

The present invention in one aspect provides immune cells (such as lymphocytes, for example T cells) expressing a caTCR and a CSR according to any of the embodiments described herein. Exemplary methods of preparing immune cells (such as T cells) expressing a caTCR and a CSR (caTCR plus CSR immune cells, such as caTCR plus CSR T cells) are provided herein.

In some embodiments, a caTCR plus CSR immune cell (such as a caTCR plus CSR T cell) can be generated by introducing one or more nucleic acids (including for example a lentiviral vector) encoding a caTCR (such as any of the caTCRs described herein) that specifically binds to a target antigen (such as a disease-associated antigen) and a CSR (such as any of the CSRs described herein) that specifically binds to a target ligand into the immune cell. The introduction of the one or more nucleic acids into the immune cell can be accomplished using techniques known in the art, such as those described herein for Nucleic Acids. In some embodiments, the caTCR plus CSR immune cells (such as caTCR plus CSR T cells) of the invention are able to replicate in vivo, resulting in long-term persistence that can lead to sustained control of a disease associated with expression of the target antigen (such as cancer or viral infection).

In some embodiments, the invention relates to administering a genetically modified T cell expressing a caTCR that specifically binds to a target antigen according to any of the caTCRs described herein and a CSR that specifically binds to a target ligand according to any of the CSRs described herein for the treatment of a patient having or at risk of developing a disease and/or disorder associated with expression of the target antigen (also referred to herein as a "target antigen-positive" or "TA-positive" disease or disorder), including, for example, cancer or viral infection, using lymphocyte infusion. In some embodiments, autologous lymphocyte infusion is used in the treatment. Autologous PBMCs are collected from a patient in need of treatment and T cells are activated and expanded using the methods described herein and known in the art and then infused back into the patient.

In some embodiments, there is provided a T cell expressing a caTCR that specifically binds to a target antigen according to any of the caTCRs described herein and a CSR that specifically binds to a target ligand according to any of the CSRs described herein (also referred to herein as an "caTCR plus CSR T cell"). The caTCR plus CSR T cells of the invention can undergo robust in vivo T cell expansion and can establish target antigen-specific memory cells that persist at high levels for an extended amount of time in blood and bone marrow. In some embodiments, the caTCR plus CSR T cells of the invention infused into a patient can eliminate target antigen-presenting cells, such as target antigen-presenting cancer or virally-infected cells, in vivo in patients having a target antigen-associated disease. In some embodiments, the caTCR plus CSR T cells of the invention infused into a patient can eliminate target antigen-presenting cells, such as target antigen-presenting cancer or virally-infected cells, in vivo in patients having a target antigen-associated disease that is refractory to at least one conventional treatment.

Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art may be used. In some embodiments of the present invention, T cells can be obtained from a unit of blood collected from a subject using any number of techniques known to the skilled artisan, such as FICOLL™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer (including all ranges between these values). In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express $CD4^+$, $CD25^+$, CD62Lhi, $GITR^+$, and $FoxP3^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In some embodiments of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a desirable caTCR, CSR and optionally SSE, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

Genetic Modification

In some embodiments, the caTCR plus CSR immune cells (such as caTCR plus CSR T cells) of the invention are generated by transducing immune cells (such as T cells prepared by the methods described herein) with one or more viral vectors encoding a caTCR as described herein and a CSR as described herein. Viral vector delivery systems include DNA and RNA viruses, which have either episomal or integrated genomes after delivery to the immune cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11: 167-175 (1993); Miller, Nature 357:455-460 (1992); Van Brunt, Biotechnology 6(10): 1149-1 154 (1988); Vigne, Restorative Neurology and Neuroscience 8:35-36 (1995); Kremer & Perricaudet, British Medical Bulletin 51(1):31-44 (1995); and Yu et al., Gene Therapy 1:13-26 (1994). In some embodiments, the caTCR plus CSR immune cell comprises the one or more vectors integrated into the caTCR plus CSR immune cell genome. In some embodiments, the one or more viral vectors are lentiviral vectors. In some embodiments, the caTCR plus CSR immune cell is a caTCR plus CSR T cell comprising the lentiviral vectors integrated into its genome.

In some embodiments, the caTCR plus CSR immune cell is a T cell modified to block or decrease the expression of one or both of its endogenous TCR chains. For example, in some embodiments, the caTCR plus CSR immune cell is an $\alpha\beta$ T cell modified to block or decrease the expression of the TCR $\alpha$ and/or $\beta$ chains, or the caTCR plus CSR immune cell is a $\gamma\delta$ T cell modified to block or decrease the expression of the TCR $\gamma$ and/or $\delta$ chains. Modifications of cells to disrupt gene expression include any such techniques known in the art, including for example RNA interference (e.g., siRNA, shRNA, miRNA), gene editing (e.g., CRISPR- or TALEN-based gene knockout), and the like.

In some embodiments, caTCR plus CSR T cells with reduced expression of one or both of the endogenous TCR chains of the T cell are generated using the CRISPR/Cas system. For a review of the CRISPR/Cas system of gene editing, see for example Jian W & Marraffini L A, *Annu. Rev. Microbiol.* 69, 2015; Hsu P D et al., *Cell*, 157(6):1262-1278, 2014; and O'Connell M R et al., *Nature* Volume: 516: Pages: 263-266, 2014. In some embodiments, caTCR plus CSR T cells with reduced expression of one or both of the endogenous TCR chains of the T cell are generated using TALEN-based genome editing.

Enrichment

In some embodiments, there is provided a method of enriching a heterogeneous cell population for a caTCR plus CSR immune cell according to any of the caTCR plus CSR immune cells described herein.

A specific subpopulation of caTCR plus CSR immune cells (such as caTCR plus CSR T cells) that specifically bind to a target antigen and target ligand can be enriched for by positive selection techniques. For example, in some embodiments, caTCR plus CSR immune cells (such as caTCR plus CSR T cells) are enriched for by incubation with target antigen-conjugated beads and/or target ligand-conjugated beads for a time period sufficient for positive selection of the desired caTCR plus CSR immune cells. In some embodiments, the time period is about 30 minutes. In some embodiments, the time period ranges from 30 minutes to 36 hours or longer (including all ranges between these values). In some embodiments, the time period is at least one, 2, 3, 4, 5, or 6 hours. In some embodiments, the time period is 10 to 24 hours. In some embodiments, the incubation time period is 24 hours. For isolation of caTCR plus CSR immune cells present at low levels in the heterogeneous cell population, use of longer incubation times, such as 24 hours, can increase cell yield. Longer incubation times may be used to isolate caTCR plus CSR immune cells in any situation where there are few caTCR plus CSR immune cells as compared to other cell types. The skilled artisan would recognize that multiple rounds of selection can also be used in the context of this invention.

For isolation of a desired population of caTCR plus CSR immune cells by positive selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of caTCR plus CSR immune cells that may weakly express the caTCR and/or CSR.

In some of any such embodiments described herein, enrichment results in minimal or substantially no exhaustion of the caTCR plus CSR immune cells. For example, in some embodiments, enrichment results in fewer than about 50% (such as fewer than about any of 45, 40, 35, 30, 25, 20, 15, 10, or 5%) of the caTCR plus CSR immune cells becoming exhausted. Immune cell exhaustion can be determined by any means known in the art, including any means described herein.

In some of any such embodiments described herein, enrichment results in minimal or substantially no terminal differentiation of the caTCR plus CSR immune cells. For example, in some embodiments, enrichment results in fewer than about 50% (such as fewer than about any of 45, 40, 35, 30, 25, 20, 15, 10, or 5%) of the caTCR plus CSR immune cells becoming terminally differentiated. Immune cell differentiation can be determined by any means known in the art, including any means described herein.

In some of any such embodiments described herein, enrichment results in minimal or substantially no internalization of caTCRs and/or CSRs on the caTCR plus CSR immune cells. For example, in some embodiments, enrichment results in less than about 50% (such as less than about any of 45, 40, 35, 30, 25, 20, 15, 10, or 5%) of caTCRs and/or CSRs on the caTCR plus CSR immune cells becoming internalized. Internalization of caTCRs and/or CSRs on caTCR plus CSR immune cells can be determined by any means known in the art, including any means described herein.

In some of any such embodiments described herein, enrichment results in increased proliferation of the caTCR plus CSR immune cells. For example, in some embodiments, enrichment results in an increase of at least about 10% (such as at least about any of 20, 30, 40, 50, 60, 70, 80, 90, 100, 200, 300, 400, 500, 1000% or more) in the number of caTCR plus CSR immune cells following enrichment.

Thus, in some embodiments, there is provided a method of enriching a heterogeneous cell population for caTCR plus CSR immune cells expressing a caTCR that specifically binds to a target antigen and a CSR that specifically binds to a target ligand comprising: a) contacting the heterogeneous cell population with a first molecule comprising the target antigen or one or more epitopes contained therein and/or a second molecule comprising the target ligand or one or more epitopes contained therein to form complexes comprising the caTCR plus CSR immune cell bound to the first molecule and/or complexes comprising the caTCR plus CSR immune cell bound to the second molecule; and b) separating the complexes from the heterogeneous cell population, thereby generating a cell population enriched for the caTCR plus CSR immune cells. In some embodiments, the first and/or second molecules are immobilized, individually, to a solid support. In some embodiments, the solid support is particulate (such as beads). In some embodiments, the solid support is a surface (such as the bottom of a well). In some embodiments, the first and/or second molecules are labelled, individually, with a tag. In some embodiments, the tag is a fluorescent molecule, an affinity tag, or a magnetic tag. In some embodiments, the method further comprises eluting the caTCR plus CSR immune cells from the first and/or second molecules and recovering the eluate.

Library Screening

In some embodiments, to isolate candidate caTCR constructs specific for a target antigen, a caTCR library, for example cells expressing a library of nucleic acids encoding a plurality of caTCRs, may be exposed to a capture molecule comprising the target antigen or one or more epitopes contained therein, followed by isolation of affinity members of the library that specifically bind the capture molecule. In some embodiments, the capture molecule is immobilized on a solid support. In some embodiments, the support may be the surfaces of beads, microtitre plates, immunotubes, or any material known in the art useful for such purposes. In some embodiments, the interaction takes place in solution with a tagged capture molecule (e.g. biotinylated capture molecule). In some embodiments, the procedure involves one or more washing steps to remove unspecific and non-reactive library members (panning). In some embodiments, to purify complexes in solution, they are collected by either immobilization or by centrifugation. In some embodiments, affinity members are captured on a soluble biotinylated capture molecule, followed by immobilization of the affinity complex (affinity member and capture molecule) on streptavidin beads. In some embodiments, the solid support is a bead. In some embodiments, the beads include, for example, magnetic beads (e.g. from Bangs Laboratories, Polysciences inc., Dynal Biotech, Miltenyi Biotech or Quantum Magnetic), nonmagnetic beads (e.g. Pierce and Upstate technology), monodisperse beads (e.g. Dynal Biotech and Microparticle Gmbh), and polydisperse beads (e.g. Chemagen). The use of magnetic beads has been described exhaustingly in literature (Uhlen, M, et al (1994) in Advances in Biomagnetic Separation, BioTechniques press, Westborough, MA). In some embodiments, the affinity members are purified by positive selection. In some embodiments, the affinity members are purified by negative selection to remove unwanted library members. In some embodiments, the affinity members are purified by both positive and negative selection steps.

In some embodiments, to isolate candidate CSR constructs specific for a target ligand, a CSR library, for example cells expressing a library of nucleic acids encoding a plurality of CSRs, may be exposed to a capture molecule comprising the target ligand or one or more epitopes contained therein, followed by isolation of affinity members of the library that specifically bind the capture molecule. In some embodiments, the capture molecule is immobilized on a solid support. In some embodiments, the support may be the surfaces of beads, microtitre plates, immunotubes, or any material known in the art useful for such purposes. In some embodiments, the interaction takes place in solution with a tagged capture molecule (e.g. biotinylated capture molecule). In some embodiments, the procedure involves one or more washing steps to remove unspecific and non-reactive library members (panning). In some embodiments, to purify complexes in solution, they are collected by either immobilization or by centrifugation. In some embodiments, affinity members are captured on a soluble biotinylated capture molecule, followed by immobilization of the affinity complex (affinity member and capture molecule) on streptavidin beads. In some embodiments, the solid support is a bead. In some embodiments, the beads include, for example, magnetic beads (e.g. from Bangs Laboratories, Polysciences inc., Dynal Biotech, Miltenyi Biotech or Quantum Magnetic), nonmagnetic beads (e.g. Pierce and Upstate technology), monodisperse beads (e.g. Dynal Biotech and Microparticle Gmbh), and polydisperse beads (e.g. Chemagen). In some embodiments, the affinity members are purified by positive selection. In some embodiments, the affinity members are purified by negative selection to remove unwanted library members. In some embodiments, the affinity members are purified by both positive and negative selection steps.

Generally, the techniques used to prepare the library constructs will be based on known genetic engineering techniques. In this regard, nucleic acid sequences encoding the caTCRs or CSRs to be expressed in the library are incorporated into expression vectors appropriate for the type of expression system to be used. Appropriate expression vectors for use in display in cells, such as CD3+ cells, are well known and described in the art. For example, in some embodiments, the expression vector is a viral vector, such as a lentiviral vector.

In some embodiments, there is provided a nucleic acid library comprising sequences encoding a plurality of caTCRs according to any one of the embodiments described herein. In some embodiments, the nucleic acid library comprises viral vectors encoding the plurality of caTCRs. In some embodiments, the viral vectors are lentiviral vectors.

In some embodiments, there is provided a nucleic acid library comprising sequences encoding a plurality of CSRs according to any one of the embodiments described herein. In some embodiments, the nucleic acid library comprises viral vectors encoding the plurality of CSRs. In some embodiments, the viral vectors are lentiviral vectors.

In some embodiments, there is provided a method of screening a nucleic acid library according to any of the embodiments described herein for sequences encoding caTCRs specific for a target antigen, comprising: a) introducing the nucleic acid library into a plurality of cells, such that the caTCRs are expressed on the surface of the plurality of cells; b) incubating the plurality of cells with a capture molecule comprising the target antigen or one or more epitopes contained therein; c) collecting cells bound to the capture molecule; and d) isolating sequences encoding the caTCRs from cells collected in step c), thereby identifying caTCRs specific for the target antigen. In some embodiments, the method further comprises one or more wash steps. In some embodiments, the one or more wash steps are carried out between steps b) and c). In some embodiments, the plurality of cells is a plurality of CD3+ cells. In some embodiments, the capture molecule is immobilized on a solid support. In some embodiments, the solid support is a bead. In some embodiments, collecting cells bound to the capture molecule comprises eluting cells from the capture ligand bound to the solid support and collecting the eluate. In some embodiments, the capture molecule is labelled with a tag. In some embodiments, the tag is a fluorescent molecule, an affinity tag, or a magnetic tag. In some embodiments, collecting cells bound to the capture molecule comprises isolating complexes comprising the cells and the labelled ligand. In some embodiments, the cells are dissociated from the complexes.

In some embodiments, there is provided a method of screening a nucleic acid library according to any of the embodiments described herein for sequences encoding CSRs specific for a target ligand, comprising: a) introducing the nucleic acid library into a plurality of cells, such that the CSRs are expressed on the surface of the plurality of cells; b) incubating the plurality of cells with a capture molecule comprising the target ligand or one or more epitopes contained therein; c) collecting cells bound to the capture molecule; and d) isolating sequences encoding the CSRs from cells collected in step c), thereby identifying CSRs specific for the target ligand. In some embodiments, the method further comprises one or more wash steps. In some embodiments, the one or more wash steps are carried out between steps b) and c). In some embodiments, the plurality of cells is a plurality of CD3+ cells. In some embodiments, the capture molecule is immobilized on a solid support. In some embodiments, the solid support is a bead. In some embodiments, collecting cells bound to the capture molecule comprises eluting cells from the capture ligand bound to the solid support and collecting the eluate. In some embodiments, the capture molecule is labelled with a tag. In some embodiments, the tag is a fluorescent molecule, an affinity tag, or a magnetic tag. In some embodiments, collecting cells bound to the capture molecule comprises isolating complexes comprising the cells and the labelled ligand. In some embodiments, the cells are dissociated from the complexes.

MHC Proteins

MHC class I proteins are one of two primary classes of major histocompatibility complex (MHC) molecules (the other being MHC class II) and are found on nearly every nucleated cell of the body. Their function is to display fragments of proteins from within the cell to T cells; healthy cells will be ignored, while cells containing foreign or mutated proteins will be attacked by the immune system. Because MHC class I proteins present peptides derived from cytosolic proteins, the pathway of MHC class I presentation is often called the cytosolic or endogenous pathway. Class I MHC molecules bind peptides generated mainly from degradation of cytosolic proteins by the proteasome. The MHC I:peptide complex is then inserted into the plasma membrane of the cell. The peptide is bound to the extracellular part of the class I MHC molecule. Thus, the function of the class I MHC is to display intracellular proteins to cytotoxic T cells (CTLs). However, class I MHC can also present peptides generated from exogenous proteins, in a process known as cross-presentation.

MHC class I proteins consist of two polypeptide chains, $\alpha$ and $\beta$2-microglobulin ($\beta$2M). The two chains are linked noncovalently via interaction of $\beta$2M and the $\alpha$3 domain. Only the $\alpha$ chain is polymorphic and encoded by a HLA gene, while the $\beta$2M subunit is not polymorphic and encoded by the $\beta$-2 microglobulin gene. The $\alpha$3 domain is plasma membrane-spanning and interacts with the CD8 co-receptor of T-cells. The $\alpha$3-CD8 interaction holds the MHC I molecule in place while the T cell receptor (TCR) on the surface of the cytotoxic T cell binds its $\alpha$1-$\alpha$2 heterodimer ligand, and checks the coupled peptide for antigenicity. The $\alpha$1 and $\alpha$2 domains fold to make up a groove for peptides to bind. MHC class I proteins bind peptides that are 8-10 amino acid in length.

MHC class II molecules are a family of molecules normally found only on antigen-presenting cells such as dendritic cells, mononuclear phagocytes, some endothelial cells, thymic epithelial cells, and B cells. The antigens presented by class II peptides are derived from extracellular proteins (not cytosolic as in class I); hence, the MHC class II-dependent pathway of antigen presentation is called the endocytic or exogenous pathway. Loading of an MHC class II molecule occurs by phagocytosis; extracellular proteins are endocytosed, digested in lysosomes, and the resulting epitopic peptide fragments are loaded onto MHC class II molecules prior to their migration to the cell surface.

Like MHC class I molecules, class II molecules are also heterodimers, but in this case consist of two homogenous peptides, an $\alpha$ and $\beta$ chain. The subdesignation $\alpha$1, $\alpha$2, etc. refers to separate domains within the HLA gene; each domain is usually encoded by a different exon within the gene, and some genes have further domains that encode leader sequences, transmembrane sequences, etc. Because the antigen-binding groove of MHC class II molecules is open at both ends while the corresponding groove on class I molecules is closed at each end, the antigens presented by MHC class II molecules are longer, generally between 15 and 24 amino acid residues long.

The human leukocyte antigen (HLA) genes are the human versions of the MHC genes. The three major MHC class I proteins in humans are HLA-A, HLA-B, and HLA-C, while the 3 minor ones are HLA-E, HLA-F, and HLA-G. The three major MHC class II proteins involved in antigen presentation in humans are HLA-DP, HLDA-DQ, and HLA-DR, while the other MHC class II proteins, HLA-DM and HLA-DO, are involved in the internal processing and loading of antigens. HLA-A is ranked among the genes in humans with the fastest-evolving coding sequence. As of December 2013, there were 2432 known HLA-A alleles coding for 1740 active proteins and 117 null proteins. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface, enhancing the likelihood that a subset of the population will be resistant to any given foreign invader. This decreases the likelihood that a single pathogen has the capability to wipe out the entire human population. Each individual can express up to two types of HLA-A, one from each of their parents. Some individuals will inherit the same HLA-A from both parents, decreasing their individual HLA diversity; however, the majority of individuals will receive two different copies of HLA-A. This same pattern follows for all HLA groups. In other words, a person can only express either one or two of the 2432 known HLA-A alleles.

All alleles receive at least a four digit classification, e.g., HLA-A*02:12. The A signifies which HLA gene the allele belongs to. There are many HLA-A alleles, so that classification by serotype simplifies categorization. The next pair of digits indicates this assignment. For example, HLA-A*02:02, HLA-A*02:04, and HLA-A*02:324 are all members of the A2 serotype (designated by the *02 prefix). This group is the primary factor responsible for HLA compatibility. All numbers after this cannot be determined by serotyping and are designated through gene sequencing. The second set of digits indicates what HLA protein is produced. These are assigned in order of discovery and as of December 2013 there are 456 different HLA-A02 proteins known (assigned names HLA-A*02:01 to HLA-A*02:456). The shortest possible HLA name includes both of these details. Each extension beyond that signifies a nucleotide change that may or may not change the protein.

In some embodiments, the Fab-like antigen-binding module specifically binds to a complex comprising a peptide derived from a disease-associated antigen (such as a tumor-associated or virally-encoded antigen) and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01. HLA-A*02:01 is expressed in 39-46% of all Caucasians, and therefore represents a suitable choice of MHC class I protein for use in the present invention.

In some embodiments, the Fab-like antigen-binding module specifically binds to a complex comprising a peptide derived from a disease-associated antigen (such as a tumor-associated or virally-encoded antigen) and an MHC class II protein, wherein the MHC class II protein is HLA-DP, HLA-DQ, or HLA-DR. In some embodiments, the MHC class II protein is HLA-DP. In some embodiments, the MHC class II protein is HLA-DQ. In some embodiments, the MHC class II protein is HLA-DR.

Peptides suitable for use in generating Fab-like antigen-binding modules can be determined, for example, based on the presence of HLA (such as HLA-A*02:01) binding motifs and cleavage sites for proteasomes and immune-proteasomes using computer prediction models known to those of skill in the art. For predicting MHC binding sites, such models include, but are not limited to, ProPred1 (described in more detail in Singh and Raghava, *ProPred: prediction of HLA-DR binding sites. BIOINFORMATICS* 17(12):1236-1237, 2001), and SYFPEITHI (see Schuler et al. *SYFPEITHI, Database for Searching and T-Cell Epitope Prediction. in Immunoinformatics Methods in Molecular Biology*, vol 409(1): 75-93, 2007).

Once appropriate peptides have been identified, peptide synthesis may be done in accordance with protocols well known to those of skill in the art. Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention (See for example, Solid Phase Peptide Synthesis by John Morrow Stewart and Martin et al. *Application of Almez-mediated Amidation Reactions to Solution Phase Peptide Synthesis*, Tetrahedron Letters Vol. 39, pages 1517-1520, 1998).

Pharmaceutical Compositions

Also provided herein are caTCR plus CSR immune cell compositions (such as pharmaceutical compositions, also referred to herein as formulations) comprising an immune cell (such as a T cell) presenting on its surface a caTCR according to any of the caTCRs described herein and a CSR according to any of the CSRs described herein. In some embodiments, the caTCR plus CSR immune cell composition is a pharmaceutical composition.

The composition may comprise a homogenous cell population comprising caTCR plus CSR immune cells of the same cell type and expressing the same caTCR and CSR, or a heterogeneous cell population comprising a plurality of caTCR plus CSR immune cell populations comprising caTCR plus CSR immune cells of different cell types, expressing different caTCRs, and/or expressing different CSRs. The composition may further comprise cells that are not caTCR plus CSR immune cells.

Thus, in some embodiments, there is provided a caTCR plus CSR immune cell composition comprising a homogeneous cell population of caTCR plus CSR immune cells (such as caTCR plus CSR T cells) of the same cell type and expressing the same caTCR and CSR. In some embodiments, the caTCR plus CSR immune cell is a T cell. In some embodiments, the caTCR plus CSR immune cell is selected from the group consisting of a cytotoxic T cell, a helper T cell, a natural killer T cell, and a suppressor T cell. In some embodiments, the caTCR plus CSR immune cell composition is a pharmaceutical composition.

In some embodiments, there is provided a caTCR plus CSR immune cell composition comprising a heterogeneous cell population comprising a plurality of caTCR plus CSR immune cell populations comprising caTCR plus CSR immune cells of different cell types, expressing different caTCRs, and/or expressing different CSRs. In some embodiments, the caTCR plus CSR immune cells are T cells. In some embodiments, each population of caTCR plus CSR immune cells is, independently from one another, of a cell type selected from the group consisting of cytotoxic T cells, helper T cells, natural killer T cells, and suppressor T cells. In some embodiments, all of the caTCR plus CSR immune cells in the composition are of the same cell type (e.g., all of the caTCR plus CSR immune cells are cytotoxic T cells). In some embodiments, at least one population of caTCR plus CSR immune cells is of a different cell type than the others (e.g., one population of caTCR plus CSR immune cells consists of cytotoxic T cells and the other populations of caTCR plus CSR immune cells consist of natural killer T cells). In some embodiments, each population of caTCR plus CSR immune cells expresses the same caTCR. In some embodiments, at least one population of caTCR plus CSR immune cells expresses a different caTCR than the others. In some embodiments, each population of caTCR plus CSR immune cells expresses a different caTCR than the others. In some embodiments, each population of caTCR plus CSR immune cells expresses a caTCR that specifically binds to the same target antigen. In some embodiments, at least one population of caTCR plus CSR immune cells expresses a caTCR that specifically binds to a different target antigen than the others (e.g., one population of caTCR plus CSR immune cells specifically binds to a pMMC complex and the other populations of caTCR plus CSR immune cells specifically bind to a cell surface receptor). In some embodiments, where at least one population of caTCR plus CSR immune cells expresses a caTCR that specifically binds to a different target antigen, each population of caTCR plus CSR immune cells expresses a caTCR that specifically binds to a target antigen associated with the same disease or disorder (e.g., each of the target antigens are associated with a cancer, such as breast cancer). In some embodiments, each population of caTCR plus CSR immune cells expresses the same CSR. In some embodiments, at least one population of caTCR plus CSR immune cells expresses a different CSR than the others. In some embodiments, each population of caTCR plus CSR immune cells expresses a different CSR than the others. In some embodiments, each population of caTCR plus CSR immune cells expresses a CSR that specifically binds to the same target ligand. In some embodiments, at least one population of caTCR plus CSR immune cells expresses a CSR that specifically binds to a different target ligand than the others (e.g., one population of caTCR plus CSR immune cells specifically binds to a pMHC complex and the other populations of caTCR plus CSR immune cells specifically bind to a cell surface receptor). In some embodiments, where at least one population of caTCR plus CSR immune cells expresses a CSR that specifically binds to a different target ligand, each population of caTCR plus CSR immune cells expresses a CSR that specifically binds to a target ligand associated with the same disease or disorder (e.g., each of the target ligands are associated with a cancer, such as breast cancer). In some embodiments, the caTCR plus CSR immune cell composition is a pharmaceutical composition.

Thus, in some embodiments, there is provided a caTCR plus CSR immune cell composition comprising a plurality of caTCR plus CSR immune cell populations according to any of the embodiments described herein, wherein all of the caTCR plus CSR immune cells in the composition are of the same cell type (e.g., all of the caTCR plus CSR immune cells are cytotoxic T cells), and wherein each population of caTCR plus CSR immune cells expresses a different caTCR than the others. In some embodiments, the caTCR plus CSR immune cells are T cells. In some embodiments, the caTCR plus CSR immune cells are selected from the group consisting of cytotoxic T cells, helper T cells, natural killer T cells, and suppressor T cells. In some embodiments, each population of caTCR plus CSR immune cells expresses a caTCR that specifically binds to the same target antigen. In some embodiments, at least one population of caTCR plus CSR immune cells expresses a caTCR that specifically binds to a different target antigen than the others (e.g., one population of caTCR plus CSR immune cells specifically binds to a pMHC complex and the other populations of caTCR plus CSR immune cells specifically bind to a cell surface receptor). In some embodiments, where at least one population of caTCR plus CSR immune cells expresses a caTCR that specifically binds to a different target antigen, each population of caTCR plus CSR immune cells expresses a caTCR that specifically binds to a target antigen associated with the same disease or disorder (e.g., each of the target antigens are associated with a cancer, such as breast cancer). In some embodiments, the caTCR plus CSR immune cell composition is a pharmaceutical composition.

In some embodiments, there is provided a caTCR plus CSR immune cell composition comprising a plurality of caTCR plus CSR immune cell populations according to any of the embodiments described herein, wherein all of the caTCR plus CSR immune cells in the composition are of the same cell type (e.g., all of the caTCR plus CSR immune cells are cytotoxic T cells), and wherein each population of caTCR plus CSR immune cells expresses a different CSR than the others. In some embodiments, the caTCR plus CSR immune cells are T cells. In some embodiments, the caTCR plus CSR immune cells are selected from the group consisting of cytotoxic T cells, helper T cells, natural killer T cells, and suppressor T cells. In some embodiments, each population of caTCR plus CSR immune cells expresses a CSR that specifically binds to the same target ligand. In some embodiments, at least one population of caTCR plus CSR immune cells expresses a CSR that specifically binds to a different target ligand than the others (e.g., one population of caTCR plus CSR immune cells specifically binds to a pMHC complex and the other populations of caTCR plus CSR immune cells specifically bind to a cell surface receptor). In some embodiments, where at least one population of caTCR plus CSR immune cells expresses a CSR that specifically binds to a different target ligand, each population of caTCR plus CSR immune cells expresses a CSR that specifically binds to a target ligand associated with the same disease or disorder (e.g., each of the target ligands are associated with a cancer, such as breast cancer). In some embodiments, the caTCR plus CSR immune cell composition is a pharmaceutical composition.

In some embodiments, there is provided a composition comprising a plurality of caTCR plus CSR immune cell populations according to any of the embodiments described herein, wherein at least one population of caTCR plus CSR immune cells is of a different cell type than the others. In some embodiments, all of the populations of caTCR plus CSR immune cells are of different cell types. In some embodiments, the caTCR plus CSR immune cells are T cells. In some embodiments, each population of caTCR plus CSR immune cells is, independently from one another, of a cell type selected from the group consisting of cytotoxic T cells, helper T cells, natural killer T cells, and suppressor T cells. In some embodiments, each population of caTCR plus CSR immune cells expresses the same caTCR. In some embodiments, at least one population of caTCR plus CSR immune cells expresses a different caTCR than the others. In some embodiments, each population of caTCR plus CSR immune cells expresses a different caTCR than the others. In some embodiments, each population of caTCR plus CSR immune cells expresses a caTCR that specifically binds to the same target antigen. In some embodiments, at least one population of caTCR plus CSR immune cells expresses a caTCR that specifically binds to a different target antigen than the others (e.g., one population of caTCR plus CSR immune cells specifically binds to a pMHC complex and the other populations of caTCR plus CSR immune cells specifically bind to a cell surface receptor). In some embodiments, where at least one population of caTCR plus CSR immune cells expresses a caTCR that specifically binds to a different target antigen, each population of caTCR plus CSR immune cells expresses a caTCR that specifically binds to a target antigen associated with the same disease or disorder (e.g., each of the target antigens are associated with a cancer, such as breast cancer). In some embodiments, each population of caTCR plus CSR immune cells expresses the same CSR. In some embodiments, at least one population of caTCR plus CSR immune cells expresses a different CSR than the others. In some embodiments, each population of caTCR plus CSR immune cells expresses a different CSR than the others. In some embodiments, each population of caTCR plus CSR immune cells expresses a CSR that specifically binds to the same target ligand. In some embodiments, at least one population of caTCR plus CSR immune cells expresses a CSR that specifically binds to a different target ligand than the others (e.g., one population of caTCR plus CSR immune cells specifically binds to a pMHC complex and the other populations of caTCR plus CSR immune cells specifically bind to a cell surface receptor). In some embodiments, where at least one population of caTCR plus CSR immune cells expresses a CSR that specifically binds to a different target ligand, each population of caTCR plus CSR immune cells expresses a CSR that specifically binds to a target ligand associated with the same disease or disorder (e.g., each of the target ligands are associated with a cancer, such as breast cancer). In some embodiments, the caTCR plus CSR immune cell composition is a pharmaceutical composition.

At various points during preparation of a composition, it can be necessary or beneficial to cryopreserve a cell. The terms "frozen/freezing" and "cryopreserved/cryopreserving" can be used interchangeably. Freezing includes freeze drying.

As is understood by one of ordinary skill in the art, the freezing of cells can be destructive (see Mazur, P., 1977, Cryobiology 14:251-272) but there are numerous procedures available to prevent such damage. For example, damage can be avoided by (a) use of a cryoprotective agent, (b) control of the freezing rate, and/or (c) storage at a temperature sufficiently low to minimize degradative reactions. Exemplary cryoprotective agents include dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In particular embodiments, DMSO can be used. Addition of plasma (e.g., to a concentration of 20-25%) can augment the protective effects of DMSO. After addition of DMSO, cells can be kept at 0° C. until freezing, because DMSO concentrations of 1% can be toxic at temperatures above 4° C.

In the cryopreservation of cells, slow controlled cooling rates can be critical and different cryoprotective agents (Rapatz et al., 1968, Cryobiology 5(1): 18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1): 17-32; and Mazur, 1970, Science 168:939-949 for effects of cooling velocity on survival of stem cells and on their transplantation potential). The heat of fusion phase where water turns to ice should be minimal. The cooling procedure can be carried out by use of, e.g., a programmable freezing device or a methanol bath procedure. Programmable freezing apparatuses allow determination of optimal cooling rates and facilitate standard reproducible cooling.

In particular embodiments, DMSO-treated cells can be pre-cooled on ice and transferred to a tray containing chilled methanol which is placed, in turn, in a mechanical refrigerator (e.g., Harris or Revco) at −80° C. Thermocouple measurements of the methanol bath and the samples indicate a cooling rate of 1° to 3° C./minute can be preferred. After at least two hours, the specimens can have reached a temperature of −80° C. and can be placed directly into liquid nitrogen (−196° C.).

After thorough freezing, the cells can be rapidly transferred to a long-term cryogenic storage vessel. In a preferred embodiment, samples can be cryogenically stored in liquid nitrogen (−196° C.) or vapor (−1° C.). Such storage is facilitated by the availability of highly efficient liquid nitrogen refrigerators.

Further considerations and procedures for the manipulation, cryopreservation, and long-term storage of cells, can be found in the following exemplary references: U.S. Pat. Nos. 4,199,022; 3,753,357; and 4,559,298; Gorin, 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186; Livesey and Linner, 1987, Nature 327:255; Linner et al., 1986, J. Histochem. Cytochem. 34(9):1 123-1 135; Simione, 1992, J. Parenter. Sci. Technol. 46(6):226-32).

Following cryopreservation, frozen cells can be thawed for use in accordance with methods known to those of ordinary skill in the art. Frozen cells are preferably thawed quickly and chilled immediately upon thawing. In particular embodiments, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed on ice.

In particular embodiments, methods can be used to prevent cellular clumping during thawing. Exemplary methods include: the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc. [0162] As is understood by one of ordinary skill in the art, if a cryoprotective agent that is toxic to humans is used, it should be removed prior to therapeutic use. DMSO has no serious toxicity.

Exemplary carriers and modes of administration of cells are described at pages 14-15 of U.S. Patent Publication No. 2010/0183564. Additional pharmaceutical carriers are described in Remington: The Science and Practice of Pharmacy, 21 st Edition, David B. Troy, ed., Lippicott Williams & Wilkins (2005).

In particular embodiments, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), Plasma-Lyte A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

In compositions and formulations disclosed herein, cells are generally in a volume of a liter or less, 500 ml or less, 250 ml or less or 100 ml or less. Hence the density of administered cells is typically greater than $10^4$ cells/ml, $10^7$ cells/ml or $10^8$ cells/ml.

Also provided herein are nucleic acid compositions (such as pharmaceutical compositions, also referred to herein as formulations) comprising any of the nucleic acids encoding a caTCR and/or CSR and/or SSE described herein. In some embodiments, the nucleic acid composition is a pharmaceutical composition. In some embodiments, the nucleic acid composition further comprises any of an isotonizing agent, an excipient, a diluent, a thickener, a stabilizer, a buffer, and/or a preservative; and/or an aqueous vehicle, such as purified water, an aqueous sugar solution, a buffer solution, physiological saline, an aqueous polymer solution, or RNase free water. The amounts of such additives and aqueous vehicles to be added can be suitably selected according to the form of use of the nucleic acid composition.

The compositions and formulations disclosed herein can be prepared for administration by, for example, injection, infusion, perfusion, or lavage. The compositions and formulations can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

The formulations to be used for in vivo administration must be sterile. This is readily accomplished by, e.g., filtration through sterile filtration membranes.

Methods of Treatment Using caTCR Plus CSR Immune Cells

The caTCR plus CSR immune cells of the invention can be administered to individuals (e.g., mammals such as humans) to treat a disease and/or disorder associated with target antigen (TA) expression (also referred to herein as a "target-antigen positive" or "TA-positive" disease or disorder), including, for example, cancer and infectious disease (such as viral infection). The present application thus in some embodiments provides a method for treating a target antigen-positive disease (such as cancer or viral infection) in an individual comprising administering to the individual an effective amount of a composition (such as a pharmaceutical composition) comprising caTCR plus CSR immune cells according to any one of the embodiments described herein. In some embodiments, the cancer is selected, for example, from the group consisting of adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lung cancer, lymphoma, melanoma, mesothelioma, multiple myeloma, pancreatic cancer, pheochromocytoma, plasmacytoma, neuroblastoma, ovarian cancer, prostate cancer, sarcoma, stomach cancer, uterine cancer and thyroid cancer. In some embodiments, the viral infection is caused by a virus selected, for example, from the group consisting of Cytomegalovirus (CMV), Epstein-Barr Virus (EBV), Hepatitis B Virus (HBV), Kaposi's Sarcoma associated herpesvirus (KSHV), Human papillomavirus (HPV), Molluscum contagiosum virus (MCV), Human T cell leukemia virus 1 (HTLV-1), HIV (Human immunodeficiency virus), and Hepatitis C Virus (HCV).

For example, in some embodiments, there is provided a method of treating a target antigen-associated disease (such as cancer or viral infection) in an individual in need thereof comprising administering to the individual an effective amount of a composition comprising immune cells (such as T cells or natural killer cells) presenting on their surface a) a caTCR comprising i) a first TCRD comprising a first TCR-TM derived from one of the transmembrane domains of a TCR and a second TCRD comprising a second TCR-TM derived from the other transmembrane domain of the TCR, wherein the first and second TCRDs form a TCRM that is capable of recruiting at least one TCR-associated signaling molecule, and ii) an antigen-binding module that specifically binds to the target antigen, wherein the antigen-binding module is linked to the first and/or second TCRDs; and b) a chimeric signaling receptor (CSR) comprising i) a ligand-binding domain that specifically binds to a target ligand, ii) a transmembrane domain, and iii) an intracellular signaling domain that is capable of providing a co-stimulatory signal to the immune cell. In some embodiments, both of the TCR-TMs are naturally occurring. In some embodiments, at least one of the TCR-TMs is non-naturally occurring. In some embodiments, the TCR is an αβ TCR and the first and second TCR-TMs are derived from TCR α and β subunit transmembrane domains. In some embodiments, the TCR is a γδ TCR and the first and second TCR-TMs are derived from TCR γ and δ subunit transmembrane domains. In some embodiments, the first TCRD further comprises a first TCR connecting peptide or a fragment thereof and/or the second TCRD further comprises a second TCR connecting peptide or a fragment thereof. In some embodiments, the first connecting peptide comprises all or a portion of the connecting peptide of the TCR subunit from which the first TCR-TM is derived, or a variant thereof, and/or the second connecting peptide comprises all or a portion of the connecting peptide of the TCR subunit from which the second TCR-TM is derived, or a variant thereof. In some embodiments, the first and second connecting peptides are linked by a disulfide bond. In some embodiments, the first TCRD further comprises a first TCR intracellular domain and/or the second TCRD further comprises a second TCR intracellular domain. In some embodiments, the first TCR intracellular domain comprises a sequence from the intracellular domain of the TCR subunit from which the first TCR-TM is derived and/or the second TCR intracellular domain comprises a sequence from the intracellular domain of the TCR subunit from which the second TCR-TM is derived. In some embodiments, the first TCRD is a fragment of the TCR subunit from which the first TCR-TM is derived and/or the second TCRD is a fragment of the TCR subunit from which the second TCR-TM is derived. In some embodiments, the caTCR further comprises at least one accessory intracellular domain comprising a T cell co-stimulatory signaling sequence (such as from CD27, CD28, 4-1BB (CD137), OX40, CD30, or CD40). In some embodiments, the caTCR further comprises a stabilization module comprising a first stabilization domain and a second stabilization domain, wherein the first and second stabilization domains have a binding affinity for each other that stabilizes the caTCR. In some embodiments, the first and second stabilization domains are linked by a disulfide bond. In some embodiments, the first and second stabilization domains comprise antibody domains, such as $C_H 1$ and $C_L$ antibody domains, or variants thereof. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the T cell receptor transmembrane domains. In some embodiments, the TCRM promotes caTCR-CD3 complex formation. In some embodiments, there is a spacer module between any two caTCR modules or domains. In some embodiments, the antigen-binding module is an antibody moiety. In some embodiments, the antibody moiety is a Fab, a Fab', a (Fab')2, an Fv, or a single chain Fv (scFv). In some embodiments, the antigen-binding module is multispecific (e.g., bispecific). In some embodiments, the target antigen is a cell surface antigen. In some embodiments, the cell surface antigen is selected from the group consisting of a protein, a carbohydrate, and a lipid. In some embodiments, the cell surface antigen is a disease-associated antigen, such as a tumor-associated or virally-encoded antigen. In some embodiments, the cell surface antigen is CD19, ROR1, ROR2, BCMA, GPRC5D, or FCRL5. In some embodiments, the target antigen is a surface-presented peptide/MHC complex. In some embodiments, the peptide/MHC complex comprises a peptide derived from a disease-associated antigen (such as a tumor-associated or virally-encoded antigen) and an MHC protein. In some embodiments, the peptide/MHC complex comprises a peptide and an MHC protein, wherein the peptide is derived from a protein selected from the group consisting of WT-1, AFP, HPV16-E7, NY-ESO-1, PRAME, EBV-LMP2A, and PSA. In some embodiments, the MHC protein is an MHC class I protein. In some embodiments, the MHC class I protein is HLA-A. In some embodiments, the HLA-A is HLA-A02. In some embodiments, the HLA-A02 is HLA-A*02:01. In some embodiments, the target ligand of the CSR is a cell surface antigen. In some embodiments, the target ligand is a peptide/MHC complex. In some embodiments, the target ligand of the CSR and the target antigen of the caTCR are the same. In some embodiments, the target ligand and the target antigen are different. In some embodiments, the target ligand is a disease-associated ligand. In some embodiments, the target ligand is a cancer-associated ligand. In some embodiments, the cancer-associated ligand is, for example, CD19, CD20, CD22, CD47, IL4, GPC-3, ROR1, ROR2, BCMA, GPRC5D, or FCRL5. In some embodiments, the cancer-associated ligand is a peptide/MHC complex comprising a peptide derived from a protein including WT-1, AFP, HPV16-E7, NY-ESO-1, PRAME, EBV-LMP2A, and PSA. In some embodiments, the target ligand is a virus-associated ligand. In some embodiments, the target ligand is an immune checkpoint molecule. In some embodiments, the immune checkpoint molecule includes PD-L1, PD-L2, CD80, CD86, ICOSL, B7-H3, B7-H4, HVEM, 4-1BBL, OX40L, CD70, CD40, and GAL9. In some embodiments, the target ligand is an apoptotic molecule. In some embodiments, the apoptotic molecule includes FasL, FasR, TNFR1, and TNFR2. In some embodiments, the ligand-binding domain is an antibody moiety. In some embodiments, the ligand-binding domain antibody moiety is a Fab, a Fab', a (Fab')2, an Fv, or a single chain Fv (scFv). In some embodiments, the ligand-binding domain is (or is derived from) all or a portion of the extracellular domain of a receptor for the target ligand. In some embodiments, the receptor includes, for example, FasR, TNFR1, TNFR2, PD-1, CD28, CTLA-4, ICOS, BTLA, KIR, LAG-3, 4-1BB, OX40, CD27, and TIM-3. In some embodiments, the transmembrane domain of the CSR comprises a transmembrane domain derived from, for example, CD28, CD3ε, CD3ζ, CD45, CD4, CD5, CD8, CD9, CD16, CD22, CD33, CD37, CD64, CD80, CD86, CD134, CD137, or CD154. In some embodiments, the co-stimulatory signaling domain of the CSR comprises, consists essentially of, or consists of all or a portion of the intracellular domain of an immune cell co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the CSR further comprises a spacer domain between any of the ligand-binding domain, the transmembrane domain, and the co-stimulatory signaling domain. In some embodiments, the spacer domain comprises a peptide linker connecting two CSR domains. In some embodiments, the immune cell is a γδ T cell. In some embodiments, the immune cell is an αβ T cell modified to block or decrease the expression of the TCR α and/or β chains. In some embodiments, the immune cell is selected from the group consisting of a cytotoxic T cell, a helper T cell, a natural killer T cell, and a suppressor T cell.

In some embodiments, there is provided a method of treating a target antigen-associated disease (such as cancer or viral infection) in an individual in need thereof comprising administering to the individual an effective amount of a composition comprising immune cells (such as T cells or natural killer cells) presenting on their surface a) a caTCR that specifically binds the target antigen comprising i) a first TCRD comprising a first TCR-TM derived from one of the transmembrane domains of a naturally occurring αβ TCR and a second TCRD comprising a second TCR-TM derived from the other transmembrane domain of the naturally occurring a TCR, wherein the first and second TCRDs form a TCRM that is capable of recruiting at least one TCR-associated signaling molecule, and ii) an antigen-binding module that specifically binds to the target antigen, wherein the antigen-binding module is linked to the first and/or second TCRDs; and b) a chimeric signaling receptor (CSR) comprising i) a ligand-binding domain that specifically binds to a target ligand, ii) a transmembrane domain, and iii) an intracellular signaling domain that is capable of providing a co-stimulatory signal to the immune cell.

In some embodiments, there is provided a method of treating a target antigen-associated disease (such as cancer or viral infection) in an individual in need thereof comprising administering to the individual an effective amount of a composition comprising immune cells (such as T cells or natural killer cells) presenting on their surface a) a caTCR that specifically binds the target antigen comprising i) a first TCRD comprising a first TCR-TM derived from one of the transmembrane domains of a naturally occurring γδ TCR and a second TCRD comprising a second TCR-TM derived from the other transmembrane domain of the naturally occurring γδ TCR, wherein the first and second TCRDs form a TCRM that is capable of recruiting at least one TCR-associated signaling molecule, and ii) an antigen-binding module that specifically binds to the target antigen, wherein the antigen-binding module is linked to the first and/or second TCRDs; and b) a chimeric signaling receptor (CSR) comprising i) a ligand-binding domain that specifically binds to a target ligand, ii) a transmembrane domain, and iii) an intracellular signaling domain that is capable of providing a co-stimulatory signal to the immune cell.

In some embodiments, there is provided a method of treating a target antigen-associated disease (such as cancer or viral infection) in an individual in need thereof comprising administering to the individual an effective amount of a composition comprising immune cells (such as T cells or natural killer cells) presenting on their surface a) a caTCR that specifically binds the target antigen comprising i) a first TCRD comprising a first TCR-TM derived from the amino acid sequence of SEQ ID NO: 5 and a second TCRD comprising a second TCR-TM derived from the amino acid sequence of SEQ ID NO: 6, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs; and b) a chimeric signaling receptor (CSR) comprising i) a ligand-binding domain that specifically binds to a target ligand, ii) a transmembrane domain, and iii) an intracellular signaling domain that is capable of providing a co-stimulatory signal to the immune cell. In some embodiments, at least one of the TCR-TMs comprises one or more (such as 2, 3, 4, 5, or more) amino acid substitutions compared to the amino acid sequence from which it is derived. In some embodiments, each of the TCR-TMs comprises, independently from one another, one or more (such as 2, 3, 4, 5, or more) amino acid substitutions compared to the amino acid sequence from which it is derived. In some embodiments, the first TCR-TM and/or the second TCR-TM each comprise, independently from one another, no more than 5 amino acid substitutions compared to the amino acid sequences from which they are derived. In some embodiments, at least one of the TCR-TMs comprises a single amino acid substitution compared to the amino acid sequence from which it is derived. In some embodiments, each of the TCR-TMs comprises a single amino acid substitution compared to the amino acid sequence from which it is derived. In some embodiments, at least one of the substituted amino acids in the first TCR-TM is positioned such that in the caTCR it can interact with at least one of the substituted amino acids in the second TCR-TM.

In some embodiments, there is provided a method of treating a target antigen-associated disease (such as cancer or viral infection) in an individual in need thereof comprising administering to the individual an effective amount of a composition comprising immune cells (such as T cells or natural killer cells) presenting on their surface a) a caTCR that specifically binds the target antigen comprising i) a first TCRD comprising a first TCR-TM derived from the amino acid sequence of SEQ ID NO: 7 and a second TCRD comprising a second TCR-TM derived from the amino acid sequence of SEQ ID NO: 8, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs; and b) a chimeric signaling receptor (CSR) comprising i) a ligand-binding domain that specifically binds to a target ligand, ii) a transmembrane domain, and iii) an intracellular signaling domain that is capable of providing a co-stimulatory signal to the immune cell. In some embodiments, at least one of the TCR-TMs comprises one or more (such as 2, 3, 4, 5, or more) amino acid substitutions compared to the amino acid sequence from which it is derived. In some embodiments, each of the TCR-TMs comprises, independently from one another, one or more (such as 2, 3, 4, 5, or more) amino acid substitutions compared to the amino acid sequence from which it is derived. In some embodiments, the first TCR-TM and/or the second TCR-TM each comprise, independently from one another, no more than 5 amino acid substitutions compared to the amino acid sequences from which they are derived. In some embodiments, at least one of the TCR-TMs comprises a single amino acid substitution compared to the amino acid sequence from which it is derived. In some embodiments, each of the TCR-TMs comprises a single amino acid substitution compared to the amino acid sequence from which it is derived. In some embodiments, at least one of the substituted amino acids in the first TCR-TM is positioned such that in the caTCR it can interact with at least one of the substituted amino acids in the second TCR-TM. In some embodiments, the first TCR-TM and second TCR-TM are selected according to any of the caTCRs listed in Table 2. In some embodiments, the CSR domains are selected according to any of the CSRs listed in Table 3.

In some embodiments, there is provided a method of treating a target antigen-associated disease (such as cancer or viral infection) in an individual in need thereof comprising administering to the individual an effective amount of a composition comprising immune cells (such as T cells or natural killer cells) presenting on their surface a) a caTCR that specifically binds the target antigen comprising i) a first TCRD comprising a first TCR-TM having the amino acid sequence of SEQ ID NO: 10 and a second TCRD comprising a second TCR-TM having the amino acid sequence of SEQ ID NO: 16, wherein the first and second TCRDs form a TCRM that is capable of recruiting at least one TCR-associated signaling molecule; and b) an antigen-binding module that specifically binds to the target antigen, wherein the antigen-binding module is linked to the first and/or second TCRDs; and b) a chimeric signaling receptor (CSR) comprising i) a ligand-binding domain that specifically binds to a target ligand, ii) a transmembrane domain, and iii) a fragment of an immune cell co-stimulatory molecule (fCSM) comprising an intracellular signaling domain that is capable of providing a co-stimulatory signal to the immune cell, wherein the co-stimulatory molecule fragment comprises the amino acid sequence of any one of SEQ ID NOs: 51-56 and 86-89. In some embodiments, the CSR transmembrane domain is derived from CD8. In some embodiments, the CSR comprises a fragment of a transmembrane protein (fTMP), wherein the transmembrane protein fragment comprises the amino acid sequence of SEQ ID NO: 57. In some embodiments, the CSR comprises a spacer peptide following the ligand-binding domain. In some embodiments, the spacer peptide comprises the amino acid sequence of SEQ ID NO: 103 or 104. In some embodiments, the CSR domains are selected according to any of the CSRs listed in Table 3. In some embodiments, the target antigen is CD19. In some embodiments, the target ligand is CD19. In some embodiments, the caTCR antigen-binding module is a Fab-like antigen-binding moiety comprising a $V_H$ domain comprising the amino acid sequence of SEQ ID NO: 58 and a $V_L$ domain comprising the amino acid sequence of SEQ ID NO: 59. In some embodiments, the target antigen is CD19 and the target ligand is CD19. In some embodiments, the CSR ligand-binding domain is an scFv comprising the amino acid sequence of SEQ ID NO: 77. In some embodiments, the target antigen is CD19 and the target ligand is CD20. In some embodiments, the CSR ligand-binding domain is an scFv comprising the amino acid sequence of SEQ ID NO: 78. In some embodiments, the target antigen is an AFP peptide/MHC complex (e.g., AFP158/HLA-A02 complex) and the target ligand is GPC3. In some embodiments, the caTCR antigen-binding module is a Fab-like antigen-binding moiety comprising a $V_H$ domain comprising the amino acid sequence of SEQ ID NO: 62 and a $V_L$ domain comprising the amino acid sequence of SEQ ID NO: 63. In some embodiments, the CSR ligand-binding domain is an scFv comprising the amino acid sequence of SEQ ID NO: 79.

In some embodiments, there is provided a method of treating a CD19-associated disease (such as cancer) in an individual in need thereof comprising administering to the individual an effective amount of a composition comprising immune cells (such as T cells or natural killer cells) presenting on their surface a) a caTCR that specifically binds CD19 comprising i) a first TCRD comprising a first TCR-TM having the amino acid sequence of SEQ ID NO: 10 and a second TCRD comprising a second TCR-TM having the amino acid sequence of SEQ ID NO: 16, wherein the first and second TCRDs form a TCRM that is capable of recruiting at least one TCR-associated signaling molecule; and b) a Fab-like antigen-binding module comprising a first Fab chain comprising a $V_H$ domain comprising the amino acid sequence of SEQ ID NO: 58 and a second Fab chain comprising a $V_L$ domain comprising the amino acid sequence of SEQ ID NO: 59, wherein the first Fab chain is linked to one of the first and second TCRDs, and the second Fab chain is linked to the other TCRD; and b) a chimeric signaling receptor (CSR) comprising i) an scFv that specifically binds CD19 comprising a $V_H$ domain comprising the amino acid sequence of SEQ ID NO: 58 and a $V_L$ domain comprising the amino acid sequence of SEQ ID NO: 59, ii) a transmembrane domain, and iii) a fragment of an immune cell co-stimulatory molecule (fCSM) comprising an intracellular signaling domain that is capable of providing a co-stimulatory signal to the immune cell, wherein the co-stimulatory molecule fragment comprises the amino acid sequence of any one of SEQ ID NOs: 51-56 and 86-89. In some embodiments, the CSR transmembrane domain is derived from CD8. In some embodiments, the CSR comprises a fragment of a transmembrane protein (fTMP), wherein the transmembrane protein fragment comprises the amino acid sequence of SEQ ID NO: 57. In some embodiments, the CSR comprises a spacer peptide following the ligand-binding domain. In some embodiments, the spacer peptide comprises the amino acid sequence of SEQ ID NO: 103 or 104. In some embodiments, the CSR domains are selected according to any of the CSRs listed in Table 3. In some embodiments, the CSR ligand-binding domain is an scFv comprising the amino acid sequence of SEQ ID NO: 77. In some embodiments, the CD19-associated disease is leukemia, e.g., acute lymphoblastic leukemia (ALL).

In some embodiments, there is provided a method of treating a CD19/CD20-associated disease (such as cancer) in an individual in need thereof comprising administering to the individual an effective amount of a composition comprising immune cells (such as T cells or natural killer cells) presenting on their surface a) a caTCR that specifically binds CD19 comprising i) a first TCRD comprising a first TCR-TM having the amino acid sequence of SEQ ID NO: 10 and a second TCRD comprising a second TCR-TM having the amino acid sequence of SEQ ID NO: 16, wherein the first and second TCRDs form a TCRM that is capable of recruiting at least one TCR-associated signaling molecule; and b) a Fab-like antigen-binding module comprising a first Fab chain comprising a $V_H$ domain comprising the amino acid sequence of SEQ ID NO: 58 and a second Fab chain comprising a $V_L$ domain comprising the amino acid sequence of SEQ ID NO: 59, wherein the first Fab chain is linked to one of the first and second TCRDs, and the second Fab chain is linked to the other TCRD; and b) a chimeric signaling receptor (CSR) comprising i) an scFv that specifically binds CD20 comprising a $V_H$ domain comprising the amino acid sequence of SEQ ID NO: 60 and a $V_L$ domain comprising the amino acid sequence of SEQ ID NO: 61, ii) a transmembrane domain, and iii) a fragment of an immune cell co-stimulatory molecule (fCSM) comprising an intracellular signaling domain that is capable of providing a co-stimulatory signal to the immune cell, wherein the co-stimulatory molecule fragment comprises the amino acid sequence of any one of SEQ ID NOs: 51-56 and 86-89. In some embodiments, the CSR transmembrane domain is derived from CD8. In some embodiments, the CSR comprises a fragment of a transmembrane protein (fTMP), wherein the transmembrane protein fragment comprises the amino acid sequence of SEQ ID NO: 57. In some embodiments, the CSR comprises a spacer peptide following the ligand-binding domain. In some embodiments, the spacer peptide comprises the amino acid sequence of SEQ ID NO: 103 or 104. In some embodiments, the CSR domains are selected according to any of the CSRs listed in Table 3. In some embodiments, the CSR ligand-binding domain is an scFv comprising the amino acid sequence of SEQ ID NO: 81.

In some embodiments, there is provided a method of treating a AFP/GPC3-associated disease (such as cancer, e.g., liver cancer) in an individual in need thereof comprising administering to the individual an effective amount of a composition comprising immune cells (such as T cells or natural killer cells) presenting on their surface a) a caTCR that specifically binds an AFP peptide/MHC complex (e.g., AFP158/HLA-A02 complex) comprising i) a first TCRD comprising a first TCR-TM having the amino acid sequence of SEQ ID NO: 10 and a second TCRD comprising a second TCR-TM having the amino acid sequence of SEQ ID NO: 16, wherein the first and second TCRDs form a TCRM that is capable of recruiting at least one TCR-associated signaling molecule; and b) a Fab-like antigen-binding module comprising a first Fab chain comprising a $V_H$ domain comprising the amino acid sequence of SEQ ID NO: 62 and a second Fab chain comprising a $V_L$ domain comprising the amino acid sequence of SEQ ID NO: 63, wherein the first Fab chain is linked to one of the first and second TCRDs, and the second Fab chain is linked to the other TCRD; and b) a chimeric signaling receptor (CSR) comprising i) an scFv that specifically binds GPC3 comprising a $V_H$ domain comprising the amino acid sequence of SEQ ID NO: 64 and a $V_L$ domain comprising the amino acid sequence of SEQ ID NO: 65, ii) a transmembrane domain, and iii) a fragment of an immune cell co-stimulatory molecule (fCSM) comprising an intracellular signaling domain that is capable of providing a co-stimulatory signal to the immune cell, wherein the co-stimulatory molecule fragment comprises the amino acid sequence of any one of SEQ ID NOs: 51-56 and 86-89. In some embodiments, the CSR transmembrane domain is derived from CD8. In some embodiments, the CSR comprises a fragment of a transmembrane protein (fTMP), wherein the transmembrane protein fragment comprises the amino acid sequence of SEQ ID NO: 57. In some embodiments, the CSR comprises a spacer peptide following the ligand-binding domain. In some embodiments, the spacer peptide comprises the amino acid sequence of SEQ ID NO: 103 or 104. In some embodiments, the CSR domains are selected according to any of the CSRs listed in Table 3. In some embodiments, the CSR ligand-binding domain is an scFv comprising the amino acid sequence of SEQ ID NO: 82.

Also contemplated are methods of treating a target antigen-associated disease in an individual in need thereof comprising administering to the individual a composition comprising a plurality of immune cells expressing different caTCRs and/or different CSRs. Thus, in some embodiments, according to any of the methods for treating a target antigen-associated disease in an individual described herein, the composition is a heterogeneous caTCR plus CSR immune cell composition as described herein.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or environmentally or genetically prone to one or more of the diseases or disorders described herein (such as cancer or viral infection). In some embodiments, the individual has one or more risk factors associated with one or more diseases or disorders described herein.

In some embodiments, the caTCR plus CSR immune cell compositions of the invention are administered in combination with a second, third, or fourth agent (including, e.g., an antineoplastic agent, a growth inhibitory agent, a cytotoxic agent, or a chemotherapeutic agent) to treat diseases or disorders involving target antigen expression. In some embodiments, the caTCR plus CSR immune cell composition is administered in combination with a cytokine (such as IL-2). In some embodiments, the caTCR plus CSR immune cell composition is administered in combination with an agent that increases the expression of MHC proteins and/or enhances the surface presentation of peptides by MHC proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

In some embodiments, there is provided a method of treating a target antigen-positive disease in an individual in need thereof comprising administering to the individual a caTCR plus CSR immune cell composition according to any of the embodiments described herein in combination with a cytokine (such as IL-2). In some embodiments, the caTCR plus CSR immune cell composition and the cytokine are administered simultaneously. In some embodiments, the caTCR plus CSR immune cell composition and the cytokine are administered sequentially.

In some embodiments, there is provided a method of treating a target antigen-positive disease in an individual in need thereof, wherein the cells expressing the target antigen do not normally present, or present at relatively low levels, a complex comprising the target antigen and an MHC class I protein on their surface, the method comprising administering to the individual a caTCR plus CSR immune cell compositions according to any of the embodiments described herein in combination with an agent that increases the expression of MHC class I proteins and/or enhances the surface presentation of target antigens by MHC class I proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine. In some embodiments, the caTCR plus CSR immune cell composition and the agent are administered simultaneously. In some embodiments, the caTCR plus CSR immune cell composition and the agent are administered sequentially.

In some embodiments, there is provided a method of treating a target antigen-associated disease (such as cancer or viral infection) in an individual in need thereof comprising administering to the individual an effective amount of a composition comprising nucleic acid encoding a caTCR and a CSR according to any of the embodiments described herein. Methods for gene delivery are known in the art. See, e.g., U.S. Pat. Nos. 5,399,346, 5,580,859, 5,589,466, incorporated by reference herein in their entireties.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C\times100)$, where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%.

Viral infection treatments can be evaluated, for example, by viral load, duration of survival, quality of life, protein expression and/or activity.

Diseases

The caTCR plus CSR immune cells in some embodiments can be useful for treating cancers associated with a target antigen. Cancers that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the caTCR plus CSR immune cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, plasmacytoma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include adrenocortical carcinoma, cholangiocarcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

The caTCR plus CSR immune cells in other embodiments can be useful for treating infectious diseases by targeting pathogen-associated (such as virally-encoded) antigens. The infection to be prevented or treated, for example, may be caused by a virus, bacteria, protozoa, or parasite. The target antigen may be a pathogenic protein, polypeptide or peptide that is responsible for a disease caused by the pathogen, or is capable of inducing an immunological response in a host infected by the pathogen. Pathogenic antigens which can be targeted by caTCR plus CSR immune cells include, but are not limited to, antigens derived from *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, *Enterovirus* genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Human T cell leukemia virus 1 (HTLV-1), Japanese encephalitis virus, JC virus, Junin virus, Kaposi's Sarcoma associated herpesvirus (KSHV), *Kingella kingae*, *Klebsiella granulomatis*, Kuru prion, Lassa virus, *Legionella pneumophila*, *Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family (Influenza), *Paracoccidioides brasiliensis*, *Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In some embodiments, the caTCR plus CSR immune cells are used for treating oncogenic infectious diseases, such as infection by oncogenic viruses. Oncogenic viruses include, but are not limited to, CMV, EBV, HBV, KSHV, HPV, MCV, HTLV-1, HIV-1, and HCV. The target antigen of the caTCR can be a viral oncoprotein including, but not limited to, Tax, E7, E6/E7, E6, HBx, EBNA proteins (e.g., EBNA3 A, EBNA3 C, and EBNA 2), v-cyclin, LANA1, LANA2, LMP-1, k-bZIP, RTA, KSHV K8, and fragments thereof. See Ahuja, Richa, et al., Curr. Sci., 2014.

Articles of Manufacture and Kits

In some embodiments of the invention, there is provided an article of manufacture containing materials useful for the treatment of a target antigen-positive disease such as cancer (for example adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lung cancer, lymphoma, melanoma, mesothelioma, multiple myeloma, pancreatic cancer, pheochromocytoma, plasmacytoma, neuroblastoma, ovarian cancer, prostate cancer, sarcoma, stomach cancer, uterine cancer or thyroid cancer) or viral infection (for example infection by CMV, EBV, HBV, KSHV, HPV, MCV, HTLV-1, HIV-1, or HCV). The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an immune cell presenting on its surface a caTCR and a CSR of the invention. The label or package insert indicates that the composition is used for treating the particular condition. The label or package insert will further comprise instructions for administering the caTCR plus CSR immune cell composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a target antigen-positive cancer (such as adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lung cancer, lymphoma, melanoma, mesothelioma, multiple myeloma, pancreatic cancer, pheochromocytoma, plasmacytoma, neuroblastoma, ovarian cancer, prostate cancer, sarcoma, stomach cancer, uterine cancer or thyroid cancer). In other embodiments, the package insert indicates that the composition is used for treating a target antigen-positive viral infection (for example infection by CMV, EBV, HBV, KSHV, HPV, MCV, HTLV-1, HIV-1, or HCV).

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a target antigen-positive disease or disorder described herein, optionally in combination with the articles of manufacture. Kits of the invention include one or more containers comprising a caTCR plus CSR immune cell composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an immune cell presenting on its surface a caTCR and a CSR. In some embodiments, the kit comprises a) a composition comprising an immune cell presenting on its surface a caTCR and a CSR, and b) an effective amount of at least one other agent, wherein the other agent increases the expression of MHC proteins and/or enhances the surface presentation of peptides by MHC proteins (e.g., IFNγ, IFNβ, IFNα, or Hsp90 inhibitor). In some embodiments, the kit comprises a) a composition comprising an immune cell presenting on its surface a caTCR and a CSR, and b) instructions for administering the caTCR plus CSR immune cell composition to an individual for treatment of a target antigen-positive disease (such as cancer or viral infection). In some embodiments, the kit comprises a) a composition comprising an immune cell presenting on its surface a caTCR and a CSR, b) an effective amount of at least one other agent, wherein the other agent increases the expression of MHC proteins and/or enhances the surface presentation of peptides by MHC proteins (e.g., IFNγ, IFNβ, IFNα, or Hsp90 inhibitor), and c) instructions for administering the caTCR plus CSR immune cell composition and the other agent(s) to an individual for treatment of a target antigen-positive disease (such as cancer or viral infection). The caTCR plus CSR immune cell composition and the other agent(s) can be present in separate containers or in a single container. For example, the kit may comprise one distinct composition or two or more compositions wherein one composition comprises the caTCR plus CSR immune cell and another composition comprises the other agent.

In some embodiments, the kit comprises a) one or more compositions comprising a caTCR and a CSR, and b) instructions for combining the caTCR and CSR with immune cells (such as immune cells, e.g., T cells or natural killer cells, derived from an individual) to form a composition comprising the immune cells presenting on their surface the caTCR and CSR, and administering the caTCR plus CSR immune cell composition to the individual for treatment of a target antigen-positive disease (such as cancer or viral infection). In some embodiments, the kit comprises a) one or more compositions comprising a caTCR and a CSR, and b) an immune cell (such as a cytotoxic cell). In some embodiments, the kit comprises a) one or more compositions comprising a caTCR and a CSR, b) an immune cell (such as a cytotoxic cell), and c) instructions for combining the caTCR and CSR with the immune cell to form a composition comprising the immune cell presenting on its surface the caTCR and CSR, and administering the caTCR plus CSR immune cell composition to an individual for the treatment of a target antigen-positive disease (such as cancer or viral infection).

In some embodiments, the kit comprises a nucleic acid (or set of nucleic acids) encoding a caTCR and a CSR. In some embodiments, the kit comprises a) a nucleic acid (or set of nucleic acids) encoding a caTCR and a CSR, and b) a host cell (such as an immune cell) for expressing the nucleic acid (or set of nucleic acids). In some embodiments, the kit comprises a) a nucleic acid (or set of nucleic acids) encoding a caTCR and a CSR, and b) instructions for i) expressing the caTCR and CSR in a host cell (such as an immune cell, e.g., a T cell), ii) preparing a composition comprising the host cell expressing the caTCR and CSR, and iii) administering the composition comprising the host cell expressing the caTCR and CSR to an individual for the treatment of a target antigen-positive disease (such as cancer or viral infection). In some embodiments, the host cell is derived from the individual. In some embodiments, the kit comprises a) a nucleic acid (or set of nucleic acids) encoding a caTCR and a CSR, b) a host cell (such as an immune cell) for expressing the nucleic acid (or set of nucleic acids), and c) instructions for i) expressing the caTCR and CSR in the host cell, ii) preparing a composition comprising the host cell expressing the caTCR and CSR, and iii) administering the composition comprising the host cell expressing the caTCR and CSR to an individual for the treatment of a target antigen-positive disease (such as cancer or viral infection).

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the caTCR plus CSR immune cell compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of a caTCR plus CSR immune cell composition as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the caTCR and CSR, and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Exemplary Embodiments

Embodiment 1. In one embodiment, there is provided an immune cell comprising:
a) a chimeric antibody-T cell receptor (TCR) construct (caTCR) comprising:
i) an antigen binding module that specifically binds to a target antigen; and
ii) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule; and
b) a chimeric signaling receptor (CSR) comprising:
i) a ligand-binding module that is capable of binding or interacting with a target ligand;
ii) a transmembrane module; and
iii) a co-stimulatory immune cell signaling module that is capable of providing a co-stimulatory signal to the immune cell,
wherein the ligand-binding module and the co-stimulatory immune cell signaling module are not derived from the same molecule, and wherein the CSR lacks a functional primary immune cell signaling domain.

Embodiment 2. The immune cell of embodiment 1, wherein the CSR lacks any primary immune cell signaling sequences.

Embodiment 3. The immune cell of embodiment 1 or 2, wherein the target antigen is a cell surface antigen.

Embodiment 4. The immune cell of embodiment 3, wherein the cell surface antigen is selected from the group consisting of a protein, a carbohydrate, and a lipid.

Embodiment 5. The immune cell of embodiment 4, wherein the cell surface antigen is selected from the group consisting of CD19, ROR1, ROR2, BCMA, GPRC5D, and FCRL5.

Embodiment 6. The immune cell of embodiment 1 or 2, wherein the target antigen is a complex comprising a peptide and a major histocompatibility complex (MHC) protein.

Embodiment 7. The immune cell of embodiment 6, wherein the peptide is derived from a protein selected from the group consisting of WT-1, AFP, HPV16-E7, NY-ESO-1, PRAME, EBV-LMP2A, and PSA.

Embodiment 8. The immune cell of any one of embodiments 1-7, wherein the first TCR-TM is derived from one of the transmembrane domains of a first T cell receptor and the second TCR-TM is derived from the other transmembrane domain of the first T cell receptor.

Embodiment 9. The immune cell of embodiment 8, wherein at least one of the TCR-TMs is non-naturally occurring.

Embodiment 10. The immune cell of embodiment 9, wherein the TCRM allows for enhanced recruitment of the at least one TCR-associated signaling molecule as compared to a TCRM comprising the first T cell receptor transmembrane domains.

Embodiment 11. The immune cell of anyone of embodiments 8-10, wherein the first TCR-TM comprises up to 5 amino acid substitutions compared to the transmembrane domain from which it is derived and/or the second TCR-TM comprises up to 5 amino acid substitutions compared to the transmembrane domain from which it is derived.

Embodiment 12. The immune cell of embodiment 11, wherein the first TCR-TM comprises a single amino acid substitution and/or the second TCR-TM comprises a single amino acid substitution.

Embodiment 13. The immune cell of any one of embodiments 8-12, wherein the first T cell receptor is a γ/δ T cell receptor.

Embodiment 14. The immune cell of any one of embodiments 8-12, wherein the first T cell receptor is an α/β cell receptor.

Embodiment 15. The immune cell of any one of embodiments 1-14, wherein the antigen-binding module is an antibody moiety selected from the group consisting of a Fab, a Fab', a (Fab')2, an Fv, and a single chain Fv (scFv).

Embodiment 16. The immune cell of embodiment 15, wherein the antigen binding module comprises a $V_H$ domain and a $V_L$ domain, and wherein the $V_H$ domain is linked to the amino-terminus of one of the TCRDs and the $V_L$ domain is linked to the amino-terminus of the other TCRD.

Embodiment 17. The immune cell of embodiment 16, wherein the $V_H$ domain is linked to one of the TCRDs via a $C_H 1$ domain and the $V_L$ domain is linked to the other TCRD via a $C_L$ domain.

Embodiment 18. The immune cell of embodiment 15, wherein the caTCR further comprises at least one additional antigen-binding module.

Embodiment 19. The immune cell of embodiment 18, wherein the at least one additional antigen-binding module is an antibody moiety.

Embodiment 20. The immune cell of embodiment 18 or 19, wherein the caTCR is multispecific.

Embodiment 21. The immune cell of anyone of embodiments 15-20, wherein the antigen binding module comprises an scFv fused to the amino-terminus of one of the TCRDs.

Embodiment 22. The immune cell of embodiment 21, wherein the caTCR comprises a first scFv fused to the amino terminus of the first TCRD and a second scFv fused to the amino-terminus of the second TCRD.

Embodiment 23. The immune cell of embodiment 22, wherein the first scFv binds to a different target than the second scFv.

Embodiment 24. The immune cell of any one of embodiments 1-23, wherein the caTCR is a heterodimer comprising a first polypeptide chain comprising the first TCRD and a second polypeptide chain comprising the second TCRD, and wherein the antigen-binding module is linked to the amino-terminus of one or both of the first and second TCRDs.

Embodiment 25. The immune cell of any one of embodiments 1-24, wherein the caTCR further comprises a stabilization module comprising a first stabilization domain and a second stabilization domain, wherein the first and second stabilization domains have a binding affinity for each other that stabilizes the caTCR.

Embodiment 26. The immune cell of embodiment 25, wherein the stabilization module is selected from the group consisting of a $C_H1$-$C_L$ module, a $C_H2$-$C_H2$ module, a $C_H3$-$C_H3$ module, and a $C_H4$-$C_H4$ module.

Embodiment 27. The immune cell of embodiment 25 or 26, wherein there is a covalent linkage between the first and second stabilization domains.

Embodiment 28. The immune cell of embodiment 27, wherein the covalent linkage is a disulfide linkage.

Embodiment 29. The immune cell of any one of embodiments 25-28, wherein the stabilization module is located between the antigen-binding module and the TCRM.

Embodiment 30. The immune cell of any one of embodiments 25-29, wherein the caTCR is a heterodimer comprising:
 a) a first polypeptide chain comprising the first stabilization domain fused to the amino-terminus of the first TCRD and a second polypeptide chain comprising the second stabilization domain fused to the amino-terminus of the second TCRD, and wherein the antigen-binding module is fused to the amino-terminus of one or both of the first and second stabilization domains.

Embodiment 31. The immune cell of anyone of embodiments 1-30, wherein the caTCR binds to the target antigen with an equilibrium dissociation constant (Kd) from about 0.1 pM to about 500 nM.

Embodiment 32. The immune cell of anyone of embodiments 1-31, wherein the TCR-associated signaling molecule is selected from the group consisting of CD3δε, CD3γε, and ζζ.

Embodiment 33. The immune cell of anyone of embodiments 1-32, wherein the target antigen and the target ligand are the same.

Embodiment 34. The immune cell of any one of embodiments 1-32, wherein the target antigen and the target ligand are different.

Embodiment 35. The immune cell of embodiment 34, wherein the target ligand is a ligand expressed on the surface of a cell presenting the target antigen.

Embodiment 36. The immune cell of anyone of embodiments 1-35, where the target ligand is a disease-associated ligand.

Embodiment 37. The immune cell of embodiment 36, wherein the target ligand is a cancer-associated ligand.

Embodiment 38. The immune cell of embodiment 37, wherein the cancer-associated ligand is selected from the group consisting of CD19, CD20, CD22, CD47, IL4, GPC-3, ROR1, ROR2, BCMA, GPRC5D, and FCRL5.

Embodiment 39. The immune cell of embodiment 37, wherein the cancer-associated ligand is a peptide/MHC complex comprising a peptide derived from a protein selected from the group consisting of WT-1, AFP, HPV16-E7, NY-ESO-1, PRAME, EBV-LMP2A, and PSA.

Embodiment 40. The immune cell of embodiment 36, wherein the target ligand is a virus-associated ligand.

Embodiment 41. The immune cell of anyone of embodiments 1-35, where the target ligand is an immunomodulatory molecule.

Embodiment 42. The immune cell of embodiment 41, wherein the immunomodulatory molecule is an immunosuppressive receptor, and the CSR is an antagonist of the immunosuppressive receptor.

Embodiment 43. The immune cell of embodiment 41, wherein the immunomodulatory molecule is an immunostimulatory receptor, and the CSR is an agonist of the immunostimulatory receptor.

Embodiment 44. The immune cell of embodiment 41, where the target ligand is an immune checkpoint molecule.

Embodiment 45. The immune cell of embodiment 44, wherein the immune checkpoint molecule is selected from the group consisting of PD-L1, PD-L2, CD80, CD86, ICOSL, B7-H3, B7-H4, HVEM, 4-1BBL, OX40L, CD70, CD40, and GAL9.

Embodiment 46. The immune cell of embodiment 41, wherein the target ligand is an inhibitory cytokine.

Embodiment 47. The immune cell of anyone of embodiments 1-35, where the target ligand is an apoptotic molecule.

Embodiment 48. The immune cell of embodiment 47, wherein the apoptotic molecule is selected from the group consisting of FasL, FasR, TNFR1, and TNFR2.

Embodiment 49. The immune cell of any one of embodiments 1-48, wherein the ligand-binding module is an antibody moiety.

Embodiment 50. The immune cell of embodiment 49, wherein the antibody moiety of the CSR is selected from the group consisting of a Fab, a Fab', a (Fab')2, an Fv, and a single chain Fv (scFv).

Embodiment 51. The immune cell of embodiment 50, wherein the antibody moiety of the CSR is an scFv.

Embodiment 52. The immune cell of any one of embodiments 1-48, wherein the ligand-binding module is derived from the extracellular domain of a receptor.

Embodiment 53. The immune cell of embodiment 52, wherein the receptor is selected from the group consisting of FasR, TNFR1, TNFR2, PD-1, CD28, CTLA-4, ICOS, BTLA, KIR, LAG-3, 4-1BB, OX40, CD27, TIM-3, IL-10R, IL-6R, and IL-4R.

Embodiment 54. The immune cell of any one of embodiments 1-53, wherein the transmembrane module of the CSR comprises transmembrane domains derived from CD28, CD3ε, CD3ζ, CD45, CD4, CD5, CD8, CD9, CD16, CD22, CD33, CD37, CD64, CD80, CD86, CD134, CD137, or CD154.

Embodiment 55. The immune cell of any one of embodiments 1-54, wherein the co-stimulatory immune cell signaling module is derived from the intracellular domain of a co-stimulatory receptor of a TCR.

Embodiment 56. The immune cell of embodiment 55, wherein the co-stimulatory receptor is selected from the group consisting of CD28, 4-1BB, OX40, ICOS, CD27, and CD40.

Embodiment 57. The immune cell of any one of embodiments 1-56, wherein the expression of the CSR is inducible.

Embodiment 58. The immune cell of embodiment 57, wherein the expression of the CSR is inducible upon activation of the immune cell.

Embodiment 59. The immune cell of any one of embodiments 1-32, wherein the antigen-binding module of the caTCR comprises an antibody moiety that binds to CD19, wherein the ligand-binding module of the CSR comprises an scFv that binds to CD19, and wherein the transmembrane module and co-stimulatory immune cell signaling module are both derived from CD28.

Embodiment 60. The immune cell of embodiment 59, wherein the antibody moiety that binds to CD19 comprises a $V_H$ domain comprising the amino acid sequence of SEQ ID NO: 58 and a $V_L$ domain comprising the amino acid sequence of SEQ ID NO: 59, wherein the scFv that binds to CD19 comprises a $V_L$ domain comprising the amino acid sequence of SEQ ID NO: 58 and a $V_L$ domain comprising the amino acid sequence of SEQ ID NO: 59, and wherein the CSR comprises a fragment of CD28 comprising the amino acid sequence of SEQ ID NO: 51.

Embodiment 61. The immune cell of embodiment 60, wherein the caTCR comprises two polypeptide chains comprising the amino acid sequences of SEQ ID NOs: 72 and 73 or SEQ ID NOs: 74 and 75, and/or wherein the CSR comprises the amino acid sequence of SEQ ID NO: 80.

Embodiment 62. The immune cell of any one of embodiments 1-32, wherein the antigen-binding module of the caTCR comprises an antibody moiety that binds to AFP, wherein the ligand-binding module of the CSR comprises an scFv that binds to GPC3, and wherein the transmembrane module and co-stimulatory immune cell signaling module are both derived from CD28.

Embodiment 63. The immune cell of embodiment 62, wherein the antibody moiety that binds to AFP comprises a $V_H$ domain comprising the amino acid sequence of SEQ ID NO: 62 and a $V_L$ domain comprising the amino acid sequence of SEQ ID NO: 63, wherein the scFv that binds to GPC3 comprises a $V_L$ domain comprising the amino acid sequence of SEQ ID NO: 64 and a $V_L$ domain comprising the amino acid sequence of SEQ ID NO: 65, and wherein the CSR comprises a fragment of CD28 comprising the amino acid sequence of SEQ ID NO: 51.

Embodiment 64. The immune cell of embodiment 63, wherein the caTCR comprises two polypeptide chains comprising the amino acid sequences of SEQ ID NOs: 68 and 69 or SEQ ID NOs: 70 and 71, and/or wherein the CSR comprises the amino acid sequence of SEQ ID NO: 82.

Embodiment 65. The immune cell of any one of embodiments 1-32, wherein the antigen-binding module of the caTCR comprises an antibody moiety that binds to CD19, wherein the ligand-binding module of the CSR comprises an scFv that binds to CD20, and wherein the transmembrane module and co-stimulatory immune cell signaling module are both derived from CD28.

Embodiment 66. The immune cell of embodiment 65, wherein the antibody moiety that binds to CD19 comprises a $V_H$ domain comprising the amino acid sequence of SEQ ID NO: 58 and a $V_L$ domain comprising the amino acid sequence of SEQ ID NO: 59, wherein the scFv that binds to CD20 comprises a $V_H$ domain comprising the amino acid sequence of SEQ ID NO: 60 and a $V_L$ domain comprising the amino acid sequence of SEQ ID NO: 61, and wherein the CSR comprises a fragment of CD28 comprising the amino acid sequence of SEQ ID NO: 51.

Embodiment 67. The immune cell of embodiment 66, wherein the caTCR comprises two polypeptide chains comprising the amino acid sequences of SEQ ID NOs: 72 and 73 or SEQ ID NOs: 74 and 75, and/or wherein the CSR comprises the amino acid sequence of SEQ ID NO: 81.

Embodiment 68. In one embodiment, there is provided one or more nucleic acids encoding the caTCR and CSR of any one of embodiments 1-67, wherein the caTCR and CSR each consist of one or more polypeptide chains encoded by the one or more nucleic acids.

Embodiment 69. In one embodiment, there is provided one or more nucleic acids encoding:
a) a chimeric antibody-T cell receptor (TCR) construct (caTCR) comprising:
i) an antigen binding module that specifically binds to a target antigen; and
ii) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule, and wherein the caTCR consists of one or more polypeptide chains; and
b) a chimeric signaling receptor (CSR) comprising:
i) a ligand-binding module that is capable of binding or interacting with a target ligand;
ii) a transmembrane module; and
iii) a co-stimulatory immune cell signaling module that is capable of providing a co-stimulatory signal to the immune cell, wherein the ligand-binding module and the co-stimulatory immune cell signaling module are not derived from the same molecule, wherein the CSR lacks a functional primary immune cell signaling domain, and wherein the CSR consists of one or more polypeptide chains.

Embodiment 70. The one or more nucleic acids of embodiment 68 or 69, wherein the caTCR and CSR are encoded on the same nucleic acid molecule.

Embodiment 71. The one or more nucleic acids of embodiment 68 or 69, wherein the caTCR and CSR are encoded on different nucleic acid molecules Embodiment 72. The one or more nucleic acids of anyone of embodiments 68-71, comprising a nucleotide sequence encoding the CSR operably linked to an inducible promoter.

Embodiment 73. The one or more nucleic acids of embodiment 72, wherein the inducible promoter is inducible upon activation of the immune cell.

Embodiment 74. The one or more nucleic acids of embodiment 72, wherein the inducible promoter is a nuclear-factor of the activated T-cell (NFAT)-derived promoter.

Embodiment 75. In one embodiment, there is provided one or more vectors comprising the one or more nucleic acids of any one of embodiments 68-74.

Embodiment 76. The one or more vectors of embodiment 75, wherein at least one of the vectors comprises a nucleic acid sequence encoding the caTCR and at least one other vector comprises a nucleic acid sequence encoding the CSR.

Embodiment 77. The one or more vectors of embodiment 75, comprising a single vector comprising the one or more nucleic acids.

Embodiment 78. In one embodiment, there is provided a composition comprising the one or more nucleic acids of any one of embodiments 68-74 or the one or more vectors of any one of embodiments 75-77.

Embodiment 79. In one embodiment, there is provided an immune cell comprising the one or more nucleic acids of any one of embodiments 68-74 or the one or more vectors of any one of embodiments 75-77.

Embodiment 80. The immune cell of embodiment 79, wherein the immune cell further comprises a caTCR expressed from the one or more nucleic acids of any one of embodiments 68-74 or the one or more vectors of any one of embodiments 75-77.

Embodiment 81. The immune cell of embodiment 79 or 80, wherein the immune cell further comprises a CSR expressed from the one or more nucleic acids of any one of embodiments 68-74 or the one or more vectors of any one of embodiments 75-77.

Embodiment 82. The immune cell of anyone of embodiments 1-67 and 79-81, wherein the immune cell is selected from the group consisting of a cytotoxic T cell, a helper T cell, a natural killer T cell, and a suppressor T cell.

Embodiment 83. The immune cell of any one of embodiments 1-67 and 79-82, wherein
 a) the caTCR is a heterodimer comprising a first polypeptide chain comprising the first TCRD and a second polypeptide chain comprising the second TCRD, and wherein the antigen-binding module comprises one or two polypeptide chains linked to the amino-terminus of one or both of the TCRDs, and
 b) the CSR comprises a single polypeptide chain, the immune cell comprising:
 i) a first nucleic acid sequence encoding the first polypeptide chain of the caTCR;
 ii) a second nucleic acid sequence encoding the second polypeptide chain of the caTCR; and
 iii) a third nucleic acid sequence encoding the CSR.

Embodiment 84. The immune cell of embodiment 83, comprising:
 a) a first vector comprising the first nucleic acid sequence under the control of a first promoter;
 b) a second vector comprising the second nucleic acid sequence under the control of a second promoter; and
 c) a third vector comprising the third nucleic acid sequence under the control of a third promoter.

Embodiment 85. The immune cell of embodiment 83, comprising:
 a) a first vector comprising:
 i) the first nucleic acid sequence under the control of a first promoter; and
 ii) the second nucleic acid sequence under the control of a second promoter; and
 b) a second vector comprising the third nucleic acid sequence under the control of a third promoter.

Embodiment 86. The immune cell of embodiment 83, comprising a vector comprising:
 a) the first nucleic acid sequence under the control of a first promoter;
 b) the second nucleic acid sequence under the control of a second promoter; and
 c) the third nucleic acid sequence under the control of a third promoter.

Embodiment 87. The immune cell of any one of embodiments 84-86, wherein the first promoter and/or the second promoter are constitutively active promoters.

Embodiment 88. The immune cell of any one of embodiments 84-87, wherein the third promoter is an inducible promoter.

Embodiment 89. The immune cell of embodiment 83, comprising:
 a) a first vector comprising the first nucleic acid sequence and the second nucleic acid sequence under the control of a single first promoter; and
 b) a second vector comprising the third nucleic acid sequence under the control of a second promoter.

Embodiment 90. The immune cell of embodiment 83, comprising a vector comprising:
 a) the first nucleic acid sequence and the second nucleic acid sequence under the control of a single first promoter; and
 b) the third nucleic acid sequence under the control of a second promoter.

Embodiment 91. The immune cell of embodiment 89 or 90, wherein the first promoter is a constitutively active promoter.

Embodiment 92. The immune cell of any one of embodiments 89-91, wherein the second promoter is an inducible promoter.

Embodiment 93. The immune cell of embodiment 88 or 92, wherein the inducible promoter is inducible upon activation of the immune cell.

Embodiment 94. The immune cell of embodiment 88 or 92, wherein the inducible promoter is an NFAT-derived promoter.

Embodiment 95. The immune cell of embodiment 83, comprising a vector comprising the first nucleic acid sequence, the second nucleic acid sequence, and the third nucleic acid sequence all under the control of a single promoter.

Embodiment 96. The immune cell of any one of embodiments 84-95, wherein the vectors are integrated into the immune cell genome.

Embodiment 97. In one embodiment, there is provided a pharmaceutical composition comprising the immune cell of any one of embodiments 1-67 and 79-96, and a pharmaceutically acceptable carrier.

Embodiment 98. In one embodiment, there is provided a method of killing a target cell presenting a target antigen (or treating a target antigen-associated disease), comprising contacting the target cell with the immune cell of any one of embodiments 1-67 and 79-96.

Embodiment 99. The method of embodiment 98, wherein the contacting is carried out in vivo.

Embodiment 100. The method of embodiment 98, wherein the contacting is carried out in vitro.

Embodiment 101. In one embodiment, there is provided a method of treating a target antigen-associated disease in an individual in need thereof, comprising administering to the individual an effective amount of the pharmaceutical composition of embodiment 97.

Embodiment 102. The method of embodiment 101, wherein the target antigen-associated disease is cancer.

Embodiment 103. The method of embodiment 102, wherein the cancer is selected from the group consisting of adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lung cancer, lymphoma, melanoma, mesothelioma, multiple myeloma, pancreatic cancer, pheochromocytoma, plasmacytoma, neuroblastoma, ovarian cancer, prostate cancer, sarcoma, stomach cancer, uterine cancer and thyroid cancer.

Embodiment 104. The method of embodiment 101, wherein the target antigen-associated disease is viral infection.

Embodiment 105. The method of embodiment 104, wherein the viral infection is caused by a virus selected from the group consisting of Cytomegalovirus (CMV), Epstein-Barr Virus (EBV), Hepatitis B Virus (HBV), Kaposi's Sarcoma associated herpesvirus (KSHV), Human papillomavirus (HPV), Molluscum contagiosum virus (MCV), Human T cell leukemia virus 1 (HTLV-1), Human immunodeficiency virus (HIV), and Hepatitis C Virus (HCV).

Embodiment 106. The method of anyone of embodiments 101-105, wherein the immune cell is autologous to the individual.

Embodiment 107. In one embodiment, there is provided a method of providing a co-stimulatory signal to an immune cell comprising a caTCR or transduced with a nucleic acid encoding a caTCR, comprising introducing into said cell the one or more nucleic acids of any one of embodiments 68-74 or the one or more vectors of any one of embodiments 75-77.

Examples

Materials and Methods
Cell Samples, Cell Lines, and Antibodies

The cell lines HepG2 (ATCC HB-8065; HLA-A2+, AFP+), SK-HEP-1 (ATCC HTB-52; HLA-A2+, AFP$^-$), Raji (ATCC CCL-86; CD19$^+$), CA46 (ATCC CRL-1648; CD19$^+$), Jurkat (ATCC CRL-2899, CD19$^-$), J.RT3-T3.5 (ATCC TIB-153), Jeko-1 (ATCC CRL-3006; CD19$^+$), THP-1 (ATCC TIB-202, CD19$^-$), Daudi (ATCC CCL-213; CD19$^+$), HeLa (ATCC CCL-2), MDA-MB-231 (ATCC HTB-26) and MCF-7 (ATCC HTB-22) were obtained from the American Type Culture Collection. Jurkat is a human T lymphocyte cell line derived from T cell leukemia. J.RT3-T3.5 is a mutant line derived from Jurkat cells that lacks the T cell receptor R chain. Raji is a Burkitt lymphoma cell line that expresses CD19. Raji-CD19 knockout (Raji-CD19KO) line was generated by CRISPR technology. Three different guide sequences were designed to target CD19 in Raji cells. CRISPR-Cas9 vector was purchased from Origene and each guide was cloned separately into the pCas-Guide vector. Three days after electroporation, efficiency of knock-out by each guide was evaluated by flow cytometry and the best CD19-knock-out pool was chosen for clonal selection by limiting dilution. The selected clone was confirmed as a complete CD19 knock-out by sequencing. All cell lines were cultured in RPMI 1640 or DMEM supplemented with 10% FBS and 2 mM glutamine at 37° C./5% $CO_2$.

Monoclonal Ab against human HLA-A02 (clone BB7.2) conjugated to FITC or APC, and its isotype control mouse IgG 2b conjugated to FITC or APC, antibodies against human or mouse CD3, human T cell receptor various subunit, 3×Flag tag, HA tag, goat F(ab)2 anti-human IgG conjugated with PE or FITC, and fluorescence-conjugated goat F(ab')2 anti-mouse Ig's (Invitrogen) were purchased. The anti-idiotypic antibody against an AFP158/HLLA-A*02:01-specific antibody was developed and produced in house at Eureka Therapeutics. Flow cytometry data were collected using BD FACSCanto II and analyzed using FlowJo software package.

All peptides were purchased and synthesized by Elim Biopharma. Peptides were >90% pure. The peptides were dissolved in DMSO or diluted in saline at 10 mg/mL and frozen at −80° C. Biotinylated single chain AFP158/HLA-A*02:01 and control peptides/HLA-A*02:01 complex monomers were generated by refolding the peptides with recombinant HLA-A*02:01 and beta-2 microglobulin (02M). The monomers were biotinylated via the BSP peptide linked to the C-terminal end of HLA-A*02:01 extracellular domain (ECD) by the BirA enzyme. Fluorescence-labelled streptavidin was mixed with biotinylated peptide/HLA-A*02:01 complex monomer to form fluorescence-labelled peptide/HLA-A*02:01 tetramer.

Lentiviruses containing human CD19-specific or AFP158/HLA-A*02:01-specific CAR or caTCRs were produced, for example, by transfection of 293T cells with vectors encoding the chimeric constructs. Primary human T-cells were used for transduction after one-day stimulation with CD3/CD28 beads (Dynabeads®, Invitrogen) in the presence of interleukin-2 (IL-2) at 100 U/ml. Concentrated lentiviruses were applied to T-cells in Retronectin- (Takara) coated 6-well plates for 96 hours. Transduction efficiencies of the anti-AFP and anti-CD19 chimeric constructs were assessed by flow cytometry, using biotinylated AFP158/HLA-A*02:01 tetramer ("AFP158 tetramer") with PE-conjugated streptavidin or anti-myc antibody respectively. Repeat flow cytometry analyses were done on day 5 and every 3-4 days thereafter.

Cell lines were transduced with either one or two vectors that encode the two subunits of caTCR construct. Five days post-transduction, cell lysates were generated for western blot using anti-HA (Anti-HA tag antibody—ChIP Grade, Abcam) or anti-Flag antibody (Anti-Flag Antibody Produced in Rabbit, Sigma).

Tumor cytotoxicities were assayed by Cytox 96 Non-radioactive LDH Cytotoxicity Assay (Promega). CD3$^+$ T cells were prepared from PBMC-enriched whole blood using EasySep Human T Cell Isolation Kit (StemCell Technologies) which negatively depletes CD14, CD16, CD19, CD20, CD36, CD56, CD66b, CD123, glycophorin A expressing cells. Human T cells were activated and expanded with, for example, CD3/CD28 Dynabeads (Invitrogen) according to manufacturer's protocol. Activated T cells (ATC) were cultured and maintained in RPMI1640 medium with 10% FBS plus 100 U/ml IL-2, and used at day 7-14. Activated T cells (immune cells) and target cells were co-cultured at various effector-to-target ratios (e.g., 2.5:1 or 5:1) for 16 hours and assayed for cytotoxicities.

Example 1. Chimeric Antibody-T Cell Receptor (caTCR) Designs

Various chimeric antibody-T cell receptor (caTCRs) designs are contemplated, and six different examples are shown in FIG. 1 (caTCR-1, caTCR-2, caTCR-3, caTCR-4, caTCR-5, and caTCR-6). In these designs, various antibody moieties (Fab, Fab', (Fab')2, Fv, or scFv) are fused to the amino terminus of T cell receptor α/β chains or γ/δ chains lacking variable and constant domains and including all or part of their connecting peptide (region after the constant domain), their transmembrane domain, or a variant thereof, and any intracellular domain to form caTCR heterodimers which can be expressed on the surface of T cells. In a native TCR, the Vα/Vβ or Vδ/Vγ domains form the antigen-binding domain of the TCR. Our designs replace the Vα-Cα/Vβ-Cβ or Vδ-Cδ/Vγ-Cγ regions with various antibody moieties, and introduce at least one variant TCR transmembrane domain, thus conferring an antibody's binding specificity to the construct, and resulting in an enhanced ability of the construct to recruit accessory molecules in a TCR complex, such as CD3δε, CD3γε and CD3ζζ, as compared to TCRs or related constructs with only naturally occurring TCR transmembrane domains. The caTCR constructs were named as follows: caTCR-[design #]-[variant location][#]. Design #1 corresponds to caTCR with a Fab antibody moiety, design #2 corresponds to caTCR with a Fab' antibody moiety, design #3 corresponds to caTCR with a (Fab')2 antibody moiety, design #4 corresponds to caTCR with an Fv antibody moiety, design #5 corresponds to caTCR with a single scFv antibody moiety, and design #6 corresponds to caTCR with two scFv antibody moieties (see FIG. 1). No variant location and #0 (e.g., caTCR-1-0) corresponds to a construct with naturally occurring TCR domains, and #≥1 corresponds to caTCR with specific variants in the variant location (e.g., caTCR-1-TM1 corresponds to one transmembrane domain variant, caTCR-1-EC1 corresponds to one extracellular domain variant; see Table 2).

In the caTCR-1 (IgV$_H$-IgC$_H$1-TCRδ/IgV$_L$-IgC$_L$-TCRγ) design, the variable domain and the first constant domain (IgV$_H$-IgC$_H$1) of an antibody heavy chain replaces the amino terminal portion of the TCRS chain up to a position bordering or within the connecting peptide in the extracellular domain of the TCRS chain after the Vδ-Cδ region, optionally wherein the transmembrane domain of the TCRS chain is modified, such as by substitution of one or more amino acids. The variable domain and the constant domain (IgV$_L$-IgC$_L$) of the corresponding antibody light chain replaces the amino terminal portion of the TCRγ chain up to a position bordering or within the connecting peptide in the extracellular domain of the TCRγ chain after the Vγ-Cγ region, optionally wherein the transmembrane domain of the TCRγ chain is modified, such as by substitution of one or more amino acids.

In one embodiment of caTCR-1, one chain includes the IgV$_H$ domain of an anti-AFP158/LA-A*02:01 antibody (SEQ ID NO: 62) fused to an IgC$_H$1 domain (any one of SEQ ID NOs: 37-47) fused to a carboxy-terminal portion of the TCRS chain including the transmembrane domain and all or part of the connecting peptide of the TCRS chain, and the other chain includes the IgV$_L$ domain of the anti-AFP158/HLA-A*02:01 antibody (SEQ ID NO: 63) fused to an IgC$_L$ domain (SEQ ID NO: 48) fused to a carboxy-terminal portion of the TCRγ chain including the transmembrane domain and all or part of the connecting peptide of the TCRγ chain. In some embodiments, both of the TCR transmembrane domains are naturally occurring. In some embodiments, at least one of the TCR transmembrane domains is a non-naturally occurring variant comprising one or more amino acid substitutions. In some embodiments, the carboxy terminal portion of the TCRS chain includes a connecting peptide having the amino acid sequence of SEQ ID NO: 31 or 32. In some embodiments, the carboxy terminal portion of the TCRS chain includes a transmembrane domain having the amino acid sequence of any one of SEQ ID NOs: 7, and 9-13. In some embodiments, the carboxy terminal portion of the TCR chain includes a connecting peptide having the amino acid sequence of SEQ ID NO: 33 or 34. In some embodiments, the carboxy terminal portion of the TCRγ chain includes a transmembrane domain having the amino acid sequence of any one of SEQ ID NOs: 8, and 14-26.

In the caTCR-2 (IgV$_H$-IgC$_H$1-hinge-TCRS/IgV$_L$-IgC$_L$-linker-TCRγ) design, the variable domain, the first constant domain, and the hinge (IgV$_H$-IgC$_H$1-hinge) of an antibody heavy chain replaces the amino terminal portion of the TCRS chain up to a position bordering or within the connecting peptide in the extracellular domain of the TCRS chain after the Vδ-Cδ region, optionally wherein the transmembrane domain of the TCRS chain is modified, such as by substitution of one or more amino acids. The variable domain and the constant domain of the corresponding antibody light chain fused to a linker (IgV$_L$-IgC$_L$-linker) replaces the amino terminal portion of the TCRγ chain up to a position bordering or within the connecting peptide in the extracellular domain of the TCRγ chain after the Vγ-Cγ region, optionally wherein the transmembrane domain of the TCRγ chain is modified, such as by substitution of one or more amino acids.

In the caTCR-3 (IgV$_H$-IgC$_H$1-hinge-TCRδ/IgV$_H$-IgC$_H$1-hinge-TCRγ+IgV$_L$-IgC$_L$) design, the variable domain, the first constant domain, and the hinge (IgV$_H$-IgC$_H$1-hinge) of an antibody heavy chain replaces the amino terminal portion of the TCRS chain up to a position bordering or within the connecting peptide in the extracellular domain of the TCRS chain after the Vδ-Cδ region, optionally wherein the transmembrane domain of the TCRS chain is modified, such as by substitution of one or more amino acids. The variable domain, the first constant domain, and the hinge (IgV$_H$-IgC$_H$1-hinge) of the antibody heavy chain replaces the amino terminal portion of the TCRγ chain up to a position bordering or within the connecting peptide in the extracellular domain of the TCRγ chain after the Vγ-Cγ region, optionally wherein the transmembrane domain of the TCRγ chain is modified, such as by substitution of one or more amino acids. The variable domain and the constant domain of the corresponding antibody light chain (IgV$_L$-IgC$_L$) are associated with the IgV$_H$-IgC$_H$1 domains.

In the caTCR-4 (IgV$_H$-TCR6/IgV$_L$-TCRγ) design, the variable domain (IgV$_H$) of an antibody heavy chain replaces the amino terminal portion of the TCR6 chain up to a position bordering or within the connecting peptide in the extracellular domain of the TCR6 chain after the Vδ-Cδ region, optionally wherein the transmembrane domain of the TCR6 chain is modified, such as by substitution of one or more amino acids. The variable domain (IgV$_L$) of the corresponding antibody light chain replaces the amino terminal portion of the TCRγ chain up to a position bordering or within the connecting peptide in the extracellular domain of the TCRγ chain after the Vγ-Cγ region, optionally wherein the transmembrane domain of the TCRγ chain is modified, such as by substitution of one or more amino acids.

In the caTCR-5 (IgV$_H$-IgV$_L$-TCRδ/TCRγ) design, the variable domain of an antibody heavy chain fused to the variable domain of the corresponding antibody light chain (IgV$_H$-IgV$_L$ or IgV$_L$-IgV$_H$) replaces the amino terminal portion of the TCRδ chain up to a position bordering or within the connecting peptide in the extracellular domain of the TCRδ chain after the Vδ-Cδ region, optionally wherein the transmembrane domain of the TCRδ chain is modified, such as by substitution of one or more amino acids. The amino terminal portion of the TCRγ chain up to a position bordering or within the connecting peptide in the extracellular domain of the TCRγ chain after the Vγ-Cγ region is deleted, optionally wherein the transmembrane domain of the TCRγ chain is modified, such as by substitution of one or more amino acids.

In the caTCR-6 (IgV$_H$-IgV$_L$-TCR6/IgV$_H$-IgV$_L$-TCR) design, the variable domain of an antibody heavy chain fused to the variable domain of the corresponding antibody light chain (IgV$_H$-IgV$_L$ or IgV$_L$-IgV$_H$) replaces the amino terminal portion of the TCRδ chain up to a position bordering or within the connecting peptide in the extracellular domain of the TCRδ chain after the Vδ-Cδ region, optionally wherein the transmembrane domain of the TCRδ chain is modified, such as by substitution of one or more amino acids. The variable domain of an antibody heavy chain fused to the variable domain of the corresponding antibody light chain (IgV$_H$-IgV$_L$ or IgV$_L$-IgV$_H$) replaces the amino terminal portion of the TCRγ chain up to a position bordering or within the connecting peptide in the extracellular domain of the TCRγ chain after the Vγ-Cγ region, optionally wherein the transmembrane domain of the TCRγ chain is modified, such as by substitution of one or more amino acids.

Example 2: Construction and Characterization of T Cells Transduced with Anti-CD19 caTCR-1 and Anti-CD19 Chimeric Stimulation Receptor A nucleic acid fragment encoding the anti-CD19 binding moiety (SEQ ID NOs: 58 and 59) was used to generate both a chimeric co-stimulatory receptor (CSR; also referred herein as "CSR1") comprising CD28 transmembrane and intracellular signaling sequences (SEQ ID NO: 51) and caTCR-1 constructs (caTCR-1-0 or caTCR-1-TM5). Primary T cells were transduced with either CSR alone, caTCR-1-0 alone, caTCR-1-0 in combination with CSR, or caTCR-1-TM5 in combination with CSR. Transduction efficiency was determined by cell surface staining and all caTCR-1 T-cells were matched at approximately 40% receptor positive by mixing with mock T-cells.

In Vitro Killing

CD80/86 negative NALM6 cells (leukemia cells expressing CD19) were used as target cells for T-cell stimulation at an effector-to-target ratio of 2.5:1. Specific T-cell lysis was measured after 16 hr incubation using the Cytox 96 Non-radioactive Cytotoxicity Assay (Promega).

Figure 2:
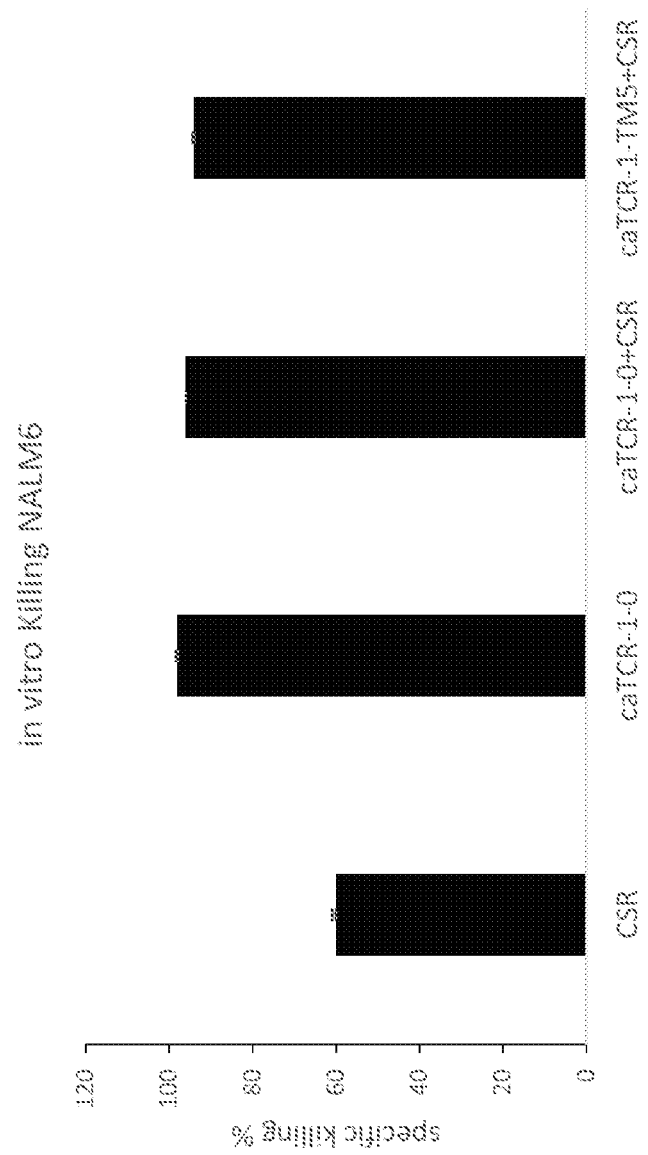
FIG. 2 shows percent specific lysis from the killing of cancer cell line NALM6 (CD19+), mediated by T cells transduced with anti-CD19 caTCR-1-0 alone, anti-CD19 CSR alone, or anti-CD19 caTCR (1-0 and 1-TM5)+anti-CD19 CSR.

Expression of anti-CD19-CSR with either anti-CD19-caTCR-1-0 or anti-CD19-caTCR-1-TM5 created fully functional cytotoxic T-cells capable of lysing NALM6 tumor cells in vitro (FIG. 2). Because the T cells expressing only the caTCR-1-0 and those expressing both caTCR-1 (caTCR-1-0 or caTCR-1-TM5) and CSR were all capable of lysing almost 100% of NALM6 target cells, no significant difference of the number of killed target cells was observed between the two types of T cells.

Cytokine Secretion

Figure 3:
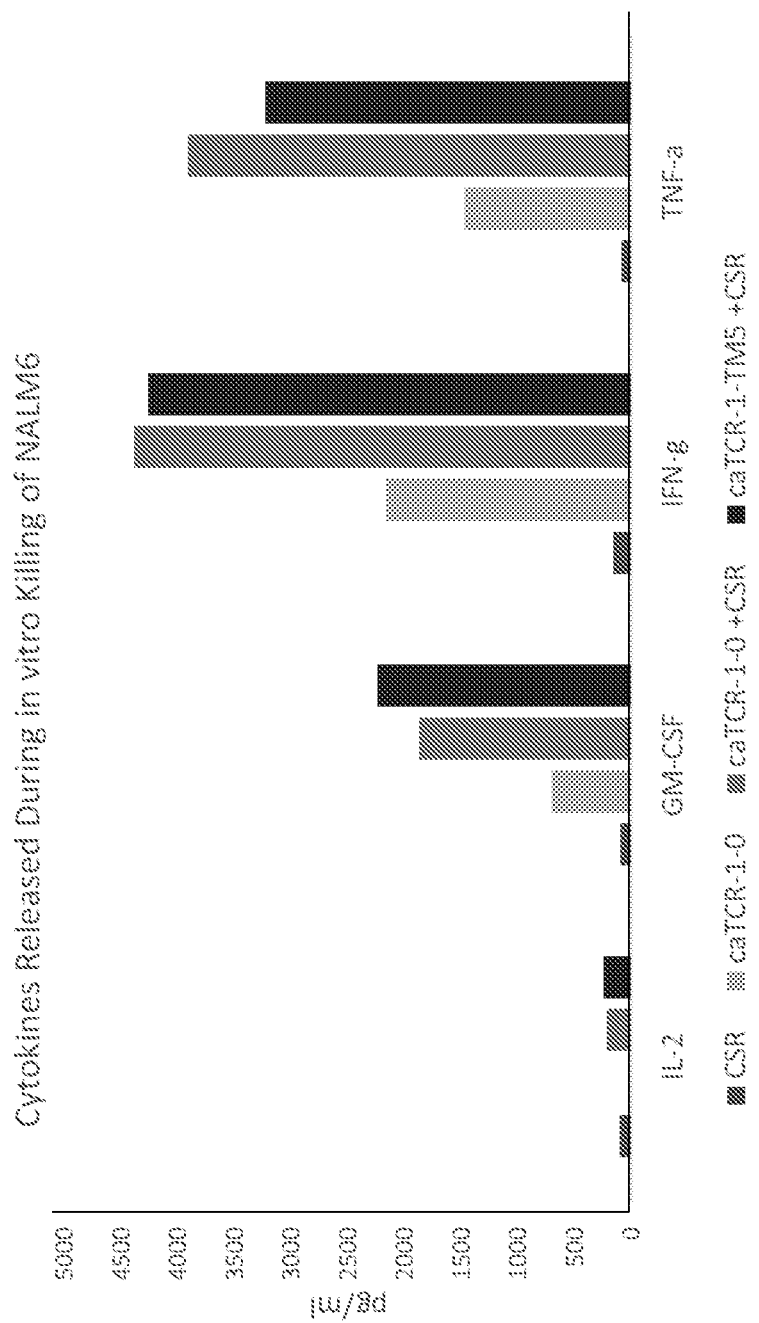
FIG. 3 shows the concentration of cytokines (IL-2, GM-CSF, IFN-γ, and TNF-α) found in the supernatant after in vitro killing of cancer cell line NALM6, mediated by T cells transduced with anti-CD19 caTCR-1-0 alone, anti-CD19 CSR alone, or anti-CD19 caTCR (1-0 and 1-TM5)+anti-CD19 CSR.

The concentration of cytokines released into the supernatant of the in vitro killing reactions was measured with a Bioplex200 (Luminex) using the Bio-plex Pro Human Cytokine 8-plex kit (BioRad). T cells expressing the CSR in combination with the caTCR (CSR-positive and caTCR-positive T-cells) released more cytotoxic cytokines than T-cells expressing ca-TCR-1-0 alone (FIG. 3).

Intracellular Cytokine Expression

T-cells were stimulated with target cells at an E:T ratio 1:2 in the presence of secretion inhibitor brefeldin A (BFA) for 4 hours. T-cells were permeabilized and cytokine specific antibodies were used to detect cytokines expressed in response to tumor stimulation. The percentage of cytokine-positive cells was determined using flow cytometry. The CSR-positive and caTCR-positive T-cells expressed more intracellular cytokines than T-cells expressing ca-TCR-1-0 alone (Table 5).

TABLE 5

| %, Positive | Raji | NALM6 | T-cell Alone |
|---|---|---|---|
| Intracellular TNFα Expression in CD8+ T-cells | | | |
| CSR | 0.58 | 0.44 | 0.04 |
| caTCR-1-0 | 24.3 | 20.1 | 0.04 |
| caTCR-1-0 + CSR | 28.7 | 28.2 | 0.07 |
| caTCR-1-TM5 + CSR | 29 | 31.5 | 0.04 |
| Intracellular IL-2 Expression in CD8+ T-cells | | | |
| CSR | 0.97 | 0.71 | 0.49 |
| caTCR-1-0 | 8.5 | 4.36 | 0.61 |
| caTCR-1-0 + CSR | 12.5 | 8.2 | 0.53 |
| caTCR-1-TM5 + CSR | 10.6 | 8.2 | 0.65 |
| Intracellular IFN-γ Expression in CD8+ T-cells | | | |
| CSR | 1.43 | 2.28 | 0.17 |
| caTCR-1-0 | 18.2 | 15.5 | 0.78 |
| caTCR-1-0+CSR | 21.8 | 18.8 | 1.72 |
| caTCR-1-TM5+CSR | 18.5 | 16.4 | 0.51 |

Taken together, the results indicate that the addition of the CSR increases the sensitivity and responsiveness of the caTCR T-cells. The increased amount of cytokines expressed in and released from CSR-caTCR double positive T cells indicates that the co-stimulation of both caTCR-1 and CSR raises the cytotoxic potential of the T-cells.

Degranulation

The primary mechanism by which T cells lyse tumor cells is by producing secretory granules of cytotoxic molecules that are released into target cells. CD107a can be used as a marker of degranulation activity and increased expression of CD107a correlates with an increase in cytotoxic T-cell function.

Figure 4:
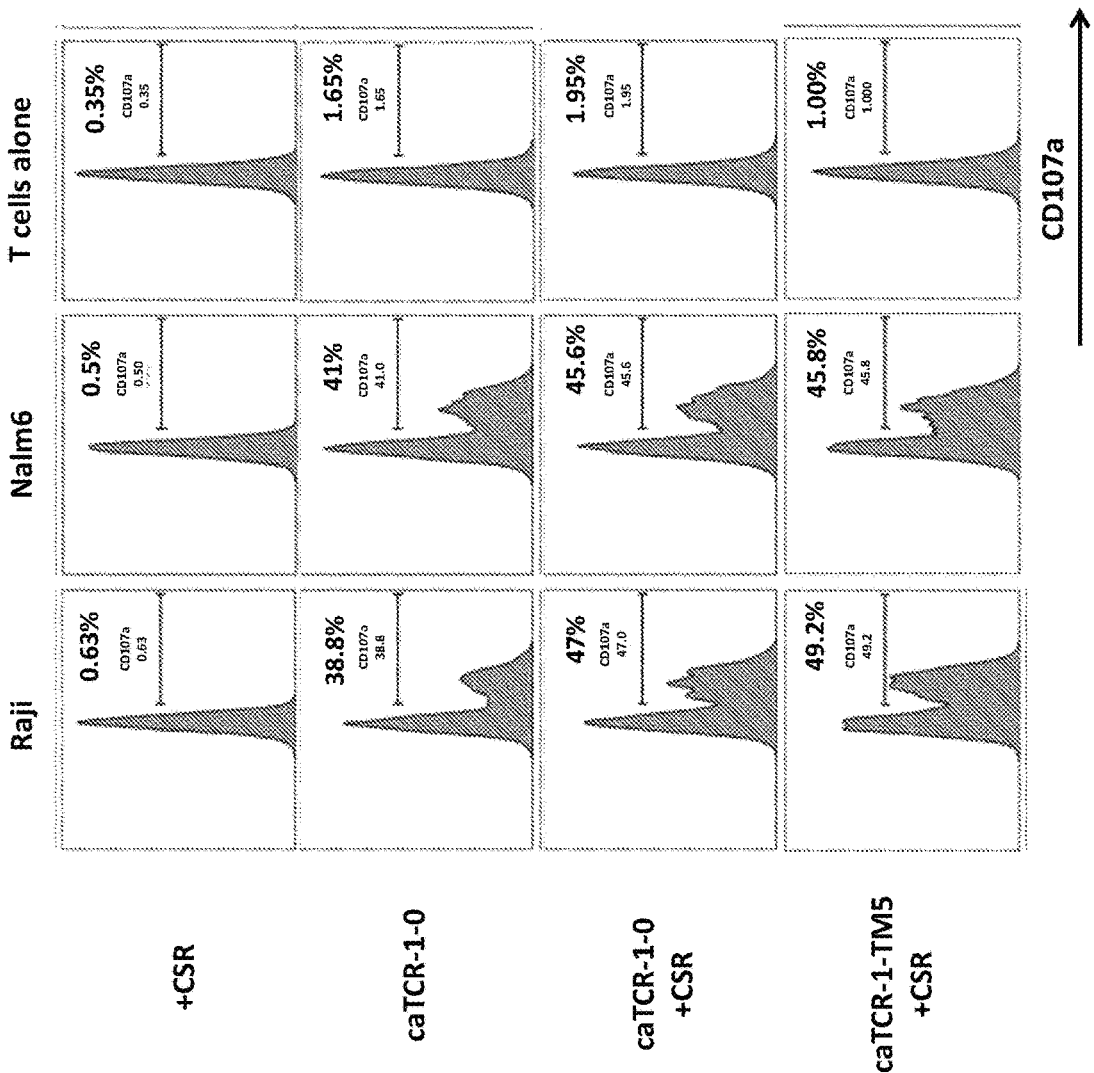
FIG. 4 shows the degranulation activity (as determined by CD107a expression) in T cells transduced with anti-CD19 caTCR-1-0 alone, anti-CD19 CSR alone, or anti-CD19 caTCR (1-0 and 1-TM5)+anti-CD19 CSR following stimulation with cancer cell line NALM6.

T cells were mixed with fluorescently-conjugated anti-CD107a and stimulated with target cells at an E:T ratio of 1:2 in the presence of the endocytosis inhibitor monensin for 4 hours. The amount of CD107a detected on the T-cell surface is a direct measure of the degree of cytotoxic degranulation induced by antigen recognition. Engagement of the CSR on caTCR T-cells increased T-cell degranulation, further demonstrating that the CSR makes the therapeutic T-cells more reactive towards the intended tumor cells (FIG. 4).

Proliferation

The proliferation and persistence of genetically modified T-cells is crucial for the success of adoptive T-cell transfer therapies when treating cancers. To assay the effect of the CSR on T-cell proliferation and persistence we labeled T-cells with the intracellular dye CFSE and observed the dilution of the dye as the T-cells divided when stimulated with tumor cells. We were also able to measure persistence of the T-cells by counting the number of CFSE-positive cells remaining at the indicated day.

Respective T-cells were serum starved overnight and labeled with CFSE using CellTrace CFSE (Thermo Fisher C34554). 100,000 T-cells were incubated at an E:T ratio of 2:1 and flow cytometry was used to observe serial dilution of the CFSE dye as the T-cells divide at the indicated day. The total number of T-cells were counted with FACs.

Figure 5:
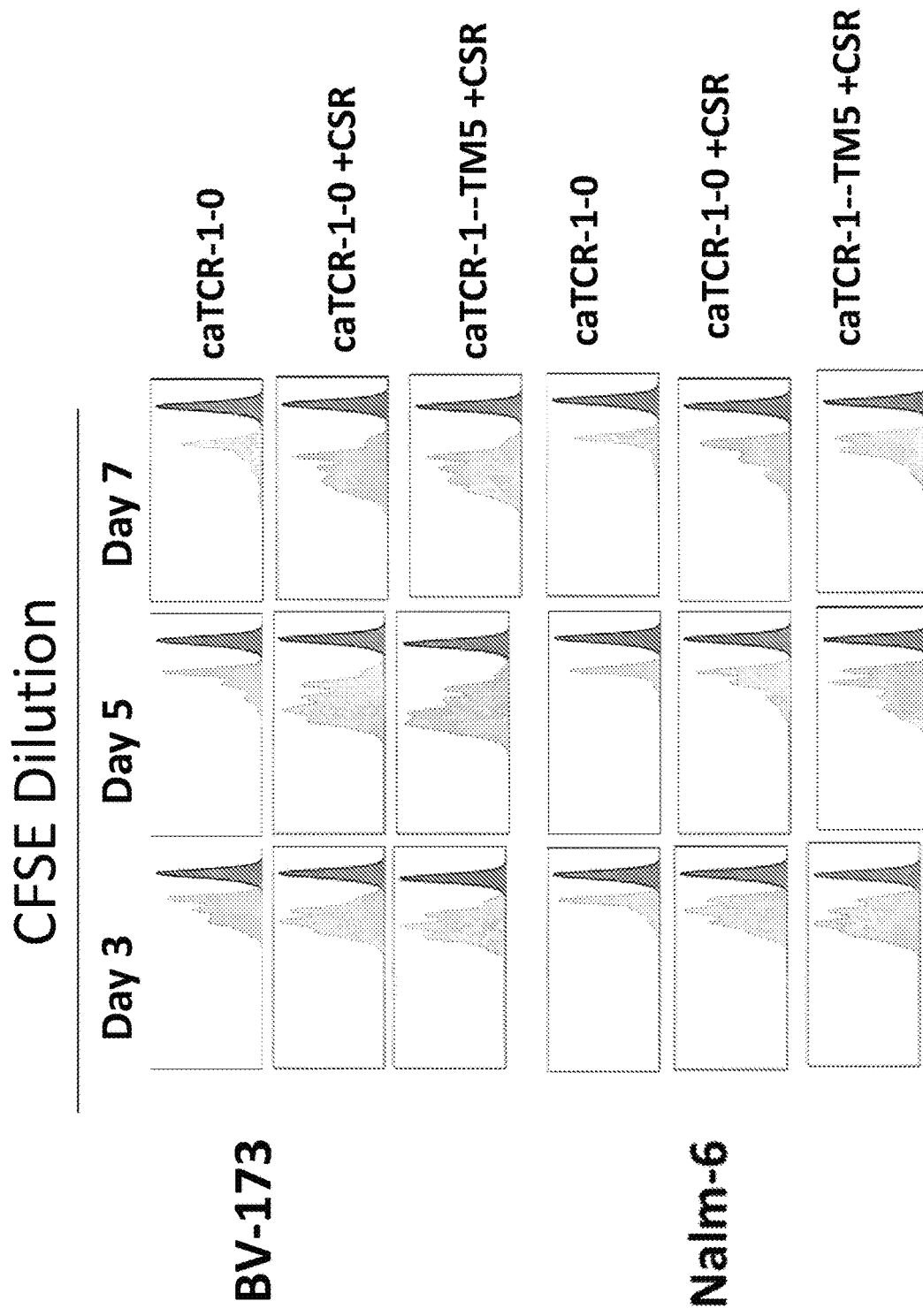
FIG. 5 shows the proliferation (as determined by CFSE dye dilution) of T cells transduced with anti-CD19 caTCR-1-0 alone or anti-CD19 caTCR (1-0 and 1-TM5)+anti-CD19 CSR following stimulation with cancer cell lines BV173 or NALM6.

CFSE dilution increased with CSR stimulation, indicating these T-cells had a higher proliferation potential (FIG. 5). Importantly there is also an increase in the cell number meaning that the cells not only proliferate better but their persistence is also maintained (Table 6).

TABLE 6 # of T cells Persisting After Engagement

| | BV173 | | | NALM6 | | |
|---|---|---|---|---|---|---|
| | -0 | -0 +CSR | -TM5 +CSR | -0 | -0 +CSR | -TM5 +CSR |
| Day 3 | 10354 | 28847 | 38830 | 6591 | 17260 | 32331 |
| Day 5 | 2945 | 16049 | 26551 | 1240 | 2988 | 8620 |
| Day 7 | 253 | 2135 | 5985 | 329 | 158 | 684 |

The results show that we were able to simultaneously stimulate both CSR and caTCR with tumor cells expressing both target ligand and target antigen, and that the co-stimulation of CSR and caTCR enhanced the cytotoxicity, proliferation potential, and persistence of caTCR T-cells. These are all characteristics that will increase the therapeutic potential of caTCR-based therapies using adoptive transfer.

Example 3. Construction and Characterization of T Cells Transduced with Anti-AFP caTCR-1 and Anti-GPC3 CSR A nucleic acid fragment encoding the anti-AFP binding moiety (SEQ ID NOs: 62 and 63) was used to generate caTCR-1 constructs (caTCR-1-0 or caTCR-1-TM5). A nucleic acid fragment encoding the anti-GPC3 binding moiety (SEQ ID NOs: 64 and 65) was used to generate a CSR (i.e., CSR1) comprising CD28 transmembrane and intracellular signaling sequences (SEQ ID NO: 51).

In Vitro Killing

HEPG2 cells (human liver cancer cells expressing AFP and GPC3) and HEPG2-GPC3.KO cells (HEPG2 cells with a targeted knockout of the GPC3 gene) were used as target cells for T-cell stimulation at an effector-to-target ratio of 2.5:1. Specific T-cell lysis was measured after 16 hr incubation using the Cytox 96 Non-radioactive Cytotoxicity Assay (Promega).

Figure 6:
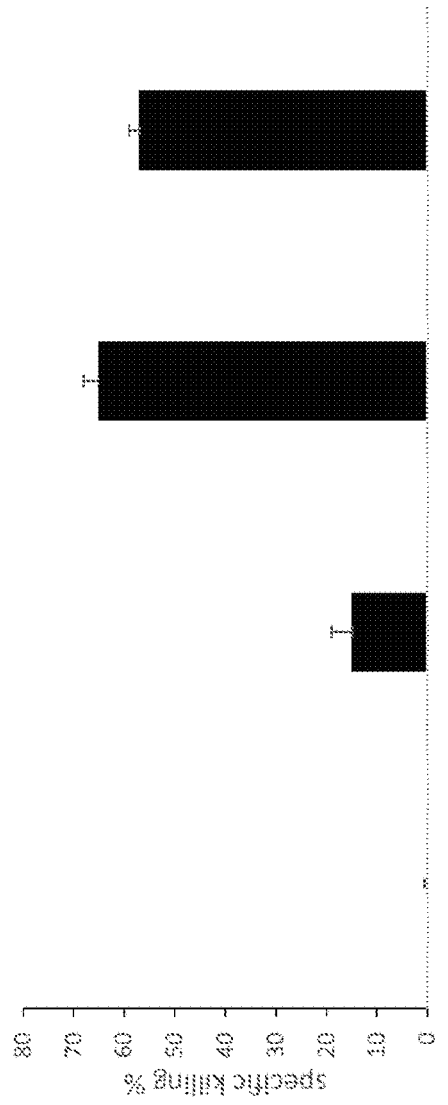
FIG. 6 shows percent specific lysis from the killing of cancer cell lines HepG2 (AFP+/GPC3+) and HepG2-GPC3.ko (AFP+/GPC3−), mediated by T cells transduced with anti-AFP158/HLA-A*2:01 caTCR-1-0 alone, anti-GPC3 CSR alone, or anti-AFP158/HLA-A*2:01 caTCR (1-0 and 1-TM5)+anti-GPC3 CSR.
Figure 6:
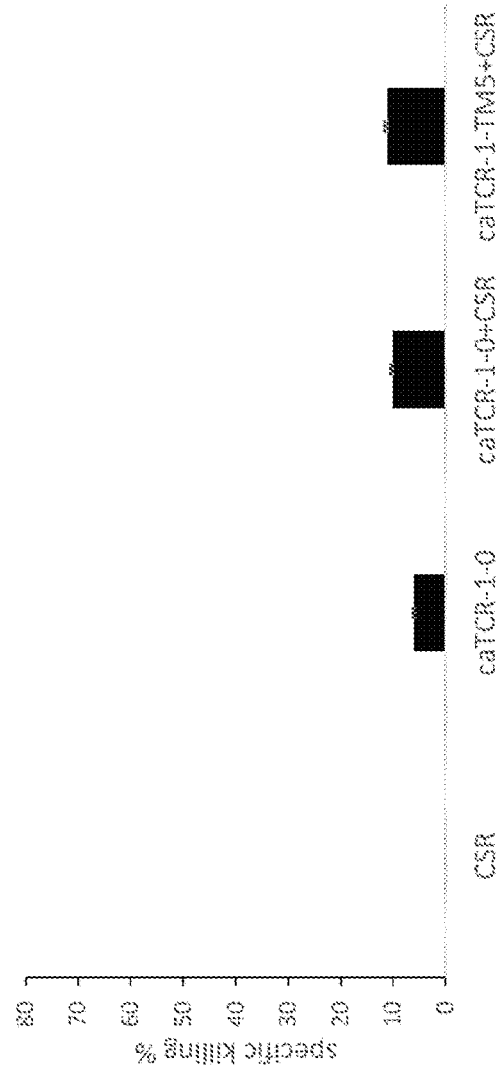

Expression of anti-GPC3-CSR with either anti-AFP-caTCR-1-0 or anti-AFP-caTCR-1-TM5 resulted in fully functional cytotoxic T-cells capable of lysing HEPG2 cells in vitro (FIG. 6). T cells expressing only the caTCR-1-0 had much less specific killing (about 15%) than those expressing both caTCR-1 (caTCR-1-0 or caTCR-1-TM5) and the CSR (between about 55% to about 65%). By contrast, specific killing was reduced to about 10% for T cells expressing both the caTCR and CSR when using HEPG2-GPC3.KO target cells (FIG. 6), indicating that engagement of the CSR with its target ligand is responsible for the increased cytotoxicity.

Cytokine Secretion

Figure 7:
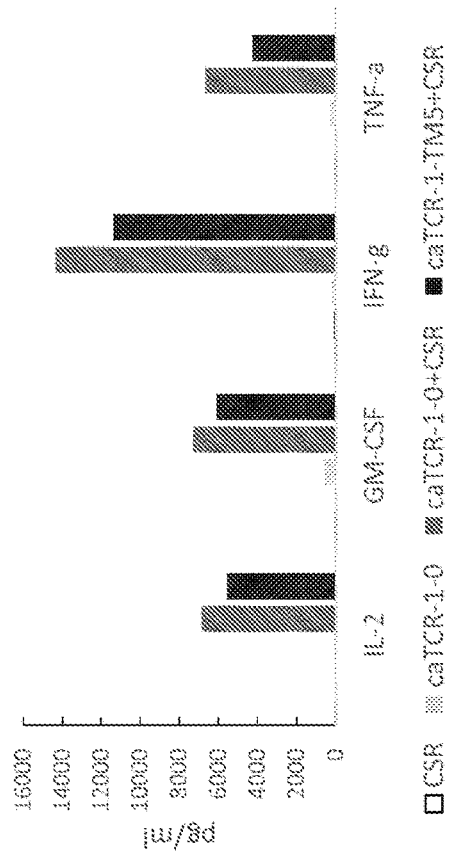
FIG. 7 shows the concentration of cytokines (IL-2, GM-CSF, IFN-γ, and TNF-α) found in the supernatant after in vitro killing of cancer cell lines HepG2 and HepG2-GPC3.ko, mediated by T cells transduced with anti-AFP158/ HLA-A*2:01 caTCR-1-0 alone, anti-GPC3 CSR alone, or anti-AFP158/HLA-A*2:01 caTCR (1-0 and 1-TM5)+anti-GPC3 CSR.
Figure 7:
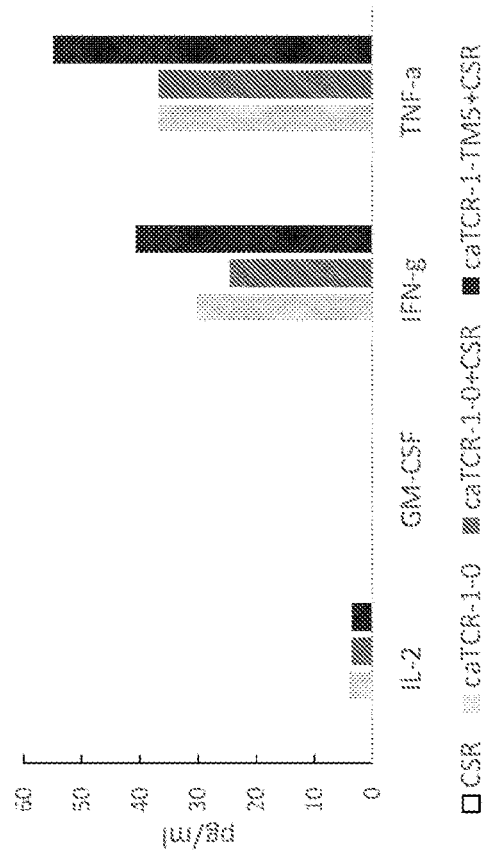

The concentration of cytokines released into the supernatant of the in vitro killing experiments was measured with a Bioplex200 (Luminex) using the Bio-plex Pro Human Cytokine 8-plex kit (BioRad). The CSR-positive and caTCR-positive T-cells released more cytotoxic cytokines than T-cells expressing ca-TCR-1-0 alone for the HEPG2 target cells expressing both the caTCR target antigen and the CSR target ligand (FIG. 7). By contrast, there was little or no difference between the T cells expressing ca-TCR-1-0 alone or both a caTCR and the CSR for the HEPG2-GPC3.KO target cells lacking the CSR target ligand (FIG. 7).

Intracellular Cytokine Expression

T-cells were stimulated with target cells (HEPG2) at an E:T ratio 1:2 in the presence of secretion inhibitor brefeldin A (BFA) for 4 hours. T-cells were permeabilized and cytokine specific antibodies were used to detect cytokines expressed in response to tumor stimulation. The percent of cytokine-positive cells was determined using flow cytometry. The CSR-positive and caTCR-positive T-cells expressed more intracellular cytokines than T-cells expressing ca-TCR-1-0 alone (Table 7).

TABLE 7

| %, Positive | HEP G2 | T-cell Alone |
|---|---|---|
| Intracellular TNFα Expression in CD8+ T-cells | | |
| CSR | 0.3 | 0.2 |
| caTCR-1-0 | 14.7 | 0.1 |
| caTCR-1-0 + CSR | 17.0 | 0.1 |
| caTCR-1-TM5 + CSR | 15.7 | 0.1 |
| Intracellular IL-2 Expression in CD4+ T-cells | | |
| CSR | 0.1 | 0.04 |
| caTCR-1-0 | 8.2 | 0.11 |
| caTCR-1-0 + CSR | 9.8 | 0.05 |
| caTCR-1-TM5 + CSR | 11.2 | 0.03 |
| Intracellular IFNγ Expression in CD8+ T-cells | | |
| CSR | 0.2 | 0.08 |
| caTCR-1-0 | 3.1 | 0.2 |
| caTCR-1-0 + CSR | 4.5 | 0.1 |
| caTCR-1-TM5 + CSR | 5.1 | 0.06 |

Taken together, the results indicate that the addition of the CSR increases the sensitivity and responsiveness of caTCR plus CSR T-cells having a different caTCR target antigen and CSR target ligand. The increased amount of cytokines expressed in and released from these CSR-caTCR double positive T cells provides further evidence that the co-stimulation of both caTCR-1 and CSR raises the cytotoxic potential of the T-cells.

Degranulation

Figure 8:
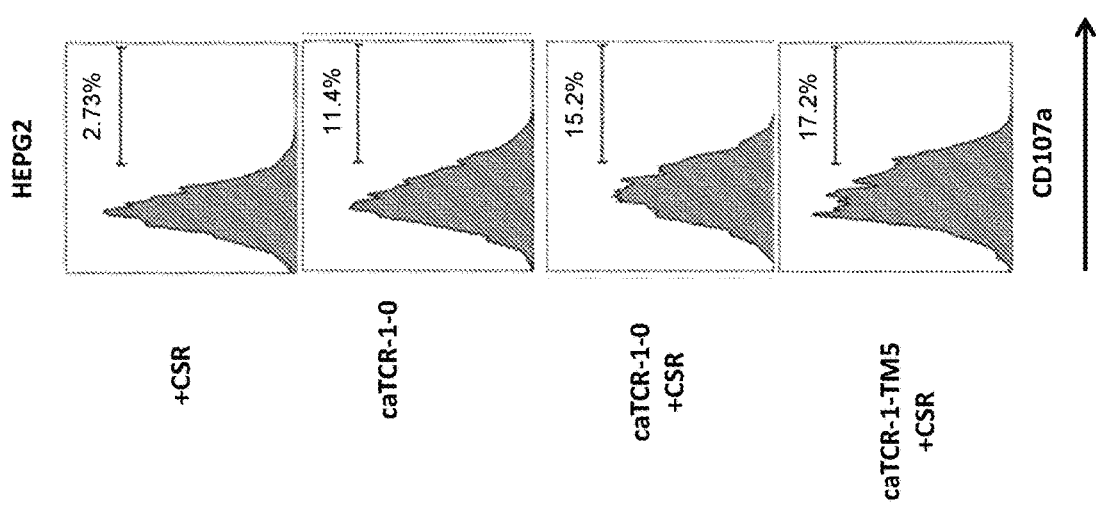
FIG. 8 shows the degranulation activity (as determined by CD107a expression) in T cells transduced with anti-AFP158/HLA-A*2:01 caTCR-1-0 alone, anti-GPC3 CSR alone, or anti-AFP158/HLA-A*2:01 caTCR (1-0 and 1-TM5)+anti-GPC3 CSR following stimulation with cancer cell line HepG2.

T cells were mixed with fluorescently-conjugated anti-CD107a and stimulated with HEPG2 target cells at an E:T ratio of 1:2 in the presence of the endocytosis inhibitor monensin for 4 hours. Engagement of the CSR on caTCR T-cells increased T-cell degranulation, further demonstrating that the CSR makes the therapeutic T-cells more reactive towards the intended tumor cells (FIG. 8).

Proliferation

T-cells were labeled with the intracellular dye CFSE, and dye dilution and number of CFSE-positive cells remaining at the indicated day was measured.

Respective T-cells were serum starved overnight and labeled with CFSE using CellTrace CFSE (Thermo Fisher C34554). 100,000 T-cells were incubated at an E:T ratio of 2:1 and flow cytometry was used to observe serial dilution of the CFSE dye as the T-cells divide at the indicated day. The total number of T-cells was counted by FACs.

Figure 9:
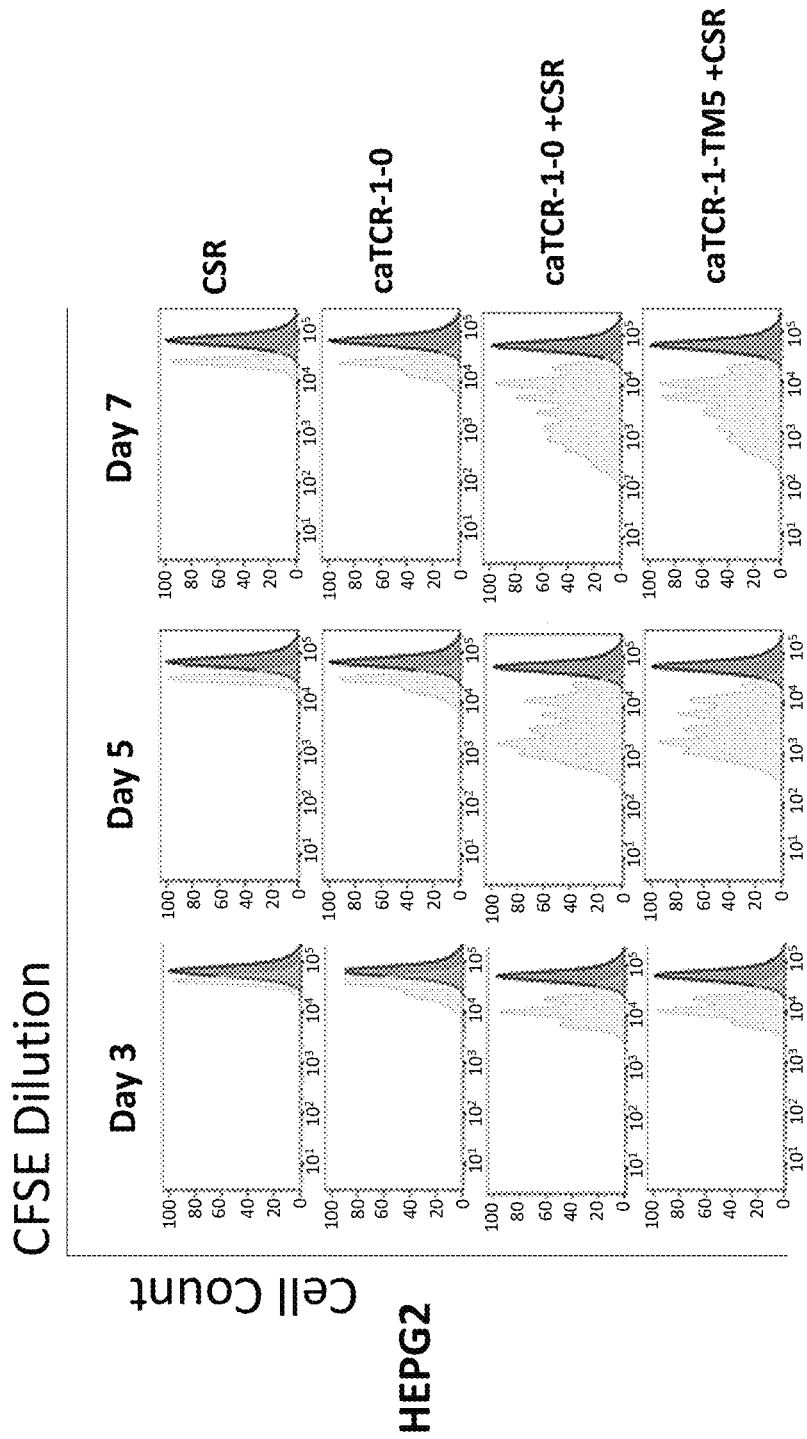
FIG. 9 shows the proliferation (as determined by CFSE dye dilution) of T cells transduced with anti-AFP158/ HLLA-A*2:01 caTCR-1-0 alone, anti-GPC3 CSR alone, or anti-AFP158/HLLA-A*2:01 caTCR (1-0 and 1-TM5)+anti-GPC3 CSR following stimulation with cancer cell line HepG2.

CFSE dilution increased with CSR stimulation, indicating these T-cells had a higher proliferation potential (FIG. 9). Importantly there is also an increase in the cell number, meaning that the cells not only proliferate better but their persistence is also maintained (Table 8).

TABLE 8 # of T-Cells Persisting After Engagement with HEPG2

| | Day3 | Day5 | Day7 |
|---|---|---|---|
| CSR | 7,147 | 4,519 | 3,055 |
| caTCR1-0 | 5,674 | 4,362 | 3,372 |
| caTCR1-0 + CSR | 31,422 | 18,689 | 8,833 |
| caTCR-1-TM5 + CSR | 28,874 | 21,978 | 9,471 |

The results show that we were able to simultaneously stimulate both CSR and caTCR with ligand positive tumor cells, and that the co-stimulation of CSR and caTCR enhanced the cytotoxicity, proliferation potential, and persistence of caTCR T-cells. These are all characteristics that will increase the therapeutic potential of caTCR-based therapies using adoptive transfer.

Example 4. Construction and Characterization of T Cells Transduced with Anti-CD19 caTCR-1 and Anti-CD20 CSR A nucleic acid fragment encoding an anti-CD20 binding moiety (SEQ ID NOs: 60 and 61) was used to generate an anti-CD20 CSR (i.e., "CSR1") that comprises CD28 transmembrane and intracellular signaling sequences (SEQ ID NO: 51), which was expressed on the same vector that expressed anti-CD19 caTCR-1-0 or caTCR-1-TM5 generated using an anti-CD19 binding moiety (SEQ ID NOs: 58 and 59).

In Vitro Killing

Raji, BV173, NALM6, and Jeko-1 cells (cell lines that express CD19 and CD20) were used as target cells for T-cell killing at an effector-to-target ratio of 2.5:1. Specific T-cell lysis was measured after 16 hr incubation using the Cytox 96 Non-radioactive Cytotoxicity Assay (Promega).

Figure 10:
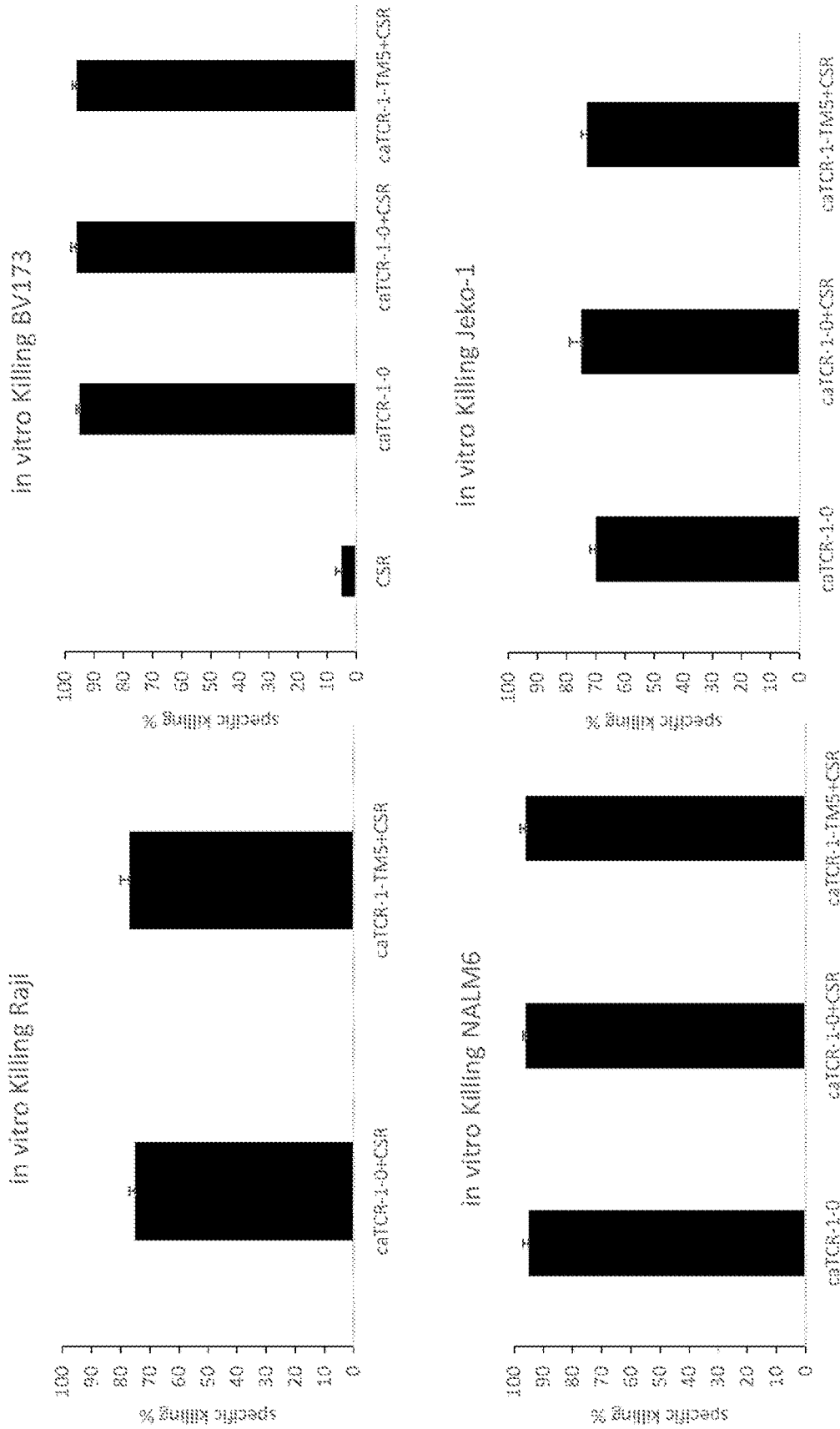
FIG. 10 shows percent specific lysis from the killing of cancer cell lines Raji, BV173, NALM6, and Jeko-1 (each CD19+/CD20+), mediated by T cells transduced with anti-CD19 caTCR (1-0 and 1-TM5)+anti-CD20 CSR.

Expression of anti-CD20-CSR with either anti-CD19-caTCR-1-0 or anti-CD19-caTCR-1-TM5 created fully functional cytotoxic T-cells capable of lysing a variety of CD19-positive, CD20-positive tumor cells in vitro (FIG. 10).

Cytokine Secretion

Figure 11:
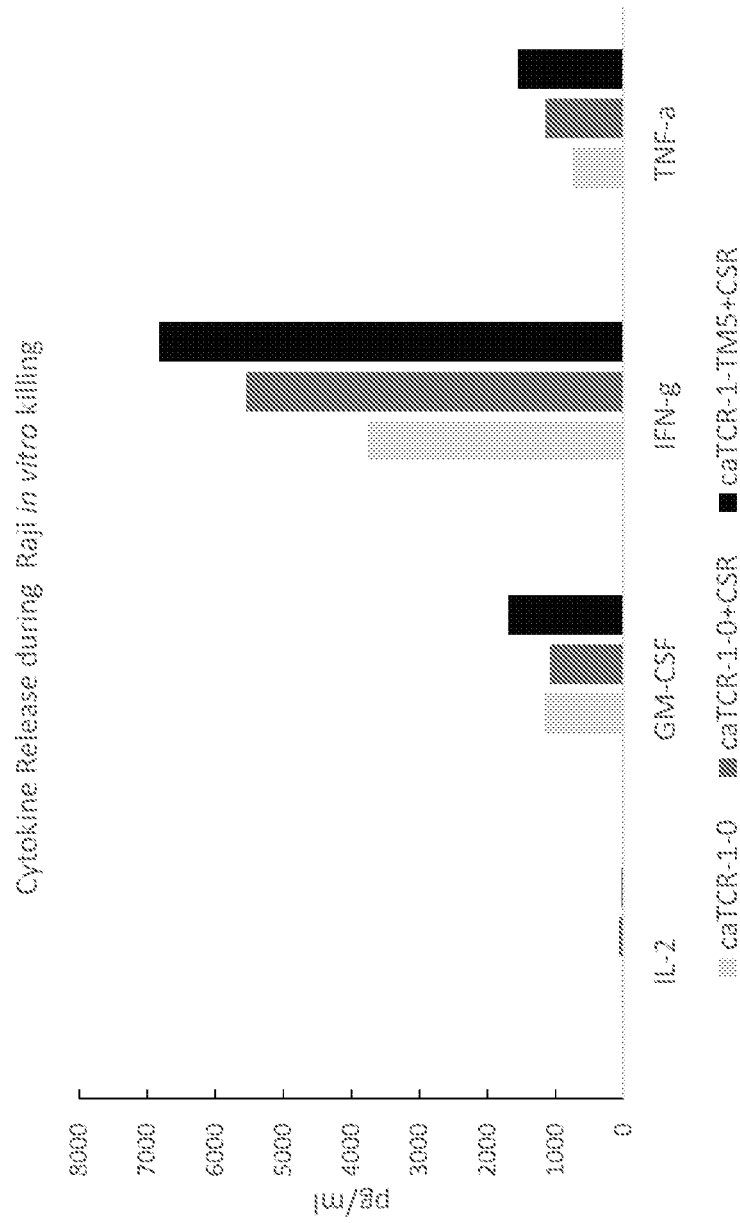
FIG. 11 shows the concentration of cytokines (IL-2, GM-CSF, IFN-γ, and TNF-α) found in the supernatant after in vitro killing of cancer cell line Raji, mediated by T cells transduced with anti-CD19 caTCR-1-0 alone or anti-CD19 caTCR (1-0 and 1-TM5)+anti-CD20 CSR.

The concentration of cytokines released into the supernatant of the Raji in vitro killing experiments was measured with a Bioplex200 (Luminex) using the Bio-plex Pro Human Cytokine 8-plex kit (BioRad). The CSR-positive and caTCR-positive T-cells released more GM-CSF, IFNγ, and TNFα than T-cells expressing ca-TCR-1-0 alone (FIG. 11).

Degranulation

Figure 12:
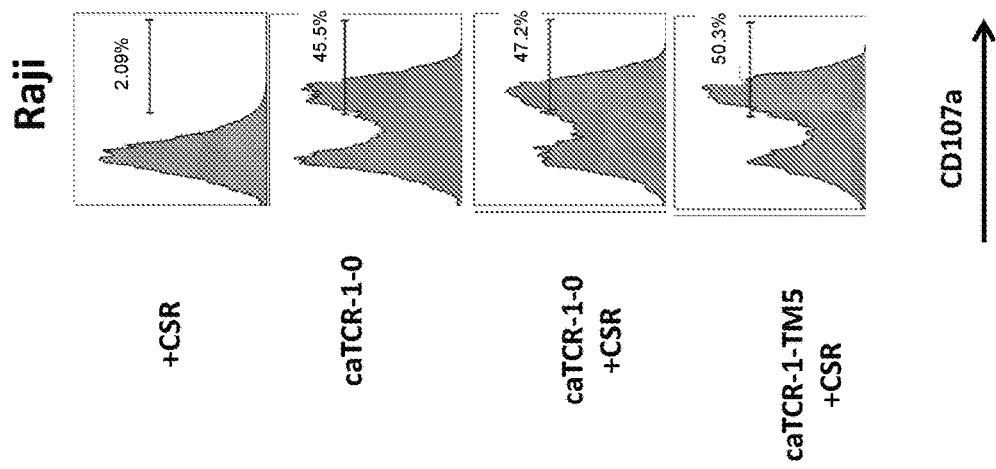
FIG. 12 shows the degranulation activity (as determined by CD107a expression) in T cells transduced with anti-CD19 caTCR-1-0 alone, anti-CD20 CSR alone, or anti-CD19 caTCR (1-0 and 1-TM5)+anti-CD20 CSR following stimulation with cancer cell line Raji.

T cells were mixed with fluorescently-conjugated anti-CD107a and stimulated with Raji target cells at an E:T ratio of 1:2 in the presence of the endocytosis inhibitor monensin for 4 hours. Engagement of the CSR on caTCR T-cells increased T-cell degranulation, further demonstrating that the CSR makes the therapeutic T-cells more reactive towards the intended tumor cells (FIG. 12).

Examples 2-4 show that the CSR is a modular molecule that can be used in combination with various antigen-targeting moieties to increase the therapeutic potential of caTCR-expressing T cells for a broad spectrum of diseased cells.

Example 5: Construction and Characterization of T Cells Transduced with Anti-CD19 caTCR-1 and Anti-CD19 Chimeric Stimulation Receptor Variants Nucleic acid fragments encoding the anti-CD19 binding moiety (SEQ ID NOs: 58 and 59) was used to generate both a chimeric co-stimulatory receptor (CSR) and a caTCR-1-0 construct (referred in this example as "caTCR-1"). Different CSRs were prepared by fusing the anti-CD19 binding moiety to the CSR sequence. CSR1 comprises CD28 transmembrane and intracellular signaling sequences (SEQ ID NO: 90). CSR2 comprises a CD8 transmembrane sequence and a 4-1BB instracellular signaling sequence (SEQ ID NO: 91). CSR3 comprises 4-1BB transmembrane and intracellular signaling sequences (SEQ ID NO: 92). CSR4 comprises a CD8 transmembrane sequence and a CD27 instracellular signaling sequence (SEQ ID NO: 93). CSR5 comprises CD27 transmembrane and intracellular signaling sequences (SEQ ID NO: 94). CSR6 comprises a CD8 transmembrane sequence and a CD30 instracellular signaling sequence (SEQ ID NO: 95). CSR7 comprises CD30 transmembrane and intracellular signaling sequences (SEQ ID NO: 96). CSR8 comprises a CD8 transmembrane sequence and a OX40 instracellular signaling sequence (SEQ ID NO: 97). CSR9 comprises OX40 transmembrane and intracellular signaling sequences (SEQ ID NO: 98).

Primary T cells were transduced with an anti-CD19 CSR alone, or with anti-CD19 caTCR-1 in combination with an anti-CD19 CSR. Transduction efficiency was determined by cell surface staining and all caTCR-transduced T-cells were matched at approximately 40% receptor positive by mixing with mock T-cells.

T Cells Expressing Anti-CD19 CSR Alone

In Vitro Killing

Raji or NALM6 cells were used as target cells for T-cell stimulation at an effector-to-target ratio of 2.5:1. Specific T-cell lysis was measured after 16 hr incubation using the Cytox 96 Non-radioactive Cytotoxicity Assay (Promega). T cells expressing anti-CD19 CSR-6, CSR-7, CSR-8 or CSR-9 alone did not result in an elevated number of killed target cells compared to untranduced mock T cells (data not shown).

Cytokine Secretion

The concentration of cytokines released into the supernatant of the in vitro killing reactions was measured with a Bioplex200 (Luminex) using the Bio-plex Pro Human Cytokine 8-plex kit (BioRad). T cells expressing anti-CD19 CSR-6, CSR-7, CSR-8 or CSR-9 alone did not release significant amount of IFNγ when incubated with Raji or NALM6 (data not shown).

T Cells Expressing Anti-CD19 caTCR-1 and Anti-CD19 CSRs

In two different batches of experiments, respective T-cells expressing both anti-CD19 caTCR-1 and an anti-CD19 CSR were serum starved overnight and labeled with CFSE using CellTrace CFSE (Thermo Fisher C34554). T-cells were incubated with NALM6 at an E:T ratio of 2:1 and flow cytometry was used to observe serial dilution of the CFSE dye as the T-cells divide at the indicated day. The total number of T-cells was counted by FACs. These experiments were repeated using primary T cells obtained from a second donor. Similar results were observed (data not shown).

Figure 14:
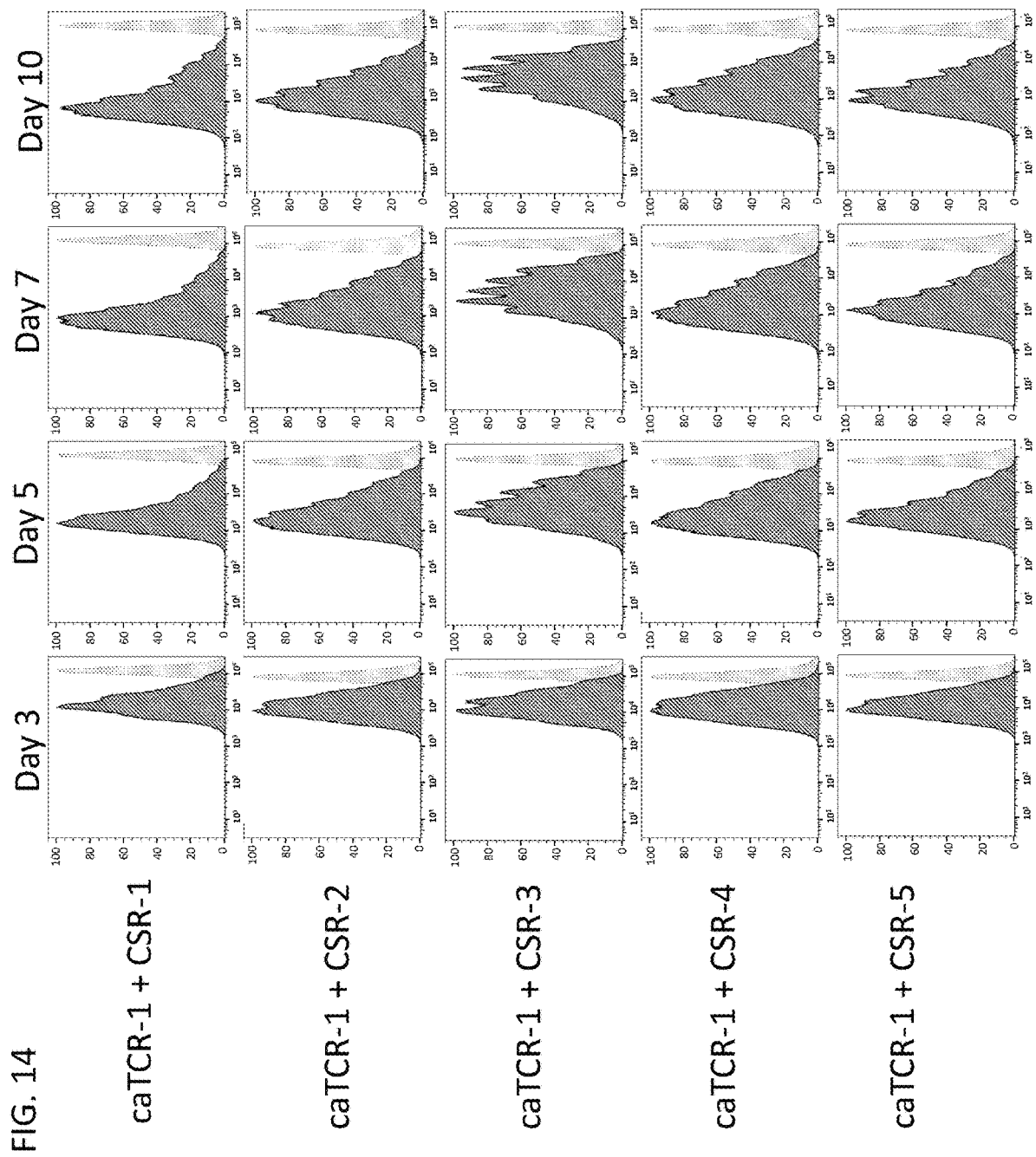
FIGS. 14-15 show the proliferation (as determined by CFSE dye dilution) of T cells expressing anti-CD19 caTCR-1-0 and anti-CD19 CSR following stimulation with cancer cell line NALM6.
Figure 15:
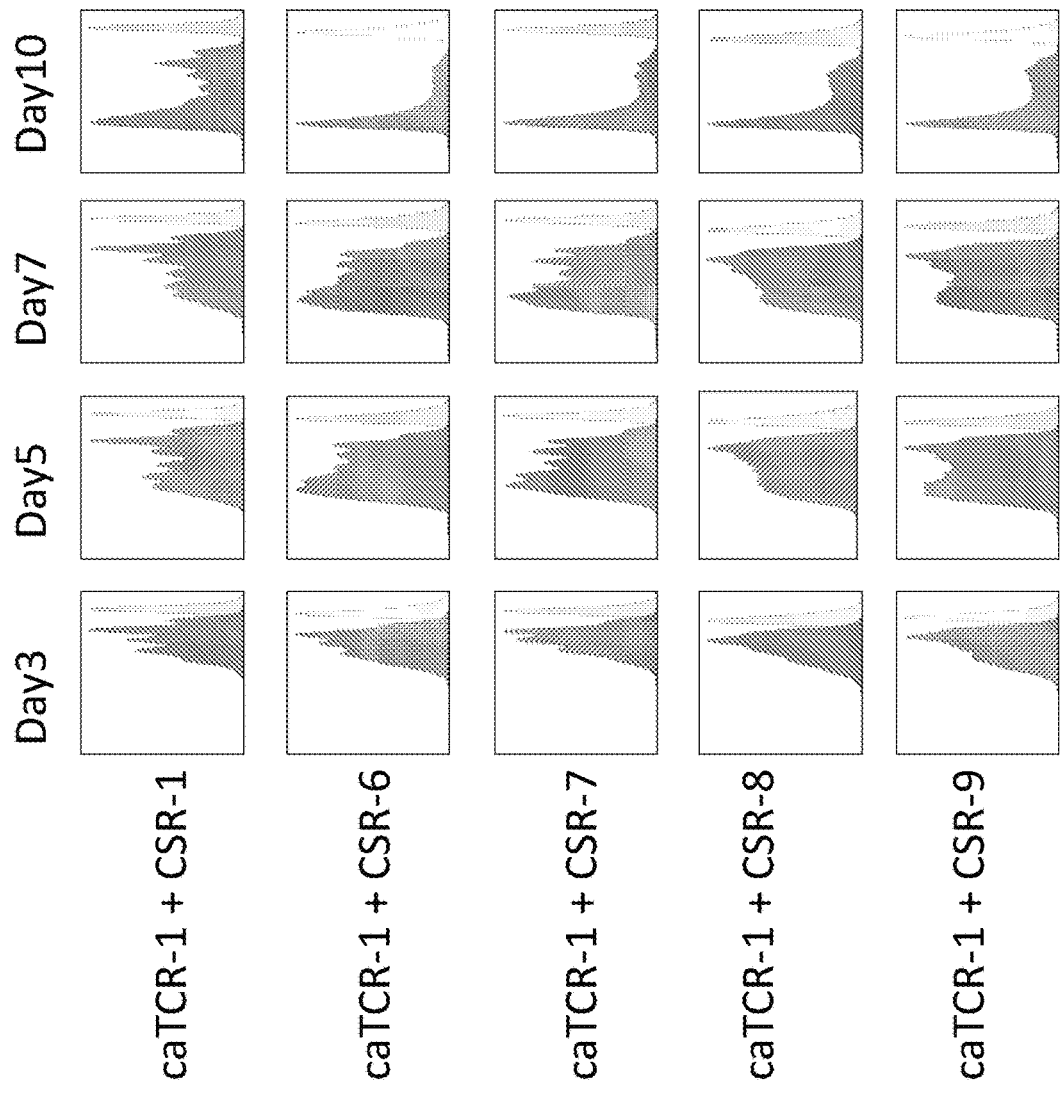

CFSE dilution was observed in all T cells expressing both anti-CD19 caTCR-1 and an anti-CD19 CSR, indicating high proliferation potential of these T cells (FIGS. 14-15). Additionally, T cells expressing both anti-CD19 caTCR-1 and an anti-CD19 CSR showed significant persistence over a period of 10 days (Table 9). In a control experiment, T cells expressing any one of anti-CD19 CSR-1 to anti-CD19 CSR-5 alone did not show increased proliferation potential or persistence over time (data not shown).

TABLE 9 # of T-Cells Persisting After Engagement with NALM6

| | caTCR-1 + CSR-1 | caTCR-1 + CSR-2 | caTCR-1 + CSR-3 | caTCR-1 + CSR-4 | caTCR-1 + CSR-5 |
|---|---|---|---|---|---|
| Day3 | 144622 | 171874 | 128353 | 158852 | 173153 |
| Day5 | 307957 | 196842 | 126643 | 237138 | 275630 |
| Day7 | 187440 | 184933 | 75822 | 163892 | 168092 |
| Day10 | 88562 | 114640 | 36480 | 111527 | 118921 |

| | caTCR-1 + CSR-1 | caTCR-1 + CSR-6 | caTCR-1 + CSR-7 | caTCR-1 + CSR-8 | caTCR-1 + CSR-9 |
|---|---|---|---|---|---|
| Day3 | 206073 | 234073 | 202600 | 264248 | 240125 |
| Day5 | 89685 | 243962 | 226587 | 264685 | 225515 |
| Day7 | 111523 | 186479 | 187614 | 175982 | 150052 |
| Day10 | 141112 | 285946 | 278322 | 274536 | 228298 |

Example 6: In Vivo Efficacy Study of T Cells Transduced with Anti-CD19 caTCR-1 and Anti-CD19 CSR The in vivo anti-tumor activity of T cells expressing both anti-CD19 caTCR-1 and anti-CD19 CSR-1 was tested in a human CD19+ NALM-6 pre-B Acute Lymphoblastic Leukemia (ALL) model. Luciferase-expressing NALM-6 cells were implanted intravenously (i.v.) into NOD SCID gamma (NSG) immune-compromised mice and tumor burden was assessed by measuring tumor-derived bioluminescence. Six days post tumor implantation, mice were randomized based on total bioluminescent flux into treatment groups: (1) i.v. injection of 5×10$^6$ un-transduced donor-matched (Mock) T cells, (2) i.v. injection of 2×10$^6$ T cells expressing anti-CD19 caTCR-1 only ("caTCR-1 T cell") and (3) i.v. injection of 2×10⁶ T cells expressing both anti-CD19 caTCR-1 and anti-CD19 CSR-1 ("caTCR-1 CSR-1 T cell"; n=6 mice/group). Health effects resulting from T cell infusions in mice were assessed by monitoring their general appearance, body weight, and other clinical signs of adverse response (including hypothermia, labored respiration, and hind-limb paralysis/weakness).

Figure 16:
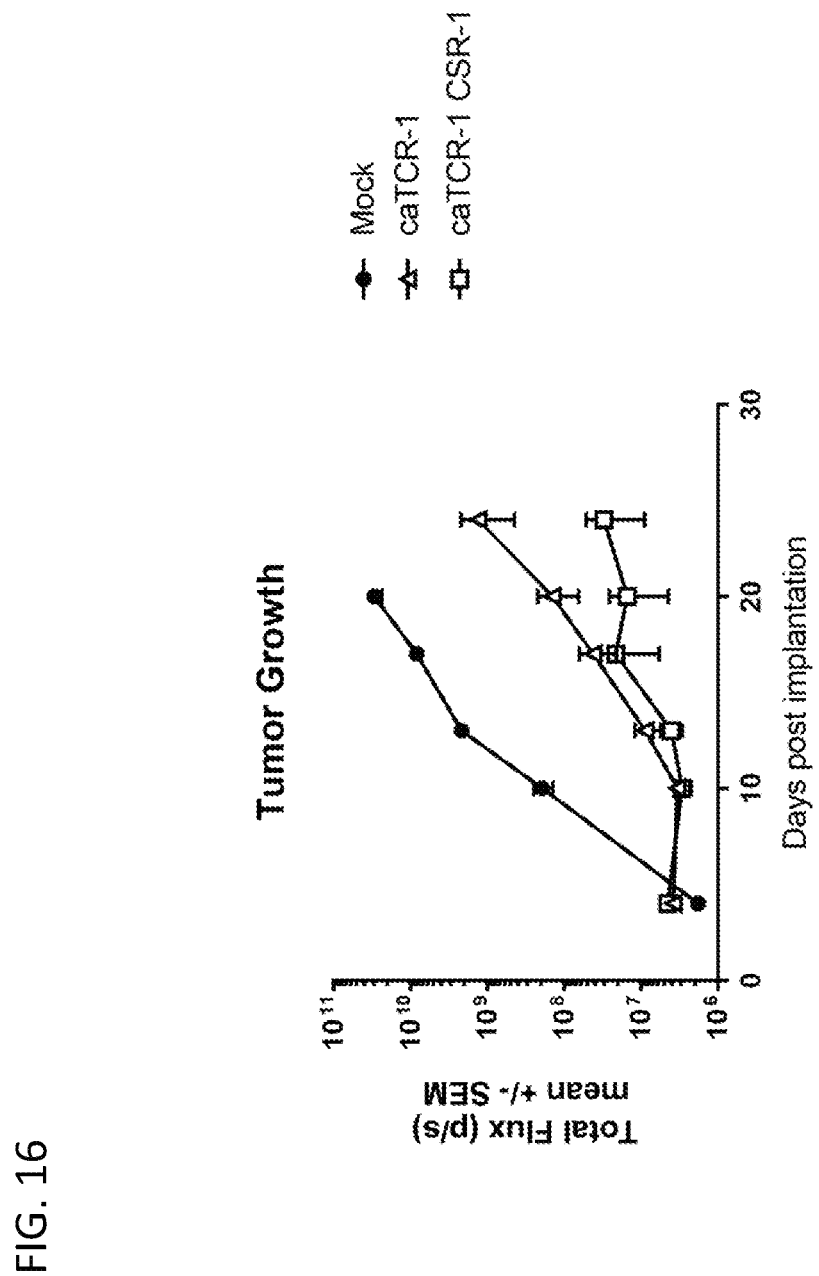
FIG. 16 shows the tumor growth in a subcutaneous mouse model of NALM6 with mock treatment or with a single intratumoral injection of T cells expressing an anti-CD19 caTCR-1, or an anti-CD19 caTCR-1 in combination with anti-CD19 CSR-1.

As shown in FIG. 16, while both caTCR-1 T cell and caTCR-1 CSR-1 T cell treatment resulted in tumor growth inhibition, caTCR-1 CSR-1 T cells showed enhanced anti-tumor activity compared to caTCR-1 T cells. All caTCR-1 T cell-treated and caTCR-1 CSR-1 T cell-treated mice demonstrated normal gait, posture, and activity/responsiveness for the duration of the study. In addition, caTCR-1 T cell-treated and caTCR-1 CSR-1 T cell-treated mice did not lose body weight during the study. Overall, the lack of observable abnormal parameters in treated mice demonstrates the safety of the caTCR-1 CSR-1 T cell therapy.

Figure 17:
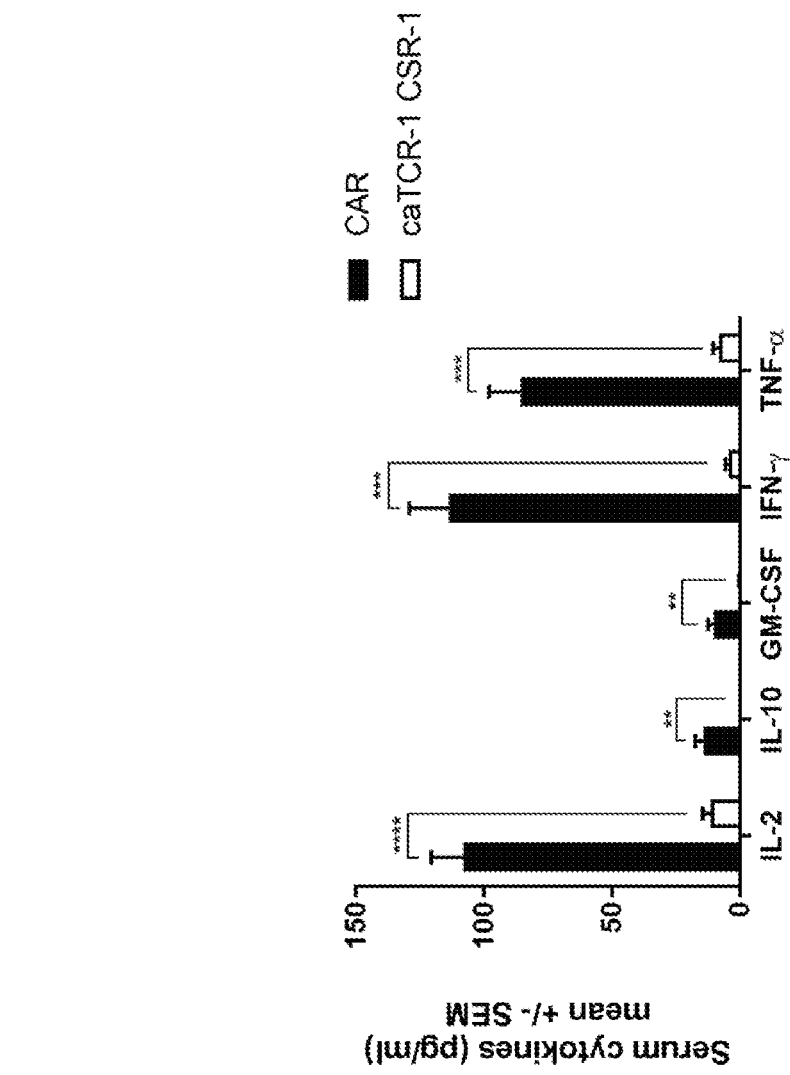
FIG. 17 shows the serum cytokine levels in mice treated with T cells expressing an anti-CD19 CAR or T cells expressing both anti-CD19 caTCR-1 and anti-CD19 CSR-1. The student t-test is used to analyze statistical significance of the serum cytokine levels in the two groups ($P<0.01$; *$P<0.001$; ****$P<0.0001$).

To determine the level of cytokine release in vivo, key cytokines, including those related to clinical cytokine release syndrome, were analyzed 24 hours after the NALM-6 tumor-bearing mice were administered with anti-CD19 CAR-T cells or caTCR-1 CSR-1 T cells. Cytokine levels were quantified with Luminex Magpix technology using BioRad Bio-Plex kits. As shown in FIG. 17, caTCR-1 CSR-1 T cell-treated mice had significantly lower level of cytokine release than CAR-T treated mice.

Example 7: In Vivo Efficacy Study of T Cells Transduced with Anti-AFP caTCR-1 and Anti-GPC3 CSR The in vivo anti-tumor activity of T cells expressing both anti-AFP caTCR-1 and anti-GPC3 CSR-1 (see, Example 3 for construct information) was tested in an established human AFP⁺/HLA-A2⁺ Hep G2 liver cancer xenograft model. Hep G2 cells were implanted subcutaneously (s.c.) over the right flank of SCID-Beige mice. When tumors reached ~100 mm³, mice were intratumorally (i.t.) injected with either (1) 5×10⁶ un-transduced donor-matched (Mock) T cells, (2) 2×10⁶ T cells expressing an anti-AFP CAR comprising the same anti-AFP binding moiety (SEQ ID NOs: 62 and 63), or (3) 2×10⁶ T cells expressing both anti-AFP caTCR-1 and anti-GPC3 CSR-1 (n6 mice/group). Health effects resulting from the T cell infusions in mice were assessed by monitoring their general appearance, body weight, and other clinical signs of adverse response (including hypothermia, labored respiration, and hind-limb paralysis/weakness).

Figure 18:
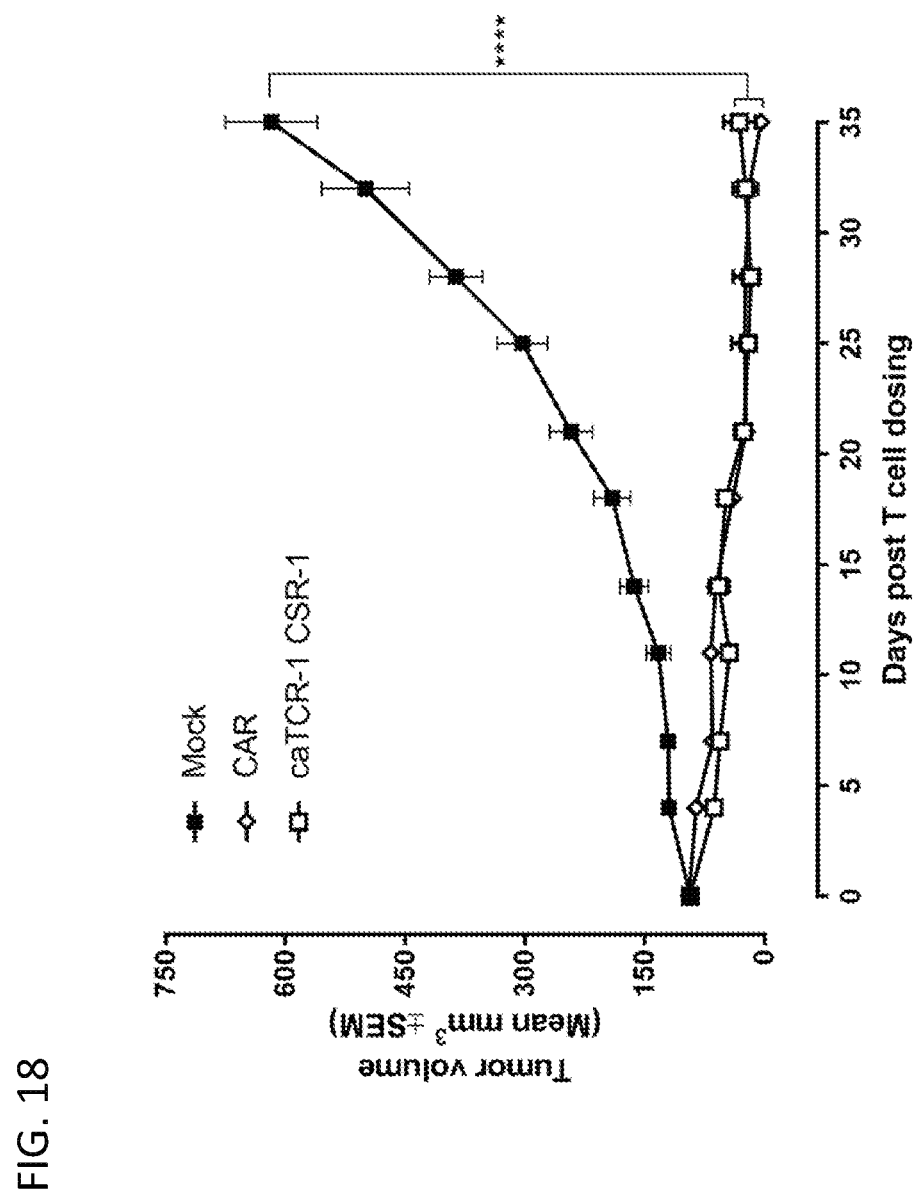
FIG. 18 shows the tumor growth in a subcutaneous mouse model of HepG2 with mock treatment or with a single intratumoral injection of T cells expressing an anti-AFP CAR, or an anti-AFP CAR in combination with an anti-GPC3 CSR.

As shown in FIG. 18, both anti-AFP CAR T cell treatment and anti-AFP caTCR-1/anti-GPC3 CSR-1 T cell treatment resulted in profound and significant (****P<0.0001; Dunnett's multiple comparison test) tumor growth inhibition. All anti-AFP CAR-T treated and anti-AFP caTCR-1/anti-GPC3 CSR-1 T cell-treated mice demonstrated normal gait, posture, and activity/responsiveness for the duration of the study. In addition, anti-AFP CAR-T treated and anti-AFP caTCR-1/anti-GPC3 CSR-1 T cell-treated mice did not lose body weight during the study. Overall, the lack of observable abnormal parameters in treated mice demonstrates the safety of the anti-AFP caTCR-1/anti-GPC3 CSR-1 T cell therapy.

Sequence Listing

| SEQ ID NO | Description | Sequence |
|---|---|---|
| 1 | TCRα constant domain | PNIQNPDPAVYQLRDSKSSDK SVCLFTDPDSQTNVSQSKDSD VYITDKTVLDMRSMDFKSNSA VAWSNKSDFACANAFNNSIIP EDTFFPSPESSCDVKLVEKSF ETDTNLNFQNLSVIGFRILLL KVAGFNLLMTLRLWSS |
| 2 | TCRβ constant domain | EDLNKVFPPEVAVFEPSEAEI SHTQKATLVCLATGFFPDHVE LSWWVNGKEVHSGVSTDPQPL KEQPALNDSRYCLSSRLRVSA TFWQNPRNHFRCQVQFYGLSE NDEWTQDRAKPVTQIVSAEAW GRADCGFTSVSYQQGVLSATI LYEILLGKATLYAVLVSALVL MAMVKRKDF |
| 3 | TCRδ constant domain | SQPHTKPSVFVMKNGTNVACL VKEFYPKDIRINLVSSKKITE FDPAIVISPSGKYNAVKLGKY EDSNSVTCSVQHDNKTVHSTD FEVKTDSTDHVKPKETENTKQ PSKSCHKPKAIVHTEKVNMMS LTVLGLRMLFAKTVAVNFLLT AKLFFL |
| 4 | TCRγ constant domain | DKQLDADVSPKPTIFLPSIAE TKLQKAGTYLCLLEKFFPDVI KIHWQEKKSNTILGSQEGNTM KTNDTYMKFSWLTVPEKSLDK EHRCIVRHENNKNGVDQEIIF PPIKTDVITMDPKDNCSKDAN DTLLLQLTNTSAYYMYLLLLL KSVVYFAIITCCLLRRTAFCC NGEKS |
| 5 | TCRα transmembrane domain | ILLLKVAGFNLLMTLRLWSS |
| 6 | TCRβ transmembrane domain | TILYEILLGKATLYAVLVSAL VL |
| 7 | TCRδ transmembrane domain | VLGLRMLFAKTVAVNFLLTAK LFFL |
| 8 | TCRγ transmembrane domain (same as uniprot) | YYMYLLLLLKSVVYFAIITCC LL |
| 9 | TCRδ transmembrane domain F24S | VLGLRMLFAKTVAVNFLLTAK LFSL |
| 10 | TCRδ transmembrane domain M6V | VLGLRVLFAKTVAVNFLLTAK LFFL |
| 11 | TCRδ transmembrane domain L4C | VLGCRMLFAKTVAVNFLLTAK LFFL |
| 12 | TCRδ transmembrane domain V12F, N15S | VLGLRMLFAKTFAVSFLLTAK LFFL |
| 13 | TCRδ transmembrane domain L25S | VLGLRMLFAKTVAVNFLLTAK LFF<u>S</u> |

| SEQ ID NO | Description | Sequence |
|---|---|---|
| 14 | TCRγ transmembrane domain V13Y | YYMYLLLLLKSVYYFAIITCC LLRRTAF |
| 15 | TCRγ transmembrane domain C21G | YYMYLLLLLKSVVYFAIITCG LLRRTAF |
| 16 | TCRγ transmembrane domain Y2L, M3V, A16V, I18V | YLVYLLLLLKSVVYFVIVTCC LLRRTAF |
| 17 | TCRγ transmembrane domain Y2L | YLMYLLLLLKSVVYFAIITCC LLRRTAF |
| 18 | TCRγ transmembrane domain M3V | YYVYLLLLLKSVVYFAIITCC LLRRTAF |
| 19 | TCRγ transmembrane domain A16V | YYMYLLLLLKSVVYFVIITCC LLRRTAF |
| 20 | TCRγ transmembrane domain I18V | YYMYLLLLLKSVVYFAIVTCC LLRRTAF |
| 21 | TCRγ transmembrane domain M3I | YYIYLLLLLKSVVYFAIITCC LLRRTAF |
| 22 | TCRγ transmembrane domain Y2I, M3I, A16I, I18L | YIIYLLLLLKSVVYFIILTCC LLRRTAF |
| 23 | TCRγ transmembrane domain L5C | YYMYCLLLLKSVVYFAIITCC LLRRTAF |
| 24 | TCRγ transmembrane domain L8F, V12F, F15S | YYMYLLLFLKSFVYSAIITCC LLRRTAF |
| 25 | TCRγ transmembrane domain C19M | YYMYLLLLLKSVVYFAIITMC LLRRTAF |
| 26 | TCRγ transmembrane domain Y1Q | QYMYLLLLLKSVVYFAIITCC LLRRTAF |
| 27 | TCRα connecting peptide | ESSCDVKLVEKSFETDTNLNF QNLSVIGFR |
| 28 | TCRα connecting peptide MD | IPEDTFFPSPESSCDVKLVEK SFETDTNLNFQNLSVIGFR |
| 29 | TCRβ connecting peptide | ADCGFTSVSYQQGVLSA |
| 30 | TCRβ connecting peptide MD | GRADCGFTSVSYQQGVLSA |
| 31 | TCRδ connecting peptide | DHVKPKETENTKQPSKSCHKP KAIVHTEKVNMMSLTVLGLR |
| 32 | TCRδ connecting peptide MD | EVKTDSTDHVKPKETENTKQP SKSCHKPKAIVHTEKVNMMSL TVLGLR |
| 33 | TCRγ connecting peptide | MDPKDNCSKDANDTLLLQLTN TSA |
| 34 | TCRγ connecting peptide MD | PIKTDVITMDPKDNCSKDAND TLLLQLTNTSA |
| 35 | TCRβ intracellular domain | MAMVKRKDF |
| 36 | TCRγ intracellular domain | RRTAFCCNGEKS |
| 37 | IgG1 $C_H1$ | ASTKGPSVFPLAPSSKSTSGG TAALGCLVKDYFPEPVTVSWN SGALTSGVHTFPAVLQSSGLY SLSSVVTVPSSSLGTQTYICN VNHKPSNTKVDKRVEPKSC |
| 38 | IgG2-0C $C_H1$ | ASTKGPSVFPLAPCSRSTSES TAALGCLVKDYFPEPVTVSWN SGALTSGVHTFPAVLQSSGLY SLSSVVTVPSSNFGTQTYTCN VDHKPSNTKVDKTVERK |
| 39 | IgG2-1C $C_H1$ | ASTKGPSVFPLAPCSRSTSES TAALGCLVKDYFPEPVTVSWN SGALTSGVHTFPAVLQSSGLY SLSSVVTVPSSNFGTQTYTCN VDHKPSNTKVDKTVERKC |
| 40 | IgG2-2C $C_H1$ | ASTKGPSVFPLAPCSRSTSES TAALGCLVKDYFPEPVTVSWN SGALTSGVHTFPAVLQSSGLY SLSSVVTVPSSNFGTQTYTCN VDHKPSNTKVDKTVERKCC |
| 41 | IgG3 $C_H1$ | ASTKGPSVFPLAPCSRSTSGG TAALGCLVKDYFPEPVTVSWN SGALTSGVHTFPAVLQSSGLY SLSSVVTVPSSSLGTQTYTCN VNHKPSNTKVDKRVELKTP |
| 42 | IgG4 $C_H1$ | ASTKGPSVFPLAPCSRSTSES TAALGCLVKDYFPEPVTVSWN SGALTSGVHTFPAVLQSSGLY SLSSVVTVPSSSLGTKTYTCN VDHKPSNTKVDKRVESKYG |
| 43 | IgA1 $C_H1$ | ASPTSPKVFPLSLCSTQPDGN VVIACLVQGFFPQEPLSVTWS ESGQGVTARNFPPSQDASGDL YTTSSQLTLPATQCLAGKSVT CHVKHYTNPSQDVTVPCPVPS TPPTPSPSTPPTPSPS |
| 44 | IgA2 $C_H1$ | ASPTSPKVFPLSLDSTPQDGN VVVACLVQGFFPQEPLSVTWS ESGQNVTARNFPPSQDASGDL YTTSSQLTLPATQCPDGKSVT CHVKHYTNPSQDVTVPCPVPP PPP |
| 45 | IgD $C_H1$ | APTKAPDVFPIISGCRHPKDN SPVVLACLITGYHPTSVTVTW YMGTQSQPQRTFPEIQRRDSY YMTSSQLSTPLQQWRQGEYKC VVQHTASKSKKEIFRWPESPK AQASSVPTAQPQAEGSLAKAT TAPATTRNTGRGGEEKKKEKE KEEQEERETKTP |

Sequence Listing

| SEQ ID NO | Description | Sequence |
|---|---|---|
| 46 | IgE C$_H$1 | ASTQSPSVFPLTRCCKNIPSN ATSVTLGCLATGYFPEPVMVT WDTGSLNGTTMTLPATTLTLS GHYATISLLTVSGAWAKQMFT CRVAHTPSSTDWVDNKTFS |
| 47 | IgM C$_H$1 | GSASAPTLFPLVSCENSPSDT SSVAVGCLAQDFLPDSITLSW KYKNNSDISSTRGFPSVLRGG KYAATSQVLLPSKDVMQGTDE HVVCKVQHPNGNKEKNVPLP |
| 48 | IgC$_L$ domain | GQPKANPTVTLFPPSSEELQA NKATLVCLISDFYPGAVTVAW KADGSPVKAGVETTKPSKQSN NKYAASSYLSLTPEQWKSHRS YSCQVTHEGSTVEKTVAPTEC S |
| 49 | fragment of CD28 | IEVMYPPPYLDNEKSNGTIIH VKGKHLCPSPLFPGPSKPFWV LVVVGGVLACYSLLVTVAFII FWVRSKRSRLLHSDYMNMTPR RPGPTRKHYQPYAPPRDFAAY RS |
| 50 | fragment of CD3-zeta | RVKFSRSADAPAYQQGQNQLY NELNLGRREEYDVLDKRRGRD PEMGGKPRRKNPQEGLYNELQ KDKMAEAYSEIGMKGERRRGK GHDGLYQGLSTATKDTYDALH MQALPPR |
| 51 | CD28 co-stimulatory fragment 1 | IEVMYPPPYLDNEKSNGTIIH VKGKHLCPSPLFPGPSKPFWV LVVVGGVLACYSLLVTVAFII FWVRSKRSRLLHSDYMNMTPR RPGPTRKHYQPYAPPRDFAAY RS |
| 52 | CD28 co-stimulatory fragment 2 | RSKRSRLLHSDYMNMTPRRPG PTRKHYQPYAPPRDFAAYRS |
| 53 | 4-1BB co-stimulatory fragment 1 | PADLSPGASSVTPPAPAREPG HSPQIISFFLALTSTALLFLL FFLTLRFSVVKRGRKKLLYIF KQPFMRPVQTTQEEDGCSCRF PEEEEGGCEL |
| 54 | 4-1BB co-stimulatory fragment 2 | KRGRKKLLYIFKQPFMRPVQT TQEEDGCSCRFPEEEEGGCEL |
| 55 | OX40 co-stimulatory fragment 1 | DPPATQPQETQGPPARPITVQ PTEAWPRTSQGPSTRPVEVPG GRAVAAILGLGLVLGLLGPLA ILLALYLLRRDQRLPPDAHKP PGGGSFRTPIQEEQADAHSTL AKI |
| 56 | OX40 co-stimulatory fragment 2 | ALYLLRRDQRLPPDAHKPPGG GSFRTPIQEEQADAHSTLAKI |
| 57 | CD8 TM fragment | TTTPAPRPPTPAPTIASQPLS LRPEACRPAAGGAVHTRGLDF ACDIYIWAPLAGTCGVLLLSL VITLYC |
| 58 | IgV$_H$ domain of anti-CD19 antibody | EVQLVQSGAEVKKPGESLKIS CKGSGYSFTSYWIGWVRQMPG KGLEWMGIIYPGDSDTRYSPS FQGQVTISADKSISTAYLQWS SLKASDTAMYYCARQVWGWQG GMYPRSNWWYNLDSWGQGTLV TVSS |
| 59 | IgV$_L$ domain of anti-CD19 antibody | LPVLTQPPSVSVAPGKTARIT CGGNNIGSKSVHWYQQKPGQA PVLVVYDDSDRPSGIPERFSG SNSGNTATLTISRVEAGDEAD YYCQVWDSSSDYVVFGGGTKL TVLG |
| 60 | IgV$_H$ domain of anti-CD20 antibody | QVQLQQPGAELVKPGASVKMS CKASGYTFTSYNMHWVKQTPG RGLEWIGAIYPGNGDTSYNQK FKGKATLTADKSSSTAYMQLS SLTSEDSAVYYCARSTYYGGD WYFNVWGAGTTVTVSS |
| 61 | IgV$_L$ domain of anti-CD20 antibody | QIVLSQSPAILSASPGEKVTM TCRASSSVSYIHWFQQKPGSS PKPWIYATSNLASGVPVRFSG SGSGTSYSLTISRVEAEDAAT YYCQQWTSNPPTFGGGTKLEI KR |
| 62 | IgV$_H$ domain of anti-AFP antibody | EVQLVQSGAEVKKPGESLTIS CKASGYSFPNYWITWVRQMSG GGLEWMGRIDPGDSYTTYNPS FQGHVTISIDKSTNTAYLHWN SLKASDTAMYYCARYYVSLVD IWGQGTLVTVSS |
| 63 | IgV$_L$ domain of anti-AFP antibody | QSVLTQPASVSGSPGQSITIS CTGTSSDVGGYNYVSWYQQHP GKAPKLMIYDVNNRPSEVSNR FSGSKSGNTASLTISGLQAED EADYYCSSYTTGSRAVFGGGT KLTVL |
| 64 | IgV$_H$ domain of anti-GPC3 antibody | QVQLVESGGGLVQPGGSLRLS CAASGFTFSSYAMSWVRQAPG KGLEWVSVIYSGGSSTYYADS VKGRFTISRDNSKNTLYLQMN SLRAEDTAVYYCARTSYLNHG DYWGQGTLVTVSS |
| 65 | IgV$_L$ domain of anti-GPC3 antibody | QSVLTQPPSVSAAPGQRVTIS CSGTRSNIGSDYVSWYQHLPG TAPKLLVYGDNLRPSGIPDRF SASKSGTSATLGITGLQTGDE ADYYCGTWDYTLNGVVFGGGT KLTVLG |
| 66 | IgV$_H$ domain of anti-CD47 | QVQLQESGPGLVKPSQTLSLT CTVSGYTFTNYYVFWVRQARG QRLEWIGDINPVNGDTNFNEK FKNRVTISADKSISTAYLQWS SLKASDTAMYYCARGGYTMDY WGQGTLVTVSS |
| 67 | IgV$_L$ domain of anti-CD47 | DIVMTQTPLSLPVTPGEPASI SCRSSQSLVHSNGNTYLHWYQ QKPGKAPKLLIYKVSYRFSGV PDRFSGSGSGTDFTLKISRVE AEDVGVYYCSQNTHVPRTFGQ GTKVEIKR |
| 68 | anti-AFP158/HLA-A*02:01-caTCR-1-0 delta | EVQLVQSGAEVKKPGESLTIS CKASGYSFPNYWITWVRQMSG GGLEWMGRIDPGDSYTTYNPS FQGHVTISIDKSTNTAYLHWN SLKASDTAMYYCARYYVSLVD IWGQGTLVTVSSASTKGPSVF PLAPSSKSTSGGTAALGCLVK |

| SEQ ID NO | Description | Sequence |
|---|---|---|
| | | DYFPEPVTVSWNSGALTSGVH TFPAVLQSSGLYSLSSVVTVP SSSLGTQTYICNVNHKPSNTK VDKRVEPKSCEVKTDSTDHVK PKETENTKQPSKSCHKPKAIV HTEKVNMMSLTVLGLRMLFAK TVAVNFLLTAKLFFL |
| 69 | anti-AFP158/HLA-A*02:01-caTCR-1-0 gamma | QSVLTQPASVSGSPGQSITIS CTGTSSDVGGYNYVSWYQQHP GKAPKLMIYDVNNRPSEVSNR FSGSKSGNTASLTISGLQAED EADYYCSSYTTGSRAVFGGGT KLTVLGQPKANPTVTLFPPSS EELQANKATLVCLISDFYPGA VTVAWKADGSPVKAGVETTKP SKQSNNKYAASSYLSLTPEQW KSHRSYSCQVTHEGSTVEKTV APTECSPIKTDVITMDPKDNC SKDANDTLLLQLTNTSAYYMY LLLLLKSVVYFAIITCCLLRR TAFCCNGEKS |
| 70 | anti-AFP158/HLA-A*02:01-caTCR-1-TM5 delta | EVQLVQSGAEVKKPGESLTIS CKASGYSFPNYWITWVRQMSG GGLEWMGRIDPGDSYTTYNPS FQGHVTISIDKSTNTAYLHWN SLKASDTAMYYCARYYVSLVD IWGQGTLVTVSSASTKGPSVF PLAPSSKSTSGGTAALGCLVK DYFPEPVTVSWNSGALTSGVH TFPAVLQSSGLYSLSSVVTVP SSSLGTQTYICNVNHKPSNTK VDKRVEPKSCEVKTDSTDHVK PKETENTKQPSKSCHKPKAIV HTEKVNMMSLTVLGLRVLFAK TVAVNFLLTAKLFFL |
| 71 | anti-AFP158/HLA-A*02:01-caTCR-1-TM5 gamma | QSVLTQPASVSGSPGQSITIS CTGTSSDVGGYNYVSWYQQHP GKAPKLMIYDVNNRPSEVSNR FSGSKSGNTASLTISGLQAED EADYYCSSYTTGSRAVFGGGT KLTVLGQPKANPTVTLFPPSS EELQANKATLVCLISDFYPGA VTVAWKADGSPVKAGVETTKP SKQSNNKYAASSYLSLTPEQW KSHRSYSCQVTHEGSTVEKTV APTECSPIKTDVITMDPKDNC SKDANDTLLLQLTNTSAYLVY LLLLLKSVVYFVIVTCCLLRR TAFCCNGEKS |
| 72 | anti-CD19-caTCR-1-0 delta | EVQLVQSGAEVKKPGESLKIS CKGSGYSFTSYWIGWVRQMPG KGLEWMGIIYPGDSDTRYSPS FQGQVTISADKSISTAYLQWS SLKASDTAMYYCARQVWGWQG GMYPRSNWWYNMDSWGQGTLV TVSSASTKGPSVFPLAPSSKS TSGGTAALGCLVKDYFPEPVT VSWNSGALTSGVHTFPAVLQS SGLYSLSSVVTVPSSSLGTQT YICNVNHKPSNTKVDKRVEPK SCEVKTDSTDHVKPKETENTK QPSKSCHKPKAIVHTEKVNMM SLTVLGLRMLFAKTVAVNFLL TAKLFFL |
| 73 | anti-CD19-caTCR-1-0 gamma | LPVLTQPPSVSVAPGKTARIT CGGNNIGSKSVHWYQQKPGQA PVLVVYDDSNRPSGIPERFSG SNSGNTATLTISRVEAGDEAD YYCQVWDSSSEYVVFGGGTKL TVLGQPKANPTVTLFPPSSEE LQANKATLVCLISDFYPGAVT VAWKADGSPVKAGVETTKPSK QSNNKYAASSYLSLTPEQWKS HRSYSCQVTHEGSTVEKTVAP TECSPIKTDVITMDPKDNCSK DANDTLLLQLTNTSAYYMYLL LLLKSVVYFAIITCCLLRRTA FCCNGEKS |
| 74 | anti-CD19-caTCR-1-TM5 delta | EVQLVQSGAEVKKPGESLKIS CKGSGYSFTSYWIGWVRQMPG KGLEWMGIIYPGDSDTRYSPS FQGQVTISADKSISTAYLQWS SLKASDTAMYYCARQVWGWQG GMYPRSNWWYNMDSWGQGTLV TVSSASTKGPSVFPLAPSSKS TSGGTAALGCLVKDYFPEPVT VSWNSGALTSGVHTFPAVLQS SGLYSLSSVVTVPSSSLGTQT YICNVNHKPSNTKVDKRVEPK SCEVKTDSTDHVKPKETENTK QPSKSCHKPKAIVHTEKVNMM SLTVLGLRVLFAKTVAVNFLL TAKLFFL |
| 75 | anti-CD19-caTCR-1-TM5 gamma | LPVLTQPPSVSVAPGKTARIT CGGNNIGSKSVHWYQQKPGQA PVLVVYDDSNRPSGIPERFSG SNSGNTATLTISRVEAGDEAD YYCQVWDSSSEYVVFGGGTKL TVLGQPKANPTVTLFPPSSEE LQANKATLVCLISDFYPGAVT VAWKADGSPVKAGVETTKPSK QSNNKYAASSYLSLTPEQWKS HRSYSCQVTHEGSTVEKTVAP TECSPIKTDVITMDPKDNCSK DANDTLLLQLTNTSAYLVYLL LLLKSVVYFVIVTCCLLRRTA FCCNGEKS |
| 76 | scFv linker | SRGGGGSGGGGSGGGGSLEMA |
| 77 | anti-CD19 scFv | LPVLTQPPSVSVAPGKTARIT CGGNNIGSKSVHWYQQKPGQA PVLVVYDDSDRPSGIPERFSG SNSGNTATLTISRVEAGDEAD YYCQVWDSSSDYVVFGGGTKL TVLGSRGGGGSGGGGSGGGGS LEMAEVQLVQSGAEVKKPGES LKISCKGSGYSFTSYWIGWVR QMPGKGLEWMGIIYPGDSDTR YSPSFQGQVTISADKSISTAY LQWSSLKASDTAMYYCARQVW GWQGGMYPRSNWWYNLDSWGQ GTLVTVSS |
| 78 | anti-CD20 scFv | QIVLSQSPAILSASPGEKVTM TCRASSSVSYIHWFQQKPGSS PKPWIYATSNLASGVPVRFSG SGSGTSYSLTISRVEAEDAAT YYCQQWTSNPPTFGGGTKLEI KRSRGGGGSGGGGSGGGGSLE QVQLQQPGAELVKPGASVKMS CKASGYTFTSYNMHWVKQTPG RGLEWIGAIYPGNGDTSYNQK FKGKATLTADKSSSTAYMQLS SLTSEDSAVYYCARSTYYGGD WYFNVWGAGTTVTVSS |
| 79 | anti-GPC3 #37 scFv | QSVLTQPPSVSAAPGQRVTIS CSGTRSNIGSDYVSWYQHLPG TAPKLLVYGDNLRPSGIPDRF SASKSGTSATLGITGLQTGDE |

Sequence Listing

| SEQ ID NO | Description | Sequence |
|---|---|---|
| | | ADYYCGTWDYTLNGVVFGGGTKLTVLGSRGGGGSGGGGSGGGGSLEMAQVQLVESGGGLVQPGGSLRLSCAASGFTFSSYAMSWVRQAPGKGLEWVSVIYSGGSSTYYADSVKGRFTISRDNSKNTLYLQMNSLRAEDTAVYYCARTSYLNHGDYWGQGTLVTVSS |
| 80 | anti-CD19 CSR | LPVLTQPPSVSVAPGKTARITCGGNNIGSKSVHWYQQKPGQAPVLVVYDDSDRPSGIPERFSGSNSGNTATLTISRVEAGDEADYYCQVWDSSSDYVVFGGGTKLTVLGSRGGGGSGGGGSGGGGSLEMAEVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARQVWGWQGGMYPRSNWWYNLDSWGQGTLVTVSSAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRS |
| 81 | anti-CD20 CSR | QIVLSQSPAILSASPGEKVTMTCRASSSVSYIHWFQQKPGSSPKPWIYATSNLASGVPVRFSGSGSGTSYSLTISRVEAEDAATYYCQQWTSNPPTFGGGTKLEIKRSRGGGGSGGGGSGGGGSLEQVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSSAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRS |
| 82 | anti-GPC3 CSR | QSVLTQPPSVSAAPGQRVTISCSGTRSNIGSDYVSWYQHLPGTAPKLLVYGDNLRPSGIPDRFSASKSGTSATLGITGLQTGDEADYYCGTWDYTLNGVVFGGGTKLTVLGSRGGGGSGGGGSGGGGSLEMAQVQLVESGGGLVQPGGSLRLSCAASGFTFSSYAMSWVRQAPGKGLEWVSVIYSGGSSTYYADSVKGRFTISRDNSKNTLYLQMNSLRAEDTAVYYCARTSYLNHGDYWGQGTLVTVSSAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRS |
| 83 | 6NFAT response element | GGAGGAAAAACTGTTTCATACAGAAGGCGTGGAGGAAAAACTGTTTCATACAGAAGGCGTGGAGGAAAAACTGTTTCATACAGAAGGCGTGGAGGAAAAACTGTTTCATACAGAAGGCGTGGAGGAAAAACTGTTTCATACAGAAGGCGT |
| 84 | TA promoter | GCCGCCCCGACTGCATCTGCGTGTTCCAATTCGCCAATGACAAGACGCTGGGCGGGGTTTGTGTCATCATAGAACTAAAGACATGCAAATATATTCTTCCGGGGACACCGCCAGCAAACGCGAGCAACGGGCCACGGGGATGAAGCAG |
| 85 | NFAT-derived promoter | GGAGGAAAAACTGTTTCATACAGAAGGCGTGGAGGAAAAACTGTTTCATACAGAAGGCGTGGAGGAAAAACTGTTTCATACAGAAGGCGTGGAGGAAAAACTGTTTCATACAGAAGGCGTGGAGGAAAAACTGTTTCATACAGAAGGCGTCTCGAGGCCGCCCCGACTGCATCTGCGTGTTCCAATTCGCCAATGACAAGACGCTGGGCGGGGTTTGTGTCATCATAGAACTAAAGACATGCAAATATATTCTTCCGGGGACACCGCCAGCAAACGCGAGCAACGGGCCACGGGGATGAAGCAG |
| 86 | CD27 co-stimulatory fragment 1 | PTHLPYVSEMLEARTAGHMQTLADFRQLPARTLSTHWPPQRSLCSSDFIRILVIFSGMFLVFTLAGALFLHQRRKYRSNKGESPVEPAEPCRYSCPREEEGSTIPIQEDYRKPEPACSP |
| 87 | CD27 co-stimulatory fragment 2 | QRRKYRSNKGESPVEPAEPCRYSCPREEEGSTIPIQEDYRKPEPACSP |
| 88 | CD30 co-stimulatory fragment 1 | APPLGTQPDCNPTPENGEAPASTSPTQSLLVDSQASKTLPIPTSAPVALSSTGKPVLDAGPVLFWVILVLVVVGSSAFLLCHRRACRKRIRQKLHLCYPVQTSQPKLELVDSRPRRSSTQLRSGASVTEPVAEEERGLMSQPLMETCHSVGAAYLESLPLQDASPAGGPSSPRDLPEPRVSTEHTNNKIEKIYIMKADTVIVGTVKAELPEGRGLAGPAEPELEEELEADHTPHYPEQETEPPLGSCSDVMLSVEEEGKEDPLPTAASGK |
| 89 | CD30 co-stimulatory fragment 2 | HRRACRKRIRQKLHLCYPVQTSQPKLELVDSRPRRSSTQLRSGASVTEPVAEEERGLMSQPLMETCHSVGAAYLESLPLQDASPAGGPSSPRDLPEPRVSTEHTNNKIEKIYIMKADTVIVGTVKAELPEGRGLAGPAEPELEEELEADHTPHYPEQETEPPLGSCSDVMLSVEEEGKEDPLPTAASGK |
| 90 | CSR1 | AAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRS |
| 91 | CSR2 | AAATGTTTPAPRPPTPAPTIASQPLSLRPEACRPAAGGAVHTRGLDFACDIYIWAPLAGTCGV |

Sequence Listing

| SEQ ID NO | Description | Sequence |
|---|---|---|
| | | LLLSLVITLYCKRGRKKLLYI FKQPFMRPVQTTQEEDGCSCR FPEEEEGGCEL |
| 92 | CSR3 | AAATGPADLSPGASSVTPPAP AREPGHSPQIISFFLALTSTA LLFLLFFLTLRFSVVKRGRKK LLYIFKQPFMRPVQTTQEEDG CSCRFPEEEEGGCEL |
| 93 | CSR4 | AAATGTTTPAPRPPTPAPTIA SQPLSLRPEACRPAAGGAVHT RGLDFACDIYIWAPLAGTCGV LLLSLVITLYCQRRKYRSNKG ESPVEPAEPCRYSCPREEEGS TIPIQEDYRKPEPACSP |
| 94 | CSR5 | AAATGPTHLPYVSEMLEARTA GHMQTLADFRQLPARTLSTHW PPQRSLCSSDFIRILVIFSGM FLVFTLAGALFLHQRRKYRSN KGESPVEPAEPCRYSCPREEE GSTIPIQEDYRKPEPACSP |
| 95 | CSR6 | AAATGTTTPAPRPPTPAPTIA SQPLSLRPEACRPAAGGAVHT RGLDFACDIYIWAPLAGTCGV LLLSLVITLYCHRRACRKRIR QKLHLCYPVQTSQPKLELVDS RPRRSSTQLRSGASVTEPVAE ERGLMSQPLMETCHSVGAAYL ESLPLQDASPAGGPSSPRDLP EPRVSTEHTNNKIEKIYIMKA DTVIVGTVKAELPEGRGLAGP AEPELEEELEADHTPHYPEQE TEPPLGSCSDVMLSVEEEGKE DPLPTAASGK |
| 96 | CSR7 | AAATGAPPLGTQPDCNPTPEN GEAPASTSPTQSLLVDSQASK TLPIPTSAPVALSSTGKPVLD AGPVLFWVILVLVVVVGSSAF LLCHRRACRKRIRQKLHLCYP VQTSQPKLELVDSRPRRSSTQ LRSGASVTEPVAEERGLMSQP LMETCHSVGAAYLESLPLQDA SPAGGPSSPRDLPEPRVSTEH TNNKIEKIYIMKADTVIVGTV KAELPEGRGLAGPAEPELEEE LEADHTPHYPEQETEPPLGSC SDVMLSVEEEGKEDPLPTAAS GK |
| 97 | CSR8 | AAATGTTTPAPRPPTPAPTIA SQPLSLRPEACRPAAGGAVHT RGLDFACDIYIWAPLAGTCGV LLLSLVITLYCALYLLRRDQR LPPDAHKPPGGSFRTPIQEE QADAHSTLAKI |
| 98 | CSR9 | AAATGDRDPPATQPQETQGPP ARPITVQPTEAWPRTSQGPST RPVEVPGGRAVAAILGLGLVL GLLGPLAILLALYLLRRDQRL PPDAHKPPGGSFRTPIQEEQ ADAHSTLAKI |
| 99 | IgV$_H$ domain of anti-CD19 antibody | EVQLVQSGAEVKKPGESLKIS CKGSGYSFTSYWIGWVRQMPG KGLEWMGIIYPGDSDTRYSPS FQGQVTIADKSISTAYLQWSS LKASDTAMYYCARQVWGWQGG MYPRSNWWYNLDSWGQGTLVT VSS |
| 100 | IgV$_L$ domain of anti-CD19 antibody | LPVLTQPPSVSVAPGKTARIT CGGNNIGSKSVHWYQQKPGQA PVLVVYDDSDRPSGIPERFSG SNSGNTATLTISRVEAGDEAD YYCQVWDSSSDYVVFGGGTKL TVL |
| 101 | IgV$_H$ domain of anti-CD22 antibody | QVQLVESGGGLVQPGGSLRLS CAASGFTFSNYAMSWVRQAPG KGLEWVSSISGSGGSTYYADS VKGRFTISRDTSKNTLYLQMN SLRAEDTAVYYCARYGSAAWM DSWGQGTLVTVSS |
| 102 | IgV$_L$ domain of anti-CD22 antibody | DIQLTQSPSSLSTSVGDRVTI TCQASHDIRNYLNWYQQKPGK APNLLIYAASNLQTGVPSRFS GRGSGTDFTLTISSLQPEDIA TYYCQQYDGLPLTFGQGTRLE IKR |
| 103 | Peptide linker | AAA |
| 104 | Peptide linker | AAATG |
| 105 | GPC3-37/CD3 BsAb | QSVLTQPPSVSAAPGQRVTIS CSGTRSNIGSDYVSWYQHLPG TAPKLLVYGDNLRPSGIPDRF SASKSGTSATLGITGLQTGDE ADYYCGTWDYTLNGVVFGGGT KLTVLGSRGGGGSGGGGSGGG GSLEMAQVLVESGGGLVQPG GSLRLSCAASGFTFSSYAMSW VRQAPGKGLEWVSVIYSGGSS TYYADSVKGRFTISRDNSKNT LYLQMNSLRAEDTAVYYCART SYLNHGDYWGQGTLVTVSSTS GGGGSDVQLVQSGAEVKKPGA SVKVSCKASGYTFTRYTMHWV RQAPGQGLEWIGYINPSRGYT NYADSVKGRFTITTDKSTSTA YMELSSLRSEDTATYYCARYY DDHYCLDYWGQGTTVTVSSGE GTSTGSGGSGGSGGADDIVLT QSPATLSLSPGERATLSCRAS QSVSYMNWYQQKPGKAPKRWI YDTSKVASGVPARFSGSGSGT DYSLTINSLEAEDAATYYCQQ WSSNPLTFGGGTKVEIK |

What is claimed is:

1. An immune cell comprising:
   a) a chimeric antibody-T cell receptor (TCR) construct (caTCR) comprising:
      i) an antigen binding module that specifically binds to a target antigen; and
      ii) a TCR module (TCRM), wherein the TCRM comprises a first TCR domain (TCRD) comprising a first TCR transmembrane domain (TCR-TM) and a second TCRD comprising a second TCR-TM,
      wherein the TCRM facilitates recruitment of at least one TCR-associated signaling molecule; and
      wherein the caTCR further comprises a stabilization module comprising a first stabilization domain and a second stabilization domain, wherein the stabilization module is selected from the group consisting of a $C_H1$-$C_L$ module, a $C_H2$-$C_H2$ module, a $C_H3$-$C_H3$ module, and a $C_H4$-$C_H4$ module;
   and
   b) a chimeric signaling receptor (CSR) comprising:
      i) a ligand-binding module that is capable of binding or interacting with a target ligand;
      ii) a transmembrane module; and
      iii) a co-stimulatory immune cell signaling module that is capable of providing a co-stimulatory signal to the immune cell,
      wherein the ligand-binding module and the co-stimulatory immune cell signaling module are not derived from the same molecule, wherein the CSR lacks a functional primary immune cell signaling domain, and wherein the co-stimulatory immune cell signaling module is derived from CD30;
      wherein the immune cell is a T cell.

2. The immune cell of claim 1, wherein the CSR lacks any primary immune cell signaling sequences.

3. The immune cell of claim 1, wherein the target antigen is a cell surface antigen.

4. The immune cell of claim 1, wherein the first TCR-TM is derived from one of the transmembrane domains of a TCR and the second TCR-TM is derived from the other transmembrane domain of the TCR.

5. The immune cell of claim 1, wherein at least one of the TCR-TMs is non-naturally occurring.

6. The immune cell of claim 4, wherein the TCR is a γ/δ TCR.

7. The immune cell of claim 6, wherein the immune cell is an αβ T cell.

8. The immune cell of claim 1, wherein the target antigen and the target ligand are the same.

9. The immune cell of claim 1, wherein the target antigen and the target ligand are different.

10. The immune cell of claim 1, wherein the target ligand is a ligand expressed on the surface of a cell presenting the target antigen.

11. The immune cell of claim 1, where the target ligand is a disease-associated ligand.

12. The immune cell of claim 1, wherein the ligand-binding module of the CSR is an antibody moiety.

13. The immune cell of claim 1, wherein the transmembrane module of the CSR comprises a transmembrane domain derived from CD28, CD3ε, CD3ζ, CD45, CD4, CD5, CD8, CD9, CD16, CD22, CD30, CD33, CD37, CD64, CD80, CD86, CD134, CD137, or CD154.

14. The immune cell of claim 1, wherein the target antigen is a complex comprising a peptide and a major histocompatibility complex (MHC) protein.

15. The immune cell of claim 1, wherein the antigen binding module of the caTCR is multispecific.

16. The immune cell of claim 1, wherein the target ligand is a cancer-associated ligand.

17. The immune cell of claim 1, wherein the ligand-binding module of the CSR comprises an scFv.

18. The immune cell of claim 1, wherein the immune cell is selected from the group consisting of a cytotoxic T cell, a helper T cell, a natural killer T cell, and a suppressor T cell.

19. The immune cell of claim 1, wherein the transmembrane module and the co-stimulatory signaling module of the CSR are derived from the same molecule.

20. The immune cell of claim 1, wherein the transmembrane module and the co-stimulatory signaling module of the CSR are derived from different molecules.

21. A T cell comprising one or more nucleic acids encoding:
   a) a chimeric antibody-T cell receptor (TCR) construct (caTCR) comprising:
      i) an antigen binding module that specifically binds to a target antigen; and
      ii) a TCR module (TCRM), wherein the TCRM comprises a first TCR domain (TCRD) comprising a first TCR transmembrane domain (TCR-TM) and a second TCRD comprising a second TCR-TM,
      wherein the TCRM facilitates recruitment of at least one TCR-associated signaling molecule;
      wherein the caTCR further comprises a stabilization module comprising a first stabilization domain and a second stabilization domain, and wherein the stabilization module is selected from the group consisting of a $C_H1$-$C_L$ module, a $C_H2$-$C_H2$ module, a $C_H3$-$C_H3$ module, and a $C_H4$-$C_H4$ module;
   and
   b) a chimeric signaling receptor (CSR) comprising:
      i) a ligand-binding module that is capable of binding or interacting with a target ligand;
      ii) a transmembrane module; and
      iii) a co-stimulatory immune cell signaling module that is capable of providing a co-stimulatory signal to the T cell,
      wherein the ligand-binding module and the co-stimulatory immune cell signaling module are not derived from the same molecule, wherein the CSR lacks a functional primary immune cell signaling domain, and wherein the co-stimulatory immune cell signaling module is derived from CD30; and
      wherein the caTCR and CSR each consists of one or more polypeptide chains encoded by the one or more nucleic acids.

22. A method of killing a target cell presenting a target antigen, comprising contacting the target cell with the immune cell of claim 1, wherein the caTCR specifically binds to the target antigen.

23. A method of treating a target antigen-associated disease in an individual in need thereof, comprising administering to the individual an effective amount of a pharmaceutical composition, wherein the pharmaceutical composition comprises the immune cell of claim 1 and a pharmaceutically acceptable carrier, wherein the caTCR specifically binds to the target antigen.

* * * * *

SEQUENCE LISTING

<160> NUMBER OF SEQ ID NOS: 105

<210> SEQ ID NO 1
<211> LENGTH: 142
<212> TYPE: PRT

<213> ORGANISM: Artificial Sequence
<220> FEATURE:
<223> OTHER INFORMATION: Synthetic Construct

<400> SEQUENCE: 1

```
Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140
```

<210> SEQ ID NO 2
<211> LENGTH: 177
<212> TYPE: PRT
<213> ORGANISM: Artificial Sequence
<220> FEATURE:
<223> OTHER INFORMATION: Synthetic Construct

<400> SEQUENCE: 2

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

-continued

```
<210> SEQ ID NO 3
<211> LENGTH: 153
<212> TYPE: PRT
<213> ORGANISM: Artificial Sequence
<220> FEATURE:
<223> OTHER INFORMATION: Synthetic Construct

<400> SEQUENCE: 3

Ser Gln Pro His Thr Lys Pro Ser Val Phe Val Met Lys Asn Gly Thr
1               5                   10                  15

Asn Val Ala Cys Leu Val Lys Glu Phe Tyr Pro Lys Asp Ile Arg Ile
            20                  25                  30

Asn Leu Val Ser Ser Lys Ile Thr Glu Phe Asp Pro Ala Ile Val
        35                  40                  45

Ile Ser Pro Ser Gly Lys Tyr Asn Ala Val Lys Leu Gly Lys Tyr Glu
50                  55                  60

Asp Ser Asn Ser Val Thr Cys Ser Val Gln His Asp Asn Lys Thr Val
65                  70                  75                  80

His Ser Thr Asp Phe Glu Val Lys Thr Asp Ser Thr Asp His Val Lys
                85                  90                  95

Pro Lys Glu Thr Glu Asn Thr Lys Gln Pro Ser Lys Ser Cys His Lys
            100                 105                 110

Pro Lys Ala Ile Val His Thr Glu Lys Val Asn Met Met Ser Leu Thr
        115                 120                 125

Val Leu Gly Leu Arg Met Leu Phe Ala Lys Thr Val Ala Val Asn Phe
    130                 135                 140

Leu Leu Thr Ala Lys Leu Phe Phe Leu
145                 150

<210> SEQ ID NO 4
<211> LENGTH: 173
<212> TYPE: PRT
<213> ORGANISM: Artificial Sequence
<220> FEATURE:
<223> OTHER INFORMATION: Synthetic Construct

<400> SEQUENCE: 4

Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Glu Gly Asn Thr Met Lys
50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160
```

```
Leu Arg Arg Thr Ala Phe Cys Cys Asn Gly Glu Lys Ser
                165                 170

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct

<400> SEQUENCE: 5

Ile Leu Leu Leu Lys Val Ala Gly Phe Asn Leu Leu Met Thr Leu Arg
1               5                   10                  15

Leu Trp Ser Ser
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic Construct

<400> SEQUENCE: 6

Thr Ile Leu Tyr Glu Ile Leu Leu Gly Lys Ala Thr Leu Tyr Ala Val
1               5                   10                  15

Leu Val Ser Ala Leu Val Leu
            20

<210> SEQ ID NO 7
<211> LENGTH: 25
<212> TYPE: PRT
<213> ORGANISM: Artificial Sequence
<220> FEATURE:
<223> OTHER INFORMATION: Synthetic Construct

<400> SEQUENCE: 7

Val Leu Gly Leu Arg Met Leu Phe Ala Lys Thr Val Ala Val Asn Phe
1               5                   10                  15

Leu Leu Thr Ala Lys Leu Phe Phe Leu
            20                  25

<210> SEQ ID NO 8
<211> LENGTH: 23
<212> TYPE: PRT
<213> ORGANISM: Artificial Sequence
<220> FEATURE:
<223> OTHER INFORMATION: Synthetic Construct

<400> SEQUENCE: 8

Tyr Tyr Met Tyr Leu Leu Leu Leu Lys Ser Val Val Tyr Phe Ala
1               5                   10                  15

Ile Ile Thr Cys Cys Leu Leu
            20

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Val Leu Gly Leu Arg Met Leu Phe Ala Lys Thr Val Ala Val Asn Phe
1               5                   10                  15
```

```
Leu Leu Thr Ala Lys Leu Phe Ser Leu
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic Construct

<400> SEQUENCE: 10

Val Leu Gly Leu Arg Val Leu Phe Ala Lys Thr Val Ala Val Asn Phe
1               5                   10                  15

Leu Leu Thr Ala Lys Leu Phe Phe Leu
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic Construct

<400> SEQUENCE: 11

Val Leu Gly Cys Arg Met Leu Phe Ala Lys Thr Val Ala Val Asn Phe
1               5                   10                  15

Leu Leu Thr Ala Lys Leu Phe Phe Leu
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Val Leu Gly Leu Arg Met Leu Phe Ala Lys Thr Phe Ala Val Ser Phe
1               5                   10                  15

Leu Leu Thr Ala Lys Leu Phe Phe Leu
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Construct

<400> SEQUENCE: 13

Val Leu Gly Leu Arg Met Leu Phe Ala Lys Thr Val Ala Val Asn Phe
1               5                   10                  15

Leu Leu Thr Ala Lys Leu Phe Phe Ser
            20                  25

<210> SEQ ID NO 14
<211> LENGTH: 28
<212> TYPE: PRT
<213> ORGANISM: Artificial Sequence
<220> FEATURE:
<223> OTHER INFORMATION: Synthetic Construct

<400> SEQUENCE: 14

Tyr Tyr Met Tyr Leu Leu Leu Leu Leu Lys Ser Val Tyr Tyr Phe Ala
```

```
1               5                   10                  15

Ile Ile Thr Cys Cys Leu Leu Arg Arg Thr Ala Phe
            20                  25
```

<210> SEQ ID NO 15
<211> LENGTH: 28
<212> TYPE: PRT
<213> ORGANISM: Artificial Sequence
<220> FEATURE:
<223> OTHER INFORMATION: Synthetic Construct

<400> SEQUENCE: 15

```
Tyr Tyr Met Tyr Leu Leu Leu Leu Lys Ser Val Val Tyr Phe Ala
1               5                   10                  15

Ile Ile Thr Cys Gly Leu Leu Arg Arg Thr Ala Phe
            20                  25
```

<210> SEQ ID NO 16
<211> LENGTH: 28
<212> TYPE: PRT
<213> ORGANISM: Artificial Sequence
<220> FEATURE:
<223> OTHER INFORMATION: Synthetic Construct

<400> SEQUENCE: 16

```
Tyr Leu Val Tyr Leu Leu Leu Leu Lys Ser Val Val Tyr Phe Val
1               5                   10                  15

Ile Val Thr Cys Cys Leu Leu Arg Arg Thr Ala Phe
            20                  25
```

<210> SEQ ID NO 17
<211> LENGTH: 28
<212> TYPE: PRT
<213> ORGANISM: Artificial Sequence
<220> FEATURE:
<223> OTHER INFORMATION: Synthetic Construct

<400> SEQUENCE: 17

```
Tyr Leu Met Tyr Leu Leu Leu Leu Lys Ser Val Val Tyr Phe Ala
1               5                   10                  15

Ile Ile Thr Cys Cys Leu Leu Arg Arg Thr Ala Phe
            20                  25
```

<210> SEQ ID NO 18
<211> LENGTH: 28
<212> TYPE: PRT
<213> ORGANISM: Artificial Sequence
<220> FEATURE:
<223> OTHER INFORMATION: Synthetic Construct

<400> SEQUENCE: 18

```
Tyr Tyr Val Tyr Leu Leu Leu Leu Lys Ser Val Val Tyr Phe Ala
1               5                   10                  15

Ile Ile Thr Cys Cys Leu Leu Arg Arg Thr Ala Phe
            20                  25
```

<210> SEQ ID NO 19
<211> LENGTH: 28
<212> TYPE: PRT
<213> ORGANISM: Artificial Sequence
<220> FEATURE:
<223> OTHER INFORMATION: Synthetic Construct

<400> SEQUENCE: 19

Tyr Tyr Met Tyr Leu Leu Leu Leu Lys Ser Val Val Tyr Phe Val
1               5                   10                  15

Ile Ile Thr Cys Cys Leu Leu Arg Arg Thr Ala Phe
            20                  25

<210> SEQ ID NO 20
<211> LENGTH: 28
<212> TYPE: PRT
<213> ORGANISM: Artificial Sequence
<220> FEATURE:
<223> OTHER INFORMATION: Synthetic Construct

<400> SEQUENCE: 20

Tyr Tyr Met Tyr Leu Leu Leu Leu Lys Ser Val Val Tyr Phe Ala
1               5                   10                  15

Ile Val Thr Cys Cys Leu Leu Arg Arg Thr Ala Phe
            20                  25

<210> SEQ ID NO 21
<211> LENGTH: 28
<212> TYPE: PRT
<213> ORGANISM: Artificial Sequence
<220> FEATURE:
<223> OTHER INFORMATION: Synthetic Construct

<400> SEQUENCE: 21

Tyr Tyr Ile Tyr Leu Leu Leu Leu Lys Ser Val Val Tyr Phe Ala
1               5                   10                  15

Ile Ile Thr Cys Cys Leu Leu Arg Arg Thr Ala Phe
            20                  25

<210> SEQ ID NO 22
<211> LENGTH: 28
<212> TYPE: PRT
<213> ORGANISM: Artificial Sequence
<220> FEATURE:
<223> OTHER INFORMATION: Synthetic Construct

<400> SEQUENCE: 22

Tyr Ile Ile Tyr Leu Leu Leu Leu Lys Ser Val Val Tyr Phe Ile
1               5                   10                  15

Ile Leu Thr Cys Cys Leu Leu Arg Arg Thr Ala Phe
            20                  25

<210> SEQ ID NO 23
<211> LENGTH: 28
<212> TYPE: PRT
<213> ORGANISM: Artificial Sequence
<220> FEATURE:
<223> OTHER INFORMATION: Synthetic Construct

<400> SEQUENCE: 23

Tyr Tyr Met Tyr Cys Leu Leu Leu Lys Ser Val Val Tyr Phe Ala
1               5                   10                  15

Ile Ile Thr Cys Cys Leu Leu Arg Arg Thr Ala Phe
            20                  25

<210> SEQ ID NO 24
<211> LENGTH: 28
<212> TYPE: PRT
<213> ORGANISM: Artificial Sequence
<220> FEATURE:
<223> OTHER INFORMATION: Synthetic Construct

<400> SEQUENCE: 24

```
Tyr Tyr Met Tyr Leu Leu Phe Leu Lys Ser Phe Val Tyr Ser Ala
1               5                   10                  15

Ile Ile Thr Cys Cys Leu Leu Arg Arg Thr Ala Phe
            20                  25
```

<210> SEQ ID NO 25
<211> LENGTH: 28
<212> TYPE: PRT
<213> ORGANISM: Artificial Sequence
<220> FEATURE:
<223> OTHER INFORMATION: Synthetic Construct

<400> SEQUENCE: 25

```
Tyr Tyr Met Tyr Leu Leu Leu Leu Lys Ser Val Val Tyr Phe Ala
1               5                   10                  15

Ile Ile Thr Met Cys Leu Leu Arg Arg Thr Ala Phe
            20                  25
```

<210> SEQ ID NO 26
<211> LENGTH: 28
<212> TYPE: PRT
<213> ORGANISM: Artificial Sequence
<220> FEATURE:
<223> OTHER INFORMATION: Synthetic Construct

<400> SEQUENCE: 26

```
Gln Tyr Met Tyr Leu Leu Leu Leu Lys Ser Val Val Tyr Phe Ala
1               5                   10                  15

Ile Ile Thr Cys Cys Leu Leu Arg Arg Thr Ala Phe
            20                  25
```

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27

```
Glu Ser Ser Cys Asp Val Lys Leu Val Glu Lys Ser Phe Glu Thr Asp
1               5                   10                  15

Thr Asn Leu Asn Phe Gln Asn Leu Ser Val Ile Gly Phe Arg
            20                  25                  30
```

<210> SEQ ID NO 28
<211> LENGTH: 40
<212> TYPE: PRT
<213> ORGANISM: Artificial Sequence
<220> FEATURE:
<223> OTHER INFORMATION: Synthetic Construct

<400> SEQUENCE: 28

```
Ile Pro Glu Asp Thr Phe Phe Pro Ser Pro Glu Ser Ser Cys Asp Val
1               5                   10                  15

Lys Leu Val Glu Lys Ser Phe Glu Thr Asp Thr Asn Leu Asn Phe Gln
            20                  25                  30

Asn Leu Ser Val Ile Gly Phe Arg
            35                  40
```

<210> SEQ ID NO 29
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 29

Ala Asp Cys Gly Phe Thr Ser Val Ser Tyr Gln Gln Gly Val Leu Ser
1               5                   10                  15
Ala

<210> SEQ ID NO 30
<211> LENGTH: 19
<212> TYPE: PRT
<213> ORGANISM: Artificial Sequence
<220> FEATURE:
<223> OTHER INFORMATION: Synthetic Construct

<400> SEQUENCE: 30

Gly Arg Ala Asp Cys Gly Phe Thr Ser Val Ser Tyr Gln Gln Gly Val
1               5                   10                  15
Leu Ser Ala

<210> SEQ ID NO 31
<211> LENGTH: 41
<212> TYPE: PRT
<213> ORGANISM: Artificial Sequence
<220> FEATURE:
<223> OTHER INFORMATION: Synthetic Construct

<400> SEQUENCE: 31

Asp His Val Lys Pro Lys Glu Thr Glu Asn Thr Lys Gln Pro Ser Lys
1               5                   10                  15

Ser Cys His Lys Pro Lys Ala Ile Val His Thr Glu Lys Val Asn Met
                20                  25                  30

Met Ser Leu Thr Val Leu Gly Leu Arg
            35                  40

<210> SEQ ID NO 32
<211> LENGTH: 48
<212> TYPE: PRT
<213> ORGANISM: Artificial Sequence
<220> FEATURE:
<223> OTHER INFORMATION: Synthetic Construct

<400> SEQUENCE: 32

Glu Val Lys Thr Asp Ser Thr Asp His Val Lys Pro Lys Glu Thr Glu
1               5                   10                  15

Asn Thr Lys Gln Pro Ser Lys Ser Cys His Lys Pro Lys Ala Ile Val
                20                  25                  30

His Thr Glu Lys Val Asn Met Met Ser Leu Thr Val Leu Gly Leu Arg
            35                  40                  45

<210> SEQ ID NO 33
<211> LENGTH: 24
<212> TYPE: PRT
<213> ORGANISM: Artificial Sequence
<220> FEATURE:
<223> OTHER INFORMATION: Synthetic Construct

<400> SEQUENCE: 33

Met Asp Pro Lys Asp Asn Cys Ser Lys Asp Ala Asn Asp Thr Leu Leu
1               5                   10                  15

Leu Gln Leu Thr Asn Thr Ser Ala
                20
```

-continued

<210> SEQ ID NO 34
<211> LENGTH: 32
<212> TYPE: PRT
<213> ORGANISM: Artificial Sequence
<220> FEATURE:
<223> OTHER INFORMATION: Synthetic Construct

<400> SEQUENCE: 34

Pro Ile Lys Thr Asp Val Ile Thr Met Asp Pro Lys Asp Asn Cys Ser
1               5                   10                  15

Lys Asp Ala Asn Asp Thr Leu Leu Leu Gln Leu Thr Asn Thr Ser Ala
            20                  25                  30

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Met Ala Met Val Lys Arg Lys Asp Phe
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

<400> SEQUENCE: 36

Arg Arg Thr Ala Phe Cys Cys Asn Gly Glu Lys Ser
1               5                   10

<210> SEQ ID NO 37
<211> LENGTH: 101
<212> TYPE: PRT
<213> ORGANISM: Artificial Sequence
<220> FEATURE:
<223> OTHER INFORMATION: Synthetic Construct

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Ser Leu Ser
    50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Arg Val
                85                  90                  95

Glu Pro Lys Ser Cys
            100

<210> SEQ ID NO 38
<211> LENGTH: 99
<212> TYPE: PRT
<213> ORGANISM: Artificial Sequence
<220> FEATURE:

<223> OTHER INFORMATION: Synthetic Construct

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Ser Leu Ser
        50                  55                  60

Ser Val Val Thr Val Pro Ser Ser Asn Phe Gly Thr Gln Thr Tyr Thr
65                  70                  75                  80

Cys Asn Val Asp His Lys Pro Ser Asn Thr Lys Val Asp Lys Thr Val
                85                  90                  95

Glu Arg Lys

<210> SEQ ID NO 39
<211> LENGTH: 100
<212> TYPE: PRT
<213> ORGANISM: Artificial Sequence
<220> FEATURE:
<223> OTHER INFORMATION: Synthetic Construct

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Ser Leu Ser
        50                  55                  60

Ser Val Val Thr Val Pro Ser Ser Asn Phe Gly Thr Gln Thr Tyr Thr
65                  70                  75                  80

Cys Asn Val Asp His Lys Pro Ser Asn Thr Lys Val Asp Lys Thr Val
                85                  90                  95

Glu Arg Lys Cys
            100

<210> SEQ ID NO 40
<211> LENGTH: 101
<212> TYPE: PRT
<213> ORGANISM: Artificial Sequence
<220> FEATURE:
<223> OTHER INFORMATION: Synthetic Construct

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Ser Leu Ser
        50                  55                  60

Ser Val Val Thr Val Pro Ser Ser Asn Phe Gly Thr Gln Thr Tyr Thr
65                  70                  75                  80

```
Cys Asn Val Asp His Lys Pro Ser Asn Thr Lys Val Asp Lys Thr Val
            85                  90                  95

Glu Arg Lys Cys Cys
            100
```

<210> SEQ ID NO 41
<211> LENGTH: 101
<212> TYPE: PRT
<213> ORGANISM: Artificial Sequence
<220> FEATURE:
<223> OTHER INFORMATION: Synthetic Construct

<400> SEQUENCE: 41

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Ser Leu Ser
    50                  55                  60

Ser Val Val Thr Val Pro Ser Ser Ser Leu Gly Thr Gln Thr Tyr Thr
65                  70                  75                  80

Cys Asn Val Asn His Lys Pro Ser Asn Thr Lys Val Asp Lys Arg Val
                85                  90                  95

Glu Leu Lys Thr Pro
            100
```

<210> SEQ ID NO 42
<211> LENGTH: 101
<212> TYPE: PRT
<213> ORGANISM: Artificial Sequence
<220> FEATURE:
<223> OTHER INFORMATION: Synthetic Construct

<400> SEQUENCE: 42

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Ser Leu Ser
    50                  55                  60

Ser Val Val Thr Val Pro Ser Ser Ser Leu Gly Thr Lys Thr Tyr Thr
65                  70                  75                  80

Cys Asn Val Asp His Lys Pro Ser Asn Thr Lys Val Asp Lys Arg Val
                85                  90                  95

Glu Ser Lys Tyr Gly
            100
```

<210> SEQ ID NO 43
<211> LENGTH: 119
<212> TYPE: PRT
<213> ORGANISM: Artificial Sequence
<220> FEATURE:
<223> OTHER INFORMATION: Synthetic Construct

<400> SEQUENCE: 43

Asp Thr Ser Pro Lys Val Phe Pro Leu Ser Leu Cys Ser Thr Gln Pro
1               5                   10                  15

Asp Gly Asn Val Val Ile Ala Cys Leu Val Gln Gly Phe Phe Pro Gln
            20                  25                  30

Glu Pro Leu Ser Val Thr Trp Ser Glu Ser Gly Gln Gly Val Thr Ala
            35                  40                  45

Arg Asn Phe Pro Pro Ser Gln Asp Ala Ser Gly Asp Leu Tyr Thr Thr
        50                  55                  60

Ser Ser Gln Leu Thr Leu Pro Ala Thr Gln Cys Leu Ala Gly Lys Ser
65                  70                  75                  80

Val Thr Cys His Val Lys His Tyr Thr Asn Pro Ser Gln Asp Val Thr
                85                  90                  95

Val Pro Cys Pro Val Pro Ser Thr Pro Pro Thr Pro Ser Pro Ser Thr
            100                 105                 110

Pro Pro Thr Pro Ser Pro Ser
            115

<210> SEQ ID NO 44
<211> LENGTH: 106
<212> TYPE: PRT
<213> ORGANISM: Artificial Sequence
<220> FEATURE:
<223> OTHER INFORMATION: Synthetic Construct

<400> SEQUENCE: 44

Asp Thr Ser Pro Lys Val Phe Pro Leu Ser Leu Asp Ser Thr Pro Gln
1               5                   10                  15

Asp Gly Asn Val Val Val Ala Cys Leu Val Gln Gly Phe Phe Pro Gln
            20                  25                  30

Glu Pro Leu Ser Val Thr Trp Ser Glu Ser Gly Gln Asn Val Thr Ala
            35                  40                  45

Arg Asn Phe Pro Pro Ser Gln Asp Ala Ser Gly Asp Leu Tyr Thr Thr
        50                  55                  60

Ser Ser Gln Leu Thr Leu Pro Ala Thr Gln Cys Pro Asp Gly Lys Ser
65                  70                  75                  80

Val Thr Cys His Val Lys His Tyr Thr Asn Pro Ser Gln Asp Val Thr
                85                  90                  95

Val Pro Cys Pro Val Pro Pro Pro Pro
            100                 105

<210> SEQ ID NO 45
<211> LENGTH: 159
<212> TYPE: PRT
<213> ORGANISM: Artificial Sequence
<220> FEATURE:
<223> OTHER INFORMATION: Synthetic Construct

<400> SEQUENCE: 45

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
130                 135                 140

Glu Lys Glu Lys Glu Glu Gln Glu Glu Arg Glu Thr Lys Thr Pro
145                 150                 155

<210> SEQ ID NO 46
<211> LENGTH: 103
<212> TYPE: PRT
<213> ORGANISM: Artificial Sequence
<220> FEATURE:
<223> OTHER INFORMATION: Synthetic Construct

<400> SEQUENCE: 46

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser
            100

<210> SEQ ID NO 47
<211> LENGTH: 104
<212> TYPE: PRT
<213> ORGANISM: Artificial Sequence
<220> FEATURE:
<223> OTHER INFORMATION: Synthetic Construct

<400> SEQUENCE: 47

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro
            100

```
<210> SEQ ID NO 48
<211> LENGTH: 106
<212> TYPE: PRT
<213> ORGANISM: Artificial Sequence
<220> FEATURE:
<223> OTHER INFORMATION: Synthetic Construct

<400> SEQUENCE: 48
```

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

```
<210> SEQ ID NO 49
<211> LENGTH: 105
<212> TYPE: PRT
<213> ORGANISM: Artificial Sequence
<220> FEATURE:
<223> OTHER INFORMATION: Synthetic Construct

<400> SEQUENCE: 49
```

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Leu Leu Val Thr Val Ala Phe Ile Ile Phe Trp Val
    50                  55                  60

Arg Ser Lys Arg Ser Arg Leu Leu His Ser Asp Tyr Met Asn Met Thr
65                  70                  75                  80

Pro Arg Arg Pro Gly Pro Thr Arg Lys His Tyr Gln Pro Tyr Ala Pro
                85                  90                  95

Pro Arg Asp Phe Ala Ala Tyr Arg Ser
            100                 105

```
<210> SEQ ID NO 50
<211> LENGTH: 108
<212> TYPE: PRT
<213> ORGANISM: Artificial Sequence
<220> FEATURE:
<223> OTHER INFORMATION: Synthetic Construct

<400> SEQUENCE: 50
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

-continued

```
Pro Arg Arg Lys Asn Pro Gln Glu Gly Asn Glu Leu Gln Lys Asp Lys
        50                  55                  60

Met Ala Glu Ala Tyr Ser Glu Ile Gly Met Lys Gly Glu Arg Arg Arg
 65                  70                  75                  80

Gly Lys Gly His Asp Gly Gln Gly Leu Ser Thr Ala Thr Lys Asp Thr
                 85                  90                  95

Tyr Asp Ala Leu His Met Gln Ala Leu Pro Pro Arg
            100                 105

<210> SEQ ID NO 51
<211> LENGTH: 105
<212> TYPE: PRT
<213> ORGANISM: Artificial Sequence
<220> FEATURE:
<223> OTHER INFORMATION: Synthetic Construct

<400> SEQUENCE: 51

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
             35                  40                  45

Val Leu Ala Cys Leu Leu Val Thr Val Ala Phe Ile Ile Phe Trp Val
 50                  55                  60

Arg Ser Lys Arg Ser Arg Leu Leu His Ser Asp Tyr Met Asn Met Thr
 65                  70                  75                  80

Pro Arg Arg Pro Gly Pro Thr Arg Lys His Tyr Gln Pro Tyr Ala Pro
                 85                  90                  95

Pro Arg Asp Phe Ala Ala Tyr Arg Ser
            100                 105

<210> SEQ ID NO 52
<211> LENGTH: 41
<212> TYPE: PRT
<213> ORGANISM: Artificial Sequence
<220> FEATURE:
<223> OTHER INFORMATION: Synthetic Construct

<400> SEQUENCE: 52

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
         35                  40

<210> SEQ ID NO 53
<211> LENGTH: 94
<212> TYPE: PRT
<213> ORGANISM: Artificial Sequence
<220> FEATURE:
<223> OTHER INFORMATION: Synthetic Construct

<400> SEQUENCE: 53

Pro Ala Asp Leu Ser Pro Gly Ala Ser Ser Val Thr Pro Pro Ala Pro
 1               5                  10                  15

Ala Arg Glu Pro Gly His Ser Pro Gln Ile Ile Ser Phe Phe Leu Ala
                20                  25                  30
```

```
Leu Thr Ser Thr Ala Leu Leu Phe Leu Leu Phe Phe Leu Thr Leu Arg
            35                  40                  45

Phe Ser Val Val Lys Arg Gly Arg Lys Leu Leu Tyr Ile Phe Lys
 50                  55                  60

Gln Pro Phe Met Arg Pro Val Gln Thr Thr Gln Glu Glu Asp Gly Cys
 65                  70                  75                  80

Ser Cys Arg Phe Pro Glu Glu Glu Gly Gly Cys Glu Leu
                 85                  90
```

<210> SEQ ID NO 54
<211> LENGTH: 42
<212> TYPE: PRT
<213> ORGANISM: Artificial Sequence
<220> FEATURE:
<223> OTHER INFORMATION: Synthetic Construct

<400> SEQUENCE: 54

```
Lys Arg Gly Arg Lys Lys Leu Leu Tyr Ile Phe Lys Gln Pro Phe Met
 1               5                   10                  15

Arg Pro Val Gln Thr Thr Gln Glu Glu Asp Gly Cys Ser Cys Arg Phe
             20                  25                  30

Pro Glu Glu Glu Gly Gly Cys Glu Leu
             35                  40
```

<210> SEQ ID NO 55
<211> LENGTH: 106
<212> TYPE: PRT
<213> ORGANISM: Artificial Sequence
<220> FEATURE:
<223> OTHER INFORMATION: Synthetic Construct

<400> SEQUENCE: 55

```
Asp Pro Pro Ala Thr Gln Pro Gln Glu Thr Gln Gly Pro Pro Ala Arg
 1               5                   10                  15

Pro Ile Thr Val Gln Pro Thr Glu Ala Trp Pro Arg Thr Ser Gln Gly
             20                  25                  30

Pro Ser Trp Val Glu Val Pro Gly Gly Arg Ala Val Ala Ala Ile Leu
             35                  40                  45

Gly Leu Gly Leu Val Leu Gly Leu Leu Gly Pro Leu Ala Ile Leu Leu
 50                  55                  60

Ala Leu Tyr Leu Leu Arg Arg Asp Gln Arg Leu Pro Pro Asp Ala His
 65                  70                  75                  80

Lys Pro Pro Gly Gly Gly Ser Phe Arg Thr Pro Ile Gln Glu Glu Gln
                 85                  90                  95

Ala Asp Ala His Ser Thr Leu Ala Lys Ile
                100                 105
```

<210> SEQ ID NO 56
<211> LENGTH: 42
<212> TYPE: PRT
<213> ORGANISM: Artificial Sequence
<220> FEATURE:
<223> OTHER INFORMATION: Synthetic Construct

<400> SEQUENCE: 56

```
Ala Leu Tyr Leu Leu Arg Arg Asp Gln Arg Leu Pro Pro Asp Ala His
 1               5                   10                  15

Lys Pro Pro Gly Gly Gly Ser Phe Arg Thr Pro Ile Gln Glu Glu Gln
             20                  25                  30

Ala Asp Ala His Ser Thr Leu Ala Lys Ile
```

<210> SEQ ID NO 57
<211> LENGTH: 69
<212> TYPE: PRT
<213> ORGANISM: Artificial Sequence
<220> FEATURE:
<223> OTHER INFORMATION: Synthetic Construct

<400> SEQUENCE: 57

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 58
<211> LENGTH: 130
<212> TYPE: PRT
<213> ORGANISM: Artificial Sequence
<220> FEATURE:
<223> OTHER INFORMATION: Synthetic Construct

<400> SEQUENCE: 58

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
            100                 105                 110

Trp Trp Tyr Asn Leu Asp Ser Trp Gly Gln Gly Thr Leu Val Thr Val
        115                 120                 125

Ser Ser
    130
```

<210> SEQ ID NO 59
<211> LENGTH: 109
<212> TYPE: PRT
<213> ORGANISM: Artificial Sequence
<220> FEATURE:
<223> OTHER INFORMATION: Synthetic Construct

<400> SEQUENCE: 59

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30
```

```
His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp Tyr
                 85                  90                  95

Val Val Phe Gly Gly Gly Thr Lys Leu Thr Val Leu Gly
                100                 105

<210> SEQ ID NO 60
<211> LENGTH: 121
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ser
            115                 120

<210> SEQ ID NO 61
<211> LENGTH: 105
<212> TYPE: PRT
<213> ORGANISM: Artificial Sequence
<220> FEATURE:
<223> OTHER INFORMATION: Synthetic Construct

<400> SEQUENCE: 61

Gln Ile Val Leu Ser Gln Ser Pro Ala Ile Leu Ser Asp Gly Glu Lys
1               5                   10                  15

Val Thr Met Thr Cys Arg Ala Ser Ser Val Ser Tyr Ile His Trp
                20                  25                  30

Phe Gln Gln Lys Pro Gly Ser Ser Pro Lys Pro Trp Ile Tyr Ala Thr
            35                  40                  45

Ser Asn Leu Ala Ser Gly Val Pro Val Arg Phe Ser Gly Ser Gly Ser
        50                  55                  60

Gly Thr Ser Tyr Ser Leu Thr Ile Ser Arg Val Glu Ala Glu Asp Ala
65                  70                  75                  80

Ala Thr Tyr Tyr Cys Gln Gln Trp Thr Ser Asn Pro Pro Thr Phe Gly
                85                  90                  95

Gly Gly Thr Lys Leu Glu Ile Lys Arg
```

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

```
Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30

Trp Ile Thr Trp Val Arg Gln Met Ser Gly Gly Gly Leu Glu Trp Met
        35                  40                  45

Gly Arg Ile Asp Pro Gly Asp Ser Tyr Thr Thr Tyr Asn Pro Ser Phe
    50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser
        115
```

<210> SEQ ID NO 63
<211> LENGTH: 110
<212> TYPE: PRT
<213> ORGANISM: Artificial Sequence
<220> FEATURE:
<223> OTHER INFORMATION: Synthetic Construct

<400> SEQUENCE: 63

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu
            100                 105                 110
```

<210> SEQ ID NO 64
<211> LENGTH: 118
<212> TYPE: PRT
<213> ORGANISM: Artificial Sequence
<220> FEATURE:
<223> OTHER INFORMATION: Synthetic Construct

<400> SEQUENCE: 64

```
Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Val Ile Tyr Ser Gly Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Ser Tyr Leu Asn His Gly Asp Tyr Trp Gly Gln Gly Thr
             100                 105                 110

Leu Val Thr Val Ser Ser
             115

<210> SEQ ID NO 65
<211> LENGTH: 111
<212> TYPE: PRT
<213> ORGANISM: Artificial Sequence
<220> FEATURE:
<223> OTHER INFORMATION: Synthetic Construct

<400> SEQUENCE: 65

Gln Ser Val Leu Thr Gln Pro Pro Ser Val Ser Ala Ala Pro Gly Gln
 1               5                  10                  15

Arg Val Thr Ile Ser Cys Ser Gly Thr Arg Ser Asn Ile Gly Ser Asp
             20                  25                  30

Tyr Val Ser Trp Tyr Gln His Leu Pro Gly Thr Ala Pro Lys Leu Leu
         35                  40                  45

Val Tyr Gly Asp Asn Leu Arg Pro Ser Gly Ile Pro Asp Arg Phe Ser
 50                  55                  60

Ala Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Tyr Thr Leu
                 85                  90                  95

Asn Gly Val Val Phe Gly Gly Gly Thr Lys Leu Thr Val Leu Gly
             100                 105                 110

<210> SEQ ID NO 66
<211> LENGTH: 112
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Thr Phe Thr Asn Tyr
             20                  25                  30

Tyr Val Phe Trp Val Arg Gln Arg Gln Arg Leu Glu Trp Ile Gly Asp
         35                  40                  45

Ile Asn Pro Val Asn Gly Asp Thr Asn Phe Asn Glu Lys Phe Lys Asn
 50                  55                  60

Arg Val Thr Ile Ser Ala Asp Lys Ser Ile Ser Thr Ala Tyr Leu Gln
 65                  70                  75                  80

Trp Ser Ser Leu Lys Ala Ser Asp Thr Ala Met Tyr Tyr Cys Arg Gly
```

```
                    85                  90                  95
Tyr Thr Met Asp Tyr Trp Gly Gln Gly Thr Leu Val Thr Val Ser Ser
                100                 105                 110
```

<210> SEQ ID NO 67
<211> LENGTH: 113
<212> TYPE: PRT
<213> ORGANISM: Artificial Sequence
<220> FEATURE:
<223> OTHER INFORMATION: Synthetic Construct

<400> SEQUENCE: 67

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Gln Gln Lys Pro Gly Lys Ala
            35                  40                  45

Pro Lys Leu Leu Ile Tyr Lys Val Ser Tyr Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly Thr Lys Val Glu Ile Lys
                100                 105                 110

Arg
```

<210> SEQ ID NO 68
<211> LENGTH: 286
<212> TYPE: PRT
<213> ORGANISM: Artificial Sequence
<220> FEATURE:
<223> OTHER INFORMATION: Synthetic Construct

<400> SEQUENCE: 68

```
Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
                20                  25                  30

Trp Ile Thr Trp Val Arg Gln Met Ser Gly Gly Leu Glu Trp Met
            35                  40                  45

Gly Arg Ile Asp Pro Gly Asp Ser Tyr Thr Thr Tyr Asn Pro Ser Phe
        50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
                165                 170                 175
Ser Gly Ser Leu Ser Val Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Glu Val Lys Thr Asp Ser
210                 215                 220

Thr Asp His Val Lys Pro Lys Glu Thr Asn Thr Lys Gln Pro Ser
225                 230                 235                 240

Lys Ser Cys His Lys Pro Lys Ala Ile Val His Thr Glu Lys Val Asn
            245                 250                 255

Met Met Ser Leu Thr Val Leu Gly Leu Arg Met Leu Phe Ala Lys Thr
            260                 265                 270

Val Ala Val Asn Phe Leu Leu Thr Ala Lys Leu Phe Phe Leu
            275                 280                 285

<210> SEQ ID NO 69
<211> LENGTH: 283
<212> TYPE: PRT
<213> ORGANISM: Artificial Sequence
<220> FEATURE:
<223> OTHER INFORMATION: Synthetic Construct

<400> SEQUENCE: 69

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Pro Ile Lys Thr Asp Val Ile Thr
    210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
```

```
                    245                 250                 255
Leu Lys Ser Val Val Tyr Phe Ala Ile Ile Thr Cys Cys Leu Leu Arg
                260                 265                 270

Arg Thr Ala Phe Cys Cys Asn Gly Glu Lys Ser
            275                 280

<210> SEQ ID NO 70
<211> LENGTH: 286
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
                20                  25                  30

Trp Ile Thr Trp Val Arg Gln Met Ser Gly Gly Leu Glu Trp Met
            35                  40                  45

Gly Arg Ile Asp Pro Gly Asp Ser Tyr Thr Thr Tyr Asn Pro Ser Phe
        50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Val Lys Thr Asp Ser
    210                 215                 220

Thr Asp His Val Lys Pro Lys Glu Thr Glu Asn Thr Lys Gln Pro Ser
225                 230                 235                 240

Lys Ser Cys His Lys Pro Lys Ala Ile Val His Thr Glu Lys Val Asn
                245                 250                 255

Met Met Ser Leu Thr Val Leu Gly Leu Arg Val Leu Phe Ala Lys Thr
            260                 265                 270

Val Ala Val Asn Phe Leu Leu Thr Ala Lys Leu Phe Phe Leu
        275                 280                 285

<210> SEQ ID NO 71
<211> LENGTH: 283
<212> TYPE: PRT
<213> ORGANISM: Artificial Sequence
<220> FEATURE:
<223> OTHER INFORMATION: Synthetic Construct
```

<400> SEQUENCE: 71

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Pro Ile Lys Thr Asp Val Ile Thr
210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Leu Val Tyr Leu Leu Leu Leu
                245                 250                 255

Leu Lys Ser Val Val Tyr Phe Val Ile Val Thr Cys Cys Leu Leu Arg
            260                 265                 270

Arg Thr Ala Phe Cys Cys Asn Gly Glu Lys Ser
        275                 280
```

<210> SEQ ID NO 72
<211> LENGTH: 299
<212> TYPE: PRT
<213> ORGANISM: Artificial Sequence
<220> FEATURE:
<223> OTHER INFORMATION: Synthetic Construct

<400> SEQUENCE: 72

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60
```

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gln Val Trp Gly Trp Gln Gly Gly Met Tyr Pro Arg Ser Asn
            100                 105                 110

Trp Trp Tyr Asn Met Asp Ser Trp Gly Gln Gly Thr Leu Val Thr Val
            115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
210                 215                 220

Arg Val Glu Pro Lys Ser Cys Glu Val Lys Thr Asp Ser Thr Asp His
225                 230                 235                 240

Val Lys Pro Lys Glu Thr Asn Thr Lys Gln Pro Ser Lys Ser Ser Cys
            245                 250                 255

His Lys Pro Lys Ala Ile Val His Thr Glu Lys Val Asn Met Met Ser
            260                 265                 270

Leu Thr Val Leu Gly Leu Arg Met Leu Phe Ala Lys Thr Val Ala Val
            275                 280                 285

Asn Phe Leu Leu Thr Ala Lys Leu Phe Phe Leu
            290                 295

<210> SEQ ID NO 73
<211> LENGTH: 281
<212> TYPE: PRT
<213> ORGANISM: Artificial Sequence
<220> FEATURE:
<223> OTHER INFORMATION: Synthetic Construct

<400> SEQUENCE: 73

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asn Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Tyr
            85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
            115                 120                 125

```
Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Pro Ile Lys Thr Asp Val Ile Thr Met Asp
    210                 215                 220

Pro Lys Asp Asn Cys Ser Lys Asp Ala Asn Asp Thr Leu Leu Leu Gln
225                 230                 235                 240

Leu Thr Asn Thr Ser Ala Tyr Tyr Met Tyr Leu Leu Leu Leu Leu Lys
                245                 250                 255

Ser Val Val Tyr Phe Ala Ile Ile Thr Cys Cys Leu Leu Arg Arg Thr
            260                 265                 270

Ala Phe Cys Cys Asn Gly Glu Lys Ser
        275                 280

<210> SEQ ID NO 74
<211> LENGTH: 299
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Val Trp Gly Trp Gln Gly Met Tyr Pro Arg Ser Asn
            100                 105                 110

Trp Trp Tyr Asn Met Asp Ser Trp Gly Gln Gly Thr Leu Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Ser
            180                 185                 190

Leu Ser Ser Val Val Thr Val Pro Ser Ser Ser Leu Gly Thr Gln Thr
        195                 200                 205
```

```
Tyr Ile Cys Asn Val Asn His Lys Pro Ser Asn Thr Lys Val Asp Lys
    210                 215                 220

Arg Val Glu Pro Lys Ser Cys Glu Val Lys Thr Asp Ser Thr Asp His
225                 230                 235                 240

Val Lys Pro Lys Glu Thr Glu Asn Thr Lys Gln Pro Ser Lys Ser Cys
                245                 250                 255

His Lys Pro Lys Ala Ile Val His Thr Glu Lys Val Asn Met Met Ser
                260                 265                 270

Leu Thr Val Leu Gly Leu Arg Val Leu Phe Ala Lys Thr Val Ala Val
                275                 280                 285

Asn Phe Leu Leu Thr Ala Lys Leu Phe Phe Leu
                290                 295

<210> SEQ ID NO 75
<211> LENGTH: 281
<212> TYPE: PRT
<213> ORGANISM: Artificial Sequence
<220> FEATURE:
<223> OTHER INFORMATION: Synthetic Construct

<400> SEQUENCE: 75

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Tyr
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Pro Ile Lys Thr Asp Val Ile Thr Met Asp
    210                 215                 220

Pro Lys Asp Asn Cys Ser Lys Asp Ala Asn Asp Thr Leu Leu Leu Gln
225                 230                 235                 240

Leu Thr Asn Thr Ser Ala Tyr Leu Val Tyr Leu Leu Leu Leu Leu Lys
                245                 250                 255

Ser Val Val Tyr Phe Val Ile Val Thr Cys Cys Leu Leu Arg Arg Thr
                260                 265                 270
```

Ala Phe Cys Cys Asn Gly Glu Lys Ser
            275                 280

<210> SEQ ID NO 76
<211> LENGTH: 21
<212> TYPE: PRT
<213> ORGANISM: Artificial Sequence
<220> FEATURE:
<223> OTHER INFORMATION: Synthetic Construct

<400> SEQUENCE: 76

Ser Arg Gly Gly Gly Ser Gly Gly Gly Gly Ser Gly Gly Gly Gly
1               5                   10                  15

Ser Leu Glu Met Ala
            20

<210> SEQ ID NO 77
<211> LENGTH: 260
<212> TYPE: PRT
<213> ORGANISM: Artificial Sequence
<220> FEATURE:
<223> OTHER INFORMATION: Synthetic Construct

<400> SEQUENCE: 77

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Leu Asp Ser Trp Gly Gln Gly Thr Leu Val
                245                 250                 255

Thr Val Ser Ser
            260

<210> SEQ ID NO 78
<211> LENGTH: 245
<212> TYPE: PRT
<213> ORGANISM: Artificial Sequence
<220> FEATURE:
<223> OTHER INFORMATION: Synthetic Construct

<400> SEQUENCE: 78

Gln Ile Val Leu Ser Gln Ser Pro Ala Ile Leu Ser Asp Gly Glu Lys
1               5                   10                  15

Val Thr Met Thr Cys Arg Ala Ser Ser Val Ser Tyr Ile His Trp
            20                  25                  30

Phe Gln Gln Lys Pro Gly Ser Ser Pro Lys Pro Trp Ile Tyr Ala Thr
            35                  40                  45

Ser Asn Leu Ala Ser Gly Val Pro Val Arg Phe Ser Gly Ser Gly Ser
    50                  55                  60

Gly Thr Ser Tyr Ser Leu Thr Ile Ser Arg Val Glu Ala Glu Asp Ala
65                  70                  75                  80

Ala Thr Tyr Tyr Cys Gln Gln Trp Thr Ser Asn Pro Pro Thr Phe Gly
                85                  90                  95

Gly Gly Thr Lys Leu Glu Ile Lys Arg Ser Arg Gly Gly Gly Gly Ser
            100                 105                 110

Gly Gly Gly Gly Ser Gly Gly Gly Gly Ser Leu Glu Gln Val Gln Leu
        115                 120                 125

Gln Gln Pro Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Arg Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Thr Ala Tyr Met Gln Leu Ser
        195                 200                 205

Ser Leu Thr Ser Glu Asp Ser Ala Val Tyr Tyr Cys Ala Arg Ser Thr
    210                 215                 220

Tyr Tyr Gly Gly Asp Trp Tyr Phe Asn Val Trp Gly Ala Gly Thr Thr
225                 230                 235                 240

Val Thr Val Ser Ser
                245

<210> SEQ ID NO 79
<211> LENGTH: 250
<212> TYPE: PRT
<213> ORGANISM: Artificial Sequence
<220> FEATURE:
<223> OTHER INFORMATION: Synthetic Construct

<400> SEQUENCE: 79

Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser

```
                50                  55                  60
Ala Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Tyr Thr Leu
                 85                  90                  95

Asn Gly Val Val Phe Gly Gly Gly Thr Lys Leu Thr Val Leu Gly Ser
                100                 105                 110

Arg Gly Gly Gly Gly Ser Gly Gly Gly Ser Gly Gly Gly Gly Gly Ser
                115                 120                 125

Leu Glu Met Ala Gln Val Gln Leu Val Glu Ser Gly Gly Gly Leu Val
                130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Ser Thr Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ser
                245                 250

<210> SEQ ID NO 80
<211> LENGTH: 368
<212> TYPE: PRT
<213> ORGANISM: Artificial Sequence
<220> FEATURE:
<223> OTHER INFORMATION: Synthetic Construct

<400> SEQUENCE: 80

Leu Pro Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Val Tyr
                 35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp Tyr
                 85                  90                  95

Val Val Phe Gly Gly Gly Thr Lys Leu Thr Val Leu Gly Ser Arg Gly
                100                 105                 110

Gly Gly Gly Ser Gly Gly Gly Ser Gly Gly Gly Gly Ser Leu Glu
                115                 120                 125

Met Ala Glu Val Gln Leu Val Gln Ser Gly Ala Glu Val Lys Lys Pro
                130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
```

```
               165                 170                 175
Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Leu Asp Ser Trp Gly Gln Gly Thr Leu Val
                245                 250                 255

Thr Val Ser Ser Ala Ala Ile Glu Val Met Tyr Pro Pro Pro Tyr
            260                 265                 270

Leu Asp Asn Glu Lys Ser Asn Gly Thr Ile Ile His Val Lys Gly Lys
                275                 280                 285

His Leu Cys Pro Ser Pro Leu Phe Pro Gly Pro Ser Lys Pro Phe Trp
            290                 295                 300

Val Leu Val Val Val Gly Gly Val Leu Ala Cys Leu Leu Val Thr Val
305                 310                 315                 320

Ala Phe Ile Ile Phe Trp Val Arg Ser Lys Arg Ser Arg Leu Leu His
                325                 330                 335

Ser Asp Tyr Met Asn Met Thr Pro Arg Arg Pro Gly Pro Thr Arg Lys
            340                 345                 350

His Tyr Gln Pro Tyr Ala Pro Pro Arg Asp Phe Ala Ala Tyr Arg Ser
            355                 360                 365

<210> SEQ ID NO 81
<211> LENGTH: 353
<212> TYPE: PRT
<213> ORGANISM: Artificial Sequence
<220> FEATURE:
<223> OTHER INFORMATION: Synthetic Construct

<400> SEQUENCE: 81

Gln Ile Val Leu Ser Gln Ser Pro Ala Ile Leu Ser Asp Gly Glu Lys
1               5                   10                  15

Val Thr Met Thr Cys Arg Ala Ser Ser Val Ser Tyr Ile His Trp
            20                  25                  30

Phe Gln Gln Lys Pro Gly Ser Ser Pro Lys Pro Trp Ile Tyr Ala Thr
        35                  40                  45

Ser Asn Leu Ala Ser Gly Val Pro Val Arg Phe Ser Gly Ser Gly Ser
    50                  55                  60

Gly Thr Ser Tyr Ser Leu Thr Ile Ser Arg Val Glu Ala Glu Asp Ala
65                  70                  75                  80

Ala Thr Tyr Tyr Cys Gln Gln Trp Thr Ser Asn Pro Pro Thr Phe Gly
                85                  90                  95

Gly Gly Thr Lys Leu Glu Ile Lys Arg Ser Arg Gly Gly Gly Gly Ser
            100                 105                 110

Gly Gly Gly Gly Ser Gly Gly Gly Ser Leu Glu Gln Val Gln Leu
        115                 120                 125

Gln Gln Pro Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Arg Gly Leu Glu Trp Ile Gly Ala Ile Tyr
```

```
                      165                 170                 175

Pro Gly Asn Gly Asp Thr Ser Tyr Asn Gln Lys Phe Lys Gly Lys Ala
                180                 185                 190

Thr Leu Thr Ala Asp Lys Ser Ser Thr Ala Tyr Met Gln Leu Ser
            195                 200                 205

Ser Leu Thr Ser Glu Asp Ser Ala Val Tyr Tyr Cys Ala Arg Ser Thr
210                 215                 220

Tyr Tyr Gly Gly Asp Trp Tyr Phe Asn Val Trp Gly Ala Gly Thr Thr
225                 230                 235                 240

Val Thr Val Ser Ser Ala Ala Ile Glu Val Met Tyr Pro Pro Pro
                245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Val Gly Gly Val Leu Ala Cys Leu Leu Val Thr
    290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
            340                 345                 350

Ser

<210> SEQ ID NO 82
<211> LENGTH: 358
<212> TYPE: PRT
<213> ORGANISM: Artificial Sequence
<220> FEATURE:
<223> OTHER INFORMATION: Synthetic Construct

<400> SEQUENCE: 82

Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
                20                  25                  30

Tyr Val Ser Trp Tyr Gln His Leu Pro Gly Thr Ala Pro Lys Leu Leu
            35                  40                  45

Val Tyr Gly Asp Asn Leu Arg Pro Ser Gly Ile Pro Asp Arg Phe Ser
        50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175
```

```
Leu Glu Trp Val Ser Val Ile Tyr Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ala Ala Ile Glu Val
                245                 250                 255

Met Tyr Pro Pro Pro Tyr Leu Asp Asn Glu Lys Ser Asn Gly Thr Ile
            260                 265                 270

Ile His Val Lys Gly Lys His Leu Cys Pro Ser Pro Leu Phe Pro Gly
        275                 280                 285

Pro Ser Lys Pro Phe Trp Val Leu Val Val Val Gly Gly Val Leu Ala
    290                 295                 300

Cys Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
                325                 330                 335

Pro Gly Pro Thr Arg Lys His Tyr Gln Pro Tyr Ala Pro Pro Arg Asp
            340                 345                 350

Phe Ala Ala Tyr Arg Ser
            355
```

```
<210> SEQ ID NO 83
<211> LENGTH: 180
<212> TYPE: DNA
<213> ORGANISM: Artificial Sequence
<220> FEATURE:
<223> OTHER INFORMATION: Synthetic Construct

<400> SEQUENCE: 83
ggaggaaaaa ctgtttcata cagaaggcgt ggaggaaaaa ctgtttcata cagaaggcgt      60
ggaggaaaaa ctgtttcata cagaaggcgt ggaggaaaaa ctgtttcata cagaaggcgt     120
ggaggaaaaa ctgtttcata cagaaggcgt ggaggaaaaa ctgtttcata cagaaggcgt     180

<210> SEQ ID NO 84
<211> LENGTH: 149
<212> TYPE: DNA
<213> ORGANISM: Artificial Sequence
<220> FEATURE:
<223> OTHER INFORMATION: Synthetic Construct

<400> SEQUENCE: 84
gccgccccga ctgcatctgc gtgttccaat tcgccaatga caagacgctg ggcggggttt      60
gtgtcatcat agaactaaag acatgcaaat atatttcttc cggggacacc gccagcaaac     120
gcgagcaacg ggccacgggg atgaagcag                                        149

<210> SEQ ID NO 85
<211> LENGTH: 335
<212> TYPE: DNA
<213> ORGANISM: Artificial Sequence
<220> FEATURE:
<223> OTHER INFORMATION: Synthetic Construct

<400> SEQUENCE: 85
```

```
ggaggaaaaa ctgtttcata cagaaggcgt ggaggaaaaa ctgtttcata cagaaggcgt    60
ggaggaaaaa ctgtttcata cagaaggcgt ggaggaaaaa ctgtttcata cagaaggcgt   120
ggaggaaaaa ctgtttcata cagaaggcgt ggaggaaaaa ctgtttcata cagaaggcgt   180
ctcgaggccg ccccgactgc atctgcgtgt tccaattcgc caatgacaag acgctgggcg   240
gggtttgtgt catcatagaa ctaaagacat gcaaatatat ttcttccggg gacaccgcca   300
gcaaacgcga gcaacgggcc acggggatga agcag                              335
```

<210> SEQ ID NO 86
<211> LENGTH: 119
<212> TYPE: PRT
<213> ORGANISM: Artificial Sequence
<220> FEATURE:
<223> OTHER INFORMATION: Synthetic Construct

<400> SEQUENCE: 86

```
Pro Thr His Leu Pro Tyr Val Ser Glu Met Leu Glu Ala Arg Thr Ala
1               5                   10                  15

Gly His Met Gln Thr Leu Ala Asp Phe Arg Gln Leu Pro Ala Arg Thr
                20                  25                  30

Leu Ser Thr His Trp Pro Pro Gln Arg Ser Leu Cys Ser Ser Asp Phe
            35                  40                  45

Ile Arg Ile Leu Val Ile Phe Ser Gly Met Phe Leu Val Phe Thr Leu
        50                  55                  60

Ala Gly Ala Leu Phe Leu His Gln Arg Arg Lys Tyr Arg Ser Asn Lys
65                  70                  75                  80

Gly Glu Ser Pro Val Glu Pro Ala Glu Pro Cys Arg Tyr Ser Cys Pro
                85                  90                  95

Arg Glu Glu Glu Gly Ser Thr Ile Pro Ile Gln Glu Asp Tyr Arg Lys
                100                 105                 110

Pro Glu Pro Ala Cys Ser Pro
            115
```

<210> SEQ ID NO 87
<211> LENGTH: 48
<212> TYPE: PRT
<213> ORGANISM: Artificial Sequence
<220> FEATURE:
<223> OTHER INFORMATION: Synthetic Construct

<400> SEQUENCE: 87

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
            35                  40                  45
```

<210> SEQ ID NO 88
<211> LENGTH: 264
<212> TYPE: PRT
<213> ORGANISM: Artificial Sequence
<220> FEATURE:
<223> OTHER INFORMATION: Synthetic Construct

<400> SEQUENCE: 88

```
Ala Pro Pro Leu Gly Thr Gln Pro Asp Cys Asn Pro Thr Pro Glu Asn
1               5                   10                  15

Gly Glu Ala Pro Ala Ser Thr Ser Pro Thr Gln Ser Leu Leu Val Asp
```

```
            20                  25                  30
Ser Gln Ala Ser Lys Thr Leu Pro Ile Pro Thr Ser Ala Pro Val Ser
            35                  40                  45

Ser Thr Gly Lys Pro Val Leu Asp Ala Gly Pro Val Leu Phe Trp Val
        50                  55                  60

Ile Leu Val Leu Val Val Val Gly Ser Ser Ala Phe Leu Leu Cys
65                  70                  75                  80

His Arg Arg Ala Cys Arg Lys Arg Ile Arg Gln Lys Leu His Leu Cys
                85                  90                  95

Tyr Pro Val Gln Thr Ser Gln Pro Lys Leu Glu Leu Val Asp Ser Arg
            100                 105                 110

Pro Arg Arg Ser Ser Thr Gln Leu Arg Ser Gly Ala Ser Val Thr Glu
        115                 120                 125

Pro Val Ala Glu Glu Arg Gly Leu Met Ser Gln Pro Leu Met Cys His
    130                 135                 140

Ser Val Gly Ala Ala Tyr Leu Glu Ser Leu Pro Leu Gln Asp Asp Ala
145                 150                 155                 160

Gly Gly Pro Ser Ser Pro Arg Asp Leu Pro Glu Pro Arg Val Ser Thr
                165                 170                 175

Glu His Thr Asn Asn Lys Ile Glu Lys Ile Tyr Ile Met Lys Ala Asp
            180                 185                 190

Thr Val Ile Val Gly Thr Val Lys Ala Glu Leu Pro Glu Gly Arg Gly
        195                 200                 205

Leu Ala Gly Pro Ala Glu Pro Glu Leu Glu Glu Leu Glu Ala Asp
    210                 215                 220

His Thr Pro His Tyr Pro Glu Gln Glu Thr Glu Pro Pro Leu Gly Ser
225                 230                 235                 240

Cys Ser Asp Val Met Leu Ser Val Glu Glu Gly Lys Glu Asp Pro
                245                 250                 255

Leu Pro Thr Ala Ala Ser Gly Lys
            260
```

<210> SEQ ID NO 89
<211> LENGTH: 184
<212> TYPE: PRT
<213> ORGANISM: Artificial Sequence
<220> FEATURE:
<223> OTHER INFORMATION: Synthetic Construct

<400> SEQUENCE: 89

```
His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

Pro Arg Arg Ser Ser Thr Gln Leu Arg Ser Gly Ala Ser Val Thr Glu
        35                  40                  45

Pro Val Ala Glu Glu Arg Gly Leu Met Ser Gln Pro Leu Met Cys His
    50                  55                  60

Ser Val Gly Ala Ala Tyr Leu Glu Ser Leu Pro Leu Gln Asp Asp Ala
65                  70                  75                  80

Gly Gly Pro Ser Ser Pro Arg Asp Leu Pro Glu Pro Arg Val Ser Thr
                85                  90                  95

Glu His Thr Asn Asn Lys Ile Glu Lys Ile Tyr Ile Met Lys Ala Asp
            100                 105                 110

Thr Val Ile Val Gly Thr Val Lys Ala Glu Leu Pro Glu Gly Arg Gly
```

```
                115                 120                 125
Leu Ala Gly Pro Ala Glu Pro Glu Leu Glu Glu Leu Glu Ala Asp
    130                 135                 140
His Thr Pro His Tyr Pro Glu Gln Glu Thr Glu Pro Pro Leu Gly Ser
145                 150                 155                 160
Cys Ser Asp Val Met Leu Ser Val Glu Glu Glu Gly Lys Glu Asp Pro
                165                 170                 175
Leu Pro Thr Ala Ala Ser Gly Lys
            180
```

<210> SEQ ID NO 90
<211> LENGTH: 108
<212> TYPE: PRT
<213> ORGANISM: Artificial Sequence
<220> FEATURE:
<223> OTHER INFORMATION: Synthetic Construct

<400> SEQUENCE: 90

```
Ala Ala Ala Ile Glu Val Met Tyr Pro Pro Pro Tyr Leu Asp Asn Glu
1               5                   10                  15
Lys Ser Asn Gly Thr Ile Ile His Val Lys Gly Lys His Leu Cys Pro
                20                  25                  30
Ser Pro Leu Phe Pro Gly Pro Ser Lys Pro Phe Trp Val Leu Val Val
            35                  40                  45
Val Gly Gly Val Leu Ala Cys Leu Leu Val Thr Val Ala Phe Ile Ile
    50                  55                  60
Phe Trp Val Arg Ser Lys Arg Ser Arg Leu Leu His Ser Asp Tyr Met
65                  70                  75                  80
Asn Met Thr Pro Arg Arg Pro Gly Pro Thr Arg Lys His Tyr Gln Pro
                85                  90                  95
Tyr Ala Pro Pro Arg Asp Phe Ala Ala Tyr Arg Ser
                100                 105
```

<210> SEQ ID NO 91
<211> LENGTH: 116
<212> TYPE: PRT
<213> ORGANISM: Artificial Sequence
<220> FEATURE:
<223> OTHER INFORMATION: Synthetic Construct

<400> SEQUENCE: 91

```
Ala Ala Ala Thr Gly Thr Thr Thr Pro Ala Pro Arg Pro Pro Thr Pro
1               5                   10                  15
Ala Pro Thr Ile Ala Ser Gln Pro Leu Ser Leu Arg Pro Glu Ala Cys
                20                  25                  30
Arg Pro Ala Ala Gly Gly Ala Val His Thr Arg Gly Leu Asp Phe Ala
            35                  40                  45
Cys Asp Ile Tyr Ile Trp Ala Pro Leu Ala Gly Thr Cys Gly Val Leu
    50                  55                  60
Leu Leu Ser Leu Val Ile Thr Leu Tyr Cys Lys Arg Gly Arg Lys Lys
65                  70                  75                  80
Leu Leu Tyr Ile Phe Lys Gln Pro Phe Met Arg Pro Val Gln Thr Thr
                85                  90                  95
Gln Glu Glu Asp Gly Cys Ser Cys Arg Phe Pro Glu Glu Glu Glu Gly
                100                 105                 110
Gly Cys Glu Leu
            115
```

<210> SEQ ID NO 92
<211> LENGTH: 99
<212> TYPE: PRT
<213> ORGANISM: Artificial Sequence
<220> FEATURE:
<223> OTHER INFORMATION: Synthetic Construct

<400> SEQUENCE: 92

```
Ala Ala Ala Thr Gly Pro Ala Asp Leu Ser Pro Gly Ala Ser Ser Val
1               5                   10                  15

Thr Pro Pro Ala Pro Ala Arg Glu Pro Gly His Ser Pro Gln Ile Ile
            20                  25                  30

Ser Phe Phe Leu Ala Leu Thr Ser Thr Ala Leu Leu Phe Leu Leu Phe
        35                  40                  45

Phe Leu Thr Leu Arg Phe Ser Val Val Lys Arg Gly Arg Lys Lys Leu
    50                  55                  60

Leu Tyr Ile Phe Lys Gln Pro Phe Met Arg Pro Val Gln Thr Thr Gln
65                  70                  75                  80

Glu Glu Asp Gly Cys Ser Cys Arg Phe Pro Glu Glu Glu Glu Gly Gly
                85                  90                  95

Cys Glu Leu
```

<210> SEQ ID NO 93
<211> LENGTH: 122
<212> TYPE: PRT
<213> ORGANISM: Artificial Sequence
<220> FEATURE:
<223> OTHER INFORMATION: Synthetic Construct

<400> SEQUENCE: 93

```
Ala Ala Ala Thr Gly Thr Thr Thr Pro Ala Pro Arg Pro Pro Thr Pro
1               5                   10                  15

Ala Pro Thr Ile Ala Ser Gln Pro Leu Ser Leu Arg Pro Glu Ala Cys
            20                  25                  30

Arg Pro Ala Ala Gly Gly Ala Val His Thr Arg Gly Leu Asp Phe Ala
        35                  40                  45

Cys Asp Ile Tyr Ile Trp Ala Pro Leu Ala Gly Thr Cys Gly Val Leu
    50                  55                  60

Leu Leu Ser Leu Val Ile Thr Leu Tyr Cys Gln Arg Arg Lys Tyr Arg
65                  70                  75                  80

Ser Asn Lys Gly Glu Ser Pro Val Glu Pro Ala Glu Pro Cys Arg Tyr
                85                  90                  95

Ser Cys Pro Arg Glu Glu Glu Gly Ser Thr Ile Pro Ile Gln Glu Asp
            100                 105                 110

Tyr Arg Lys Pro Glu Pro Ala Cys Ser Pro
        115                 120
```

<210> SEQ ID NO 94
<211> LENGTH: 124
<212> TYPE: PRT
<213> ORGANISM: Artificial Sequence
<220> FEATURE:
<223> OTHER INFORMATION: Synthetic Construct

<400> SEQUENCE: 94

```
Ala Ala Ala Thr Gly Pro Thr His Leu Pro Tyr Val Ser Glu Met Leu
1               5                   10                  15

Glu Ala Arg Thr Ala Gly His Met Gln Thr Leu Ala Asp Phe Arg Gln
            20                  25                  30
```

Leu Pro Ala Arg Thr Leu Ser Thr His Trp Pro Pro Gln Arg Ser Leu
         35                  40                  45

Cys Ser Ser Asp Phe Ile Arg Ile Leu Val Ile Phe Ser Gly Met Phe
 50                  55                  60

Leu Val Phe Thr Leu Ala Gly Ala Leu Phe Leu His Gln Arg Arg Lys
 65                  70                  75                  80

Tyr Arg Ser Asn Lys Gly Glu Ser Pro Val Glu Pro Ala Glu Pro Cys
                 85                  90                  95

Arg Tyr Ser Cys Pro Arg Glu Glu Gly Ser Thr Ile Pro Ile Gln
                100                 105                 110

Glu Asp Tyr Arg Lys Pro Glu Pro Ala Cys Ser Pro
                115                 120

<210> SEQ ID NO 95
<211> LENGTH: 258
<212> TYPE: PRT
<213> ORGANISM: Artificial Sequence
<220> FEATURE:
<223> OTHER INFORMATION: Synthetic Construct

<400> SEQUENCE: 95

Ala Ala Ala Thr Gly Thr Thr Thr Pro Ala Pro Arg Pro Pro Thr Pro
 1               5                  10                  15

Ala Pro Thr Ile Ala Ser Gln Pro Leu Ser Leu Arg Pro Glu Ala Cys
                 20                  25                  30

Arg Pro Ala Ala Gly Gly Ala Val His Thr Arg Gly Leu Asp Phe Ala
             35                  40                  45

Cys Asp Ile Tyr Ile Trp Ala Pro Leu Ala Gly Thr Cys Gly Val Leu
 50                  55                  60

Leu Leu Ser Leu Val Ile Thr Leu Tyr Cys His Arg Arg Ala Cys Arg
 65                  70                  75                  80

Lys Arg Ile Arg Gln Lys Leu His Leu Cys Tyr Pro Val Gln Thr Ser
                 85                  90                  95

Gln Pro Lys Leu Glu Leu Val Asp Ser Arg Pro Arg Arg Ser Ser Thr
                100                 105                 110

Gln Leu Arg Ser Gly Ala Ser Val Thr Glu Pro Val Ala Glu Glu Arg
             115                 120                 125

Gly Leu Met Ser Gln Pro Leu Met Cys His Ser Val Gly Ala Ala Tyr
         130                 135                 140

Leu Glu Ser Leu Pro Leu Gln Asp Asp Ala Gly Gly Pro Ser Ser Pro
145                 150                 155                 160

Arg Asp Leu Pro Glu Pro Arg Val Ser Thr Glu His Thr Asn Asn Lys
                165                 170                 175

Ile Glu Lys Ile Tyr Ile Met Lys Ala Asp Thr Val Ile Val Gly Thr
                180                 185                 190

Val Lys Ala Glu Leu Pro Glu Gly Arg Gly Leu Ala Gly Pro Ala Glu
             195                 200                 205

Pro Glu Leu Glu Glu Glu Leu Glu Ala Asp His Thr Pro His Tyr Pro
         210                 215                 220

Glu Gln Glu Thr Glu Pro Pro Leu Gly Ser Cys Ser Asp Val Met Leu
225                 230                 235                 240

Ser Val Glu Glu Glu Gly Lys Glu Asp Pro Leu Pro Thr Ala Ala Ser
                245                 250                 255

Gly Lys

-continued

```
<210> SEQ ID NO 96
<211> LENGTH: 269
<212> TYPE: PRT
<213> ORGANISM: Artificial Sequence
<220> FEATURE:
<223> OTHER INFORMATION: Synthetic Construct

<400> SEQUENCE: 96

Ala Ala Ala Thr Gly Ala Pro Pro Leu Gly Thr Gln Pro Asp Cys Asn
1               5                   10                  15

Pro Thr Pro Glu Asn Gly Glu Ala Pro Ala Ser Thr Ser Pro Thr Gln
            20                  25                  30

Ser Leu Leu Val Asp Ser Gln Ala Ser Lys Thr Leu Pro Ile Pro Thr
        35                  40                  45

Ser Ala Pro Val Ser Ser Thr Gly Lys Pro Val Leu Asp Ala Gly Pro
    50                  55                  60

Val Leu Phe Trp Val Ile Leu Val Leu Val Val Val Gly Ser Ser
65                  70                  75                  80

Ala Phe Leu Leu Cys His Arg Arg Ala Cys Arg Lys Arg Ile Arg Gln
                85                  90                  95

Lys Leu His Leu Cys Tyr Pro Val Gln Thr Ser Gln Pro Lys Leu Glu
            100                 105                 110

Leu Val Asp Ser Arg Pro Arg Arg Ser Ser Thr Gln Leu Arg Ser Gly
        115                 120                 125

Ala Ser Val Thr Glu Pro Val Ala Glu Glu Arg Gly Leu Met Ser Gln
    130                 135                 140

Pro Leu Met Cys His Ser Val Gly Ala Ala Tyr Leu Glu Ser Leu Pro
145                 150                 155                 160

Leu Gln Asp Asp Ala Gly Gly Pro Ser Ser Pro Arg Asp Leu Pro Glu
                165                 170                 175

Pro Arg Val Ser Thr Glu His Thr Asn Asn Lys Ile Glu Lys Ile Tyr
            180                 185                 190

Ile Met Lys Ala Asp Thr Val Ile Val Gly Thr Val Lys Ala Glu Leu
        195                 200                 205

Pro Glu Gly Arg Gly Leu Ala Gly Pro Ala Glu Pro Glu Leu Glu Glu
    210                 215                 220

Glu Leu Glu Ala Asp His Thr Pro His Tyr Pro Glu Gln Glu Thr Glu
225                 230                 235                 240

Pro Pro Leu Gly Ser Cys Ser Asp Val Met Leu Ser Val Glu Glu Glu
                245                 250                 255

Gly Lys Glu Asp Pro Leu Pro Thr Ala Ala Ser Gly Lys
            260                 265

<210> SEQ ID NO 97
<211> LENGTH: 116
<212> TYPE: PRT
<213> ORGANISM: Artificial Sequence
<220> FEATURE:
<223> OTHER INFORMATION: Synthetic Construct

<400> SEQUENCE: 97

Ala Ala Ala Thr Gly Thr Thr Thr Pro Ala Pro Arg Pro Pro Thr Pro
1               5                   10                  15

Ala Pro Thr Ile Ala Ser Gln Pro Leu Ser Leu Arg Pro Glu Ala Cys
            20                  25                  30

Arg Pro Ala Ala Gly Gly Ala Val His Thr Arg Gly Leu Asp Phe Ala
        35                  40                  45
```

```
Cys Asp Ile Tyr Ile Trp Ala Pro Leu Ala Gly Thr Cys Gly Val Leu
 50                  55                  60

Leu Leu Ser Leu Val Ile Thr Leu Tyr Cys Ala Leu Tyr Leu Leu Arg
 65                  70                  75                  80

Arg Asp Gln Arg Leu Pro Pro Asp Ala His Lys Pro Pro Gly Gly Gly
                 85                  90                  95

Ser Phe Arg Thr Pro Ile Gln Glu Gln Ala Asp Ala His Ser Thr
                100                 105                 110

Leu Ala Lys Ile
        115
```

<210> SEQ ID NO 98
<211> LENGTH: 113
<212> TYPE: PRT
<213> ORGANISM: Artificial Sequence
<220> FEATURE:
<223> OTHER INFORMATION: Synthetic Construct

<400> SEQUENCE: 98

```
Ala Ala Ala Thr Gly Asp Arg Asp Pro Pro Ala Thr Gln Pro Gln Glu
 1               5                  10                  15

Thr Gln Gly Pro Pro Ala Arg Pro Ile Thr Val Gln Pro Thr Glu Ala
                 20                  25                  30

Trp Pro Arg Thr Ser Gln Gly Pro Ser Trp Val Glu Val Pro Gly Gly
                 35                  40                  45

Arg Ala Val Ala Ala Ile Leu Gly Leu Gly Leu Val Leu Gly Leu Leu
 50                  55                  60

Gly Pro Leu Ala Ile Leu Leu Ala Leu Tyr Leu Leu Arg Arg Asp Gln
 65                  70                  75                  80

Arg Leu Pro Pro Asp Ala His Lys Pro Pro Gly Gly Gly Ser Phe Arg
                 85                  90                  95

Thr Pro Ile Gln Glu Glu Gln Ala Asp Ala His Ser Thr Leu Ala Lys
                100                 105                 110

Ile
```

<210> SEQ ID NO 99
<211> LENGTH: 129
<212> TYPE: PRT
<213> ORGANISM: Artificial Sequence
<220> FEATURE:
<223> OTHER INFORMATION: Synthetic Construct

<400> SEQUENCE: 99

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
                 35                  40                  45

Gly Ile Ile Tyr Pro Gly Asp Ser Asp Thr Arg Tyr Ser Pro Ser Phe
 50                  55                  60

Gln Gly Gln Val Thr Ile Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95

Arg Gln Val Trp Gly Trp Gln Gly Gly Met Tyr Pro Arg Ser Asn Trp
                100                 105                 110
```

```
<210> SEQ ID NO 100
<211> LENGTH: 108
<212> TYPE: PRT
<213> ORGANISM: Artificial Sequence
<220> FEATURE:
<223> OTHER INFORMATION: Synthetic Construct

<400> SEQUENCE: 100
```

| | | | | | | | | | | | | | | | |
|---|---|---|---|---|---|---|---|---|---|---|---|---|---|---|---|
| Trp | Tyr | Asn | Leu | Asp | Ser | Trp | Gly | Gln | Gly | Thr | Leu | Val | Thr | Val | Ser |
| | | | 115 | | | | 120 | | | | 125 | | | | |
| Ser | | | | | | | | | | | | | | | |

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu
            100                 105

<210> SEQ ID NO 101
<211> LENGTH: 118
<212> TYPE: PRT
<213> ORGANISM: Artificial Sequence
<220> FEATURE:
<223> OTHER INFORMATION: Synthetic Construct

<400> SEQUENCE: 101

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ser Ala Ala Trp Met Asp Ser Trp Gly Gln Gly Thr
            100                 105                 110

Leu Val Thr Val Ser Ser
        115

```
<210> SEQ ID NO 102
<211> LENGTH: 106
<212> TYPE: PRT
<213> ORGANISM: Artificial Sequence
<220> FEATURE:
<223> OTHER INFORMATION: Synthetic Construct
```

<400> SEQUENCE: 102

Asp Ile Gln Leu Thr Gln Ser Pro Ser Leu Ser Thr Ser Val Gly
1               5                   10                  15

Asp Arg Val Thr Ile Thr Cys Gln Ala Ser His Asp Ile Arg Asn Tyr
            20                  25                  30

Leu Asn Trp Tyr Gln Gln Lys Pro Gly Lys Ala Pro Asn Leu Leu Ile
        35                  40                  45

Tyr Ala Asn Leu Gln Thr Gly Val Pro Ser Arg Phe Ser Gly Arg Gly
50                  55                  60

Ser Gly Thr Asp Phe Thr Leu Thr Ile Ser Ser Leu Gln Pro Glu Asp
65                  70                  75                  80

Ile Ala Thr Tyr Tyr Cys Gln Gln Tyr Asp Gly Leu Pro Leu Thr Phe
                85                  90                  95

Gly Gln Gly Thr Arg Leu Glu Ile Lys Arg
            100                 105

<210> SEQ ID NO 103
<211> LENGTH: 3
<212> TYPE: PRT
<213> ORGANISM: Artificial Sequence
<220> FEATURE:
<223> OTHER INFORMATION: Synthetic Construct

<400> SEQUENCE: 103

Ala Ala Ala
1

<210> SEQ ID NO 104
<211> LENGTH: 5
<212> TYPE: PRT
<213> ORGANISM: Artificial Sequence
<220> FEATURE:
<223> OTHER INFORMATION: Synthetic Construct

<400> SEQUENCE: 104

Ala Ala Ala Thr Gly
1               5

<210> SEQ ID NO 105
<211> LENGTH: 500
<212> TYPE: PRT
<213> ORGANISM: Artificial Sequence
<220> FEATURE:
<223> OTHER INFORMATION: Synthetic Construct

<400> SEQUENCE: 105

Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

```
Arg Gly Gly Gly Gly Ser Gly Gly Gly Ser Gly Gly Gly Ser
            115                 120                 125

Leu Glu Met Ala Gln Val Gln Leu Val Glu Ser Gly Gly Gly Leu Val
        130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Ser Ser Thr Tyr Tyr
            180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ser Thr Gly Gly Gly Gly
                245                 250                 255

Ser Asp Val Gln Leu Val Gln Ser Gly Ala Glu Val Lys Lys Pro Gly
                260                 265                 270

Ala Ser Val Lys Val Ser Cys Lys Ala Ser Gly Tyr Thr Phe Thr Arg
    275                 280                 285

Tyr Thr Met His Trp Val Arg Gln Ala Pro Gly Gln Gly Leu Glu Trp
    290                 295                 300

Ile Gly Tyr Ile Asn Pro Ser Arg Gly Tyr Thr Asn Tyr Ala Asp Ser
305                 310                 315                 320

Val Lys Gly Arg Phe Thr Ile Thr Thr Asp Lys Ser Thr Ser Thr Ala
                325                 330                 335

Tyr Met Glu Leu Ser Ser Leu Arg Ser Glu Asp Thr Ala Thr Tyr Tyr
        340                 345                 350

Cys Ala Arg Tyr Tyr Asp Asp His Tyr Cys Leu Asp Tyr Trp Gly Gln
            355                 360                 365

Gly Thr Thr Val Thr Val Ser Ser Gly Glu Gly Thr Ser Thr Gly Ser
    370                 375                 380

Gly Gly Ser Gly Gly Ser Gly Gly Ala Asp Asp Ile Val Leu Thr Gln
385                 390                 395                 400

Ser Pro Ala Thr Leu Ser Leu Ser Pro Gly Glu Arg Ala Thr Leu Ser
                405                 410                 415

Cys Arg Ala Ser Gln Ser Val Ser Tyr Met Asn Trp Tyr Gln Gln Lys
            420                 425                 430

Pro Gly Lys Ala Pro Lys Arg Trp Ile Tyr Asp Thr Ser Lys Val Ala
        435                 440                 445

Ser Gly Val Pro Ala Arg Phe Ser Gly Ser Gly Ser Gly Thr Asp Tyr
    450                 455                 460

Ser Leu Thr Ile Asn Ser Leu Glu Ala Glu Asp Ala Ala Thr Tyr Tyr
465                 470                 475                 480

Cys Gln Gln Trp Ser Ser Asn Pro Leu Thr Phe Gly Gly Gly Thr Lys
                485                 490                 495

Val Glu Ile Lys
        500
```

UNITED STATES PATENT AND TRADEMARK OFFICE
CERTIFICATE OF CORRECTION

Page 1 of 2

PATENT NO. : 11,965,021 B2
APPLICATION NO. : 16/608366
DATED : April 23, 2024
INVENTOR(S) : Hong Liu et al.

It is certified that error appears in the above-identified patent and that said Letters Patent is hereby corrected as shown below:

In the Drawings

On Drawing Sheet 9 of 20, please replace

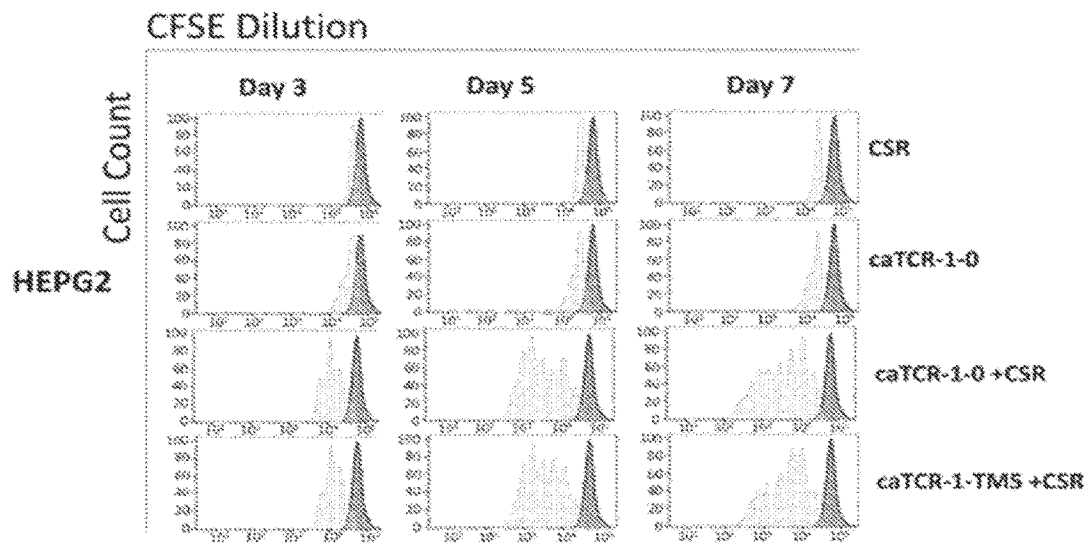

with the corrected FIG. 9 as shown on the attached drawing sheet.

Signed and Sealed this
Sixteenth Day of September, 2025

Coke Morgan Stewart
*Acting Director of the United States Patent and Trademark Office*